US009115708B2

United States Patent
van der Merwe et al.

(10) Patent No.: US 9,115,708 B2
(45) Date of Patent: Aug. 25, 2015

(54) FLUID BALANCING SYSTEMS AND METHODS

(71) Applicant: DEKA Products Limited Partnership, Manchester, NH (US)

(72) Inventors: Dirk A. van der Merwe, Canterbury, NH (US); Michael J. Wilt, Windham, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

(21) Appl. No.: 14/262,178

(22) Filed: Apr. 25, 2014

(65) Prior Publication Data

US 2014/0322053 A1 Oct. 30, 2014

Related U.S. Application Data

(60) Division of application No. 13/745,730, filed on Jan. 18, 2013, now Pat. No. 8,721,879, which is a division of application No. 12/199,452, filed on Aug. 27, 2008, now Pat. No. 8,357,298, which is a (Continued)

(51) Int. Cl.
*F04B 45/053* (2006.01)
*F04B 43/113* (2006.01)
(Continued)

(52) U.S. Cl.
CPC .............. *F04B 45/0536* (2013.01); *A61M 1/16* (2013.01); *A61M 1/1635* (2014.02);
(Continued)

(58) Field of Classification Search
CPC .......... A61M 2205/12; A61M 1/1635; A61M 1/3646; A61M 1/3441; A61M 1/16; A61M 1/365; A61M 1/1037; A61M 1/3465; A61M 2205/502; A61M 1/3652; F04B 45/0536; G06F 19/3406; G06F 19/3481
See application file for complete search history.

(56) References Cited

U.S. PATENT DOCUMENTS 1,693,526 A   11/1928   Owens
2,529,028 A   11/1950   Landon
(Continued)

FOREIGN PATENT DOCUMENTS

CN   2374187 Y   4/2000
CN   1830494 A   9/2006
(Continued)

OTHER PUBLICATIONS

Response to Examination Report dated May 16, 2012 for EP Application No. 08726213.5 filed Feb. 27, 2008, which Response is dated Nov. 21, 2012, and claims as pending for EP Application No. 08726213.5 as of Nov. 21, 2012.

(Continued)

*Primary Examiner* — John Kim
(74) *Attorney, Agent, or Firm* — Wolf, Greenfield & Sacks, P.C.

(57) ABSTRACT

Hemodialysis dialysis systems are disclosed. Hemodialysis systems of the invention may include a dialysate flow path including a balancing circuit, a mixing circuit, and/or a directing circuit. The circuits may be defined within one or more cassettes. The fluid circuits may be at least partially isolated, spatially and/or thermally, from electrical components of the system. A gas supply may be provided in fluid communication with the dialysate flow path and/or the dialyzer to, urge dialysate through the dialyzer and blood back to the patient. The hemodialysis systems may include fluid handling devices actuated using a control fluid, optionally delivered using detachable pump. Fluid handling devices may be generally rigid and of a spheroid shape, optionally with a diaphragm dividing the device into compartments.

12 Claims, 135 Drawing Sheets

Related U.S. Application Data continuation-in-part of application No. 12/072,908, filed on Feb. 27, 2008, now Pat. No. 8,246,826.

(60) Provisional application No. 60/903,582, filed on Feb. 27, 2007, provisional application No. 60/904,024, filed on Feb. 27, 2007.

(51) Int. Cl.
*A61M 1/16* (2006.01)
*G06F 19/00* (2011.01)
*A61M 1/36* (2006.01)
*A61M 1/34* (2006.01)

(52) U.S. Cl.
CPC ............ *A61M 1/3465* (2014.02); *A61M 1/365* (2014.02); *A61M 1/3646* (2014.02); *A61M 1/3652* (2014.02); *G06F 19/3406* (2013.01); *A61M 1/3441* (2013.01); *A61M 2205/12* (2013.01); *A61M 2205/502* (2013.01); *G06F 19/3481* (2013.01)

(56) References Cited

U.S. PATENT DOCUMENTS

| | | |
|---|---|---|
| 2,741,099 A | 4/1956 | Beane |
| 2,816,514 A | 12/1957 | Freese |
| 3,016,563 A | 1/1962 | De Jong |
| 3,200,648 A | 8/1965 | Waggaman |
| 3,508,656 A | 4/1970 | Serfass et al. |
| 3,539,081 A | 11/1970 | Norton et al. |
| 3,656,873 A | 4/1972 | Schiff |
| 3,759,483 A | 9/1973 | Baxter |
| RE27,849 E | 12/1973 | Wortman |
| 3,827,561 A | 8/1974 | Serfass et al. |
| 3,882,861 A | 5/1975 | Kettering et al. |
| 3,936,729 A | 2/1976 | Winslow |
| 4,096,211 A | 6/1978 | Rameau |
| 4,096,859 A | 6/1978 | Agarwal et al. |
| 4,133,312 A | 1/1979 | Burd |
| 4,155,852 A | 5/1979 | Fischel et al. |
| 4,161,264 A | 7/1979 | Malmgren et al. |
| 4,266,814 A | 5/1981 | Gallagher |
| 4,267,040 A | 5/1981 | Schal et al. |
| 4,282,099 A | 8/1981 | Jones |
| 4,299,784 A | 11/1981 | Hense |
| 4,309,592 A | 1/1982 | Le Boeuf |
| 4,322,054 A | 3/1982 | Campbell |
| 4,362,156 A | 12/1982 | Feller et al. |
| 4,369,781 A | 1/1983 | Gilson et al. |
| 4,398,908 A | 8/1983 | Siposs |
| 4,411,783 A | 10/1983 | Dickens et al. |
| 4,439,188 A | 3/1984 | Dennehy et al. |
| 4,441,357 A | 4/1984 | Kahn et al. |
| 4,479,760 A | 10/1984 | Bilstad et al. |
| 4,479,761 A | 10/1984 | Bilstad et al. |
| 4,479,762 A | 10/1984 | Bilstad et al. |
| 4,490,254 A | 12/1984 | Gordon et al. |
| 4,492,258 A | 1/1985 | Lichtenstein et al. |
| 4,501,405 A | 2/1985 | Usry |
| 4,517,081 A | 5/1985 | Amiot et al. |
| 4,574,876 A | 3/1986 | Aid |
| 4,585,442 A | 4/1986 | Mannes |
| 4,623,334 A | 11/1986 | Riddell |
| 4,623,450 A | 11/1986 | Vantard et al. |
| 4,664,891 A | 5/1987 | Cosentino et al. |
| 4,666,598 A | 5/1987 | Heath et al. |
| 4,680,445 A | 7/1987 | Ogawa |
| 4,695,385 A | 9/1987 | Boag |
| 4,718,022 A | 1/1988 | Cochran |
| 4,731,072 A | 3/1988 | Aid |
| 4,767,526 A | 8/1988 | Vantard |
| 4,770,769 A | 9/1988 | Schael et al. |
| 4,778,451 A | 10/1988 | Kamen |
| 4,784,495 A | 11/1988 | Jonsson et al. |
| 4,808,161 A | 2/1989 | Kamen |
| 4,822,343 A | 4/1989 | Beiser |
| 4,826,482 A | 5/1989 | Kamen |
| 4,828,543 A | 5/1989 | Weiss et al. |
| 4,833,329 A | 5/1989 | Quint et al. |
| 4,863,461 A | 9/1989 | Jarvik |
| 4,906,816 A | 3/1990 | van Leerdam |
| 4,927,411 A | 5/1990 | Pastrone et al. |
| 4,950,235 A | 8/1990 | Slate et al. |
| 4,971,700 A | 11/1990 | Tsuji et al. |
| 4,976,162 A | 12/1990 | Kamen |
| 4,976,729 A | 12/1990 | Holfert et al. |
| 4,997,570 A | 3/1991 | Polaschegg |
| 5,024,756 A | 6/1991 | Sternby |
| 5,033,513 A | 7/1991 | Bartholomew |
| 5,061,241 A | 10/1991 | Stephens, Jr. et al. |
| 5,062,774 A | 11/1991 | Kramer et al. |
| 5,074,838 A | 12/1991 | Kroyer |
| 5,088,515 A | 2/1992 | Kamen |
| 5,088,901 A | 2/1992 | Brauer |
| 5,100,554 A | 3/1992 | Polaschegg |
| 5,105,981 A | 4/1992 | Gehman |
| 5,110,447 A | 5/1992 | MacWilliams et al. |
| 5,110,477 A | 5/1992 | Howard et al. |
| 5,116,316 A | 5/1992 | Sertic et al. |
| 5,125,069 A | 6/1992 | O'Boyle |
| 5,160,325 A | 11/1992 | Nichols et al. |
| 5,178,182 A | 1/1993 | Kamen |
| 5,245,693 A | 9/1993 | Ford et al. |
| 5,247,434 A | 9/1993 | Peterson et al. |
| 5,267,956 A | 12/1993 | Beauchat |
| 5,278,072 A | 1/1994 | Wall et al. |
| 5,300,044 A | 4/1994 | Classey et al. |
| 5,306,242 A | 4/1994 | Joyce et al. |
| 5,324,422 A | 6/1994 | Colleran et al. |
| 5,326,476 A | 7/1994 | Grogan et al. |
| D350,823 S | 9/1994 | Lanigan |
| D350,850 S | 9/1994 | Angelini |
| 5,349,896 A | 9/1994 | Delaney, III et al. |
| 5,350,357 A | 9/1994 | Kamen et al. |
| 5,351,686 A | 10/1994 | Steuer et al. |
| 5,378,126 A | 1/1995 | Abrahamson et al. |
| 5,381,510 A | 1/1995 | Ford et al. |
| 5,385,540 A | 1/1995 | Abbott et al. |
| 5,395,316 A | 3/1995 | Martin |
| 5,410,255 A | 4/1995 | Bailey |
| 5,411,472 A | 5/1995 | Steg, Jr. et al. |
| 5,413,566 A | 5/1995 | Sevrain et al. |
| 5,420,962 A | 5/1995 | Bakke |
| 5,421,823 A | 6/1995 | Kamen et al. |
| 5,423,738 A | 6/1995 | Robinson et al. |
| 5,429,485 A | 7/1995 | Dodge |
| 5,431,626 A | 7/1995 | Bryant et al. |
| 5,438,510 A | 8/1995 | Bryant et al. |
| 5,441,231 A | 8/1995 | Payne et al. |
| 5,441,343 A | 8/1995 | Pylkki et al. |
| 5,441,636 A | 8/1995 | Chevallet et al. |
| 5,472,614 A | 12/1995 | Rossi |
| 5,474,683 A | 12/1995 | Bryant et al. |
| 5,476,368 A | 12/1995 | Rabenau et al. |
| 5,476,444 A | 12/1995 | Keeling et al. |
| 5,482,440 A | 1/1996 | Dennehey et al. |
| 5,486,286 A | 1/1996 | Peterson et al. |
| 5,487,827 A | 1/1996 | Peterson et al. |
| 5,496,273 A | 3/1996 | Pastrone et al. |
| 5,527,507 A | 6/1996 | Childers et al. |
| 5,541,344 A | 7/1996 | Becker et al. |
| 5,542,919 A | 8/1996 | Simon et al. |
| 5,558,255 A | 9/1996 | Sancoff et al. |
| 5,568,362 A | 10/1996 | Hansson |
| 5,575,310 A | 11/1996 | Kamen et al. |
| 5,578,012 A | 11/1996 | Kamen et al. |
| 5,580,460 A | 12/1996 | Polaschegg et al. |
| 5,586,438 A | 12/1996 | Fahy et al. |
| 5,591,344 A | 1/1997 | Kenley et al. |
| 5,591,389 A | 1/1997 | Esrock |
| 5,593,290 A | 1/1997 | Greisch et al. |
| 5,628,908 A | 5/1997 | Kamen et al. |
| 5,632,894 A | 5/1997 | White et al. |

(56) References Cited

U.S. PATENT DOCUMENTS

| | | |
|---|---|---|
| 5,634,896 A | 6/1997 | Bryant et al. |
| 5,645,531 A | 7/1997 | Thompson et al. |
| 5,651,765 A | 7/1997 | Haworth et al. |
| 5,651,893 A | 7/1997 | Kenley et al. |
| 5,651,898 A | 7/1997 | Imura |
| 5,690,831 A | 11/1997 | Kenley et al. |
| 5,692,729 A | 12/1997 | Harhen |
| 5,702,597 A | 12/1997 | Chevallet et al. |
| 5,729,653 A | 3/1998 | Magliochetti et al. |
| 5,730,720 A | 3/1998 | Sites et al. |
| 5,744,027 A | 4/1998 | Connell et al. |
| 5,755,275 A | 5/1998 | Rose et al. |
| 5,755,683 A | 5/1998 | Houle et al. |
| 5,776,091 A | 7/1998 | Brugger et al. |
| 5,782,508 A | 7/1998 | Bartholomew |
| 5,797,897 A | 8/1998 | Jepson et al. |
| 5,808,181 A | 9/1998 | Wamsiedler et al. |
| 5,875,282 A | 2/1999 | Jordan et al. |
| 5,879,316 A | 3/1999 | Safar et al. |
| 5,882,047 A | 3/1999 | Ostrander et al. |
| 5,899,873 A | 5/1999 | Jones et al. |
| 5,902,476 A | 5/1999 | Twardowski et al. |
| 5,931,648 A | 8/1999 | Del Canizo |
| 5,932,103 A | 8/1999 | Kenley et al. |
| 5,932,110 A | 8/1999 | Shah et al. |
| 5,938,634 A | 8/1999 | Packard |
| 5,947,931 A | 9/1999 | Bierman et al. |
| 5,948,251 A | 9/1999 | Brugger |
| 5,989,423 A | 11/1999 | Kamen et al. |
| 6,039,877 A | 3/2000 | Chevallet et al. |
| 6,041,801 A | 3/2000 | Gray et al. |
| 6,042,784 A | 3/2000 | Wamsiedler et al. |
| 6,044,868 A | 4/2000 | Gretz et al. |
| 6,047,108 A | 4/2000 | Sword et al. |
| 6,062,068 A | 5/2000 | Bowling et al. |
| 6,070,761 A | 6/2000 | Bloom et al. |
| 6,101,406 A | 8/2000 | Hacker et al. |
| 6,109,881 A | 8/2000 | Snodgrass et al. |
| 6,136,201 A | 10/2000 | Shah et al. |
| 6,139,534 A | 10/2000 | Niedospial, Jr. et al. |
| 6,139,819 A | 10/2000 | Unger et al. |
| 6,142,164 A | 11/2000 | Wier et al. |
| 6,142,446 A | 11/2000 | Leinsing |
| 6,146,354 A | 11/2000 | Beil |
| 6,146,523 A | 11/2000 | Kenley et al. |
| 6,146,536 A | 11/2000 | Twardowski |
| 6,153,102 A | 11/2000 | Kenley et al. |
| 6,159,192 A | 12/2000 | Fowles et al. |
| 6,171,261 B1 | 1/2001 | Niermann et al. |
| 6,176,904 B1 | 1/2001 | Gupta |
| 6,210,361 B1 | 4/2001 | Kamen et al. |
| 6,213,996 B1 | 4/2001 | Jepson et al. |
| 6,223,130 B1 | 4/2001 | Gray et al. |
| 6,234,997 B1 | 5/2001 | Kamen et al. |
| RE37,324 E | 8/2001 | Esrock |
| 6,274,303 B1 | 8/2001 | Wowk et al. |
| 6,277,272 B1 | 8/2001 | Nikaido et al. |
| 6,277,277 B1 | 8/2001 | Jacobi et al. |
| 6,284,131 B1 | 9/2001 | Hogard et al. |
| 6,302,653 B1 | 10/2001 | Bryant et al. |
| 6,321,597 B1 | 11/2001 | Demers et al. |
| 6,331,778 B1 | 12/2001 | Dailey et al. |
| 6,336,003 B1 | 1/2002 | Mitsunaga et al. |
| 6,336,911 B1 | 1/2002 | Westerbeck |
| 6,347,633 B1 | 2/2002 | Groth et al. |
| 6,382,923 B1 | 5/2002 | Gray |
| 6,406,426 B1 | 6/2002 | Reuss et al. |
| 6,406,452 B1 | 6/2002 | Westerbeck |
| 6,413,233 B1 | 7/2002 | Sites et al. |
| 6,415,797 B1 | 7/2002 | Groth et al. |
| 6,416,293 B1 | 7/2002 | Bouchard et al. |
| 6,423,053 B1 | 7/2002 | Lee |
| 6,464,666 B1 | 10/2002 | Augustine et al. |
| 6,480,257 B2 | 11/2002 | Cassidy et al. |
| 6,485,263 B1 | 11/2002 | Bryant et al. |
| 6,491,656 B1 | 12/2002 | Morris |
| 6,497,676 B1 | 12/2002 | Childers et al. |
| 6,517,510 B1 | 2/2003 | Stewart et al. |
| 6,520,747 B2 | 2/2003 | Gray et al. |
| 6,527,758 B2 | 3/2003 | Ko |
| 6,529,775 B2 | 3/2003 | Whitebook et al. |
| 6,535,689 B2 | 3/2003 | Augustine et al. |
| 6,537,445 B2 | 3/2003 | Muller |
| 6,539,172 B2 | 3/2003 | Akahane |
| 6,543,814 B2 | 4/2003 | Bartholomew |
| 6,579,253 B1 | 6/2003 | Burbank et al. |
| 6,579,496 B1 | 6/2003 | Fausset et al. |
| RE38,203 E | 7/2003 | Kelly |
| 6,595,944 B2 | 7/2003 | Balschat et al. |
| 6,595,948 B2 | 7/2003 | Suzuki et al. |
| 6,604,908 B1 | 8/2003 | Bryant et al. |
| 6,608,968 B2 | 8/2003 | Bakke |
| 6,620,119 B1 | 9/2003 | Utterberg et al. |
| 6,660,974 B2 | 12/2003 | Faries, Jr. et al. |
| 6,663,353 B2 | 12/2003 | Lipscomb et al. |
| 6,663,359 B2 | 12/2003 | Gray |
| 6,673,314 B1 | 1/2004 | Burbank et al. |
| 6,709,417 B1 | 3/2004 | Houle et al. |
| 6,722,865 B2 | 4/2004 | Domroese |
| 6,723,062 B1 | 4/2004 | Westberg et al. |
| 6,726,656 B2 | 4/2004 | Kamen et al. |
| 6,743,201 B1 | 6/2004 | Doing et al. |
| 6,749,403 B2 | 6/2004 | Bryant et al. |
| 6,752,172 B2 | 6/2004 | Lauer |
| 6,768,085 B2 | 7/2004 | Faries et al. |
| 6,775,473 B2 | 8/2004 | Augustine et al. |
| 6,788,885 B2 | 9/2004 | Mitsunaga et al. |
| 6,808,369 B2 | 10/2004 | Gray et al. |
| 6,814,547 B2 | 11/2004 | Childers et al. |
| 6,814,718 B2 | 11/2004 | McGuckin, Jr. et al. |
| 6,821,441 B2 | 11/2004 | Pedrini et al. |
| 6,826,948 B1 | 12/2004 | Bhatti et al. |
| 6,858,019 B2 | 2/2005 | McGuckin, Jr. et al. |
| 6,860,866 B1 | 3/2005 | Graf et al. |
| 6,868,309 B1 | 3/2005 | Begelman |
| 6,877,713 B1 | 4/2005 | Gray et al. |
| 6,905,314 B2 | 6/2005 | Danby |
| 6,905,479 B1 | 6/2005 | Bouchard et al. |
| 6,929,751 B2 | 8/2005 | Bowman et al. |
| 6,939,471 B2 | 9/2005 | Gross et al. |
| 6,949,079 B1 | 9/2005 | Westberg et al. |
| 6,953,323 B2 | 10/2005 | Childers et al. |
| 7,029,245 B2 | 4/2006 | Maianti et al. |
| 7,083,719 B2 | 8/2006 | Bowman et al. |
| 7,122,210 B2 | 10/2006 | Elisabettini et al. |
| 7,124,996 B2 | 10/2006 | Clarke et al. |
| 7,147,613 B2 | 12/2006 | Burbank et al. |
| 7,153,286 B2 | 12/2006 | Busby et al. |
| 7,168,334 B1 | 1/2007 | Drott |
| 7,169,303 B2 | 1/2007 | Sullivan et al. |
| 7,175,397 B2 | 2/2007 | Claude et al. |
| 7,175,606 B2 | 2/2007 | Bowman et al. |
| 7,214,210 B2 | 5/2007 | Kamen et al. |
| 7,238,164 B2 | 7/2007 | Childers et al. |
| 7,273,465 B2 | 9/2007 | Ash |
| 7,300,413 B2 | 11/2007 | Burbank et al. |
| 7,303,540 B2 | 12/2007 | O'Mahony et al. |
| 7,318,292 B2 | 1/2008 | Helbling et al. |
| 7,318,892 B2 | 1/2008 | Connell et al. |
| 7,410,294 B2 | 8/2008 | Shiraki et al. |
| 7,461,968 B2 | 12/2008 | Demers et al. |
| 7,465,285 B2 | 12/2008 | Hutchinson et al. |
| 7,488,448 B2 | 2/2009 | Wieting et al. |
| 7,500,962 B2 | 3/2009 | Childers et al. |
| 7,524,417 B2 | 4/2009 | Sunohara et al. |
| 7,544,179 B2 | 6/2009 | Distler et al. |
| 7,559,524 B2 | 7/2009 | Gray et al. |
| 7,601,636 B2 | 10/2009 | Dumas et al. |
| 7,632,078 B2 | 12/2009 | Demers et al. |
| 7,632,080 B2 | 12/2009 | Tracey et al. |
| 7,662,286 B2 | 2/2010 | Childers et al. |
| 7,717,682 B2 | 5/2010 | Orr |
| 7,727,176 B2 | 6/2010 | Tonelli et al. |
| 7,744,553 B2 | 6/2010 | Kelly et al. |

(56) References Cited

U.S. PATENT DOCUMENTS

| | | |
|---|---|---|
| 7,776,301 B2 | 8/2010 | Comrie et al. |
| 7,789,849 B2 | 9/2010 | Busby et al. |
| 7,794,141 B2 | 9/2010 | Perry et al. |
| 7,815,595 B2 | 10/2010 | Busby et al. |
| 7,867,214 B2 | 1/2011 | Childers et al. |
| 7,892,197 B2 | 2/2011 | Folden et al. |
| 7,896,830 B2 | 3/2011 | Gura et al. |
| 7,899,508 B2 | 3/2011 | DeArmond |
| 7,935,074 B2 | 5/2011 | Plahey et al. |
| 7,935,250 B2 | 5/2011 | Castellano et al. |
| 7,967,022 B2 | 6/2011 | Grant et al. |
| 8,002,726 B2 | 8/2011 | Karoor et al. |
| 8,029,454 B2 * | 10/2011 | Kelly et al. .................. 604/5.01 |
| 8,042,563 B2 | 10/2011 | Grant et al. |
| 8,066,671 B2 | 11/2011 | Busby et al. |
| 8,075,526 B2 | 12/2011 | Busby et al. |
| 8,246,826 B2 | 8/2012 | Wilt et al. |
| 8,273,049 B2 | 9/2012 | Demers et al. |
| 8,292,594 B2 | 10/2012 | Tracey et al. |
| 8,298,152 B2 | 10/2012 | Konig et al. |
| 8,317,492 B2 | 11/2012 | Demers et al. |
| 8,357,298 B2 | 1/2013 | Demers et al. |
| 8,393,690 B2 | 3/2013 | Grant et al. |
| 8,409,441 B2 | 4/2013 | Wilt |
| 8,425,471 B2 | 4/2013 | Grant et al. |
| 8,459,292 B2 | 6/2013 | Wilt et al. |
| 8,491,184 B2 | 7/2013 | Kamen et al. |
| 8,499,780 B2 | 8/2013 | Wilt et al. |
| 8,545,698 B2 | 10/2013 | Wilt et al. |
| 8,562,834 B2 | 10/2013 | Kamen et al. |
| 8,721,879 B2 | 5/2014 | Van der Merwe et al. |
| 8,721,884 B2 | 5/2014 | Wilt et al. |
| 8,771,508 B2 | 7/2014 | Grant et al. |
| 8,863,772 B2 | 10/2014 | Dale et al. |
| 8,870,549 B2 | 10/2014 | Tracey et al. |
| 8,888,470 B2 | 11/2014 | Demers et al. |
| 8,926,294 B2 | 1/2015 | Demers et al. |
| 2002/0056672 A1 | 5/2002 | Lyle et al. |
| 2002/0092103 A1 | 7/2002 | Bruno et al. |
| 2002/0103453 A1 | 8/2002 | Burbank et al. |
| 2002/0150476 A1 | 10/2002 | Lucke et al. |
| 2002/0179505 A1 | 12/2002 | Rovatti et al. |
| 2002/0179595 A1 | 12/2002 | Nagele |
| 2002/0182090 A1 | 12/2002 | Gray |
| 2003/0100858 A1 | 5/2003 | Utterberg et al. |
| 2003/0114795 A1 | 6/2003 | Faries et al. |
| 2003/0194328 A1 | 10/2003 | Bryant et al. |
| 2003/0194332 A1 | 10/2003 | Jahn et al. |
| 2003/0195453 A1 | 10/2003 | Han et al. |
| 2003/0195454 A1 | 10/2003 | Wariar et al. |
| 2003/0220599 A1 | 11/2003 | Lundtveit et al. |
| 2003/0220605 A1 | 11/2003 | Bowman, Jr. et al. |
| 2003/0220607 A1 | 11/2003 | Busby et al. |
| 2003/0229302 A1 | 12/2003 | Robinson et al. |
| 2003/0230191 A1 | 12/2003 | Ohrle et al. |
| 2004/0001766 A1 | 1/2004 | Maianti et al. |
| 2004/0009096 A1 | 1/2004 | Wellman |
| 2004/0019313 A1 | 1/2004 | Childers et al. |
| 2004/0091374 A1 | 5/2004 | Gray |
| 2004/0101026 A1 | 5/2004 | Nitta et al. |
| 2004/0136843 A1 | 7/2004 | Jahn et al. |
| 2004/0138607 A1 | 7/2004 | Burbank et al. |
| 2004/0245161 A1 | 12/2004 | Treu et al. |
| 2004/0249331 A1 | 12/2004 | Burbank et al. |
| 2004/0262917 A1 | 12/2004 | Sunohara et al. |
| 2005/0020958 A1 | 1/2005 | Paolini et al. |
| 2005/0045540 A1 | 3/2005 | Connell et al. |
| 2005/0069425 A1 | 3/2005 | Gray et al. |
| 2005/0069427 A1 | 3/2005 | Roemuss et al. |
| 2005/0095141 A1 | 5/2005 | Lanigan et al. |
| 2005/0095154 A1 | 5/2005 | Tracey et al. |
| 2005/0126998 A1 | 6/2005 | Childers |
| 2005/0130332 A1 | 6/2005 | Ishii et al. |
| 2005/0131332 A1 | 6/2005 | Kelly et al. |
| 2005/0145010 A1 | 7/2005 | Vanderveen et al. |
| 2005/0230292 A1 | 10/2005 | Beden et al. |
| 2005/0234385 A1 | 10/2005 | Vandlik |
| 2005/0242034 A1 | 11/2005 | Connell et al. |
| 2005/0274658 A1 | 12/2005 | Rosenbaum et al. |
| 2006/0002823 A1 | 1/2006 | Feldstein |
| 2006/0093531 A1 | 5/2006 | Tremoulet et al. |
| 2006/0184084 A1 | 8/2006 | Ware et al. |
| 2006/0195064 A1 | 8/2006 | Plahey et al. |
| 2006/0229586 A1 | 10/2006 | Faries, Jr. |
| 2006/0241550 A1 | 10/2006 | Kamen et al. |
| 2007/0060786 A1 | 3/2007 | Gura et al. |
| 2007/0060872 A1 | 3/2007 | Hall et al. |
| 2007/0077156 A1 | 4/2007 | Orr |
| 2007/0112297 A1 | 5/2007 | Plahey et al. |
| 2007/0135758 A1 | 6/2007 | Childers et al. |
| 2007/0166181 A1 | 7/2007 | Nilson |
| 2007/0253463 A1 | 11/2007 | Perry et al. |
| 2007/0255527 A1 | 11/2007 | Schick et al. |
| 2007/0278155 A1 | 12/2007 | Lo et al. |
| 2008/0015493 A1 | 1/2008 | Childers et al. |
| 2008/0015515 A1 | 1/2008 | Hopkins et al. |
| 2008/0021377 A1 | 1/2008 | Kienman et al. |
| 2008/0033346 A1 | 2/2008 | Childers et al. |
| 2008/0058697 A1 | 3/2008 | Kamen et al. |
| 2008/0058712 A1 | 3/2008 | Plahey |
| 2008/0077068 A1 | 3/2008 | Orr |
| 2008/0097283 A1 | 4/2008 | Plahey |
| 2008/0105600 A1 | 5/2008 | Connell et al. |
| 2008/0125693 A1 | 5/2008 | Gavin et al. |
| 2008/0132828 A1 | 6/2008 | Howard |
| 2008/0161751 A1 | 7/2008 | Plahey et al. |
| 2008/0175719 A1 | 7/2008 | Tracey et al. |
| 2008/0202591 A1 | 8/2008 | Grant et al. |
| 2008/0204086 A1 | 8/2008 | Park et al. |
| 2008/0205481 A1 | 8/2008 | Faries, Jr. et al. |
| 2008/0208103 A1 | 8/2008 | Demers et al. |
| 2008/0208111 A1 | 8/2008 | Kamen et al. |
| 2008/0215898 A1 | 9/2008 | Lu et al. |
| 2008/0216898 A1 | 9/2008 | Grant et al. |
| 2008/0240929 A1 | 10/2008 | Kamen et al. |
| 2008/0253427 A1 | 10/2008 | Kamen et al. |
| 2008/0253911 A1 | 10/2008 | Demers et al. |
| 2008/0253912 A1 | 10/2008 | Demers et al. |
| 2008/0287854 A1 | 11/2008 | Sun |
| 2009/0004033 A1 | 1/2009 | Demers et al. |
| 2009/0007642 A1 | 1/2009 | Busby et al. |
| 2009/0008331 A1 | 1/2009 | Wilt et al. |
| 2009/0009290 A1 | 1/2009 | Knelp et al. |
| 2009/0012447 A1 | 1/2009 | Huitt et al. |
| 2009/0012448 A1 | 1/2009 | Childers et al. |
| 2009/0012449 A1 | 1/2009 | Lee et al. |
| 2009/0012450 A1 | 1/2009 | Shah et al. |
| 2009/0012452 A1 | 1/2009 | Slepicka et al. |
| 2009/0012453 A1 | 1/2009 | Childers et al. |
| 2009/0012454 A1 | 1/2009 | Childers |
| 2009/0012455 A1 | 1/2009 | Childers et al. |
| 2009/0012456 A1 | 1/2009 | Childers et al. |
| 2009/0012457 A1 | 1/2009 | Childers et al. |
| 2009/0012458 A1 | 1/2009 | Childers et al. |
| 2009/0012460 A1 | 1/2009 | Steck et al. |
| 2009/0012461 A1 | 1/2009 | Childers et al. |
| 2009/0024070 A1 | 1/2009 | Gelfand et al. |
| 2009/0043239 A1 | 2/2009 | Gagel et al. |
| 2009/0076433 A1 | 3/2009 | Folden et al. |
| 2009/0076434 A1 | 3/2009 | Mischelevich et al. |
| 2009/0088675 A1 | 4/2009 | Kelly et al. |
| 2009/0088683 A1 | 4/2009 | Roger et al. |
| 2009/0095679 A1 | 4/2009 | Demers et al. |
| 2009/0101549 A1 | 4/2009 | Kamen et al. |
| 2009/0101550 A1 | 4/2009 | Muller et al. |
| 2009/0101566 A1 | 4/2009 | Crnkovich et al. |
| 2009/0105621 A1 | 4/2009 | Boyd et al. |
| 2009/0105629 A1 | 4/2009 | Grant et al. |
| 2009/0107335 A1 | 4/2009 | Wilt et al. |
| 2009/0107902 A1 | 4/2009 | Childers et al. |
| 2009/0112151 A1 | 4/2009 | Chapman et al. |
| 2009/0113335 A1 | 4/2009 | Sandoe et al. |
| 2009/0114582 A1 | 5/2009 | Grant et al. |
| 2009/0154524 A1 | 6/2009 | Girelli |

(56) References Cited

U.S. PATENT DOCUMENTS

| | | |
|---|---|---|
| 2009/0173682 A1 | 7/2009 | Robinson et al. |
| 2009/0182263 A1 | 7/2009 | Burbank et al. |
| 2009/0192367 A1 | 7/2009 | Braig et al. |
| 2009/0202367 A1 | 8/2009 | Gray et al. |
| 2010/0051529 A1 | 3/2010 | Grant et al. |
| 2010/0051551 A1 | 3/2010 | Grant et al. |
| 2010/0056975 A1 | 3/2010 | Dale et al. |
| 2010/0057016 A1 | 3/2010 | Dale et al. |
| 2010/0087777 A1 | 4/2010 | Hopping et al. |
| 2010/0133153 A1 | 6/2010 | Beden et al. |
| 2010/0137782 A1 | 6/2010 | Jansson et al. |
| 2010/0185134 A1 | 7/2010 | Houwen et al. |
| 2010/0187176 A1 | 7/2010 | Lopez et al. |
| 2010/0192686 A1 | 8/2010 | Kamen et al. |
| 2010/0296953 A1 | 11/2010 | Gray |
| 2010/0327849 A1 | 12/2010 | Kamen et al. |
| 2011/0009797 A1 | 1/2011 | Kelly et al. |
| 2011/0092875 A1 | 4/2011 | Beck et al. |
| 2011/0105877 A1 | 5/2011 | Wilt et al. |
| 2011/0144569 A1 | 6/2011 | Britton et al. |
| 2011/0218600 A1 | 9/2011 | Kamen et al. |
| 2011/0299358 A1 | 12/2011 | Wilt et al. |
| 2011/0303588 A1 | 12/2011 | Kelly et al. |
| 2011/0303598 A1 | 12/2011 | Lo et al. |
| 2012/0035533 A1 | 2/2012 | Britton et al. |
| 2012/0071816 A1 | 3/2012 | Busby et al. |
| 2012/0106289 A1 | 5/2012 | Wilt et al. |
| 2012/0207627 A1 | 8/2012 | Demers et al. |
| 2013/0010825 A1 | 1/2013 | Kamen et al. |
| 2013/0020237 A1 | 1/2013 | Wilt et al. |
| 2013/0022483 A1 | 1/2013 | Wilt et al. |
| 2013/0032536 A1 | 2/2013 | Wilt et al. |
| 2013/0037480 A1 | 2/2013 | Wilt et al. |
| 2013/0037485 A1 | 2/2013 | Wilt et al. |
| 2013/0074959 A1 | 3/2013 | Demers et al. |
| 2013/0115105 A1 | 5/2013 | Tracey et al. |
| 2013/0177457 A1 | 7/2013 | Demers et al. |
| 2013/0284648 A1 | 10/2013 | Grant et al. |
| 2013/0304020 A1 | 11/2013 | Wilt et al. |
| 2013/0317454 A1 | 11/2013 | Grant et al. |
| 2014/0102299 A1 | 4/2014 | Wilt et al. |
| 2014/0102958 A1 | 4/2014 | Kamen et al. |
| 2014/0102970 A1 | 4/2014 | Wilt et al. |
| 2014/0112828 A1 | 4/2014 | Grant et al. |
| 2014/0153356 A1 | 6/2014 | Grant et al. |
| 2014/0199193 A1 | 7/2014 | Wilt et al. |
| 2014/0288488 A1 | 9/2014 | Distler et al. |
| 2014/0288489 A1 | 9/2014 | Distler et al. |
| 2014/0288490 A1 | 9/2014 | Distler et al. |
| 2014/0299544 A1 | 10/2014 | Wilt et al. |
| 2014/0309611 A1 | 10/2014 | Wilt et al. |
| 2014/0319041 A1 | 10/2014 | Wilt et al. |

FOREIGN PATENT DOCUMENTS

| | | |
|---|---|---|
| DE | 3 328 744 A1 | 2/1985 |
| EP | 0 288 145 A1 | 10/1988 |
| EP | 0 687 474 A1 | 12/1995 |
| EP | 0 815 882 A2 | 1/1998 |
| EP | 0 992 255 A2 | 4/2000 |
| EP | 2 319 551 A2 | 5/2011 |
| JP | S60-077782 U | 5/1985 |
| JP | S62-5355 A | 1/1987 |
| JP | 63-106445 U | 7/1988 |
| JP | H09-099060 | 4/1997 |
| JP | H11-210633 A | 8/1999 |
| JP | 2002-126075 | 5/2002 |
| JP | 2003-265599 A | 9/2003 |
| JP | 2004-216143 | 8/2004 |
| JP | 2005-526574 A | 9/2005 |
| JP | 2006-204343 A | 8/2006 |
| JP | 2007-215557 A | 8/2007 |
| JP | 2008-006292 A | 1/2008 |
| JP | 2008-104737 A | 5/2008 |
| WO | WO 94/11093 A1 | 5/1994 |
| WO | WO 94/20158 A1 | 9/1994 |
| WO | WO 96/40320 A1 | 12/1996 |
| WO | WO 98/37801 A1 | 9/1998 |
| WO | WO 98/39058 A1 | 9/1998 |
| WO | WO 99/10028 A1 | 3/1999 |
| WO | WO 01/37895 A2 | 5/2001 |
| WO | WO 02/03879 A1 | 1/2002 |
| WO | WO 02/30267 A2 | 4/2002 |
| WO | WO 03/099354 A2 | 12/2003 |
| WO | WO 2004/041081 A1 | 5/2004 |
| WO | WO 2005/044339 A1 | 5/2005 |
| WO | WO 2005/044435 A2 | 5/2005 |
| WO | WO 2006/088419 A2 | 8/2006 |
| WO | WO 2006/120415 A1 | 11/2006 |
| WO | WO 2007/019519 A2 | 2/2007 |
| WO | WO 2007/120812 A2 | 10/2007 |
| WO | WO 2007/126360 A1 | 11/2007 |
| WO | WO 2007/149637 A2 | 12/2007 |
| WO | WO 2008/028653 A2 | 3/2008 |
| WO | WO 2008/053259 A1 | 5/2008 |
| WO | WO 2008/106191 A2 | 9/2008 |
| WO | WO 2008/106440 A1 | 9/2008 |
| WO | WO 2008/106452 A1 | 9/2008 |
| WO | WO 2008/106538 A2 | 9/2008 |
| WO | WO 2008/118600 A1 | 10/2008 |
| WO | WO 2009/051669 A1 | 4/2009 |
| WO | WO 2009/094179 A2 | 7/2009 |
| WO | WO 2009/094183 A1 | 7/2009 |
| WO | WO 2010/027435 A1 | 3/2010 |
| WO | WO 2010/027437 A2 | 3/2010 |
| WO | WO 2011/053810 A2 | 5/2011 |
| WO | WO 2012/006425 A2 | 1/2012 |
| WO | WO 2012/162515 A2 | 11/2012 |

OTHER PUBLICATIONS

Examination Report for EP Application No. 08726213.5 filed Feb. 27, 2008, published as EP 2131889 on Dec. 16, 2009, which Examination Report is dated May 16, 2012, and claims as pending for EP Application No. 08726213.5 as of May 16, 2012.
Office Action for JP Application No. 2009-551724 filed Feb. 27, 2008, which Office Action is dated Nov. 28, 2012, and claims as pending for JP Application No. 2009-551724 as of Nov. 28, 2012.
Written Opinion for Application No. PCT/US2008/002636 mailed Jul. 2, 2008.
International Preliminary Report on Patentability for Application No. PCT/US2008/002636 mailed Sep. 11, 2009.
International Search Report and Written Opinion for Application No. PCT/US2008/055000 mailed Aug. 1, 2008.
International Preliminary Report on Patentability for Application No. PCT/US2008/055000 mailed Sep. 11, 2009.
Invitation to Pay Additional Fees for Application No. PCT/US2008/055168 mailed Aug. 5, 2008.
International Search Report and Written Opinion for Application No. PCT/US2008/055168 mailed Nov. 10, 2008.
International Preliminary Report on Patentability for Application No. PCT/US2008/055168 mailed Sep. 11, 2009.
International Search Report and Written Opinion for Application No. PCT/US2008/055136 mailed Jul. 24, 2008.
International Preliminary Report on Patentability for Application No. PCT/US2008/055136 mailed Sep. 11, 2009.
Office Action for JP Application No. 2011-524994 filed Aug. 27, 2009, which Office Action is dated Sep. 3, 2013, and claims as pending for JP Application No. 2011-524994 as of Sep. 3, 2013.
Invitation to Pay Additional Fees mailed Nov. 27, 2009 for Application PCT/US2009/004866.
International Search Report and Written Opinion mailed Jan. 27, 2010 for Application PCT/US2009/004866.
International Preliminary Report on Patentability for Application No. PCT/US2009/004866 mailed Mar. 10, 2011.
Invitation to Pay Additional Fees mailed Dec. 8, 2009 for Application PCT/US2009/004877.
International Search Report and Written Opinion mailed Feb. 12, 2010 for Application PCT/US2009/004877.

(56) References Cited

OTHER PUBLICATIONS

International Preliminary Report on Patentability for Application No. PCT/US2009/004877 mailed Mar. 10, 2011.
Extended European Search Report for EP Application No. 13150786.5 filed Apr. 13, 2007, which Search Report is dated Mar. 28, 2013, and claims as pending for EP Application No. 13150786.5 as of Mar. 28, 2013.
Office Action for JP Application No. 2009-505495 filed Apr. 13, 2007, unpublished as of Aug. 3, 2012, which Office Action is dated Mar. 8, 2012, and claims as pending for JP Application No. 2009-505495 as of May 8, 2012.
Written Opinion for PCT/US2007/009107 mailed Aug. 17, 2007.
International Preliminary Report on Patentability for Application No. PCT/US2007/009107 mailed Oct. 23, 2008.
Partial European Search Report for EP Application No. 11150584.8 filed Oct. 10, 2008, published as EP 2319551 on May 11, 2011, which Search Report is dated Mar. 30, 2011, and claims as pending for EP Application No. 11150584.8 as of Mar. 30, 2011.
Extended European Search Report for EP Application No. 11150584.8 filed Oct. 10, 2008, published as EP 2319551 on May 11, 2011, which Search Report is dated Jul. 26, 2011, and claims as pending for EP Application No. 11150584.8 as of Jul. 26, 2011.
International Search Report and Written Opinion for Application No. PCT/US2008/011663 mailed Feb. 20, 2009.
International Preliminary Report on Patentability for Application No. PCT/US2008/011663 mailed Apr. 22, 2010.
Invitation to Pay Additional Fees for International Application No. PCT/US2009/000433 (published as WO 2009/094179), mailed Jun. 4, 2009.
International Search Report and Written Opinion for International Application No. PCT/US2009/000433 (published as WO 2009/094179), mailed Sep. 25, 2009.
International Preliminary Report on Patentability for Application No. PCT/US2009/000433 mailed Aug. 5, 2010
International Search Report and Written Opinion for Application No. PCT/US2008/055021 mailed Jul. 23, 2008.
International Preliminary Report on Patentability for Application No. PCT/US2008/055021 dated Sep. 11, 2009.
International Search Report and Written Opinion for International Application No. PCT/US2010/054772 mailed May 9, 2011.
International Preliminary Report on Patentability for International Application No. PCT/US2010/054772 issued May 1, 2012.
Invitation to Pay Additional Fees for PCT Application No. PCT/US2012/039369 mailed Sep. 27, 2012.
International Search Report and Written Opinion for PCT Application No. PCT/US2012/039369 mailed Jan. 16, 2013.
Office Action for U.S. Appl. No. 12/072,908, filed Feb. 27, 2008, published as US 2009-0008331 on Jan. 8, 2009 which Office Action is dated Oct. 15, 2010, and claims as pending for U.S. Appl. No. 12/072,908 as of Oct. 15, 2010.
Office Action for U.S. Appl. No. 12/072,908, filed Feb. 27, 2008, published as US 2009-0008331 on Jan. 8, 2009 which Office Action is dated Jul. 15, 2011, and claims as pending for U.S. Appl. No. 12/072,908 as of Juy 15, 2011.
Office Action for U.S. Appl. No. 12/072,908, filed Feb. 27, 2008, published as US 2009-0008331 on Jan. 8, 2009 which Office Action is dated Jan. 5, 2012, and claims as pending for U.S. Appl. No. 12/072,908 as of Jan. 5, 2012.
Office Action for U.S. Appl. No. 13/569,623, filed Aug. 8, 2012, published as US 2013-0032536 on Feb. 7, 2013, which Office Action is dated May 1, 2013, and claims as pending for U.S. Appl. No. 13/569,623 as of May 1, 2013.
Office Action for U.S. Appl. No. 11/871,712, filed Oct. 12, 2007, published as US 2009/0004033 on Jan. 1, 2009, which Office Action is dated Feb. 4, 2010, and claims as pending for U.S. Appl. No. 11/871,712 as of Feb. 4, 2010.
Office Action for U.S. Appl. No. 11/871,712, filed Oct. 12, 2007, published as US 2009-0004033 on Jan. 1, 2009, which Office Action is dated Oct. 15, 2010, and claims as pending for U.S. Appl. No. 11/871,712 as of Oct. 15, 2010.
Office Action for U.S. Appl. No. 11/871,712, filed Oct. 12, 2007, published as US 2009-0004033 on Jan. 1, 2009, which Office Action is dated Feb. 7, 2011, and claims as pending for U.S. Appl. No. 11/871,712 as of Feb. 7, 2011.
Office Action for U.S. Appl. No. 12/038,648, filed Feb. 27, 2008, published as US 2008-0216898 on Sep. 11, 2008, which Office Action is dated Oct. 1, 2010, and claims as pending for U.S. Appl. No. 12/038,648 as of Oct. 1, 2010.
Office Action for U.S. Appl. No. 12/199,176, filed Aug. 27, 2008, published as 2010-0056975 on Mar. 4, 2010, which Office Action is dated Nov. 22, 2010, and claims as pending for U.S. Appl. No. 12/199,176 as of Nov. 22, 2010.
Office Action for U.S. Appl. No. 12/199,176, filed Aug. 27, 2008, published as 2010-0056975 on Mar. 4, 2010, which Office Action is dated Sep. 2, 2011, and claims as pending for U.S. Appl. No. 12/199,176 as of Sep. 2, 2011.
Office Action for U.S. Appl. No. 12/199,176, filed Aug. 27, 2008, published as 2010-0056975 on Mar. 4, 2010, which Office Action is dated Feb. 10, 2012, and claims as pending for U.S. Appl. No. 12/199,176 as of Feb. 10, 2012.
Office Action for U.S. Appl. No. 12/199,452, filed Aug. 27, 2008, published as 2009-0095679 on Apr. 16, 2009, which Office Action is dated Jan. 12, 2012, and claims as pending for U.S. Appl. No. 12/199,452 as of Jan. 12, 2012.
Office Action for U.S. Appl. No. 13/745,730, filed Jan. 18, 2013, published as US 2013-0126413 on May 23, 2013, which Office Action is dated Apr. 10, 2013, and claims as pending for U.S. Appl. No. 13/745,730 as of Apr. 10, 2013.
Office Action for U.S. Appl. No. 11/787,212, filed Apr. 13, 2007, published as 2008-0175719 on Jul. 24, 2008, which Office Action is dated May 26, 2010, and claims as pending for U.S. Appl. No. 11/787,212 as of May 26, 2010.
Office Action for U.S. Appl. No. 11/787,212, filed Apr. 13, 2007, published as 2008-0175719 on Jul. 24, 2008, which Office Action is dated Feb. 7, 2011, and claims as pending for U.S. Appl. No. 11/787,212 as of Feb. 7, 2011.
Office Action for U.S. Appl. No. 11/787,213, filed Apr. 13, 2007, published as 2008-0058697 on Mar. 6, 2008, which Office Action is dated Mar. 18, 2010, and claims as pending for U.S. Appl. No. 11/787,213 as of Mar. 18, 2010.
Office Action for U.S. Appl. No. 11/787,112, filed Apr. 13, 2007, published as US 2007-253463 on Nov. 1, 2007, which Office Action is dated Nov. 21, 2008, and claims as pending for U.S. Appl. No. 11/787,112 as of Nov. 21, 2008.
Office Action for U.S. Appl. No. 11/871,821, filed Oct. 12, 2007, published as US 2008-0240929 on Oct. 2, 2008, which Office Action is dated Sep. 23, 2009, and claims as pending for U.S. Appl. No. 11/871,821 as of Sep. 23, 2009.
Office Action for U.S. Appl. No. 11/871,828, filed Oct. 12, 2007, published as US 2008-0208111 on Aug. 28, 2008, which Office Action is dated Mar. 11, 2010, and claims as pending for U.S. Appl. No. 11/871,828 as of Mar. 11, 2010.
Office Action for U.S. Appl. No. 11/871,828, filed Oct. 12, 2007, published as US 2008-0208111 on Aug. 28, 2008, which Office Action is dated Nov. 26, 2010, and claims as pending for U.S. Appl. No. 11/871,828 as of Nov. 26, 2010.
Bengtsson et al., Haemo dialysis software architecture design experiences. Proceedings of the 1999 International Conference on Software Engineering. ACM New York, NY. 1999:516-525.
Choppy et al., Architectural patterns for problem frames. IEE Proceedings: Software. Aug. 2005;152(4):190-208.
Gentilini et al., Multitasked closed-loop control in anesthesia. IEEE Eng Med Biol Mag. Jan.-Feb. 2001;20(1):39-53.
Harel, Statecharts: A visual formalism for complex systems. Science of Computer Programming. 1987;8:231-274.
Krasner et al., A cookbook for using the model-view-controller user interface paradigm in smalltalk-80. JOOP. Aug. 1988;1(3):26-49.
Office Action for JP Application No. 2014-137401 filed Jul. 3, 2014, which Office Action is dated Jun. 2, 2015, and claims as pending for JP Application No. 2014-137401 as of Jun. 2, 2015.

* cited by examiner

1100

1300

900

1000

900

1400

FLUID BALANCING SYSTEMS AND METHODS

RELATED APPLICATIONS

This application is a divisional of U.S. patent application Ser. No. 13/745,730, filed Jan. 18, 2013, and issued as U.S. Pat. No. 8,721,879 on May 13, 2014, entitled "Hemodialysis Systems and Methods," which is a divisional of U.S. patent application Ser. No. 12/199,452, filed Aug. 27, 2008, and issued as U.S. Pat. No. 8,357,298 on Jan. 22, 2013, entitled "Hemodialysis Systems and Methods," which is a continuation-in-part of U.S. patent application Ser. No., 12/072,908, filed Feb. 27, 2008 and issued as U.S. Pat. No. 8,246,826 on Aug. 21, 2012, entitled "Hemodialysis Systems and Methods," which claims the benefit of U.S. Provisional Patent Application Ser. No. 60/903,582, filed Feb. 27, 2007, entitled "Hemodialysis System and Methods," and U.S. Provisional Patent Application Ser. No. 60/904,024, filed February 27, 2007, entitled "Hemodialysis System and Methods." Each of these is incorporated herein by reference.

FIELD OF INVENTION

The present invention generally relates to hemodialysis and similar dialysis systems, e.g., systems able to treat blood or other bodily fluids extracorporeally. In certain aspects, the systems include a variety of systems and methods that would make hemodialysis more efficient, easier, and/or more affordable.

BACKGROUND

Many factors make hemodialysis inefficient, difficult, and expensive. These factors include the complexity of hemodialysis, the safety concerns related to hemodialysis, and the very large amount of dialysate needed for hemodialysis. Moreover, hemodialysis is typically performed in a dialysis center requiring skilled technicians. Therefore any increase in the ease and efficiency of the dialysis process could have an impact on treatment cost or patient outcome.

FIG. 1 is a schematic representation of a hemodialysis system. The system 5 includes two flow paths, a blood flow path 10 and a dialysate flow path 20. Blood is drawn from a patient. A blood flow pump 13 causes the blood to flow around blood flow path 10, drawing the blood from the patient, causing the blood to pass through the dialyzer 14, and returning the blood to the patient. Optionally, the blood may pass through other components, such as a filter and/or an air trap 19, before returning to the patient. In addition, in some cases, anticoagulant may be supplied from an anticoagulant supply 11 via an anticoagulant valve 12.

A dialysate pump 15 draws dialysate from a dialysate supply 16 and causes the dialysate to pass through the dialyzer 14, after which the dialysate can pass through a waste valve 18 and/or return to the dialysate feed via dialysate pump 15. A dialysate valve 17 controls the flow of dialysate from the dialysate supply 16. The dialyzer is constructed such that the blood from the blood flow circuit flows through tiny tubes and the dialysate solution circulates around the outside of the tubes. Therapy is achieved by the passing of waste molecules (e.g., urea, creatinine, etc.) and water from the blood through the walls of the tubes and into the dialysate solution. At the end of treatment, the dialysate solution is discarded.

SUMMARY OF THE INVENTION

The present invention generally relates to hemodialysis and similar dialysis systems. The subject matter of the present invention involves, in some cases, interrelated products, alternative solutions to a particular problem, and/or a plurality of different uses of one or more systems and/or articles. Although the various systems and methods described herein are described in relation to hemodialysis, it should be understood that the various systems and method described herein are applicable to other dialysis systems and/or in any extracorporeal system able to treat blood or other bodily fluids, such as hemofiltration, hemodiafiltration, etc.

In one aspect, the system includes four fluid paths: blood; inner dialysate; outer dialysate and dialysate mixing. In some embodiments, these four paths are combined in a single cassette. In other embodiments, these four paths are each in a respective cassette. In still other embodiments, two or more fluid paths are included on one cassette.

In one embodiment, there is provided a hemodialysis system having at least two fluid paths integrated into: 1) a blood flow pump cassette, 2) an inner dialysate cassette; 3) an outer dialysate cassette; and 4) a mixing cassette. The cassettes may be fluidly connected one to another. In some embodiments, one or more aspects of these cassettes can be combined into a single cassette.

Also provided, in another embodiment, is a hemodialysis system including a blood flow path through which untreated blood is drawn from a patient and is passed through a dialyzer and through which treated blood is returned to the patient. The blood flow path may include at least one blood flow pump located in a removable cassette. The hemodialysis system also can include a first receiving structure for receiving the blood flow path's cassette, a dialysate flow path through which dialysate flows from a dialysate supply through the dialyzer, a second receiving structure for receiving the dialysate flow path's cassette, and a control fluid path for providing a control fluid from an actuator mechanism to the cassettes for actuating each of the blood flow pump and the dialysate pump. In some instances, the dialysate flow path can include at least one dialysate pump located in a removable cassette.

In yet another embodiment, a hemodialysis system is disclosed. The hemodialysis system, in this embodiment, includes a blood flow path through which untreated blood is drawn from a patient and is passed through a dialyzer and through which treated blood is returned to the patient. The blood flow path may include at least one blood valve. The hemodialysis system may also include a control fluid path for providing a control fluid from an actuator mechanism to the blood valve for actuating the blood valve, a dialysate mixing system fluidly connected to the dialyzer (which may include at least one dialyzer valve), and a heating means or a heater for heating the dialysate.

A hemodialysis system is disclosed in yet another embodiment that includes a blood flow path through which untreated blood is drawn from a patient and passed through a dialyzer and through which treated blood is returned to the patient. The blood flow path can include at least one blood flow pump. The hemodialysis system also can include a dialysate flow path through which dialysate flows from a dialysate supply through the dialyzer. The dialysate flow path may include at least one pneumatic pump.

In one aspect, the invention is directed to a hemodialysis system. In one set of embodiments, the hemodialysis system includes a blood flow path, a first cassette defining an inner dialysate fluid path, a dialyzer in fluid communication with the blood flow path and the inner dialysate fluid path, a second cassette defining an outer dialysate fluid path, and a filter fluidly connecting the first cassette to the second cassette.

In another set of embodiments, the hemodialysis system, includes a blood flow path, an inner dialysate fluid path, a dialyzer in fluid communication with the blood flow path and the inner dialysate fluid path, an outer dialysate fluid path, a filter fluidly connecting the inner dialysate fluid path and the outer dialysate fluid path, a first dialysate pump for pumping dialysate through the inner dialysate fluid path, and a second dialysate pump for pumping dialysate through the outer dialysate fluid path, where the second dialysate pump and the first dialysate pump are operably connected such that flow through the inner dialysate fluid path is substantially equal to flow through the outer dialysate fluid path.

The hemodialysis system, in yet another set of embodiments, includes a blood flow path through which blood is drawn from a patient and passed through a dialyzer, and a dialysate flow path through which dialysate flows from a dialysate supply through the dialyzer. In some cases, the dialysate flow path comprises a balancing cassette which controls the amount of dialysate passing through the dialyzer, a mixing cassette which forms dialysate from water, and a directing cassette which passes water from a water supply to the mixing cassette and passes dialysate from the mixing cassette to the balancing cassette.

In still another set of embodiments, the hemodialysis system includes a cassette system, comprising a directing cassette, a mixing cassette and a balancing cassette. In some cases, the directing cassette is able to direct water from a water supply to the mixing cassette and direct dialysate from the mixing cassette to a balancing cassette, the mixing cassette is able to mix water from the directing cassette with dialysate from a dialysate supply precursor to produce a precursor, and the balancing cassette is able to control the amount of dialysate passing through a dialyzer.

In one set of embodiments, the hemodialysis system includes a blood flow path through which blood is drawn from a patient and passed through a dialyzer, the blood flow path including a blood flow pump, a dialysate flow path through which dialysate flows from a dialysate supply through the dialyzer, where the dialysate flow path includes a dialysate pump, and a control fluid path through which a control fluid actuates the blood flow pump and the dialysate pump.

The hemodialysis system, in another set of embodiments, comprises a blood flow path through which blood is drawn from a patient and passed through a dialyzer; and a dialysate flow path through which dialysate flows from a dialysate supply through the dialyzer. In some cases, the dialysate flow path includes at least one pneumatic pump.

The hemodialysis system, in still another set of embodiments, includes a first pump comprising a pumping chamber and an actuation chamber, a second pump comprising a pumping chamber and an actuation chamber, a control fluid in fluidic communication with each of the actuation chambers of the first and second pumps, and a controller able to pressurize the control fluid to control operation of the first and second pumps.

In yet another set of embodiments, the hemodialysis system includes a first valve comprising a valving chamber and an actuation chamber, a second valve comprising a valving chamber and an actuation chamber, a control fluid in fluidic communication with each of the actuation chambers of the first and second valves, and a controller able to pressurize the control fluid to control operation of the first and second valves.

In one set of embodiments, the hemodialysis system includes a blood flow path through which blood is drawn from a patient and passed through a dialyzer, a cassette containing at least a portion of the blood flow path, and a spike integrally formed with the cassette, the spike able to receive a vial of fluid, the integrally formed spike in fluidic communication with the blood flow path within the cassette.

The hemodialysis system, in another set of embodiments, includes a blood flow path through which untreated blood is drawn from a patient and passed through a dialyzer, a dialysate flow path through which dialysate flows from a dialysate supply through the dialyzer, the dialyzer permitting dialysate to pass from the dialysate flow path to the blood flow path, and a gas supply in fluidic communication with the dialysate flow path so that, when activated, gas from the gas supply causes the dialysate to pass through the dialyzer and urge blood in the blood flow path back to the patient.

In yet another set of embodiments, the hemodialysis system includes a blood flow path through which untreated blood is drawn from a patient and passed through a dialyzer, a dialysate flow path through which dialysate flows from a dialysate supply through the dialyzer, the dialyzer permitting dialysate to pass from the dialysate flow path to the blood flow path, a fluid supply, a chamber in fluid communication with the fluid supply and the dialysate fluid path, the chamber having a diaphragm separating fluid of the fluid supply from dialysate of the dialysate flow path, and a pressurizing device for pressurizing the fluid supply to urge the diaphragm against the dialysate in the chamber, so as to cause the dialysate to pass through the dialyzer and urge blood in the blood flow path back to the patient.

The hemodialysis system, in still another set of embodiments, includes a blood flow path through which untreated blood is drawn from a patient and passed through a dialyzer, a dialysate flow path through which dialysate flows from a dialysate supply through the dialyzer, the dialysate flow path and the blood flow path being in fluidic communication, and a pressure device able to urge dialysate in the dialysate flow path to flow into the blood flow path.

In one set of embodiments, the hemodialysis system includes a first housing containing a positive-displacement pump actuated by a control fluid, a fluid conduit fluidly connecting the positive-displacement pump with a control fluid pump, and a second housing containing the control fluid pump, where the second housing is detachable from the first housing.

In another set of embodiments, the hemodialysis system includes a housing comprising a first compartment and a second compartment separated by an insulating wall, the first compartment being sterilizable at a temperature of at least about 80° C., the second compartment containing electronic components that, when the first compartment is heated to a temperature of at least about 80° C., are not heated to a temperature of more than 60° C.

The hemodialysis system, in yet another set of embodiments, includes a blood flow path through which untreated blood is drawn from a patient and passed through a dialyzer, the blood flow path including at least one blood valve; a control fluid path for providing a control fluid from an actuator mechanism to the blood valve for actuating the blood valve; a dialysate mixing system fluidly connected to the dialyzer, including at least one dialyzer valve; and a heater for heating the dialysate.

Another aspect of the present invention is directed to a valving system. In one set of embodiments, the valving system includes a valve housing containing a plurality of valves, at least two of which valves each comprises a valving chamber and an actuation chamber, each of the at least two valves being actuatable by a control fluid in the actuation chamber; a control housing having a plurality of fluid-interface ports for providing fluid communication with a control fluid from a base unit; and a plurality of tubes extending between the valve housing and the control housing, each tube providing fluid communication between one of the fluid-interface ports and at least one of the actuation chambers, such that the base unit can actuate a valve by pressurizing control fluid in the fluid interface port.

In one set of embodiments, the invention is directed to a valve including a first plate; a second plate, the second plate having an indentation on a side facing the first plate, the indentation having a groove defined therein, the groove being open in a direction facing the first plate; a third plate, wherein the second plate is located between the first and third plate; and a diaphragm located in the indentation between the first plate and the second plate, the diaphragm having a rim, the rim being held in the groove. The second plate may include a valve seat arranged so that the diaphragm may be urged by pneumatic pressure to seal the valve seat closed, the groove surrounding the valve seat. In some cases, a valve inlet and a valve outlet are defined between the second and third plates. In one embodiment, a passage for providing pneumatic pressure is defined between the first and second plates.

Yet another aspect of the present invention is directed to a pumping system. The pumping system, in one set of embodiments, includes a pump housing containing a plurality of pumps, at least two of which pumps each includes a pumping chamber and an actuation chamber, each of the at least two pumps being actuatable by a control fluid in the actuation chamber; a control housing having a plurality of fluid-interface ports for providing fluid communication with a control fluid from a base unit; and a plurality of tubes extending between the pump housing and the control housing, each tube providing fluid communication between one of the fluid-interface ports and at least one of the actuation chambers, such that the base unit can actuate a pump by pressurizing control fluid in the fluid interface port.

The invention is generally directed to a pumping cassette in another aspect. In one set of embodiments, the pumping cassette includes at least one fluid inlet, at least one fluid outlet, a flow path connecting the at least one fluid inlet and the at least one fluid outlet, and a spike for attaching a vial to said cassette. The spike may be in fluidic communication with the flow path in some cases.

In one aspect, the invention is generally directed to a pumping cassette for balancing flow to and from a target. In one set of embodiments, the pumping cassette includes a cassette inlet, a supply line to the target, a return line from the target, a cassette outlet, a pumping mechanism for causing fluid to flow from the cassette inlet to the supply line and from the return line to the cassette outlet, and a balancing chamber. In some cases, the pumping mechanism includes a pod pump comprising a rigid curved wall defining a pumping volume and having an inlet and an outlet, a pump diaphragm mounted within the pumping volume; and an actuation port for connecting the pod pump to a pneumatic actuation system so that the diaphragm can be actuated to urge fluid into and out of the pumping volume, wherein the pump diaphragm separates the fluid from a gas in fluid communication with the pneumatic actuation system. In certain instances, the balancing chamber includes a rigid curved wall defining a balance volume; and a balance diaphragm mounted within the balance volume, where the balance diaphragm separates the balance volume into a supply side and a return side, each of the supply side and the return side having an inlet and an outlet. In some cases, fluid from the cassette inlet flows to the supply side inlet, fluid from the supply side outlet flows to the supply line, fluid from the return line flows to the return side inlet, and fluid from the return side outlet flows to the cassette outlet.

In another set of embodiments, the pumping system includes a system inlet, a supply line to the target, a return line from the target, a system outlet, a pumping mechanism for causing fluid to flow from the system inlet to the supply line and from the return line to the system outlet, and a balancing chamber.

In one embodiment, the pumping mechanism includes a pod pump comprising a rigid spheroid wall defining a pumping volume and having an inlet and an outlet, a pump diaphragm mounted within and to the spheroid wall, and a port for connecting the pod pump to a pneumatic actuation system so that the diaphragm can be actuated to urge fluid into and out of the pumping volume. In some cases, the pump diaphragm separates the fluid from a gas in fluid communication with the pneumatic actuation system;

In certain instances, the balancing chamber includes a rigid spheroid wall defining a balance volume, and a balance diaphragm mounted within and to the spheroid wall. In one embodiment, the balance diaphragm separates the balance volume into a supply side and a return side, each of the supply side and the return side having an inlet and an outlet. In some cases, fluid from the system inlet flows to the supply side inlet, fluid from the supply side outlet flows to the supply line, fluid from the return line flows to the return side inlet, and fluid from the return side outlet flows to the system outlet. The pumping mechanism may also include valving mechanisms located at each of the inlets and outlets of the supply side and the return side. The valving mechanisms may be pneumatically actuated.

Yet another aspect of the invention is directed to a cassette. In one set of embodiments, the cassette includes a first flow path connecting a first inlet to a first outlet, a second flow path connecting a second inlet to a second outlet, a pump able to pump fluid through at least a portion of the second flow path, and at least two balancing chambers, each balancing chamber comprising a rigid vessel containing a diaphragm dividing the rigid vessel into a first compartment and a second compartment, the first compartment of each balancing chamber being in fluidic communication with the first flow path and the second compartment being in fluidic communication with the second flow path.

In another set of embodiments, the cassette includes a first flow path connecting a first inlet to a first outlet; a second flow path connecting a second inlet to a second outlet; a control fluid path; at least two pumps, each pump comprising a rigid vessel containing a diaphragm dividing the rigid vessel into a first compartment and a second compartment, the first compartment of each pump being in fluidic communication with the control fluid path and the second compartment being in fluidic communication with the second flow path; and a balancing chamber able to balance flow between the first flow path and the second flow path.

The cassette, in still another set of embodiments, includes a first flow path connecting a first inlet to a first outlet, a second flow path connecting a second inlet to a second outlet, and a rigid vessel containing a diaphragm dividing the rigid vessel into a first compartment and a second compartment. In some cases, the first compartment are in fluidic communication with the first fluid path and the second compartment being in fluidic communication with the second flow path.

Still another aspect of the invention is generally directed at a pump. The pump includes, in one set of embodiments, a first rigid component; a second rigid component, the second rigid component having on a side facing the first plate a groove defined therein, the groove being open in a direction facing the first rigid component; and a diaphragm having a rim, the rim being held in the groove by a friction fit in the groove but without contact by the first rigid component against the rim. In some cases, the first and second rigid components define, at least partially, a pod-pump chamber divided by the diaphragm into separate chambers, and further define, at least partially, flow paths into the pod-pump chamber, wherein the groove surrounds the pod-pump chamber.

In another set of embodiments, the pump includes a substantially spherical vessel containing a flexible diaphragm dividing the rigid vessel into a first compartment and a second compartment, the first compartment and the second compartment not in fluidic communication with each other, whereby movement of the diaphragm due to fluid entering the first compartment causes pumping of fluid within the second compartment to occur.

In another set of embodiments, the pump is a reciprocating positive-displacement pump. In one embodiment, the pump includes a rigid chamber wall; a flexible diaphragm attached to the rigid chamber wall, so that the flexible diaphragm and rigid chamber wall define a pumping chamber; an inlet for directing flow through the rigid chamber wall into the pumping chamber; an outlet for directing flow through the rigid chamber wall out of the pumping chamber; a rigid limit wall for limiting movement of the diaphragm and limiting the maximum volume of the pumping chamber, the flexible diaphragm and the rigid limit wall forming an actuation chamber; a pneumatic actuation system that intermittently provides a control pressure to the actuation chamber. In some cases, the pneumatic actuation system includes an actuation-chamber pressure transducer for measuring the pressure of the actuation chamber, a gas reservoir having a first pressure, a variable valve mechanism for variably restricting gas flowing between the actuation chamber and the gas reservoir, and a controller that receives pressure information from the actuation-chamber pressure transducer and controls the variable valve so as to create the control pressure in the actuation chamber, the control pressure being less than the first pressure.

Still another aspect of the invention is directed to a method. The method, in one set of embodiments, includes acts of providing a first pump comprising a pumping chamber and an actuation chamber, and a second pump comprising a pumping chamber and an actuation chamber, urging a common fluid into the actuation chambers of each of the first and second pumps, and pressurizing the common fluid to pump fluids through each of the first and second pumps.

In another set of embodiments, the method includes acts of providing a first valve comprising a valving chamber and an actuation chamber, and a second valve comprising a valving chamber and an actuation chamber, urging a common fluid into the actuation chambers of each of the first and second valves, and pressurizing the common fluid to at least partially inhibit fluid flow through each of the first and second valves.

In yet another set of embodiments, the method is a method for measuring the clearance of a dialyzer, the dialyzer being located in a blood flow path, through which untreated blood can be drawn from a patient and passed through the dialyzer, and in a dialysate flow path, through which dialysate can flow from a dialysate supply through the dialyzer, the blood flow path being separated from the dialysate flow path by membranes in the dialyzer. In one embodiment, the method includes acts of urging a liquid through the dialysate flow path to the dialyzer, so as to keep the membranes wet and prevent the flow of a gas through the membranes, urging a gas through the blood flow path to the dialyzer so as to fill the blood flow path in the dialyzer with the gas, measuring the volume of gas in the dialyzer, and calculating the clearance of the dialyzer based on the volume of gas measured in the dialyzer.

The method, in still another set of embodiments, is a method for measuring the clearance of a dialyzer. In one embodiment, the method includes acts of applying a pressure differential across the dialyzer, measuring the flow rate of the dialyzer, and determining the clearance of the dialyzer based on the pressure differential and the flow rate.

In yet another set of embodiments, the method is a method for measuring the clearance of a dialyzer. In one embodiment, the method includes acts of passing water through the dialyzer, measuring the amount of ions collected by the water after passing through the dialyzer, and determining the clearance of the dialyzer based on the amount of ions collected by the water after passing through the dialyzer. In another set of embodiments, the method includes acts of passing water through the dialyzer, measuring the conductivity of the water, and determining the clearance of the dialyzer based on changes in the conductivity of the water.

In one set of embodiments, the method is a method for introducing a fluid into blood. The method includes, in one embodiment, acts of providing a cassette including an integrally formed spike for receiving a vial of fluid, and a valving mechanism for controlling flow of the fluid from the vial into the cassette, attaching a vial containing the fluid to the spike, pumping blood through the cassette, and introducing the fluid from the vial into the blood.

In one set of embodiments, the method includes acts of providing a hemodialysis system comprising a blood flow path through which untreated blood is drawn from a patient and passed through a dialyzer, and a dialysate flow path through which dialysate flows from a dialysate supply through the dialyzer, putting the blood flow path and the dialysate flow path into fluidic communication, and urging dialysate through the dialysate flow path to cause blood in the blood flow path to pass into the patient.

The method, in another set of embodiments, includes acts of providing a hemodialysis system comprising a blood flow path through which untreated blood is drawn from a patient and passed through a dialyzer, and a dialysate flow path through which dialysate flows from a dialysate supply through the dialyzer, putting the blood flow path and the dialysate flow path into fluidic communication, and urging a gas into the dialysate flow path to cause flow of blood in the blood flow path.

The method is a method of performing hemodialysis, in still another set of embodiments. In one embodiment, the method includes acts of providing a blood flow path, through which untreated blood can be drawn from a patient and passed through a dialyzer; providing a dialysate flow path, through which dialysate can flow from a dialysate supply through the dialyzer; providing ingredients for preparing a total volume of dialysate; providing water for mixing with the dialysate ingredients; mixing a volume of water with a portion of the ingredients so as to prepare a first partial volume of dialysate, the first partial volume being less than the total volume; pumping the partial volume of dialysate through the dialysate flow path and through the dialyzer; pumping blood through the blood flow path and through the dialyzer, while the first partial volume of dialysate is being pumped to the dialyzer; and mixing a volume of water with a portion of the ingredients so as to prepare a second partial volume of dialysate and storing the second partial volume of dialysate within a vessel while the blood and the first partial volume of dialysate are pumped through the dialyzer.

In another embodiment, the method includes acts of passing blood from a patient and dialysate through a dialyzer contained within a hemodialysis system at a first rate, and forming dialysate within the hemodialysis system at a second rate that is substantially different from the first rate, wherein excess dialysate is stored within a vessel contained within the hemodialysis system.

Another aspect of the invention is directed to a hemodialysis system comprising a dialysis unit and a user interface unit. The dialysis unit comprises an automation computer and dialysis equipment. The user interface unit comprises a user interface computer and a user interface, the user interface being adapted to display information and receive inputs. The automation computer is configured to receive requests for safety-critical information from the user interface computer and to access the safety-critical information on behalf of the user interface computer. The user interface computer is configured to display information related to a dialysis process via the user interface using the safety-critical information.

A further aspect of the invention is directed to a method of managing a user interface in a hemodialysis system. The method comprises receiving an input related to a dialysis process at a user interface associated with a user interface computer and, in response to the input, transmitting a request for safety-critical information from the user interface computer to an automation computer associated with dialysis equipment. The method further comprises accessing the safety-critical information on behalf of the user interface computer and, using the safety-critical information, displaying information related to the dialysis process via the user interface.

Still another aspect of the invention is directed to a computer storage media encoded with instructions that, when executed, perform a method. The method comprising acts of receiving, from a user interface associated with a user interface computer, an input related to a dialysis process and, in response to the input, transmitting a request for safety-critical information from the user interface computer to an automation computer associated with dialysis equipment. The method further comprises accessing the safety-critical information on behalf of the user interface computer, transmitting the safety-critical information to the user interface computer, accessing screen design information stored within the user interface computer and, using the safety-critical information and the screen design information, causing the user interface to display information related to the dialysis process.

In another aspect, the present invention is directed to a method of making one or more of the embodiments described herein, for example, a hemodialysis system. In another aspect, the present invention is directed to a method of using one or more of the embodiments described herein, for example, a hemodialysis system.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
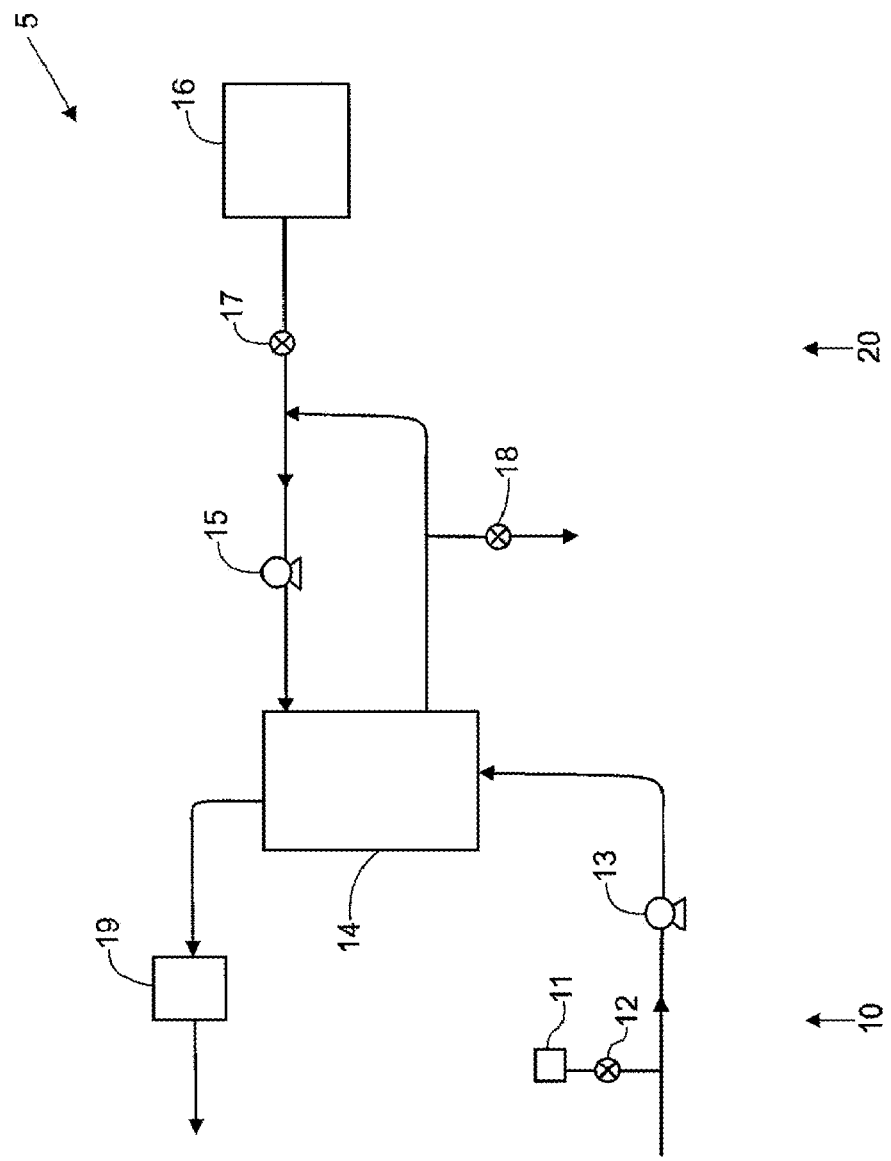
FIG. 1 is a schematic representation of a hemodialysis system.

The present invention generally relates to hemodialysis and similar dialysis systems, including a variety of systems and methods that would make hemodialysis more efficient, easier, and/or more affordable. One aspect of the invention is generally directed to new fluid circuits for fluid flow. In one set of embodiments, a hemodialysis system may include a blood flow path and a dialysate flow path, where the dialysate flow path includes one or more of a balancing circuit, a mixing circuit, and/or a directing circuit. Preparation of dialysate by the mixing circuit, in some instances, may be decoupled from patient dialysis. In some cases, the circuits are defined, at least partially, within one or more cassettes, optionally interconnected with conduits, pumps, or the like. In one embodiment, the fluid circuits and/or the various fluid flow paths may be at least partially isolated, spatially and/or thermally, from electrical components of the hemodialysis system. In some cases, a gas supply may be provided in fluid communication with the dialysate flow path and/or the dialyzer that, when activated, is able to urge dialysate to pass through the dialyzer and urge blood in the blood flow path back to the patient. Such a system may be useful, for example, in certain emergency situations (e.g., a power failure) where it is desirable to return as much blood to the patient as possible. The hemodialysis system may also include, in another aspect of the invention, one or more fluid handling devices, such as pumps, valves, mixers, or the like, which can be actuated using a control fluid, such as air. In some cases, the control fluid may be delivered to the fluid handling devices using an external pump or other device, which may be detachable in certain instances. In one embodiment, one or more of the fluid handling devices may be generally rigid (e.g., having a spheroid shape), optionally with a diaphragm contained within the device, dividing it into first and second compartments.

Various aspects of the present invention are generally directed to new systems for hemodialysis and the like, such as hemofiltration systems, hemodiafiltration systems, plasmapheresis systems, etc. Accordingly, although the various systems and methods described herein are described in relation to hemodialysis, it should be understood that the various systems and method described herein are applicable to other dialysis systems and/or in any extracorporeal system able to treat blood or other bodily fluids, such as plasma.

As discussed above, a hemodialysis system typically includes a blood flow path and a dialysate flow path. It should be noted that within such flow paths, the flow of fluid is not necessarily linear, and there may be any number of "branches" within the flow path that a fluid can flow from an inlet of the flow path to an outlet of the flow path. Examples of such branching are discussed in detail below. In the blood flow path, blood is drawn from a patient, and is passed through a dialyzer, before being returned to the patient. The blood is treated by the dialyzer, and waste molecules (e.g., urea, creatinine, etc.) and water are passed from the blood, through a semi-permeable membrane in the dialyzer, into a dialysate solution that passes through the dialyzer by the dialysate flow path. In various embodiments, blood may be drawn from the patient from two lines (e.g., an arterial line and a venous line, i.e., "dual needle" flow), or in some cases, blood may be drawn from the patient and returned through the same needle (e.g., the two lines may both be present within the same needle, i.e., "single needle" flow). In still other embodiments, a "Y" site or "T" site is used, where blood is drawn from the patient and returned to the patient through one patient connection having two branches (one being the fluid path for the drawn blood, the second the fluid path for the return blood). In an embodiment, a "Y" or "T" connection can be made with a single-lumen needle or catheter. In another embodiment, a "dual needle" flow effect can be obtained with the use of a single catheter or needle having dual lumens. The patient may be any subject in need of hemodialysis or similar treatments, although typically the patient is a human. However, hemodialysis may be performed on non-human subjects, such as dogs, cats, monkeys, and the like.

In the dialysate flow path, fresh dialysate is prepared and is passed through the dialyzer to treat the blood from the blood flow path. The dialysate may also be equalized for blood treatment within the dialyzer (i.e., the pressure between the dialysate and the blood are equalized), i.e., the pressure of dialysate through the dialyzer is closely matched to the pressure of blood through the dialyzer, often exactly, or in some embodiments, at least within about 1% or about 2% of the pressure of the blood. In some cases, it may be desirable to maintain a greater pressure difference (either positive or negative) between the blood flow path and dialysate flow path. After passing through the dialyzer, the used dialysate, containing waste molecules (as discussed below), is discarded in some fashion. In some cases, the dialysate is heated prior to treatment of the blood within the dialyzer using an appropriate heater, such as an electrical resistive heater. The dialysate may also be filtered to remove contaminants, infectious organisms, debris, and the like, for instance, using an ultrafilter. The ultrafilter may have a mesh or pore size chosen to prevent species such as these from passing therethrough. For instance, the mesh or pore size may be less than about 0.3 micrometers, less than about 0.2 micrometers, less than about 0.1 micrometers, or less than about 0.05 micrometers, etc. The dialysate is used to draw waste molecules (e.g., urea, creatinine, ions such as potassium, phosphate, etc.) and water from the blood into the dialysate through osmosis or convective transport, and dialysate solutions are well-known to those of ordinary skill in the art.

The dialysate typically contains various ions such as sodium chloride, bicarbonate, potassium and calcium that are similar in concentration to that of normal blood. In some cases, the bicarbonate, may be at a concentration somewhat higher than found in normal blood. Typically, the dialysate is prepared by mixing water from a water supply with one or more ingredients: an "acid" (which may contain various species such as acetic acid, dextrose, NaCl, CaCl, KCl, MgCl, etc.), sodium bicarbonate ($NaHCO_3$), and/or sodium chloride (NaCl). The preparation of dialysate, including using the appropriate concentrations of salts, osmolarity, pH, and the like, is well-known to those of ordinary skill in the art. As discussed in detail below, the dialysate need not be prepared at the same rate that the dialysate is used to treat the blood. For instance, the dialysate can be made concurrently or prior to dialysis, and stored within a dialysate storage vessel or the like.

Within the dialyzer, the dialysate and the blood typically do not come into physical contact with each other, and are separated by a semi-permeable membrane. Typically, the semi-permeable membrane is formed from a polymer such as cellulose, polyarylethersulfone, polyamide, polyvinylpyrrolidone, polycarbonate, polyacrylonitrile, or the like, which allows the transport of ions or small molecules (e.g., urea, water, etc.), but does not allow bulk transport or convection during treatment of the blood. In some cases, even larger molecules, such as beta-2-microglobulin, may pass through the membrane. In other cases, convective transfer of fluid, ions and small molecules can occur, for example, when there is a hydrostatic pressure difference across the semi-permeable membrane.

The dialysate and the blood do not come into contact with each other in the dialyzer, and are usually separated by the membrane. Often, the dialyzer is constructed according to a "shell-and-tube" design comprising a plurality of individual tubes or fibers (through which blood flows), formed from the semipermeable membrane, surrounded by a larger "shell" through which the dialysate flows (or vice versa in some cases). Flow of the dialysate and the blood through the dialyzer can be countercurrent, or concurrent in some instances. Dialyzers are well-known to those of ordinary skill in the art, and are obtainable from a number of different commercial sources.

In one aspect, the dialysate flow path can be divided into one or more circuits, such as a balancing circuit, a mixing circuit, and/or a directing circuit. It should be noted that a circuit, in reference to fluid flow, is not necessarily fluidically isolated, i.e., fluid may flow into a fluid circuit and out of a fluid circuit. Similarly, a fluid may pass from one fluid circuit to another fluid circuit when the fluid circuits are in fluid communication or are fluidly connected to each other. It should be noted that, as used herein, "Fluid" means anything having fluidic properties, including but not limited to, gases such as air, and liquids such as water, aqueous solution, blood, dialysate, etc.

A fluid circuit is typically a well-defined module that receives a certain number of fluid inputs and in some cases performs one or more tasks on the fluid inputs, before directing the fluids to appropriate outputs. In certain embodiments of the invention, as discussed below, the fluid circuit is defined as a cassette. As a specific example, a dialysate flow path may include a balancing circuit, a directing circuit, and a mixing circuit. As another example, a blood flow path may include a blood flow circuit. Within the balancing circuit, dialysate is introduced into the balancing circuit and pumps operate on the dialysate such that the pressure of dialysate passing through the dialyzer balances the pressure of blood passing through the dialysate, as previously discussed. Similarly, within the directing circuit, fresh dialysate is passed from the mixing circuit to the balancing circuit, while used dialysate is passed from the balancing circuit to a drain. Within the mixing circuit, ingredients and water are mixed together to form fresh dialysate. The blood flow circuit is used to draw blood from the patient, pass the blood through a dialyzer, and return the blood to the patient. These circuits will be discussed in detail below.

Figure 2A:
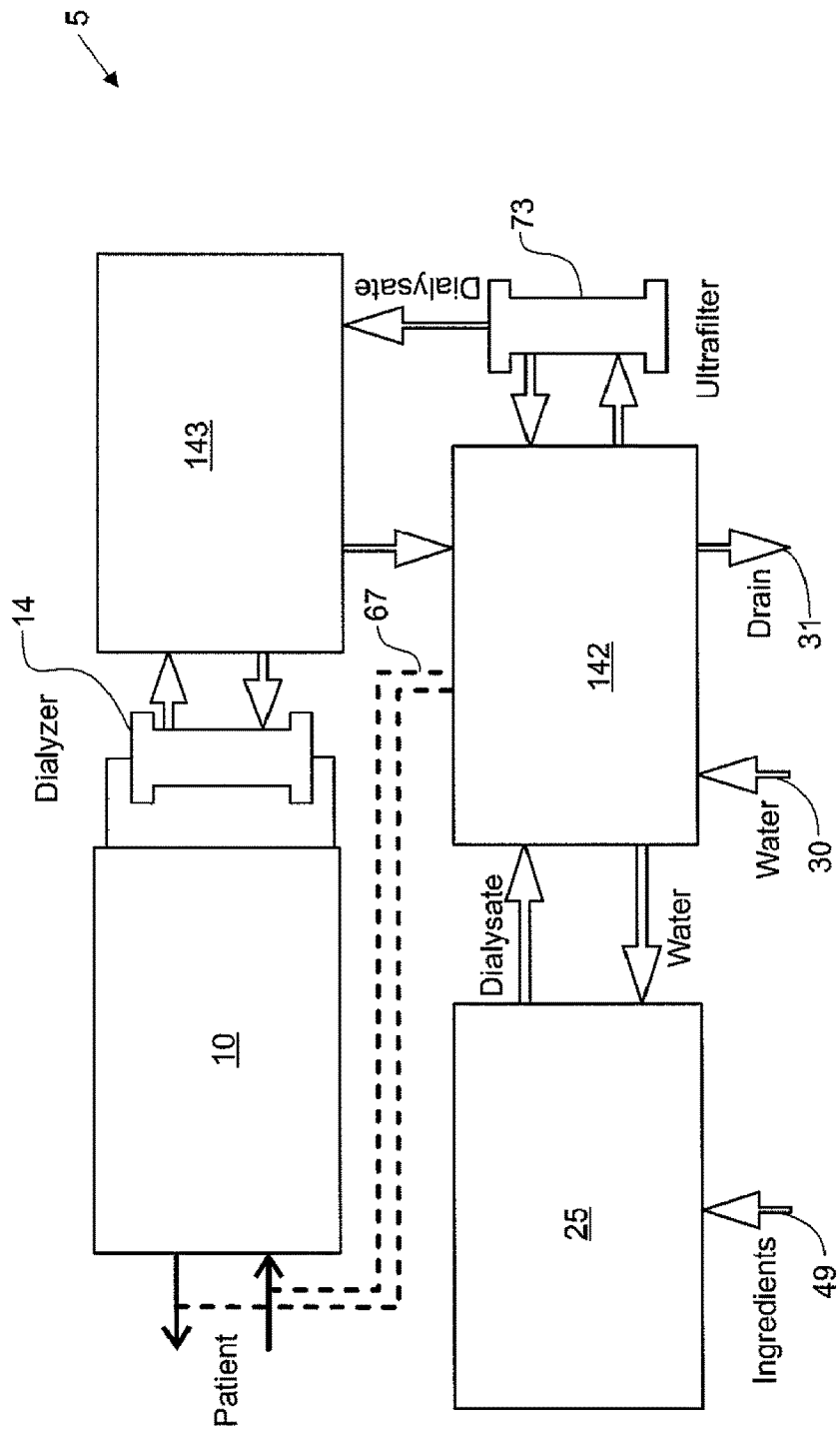
FIGS. 2A-2B are high-level schematics of various embodiments of a dialysis system.

An example of a hemodialysis system having such fluid circuits is illustrated schematically in FIG. 2A as a high-level overview. FIG. 2A illustrates a dialysis system 5 that includes a blood flow circuit 10, through which blood passes from a patient to a dialyzer 14, and through which treated blood returns to the patient. The hemodialysis system in this example also includes a balancing circuit or an internal dialysate circuit 143, which takes dialysate after it passes through an ultrafilter 73 and passes the dialysate through dialyzer 14, with used dialysate returning to balancing circuit 143 from dialyzer 14. A directing circuit or an external dialysate circuit 142 handles fresh dialysate before it passes through ultrafilter 73. A mixing circuit 25 prepares dialysate, for instance, on an as-needed basis, during and/or in advance of dialysis, etc., using various ingredients 49 and water. The directing circuit 142 can also receive water from a water supply 30 and pass it to mixing circuit 25 for preparation of the dialysate, and the directing circuit 142 can also receive used dialysate from balancing circuit 143 and pass it out of system 5 as waste via drain 31. Also shown, in dotted lines, are conduits 67 that can be connected between blood flow circuit 10, and directing circuit 142, e.g., for disinfection of the hemodialysis system. In one set of embodiments, one or more of these circuits (e.g., the blood flow circuit, the balancing circuit, the directing circuit, and/or the mixing circuit) may include a cassette incorporating the valves and pumps needed for controlling flow through that portion. Examples of such systems are discussed in detail below.

Figure 2B:
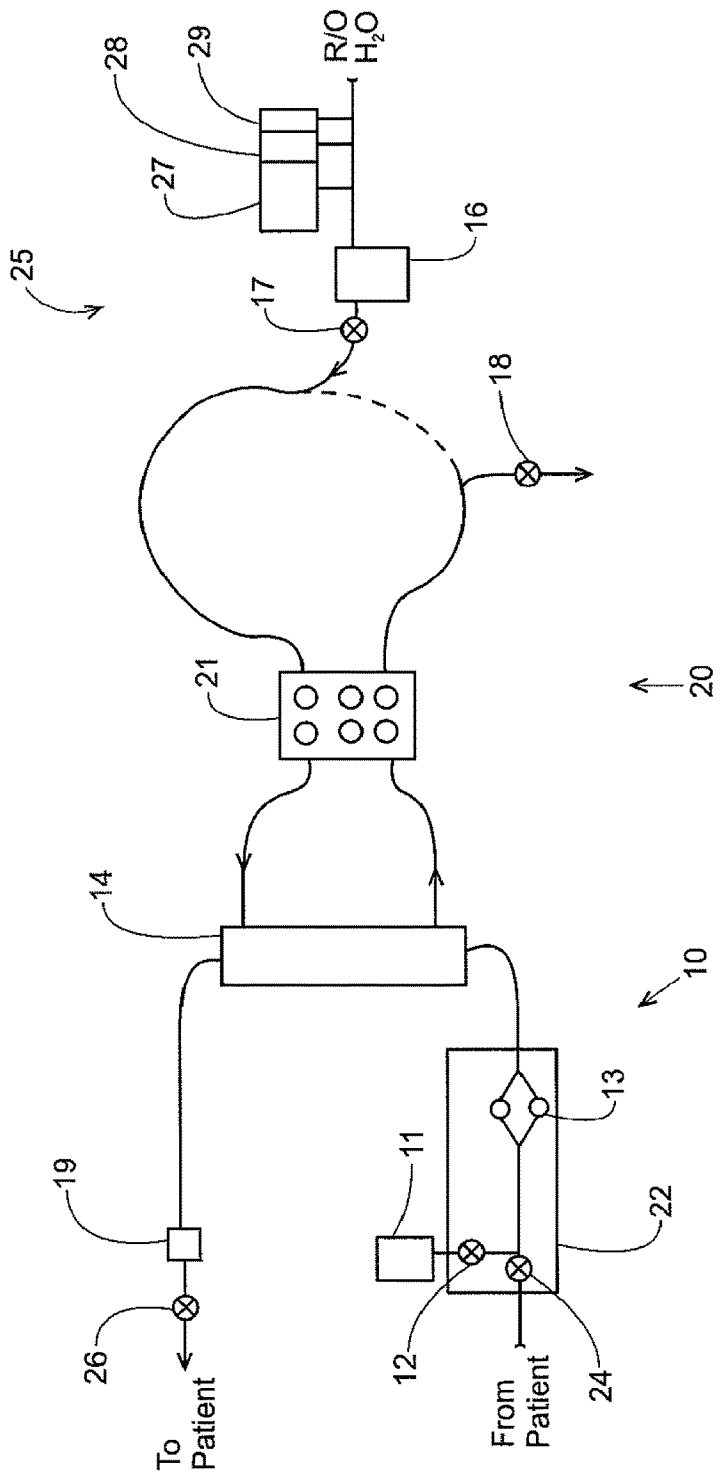

FIG. 2B is a schematic representation of a hemodialysis system according to one embodiment of the invention. In this schematic, a blood flow cassette 22 is used to control flow through the blood flow circuit 10, and a dialysate cassette 21 is used to control flow through the dialysate circuit. The blood flow cassette includes at least one inlet valve 24 (in other embodiments, more than one inlet valve is included) to control the flow of blood through cassette 22 as well as an anticoagulant valve or pump 12 to control the flow of anticoagulant into the blood, and a blood flow pump 13, which may include a pair of pod pumps in some cases. These pod pumps may be of the type (or variations of the type) as described in U.S. Provisional Patent Application Ser. No. 60/792,073, filed Apr. 14, 2006, entitled "Extracorporeal Thermal Therapy Systems and Methods"; or in U.S. patent application Ser. No. 11/787,212, filed Apr. 13, 2007 and issued as U.S. Pat. No. 8,292,594 on Oct. 23, 2012, entitled "Fluid Pumping Systems, Devices and Methods," each of which is incorporated herein in its entirety. All the pumps and valves in this example system may be controlled by a control system, e.g., an electronic and digital control system, although other control systems are possible in other embodiments.

Providing two pod pumps may allow for a more continuous flow of blood through the blood flow circuit 10; however, a single pod pump, such as a single pod pump may be used in other embodiments. The pod pumps may include active inlet and outlet valves (instead of passive check valves at their inlets and outlets) so that flow in the blood flow circuit 10 may be reversed under some conditions. For instance, by reversing flow in the blood flow circuit, the hemodialysis system can check whether the outlet of the blood flow circuit is properly connected to the patient so that the treated blood is correctly returned to the patient. If, for example, the patient connection point has been disconnected, e.g., by falling out, reversing the blood flow pump would draw air rather than blood. This air can be detected by standard air detectors incorporated into the system.

In another embodiment, blood outlet valve 26 and air trap/filter 19, which are located downstream of the dialyzer, may be incorporated into blood flow cassette 22. The pod pumps and all the valves (including the valves associated with the pod pumps' inlets and outlets) in the blood flow cassette 22 may be actuated pneumatically. Sources of positive and negative gas pressure in one embodiment, are provided by a base unit holding cassette or other device holding the cassette. However, in other embodiments, the positive and negative gas pressure may be provided by an external device fluidly connected to the cassettes, or any device build into the system The pump chamber may be actuated in the manner described in U.S. Provisional Patent Application Ser. No. 60/792,073, filed Apr. 14, 2006, entitled "Extracorporeal Thermal Therapy Systems and Methods"; or in U.S. patent application Ser. No. 11/787,212, filed Apr. 13, 2007 and issued as U.S. Pat. No. 8,292,594 on Oct. 23, 2012, entitled "Fluid Pumping Systems, Devices and Methods," referred to hereinabove. For instance, the pumps may be controlled and the end of stroke detected in the manner described below. The blood flow cassette 22 may also contain an integrally formed spike for receiving a vial of anticoagulant.

The anticoagulant pump, in one embodiment, includes three fluid valves (which may be controlled with a control fluid) and a single pumping compartment (although there may be more than one pumping compartment in other embodiments. The valves may connect the compartment to a filtered air vent, to a vial of anticoagulant (or other anticoagulant supply, such as a bag or a bottle, etc.), or to the blood flow path. The anticoagulant pump can be operated by sequencing the opening and closing of the fluid valves and controlling the pressure in the pump compartment, e.g., via the control fluid. When the anticoagulant is removed from the vial it may be replaced with an equal volume of air, e.g., to keep pressure within the vial relatively constant. This replacement of anticoagulant volume with air may be accomplished, for example, by (i) opening the valve from the filtered air vent to the pump compartment, (ii) drawing air into the compartment by connecting the negative pressure source to the chamber, (iii) closing the air vent valve, (iv) opening the valve connecting the compartment to the vial, and (v) pushing air into the vial by connecting the positive pressure source to the compartment. The anticoagulant can be pumped from the vial into the blood flow path with a similar sequence, using the valves to the vial and the blood path rather than the valves to the air vent and the vial.

Figure 3A:
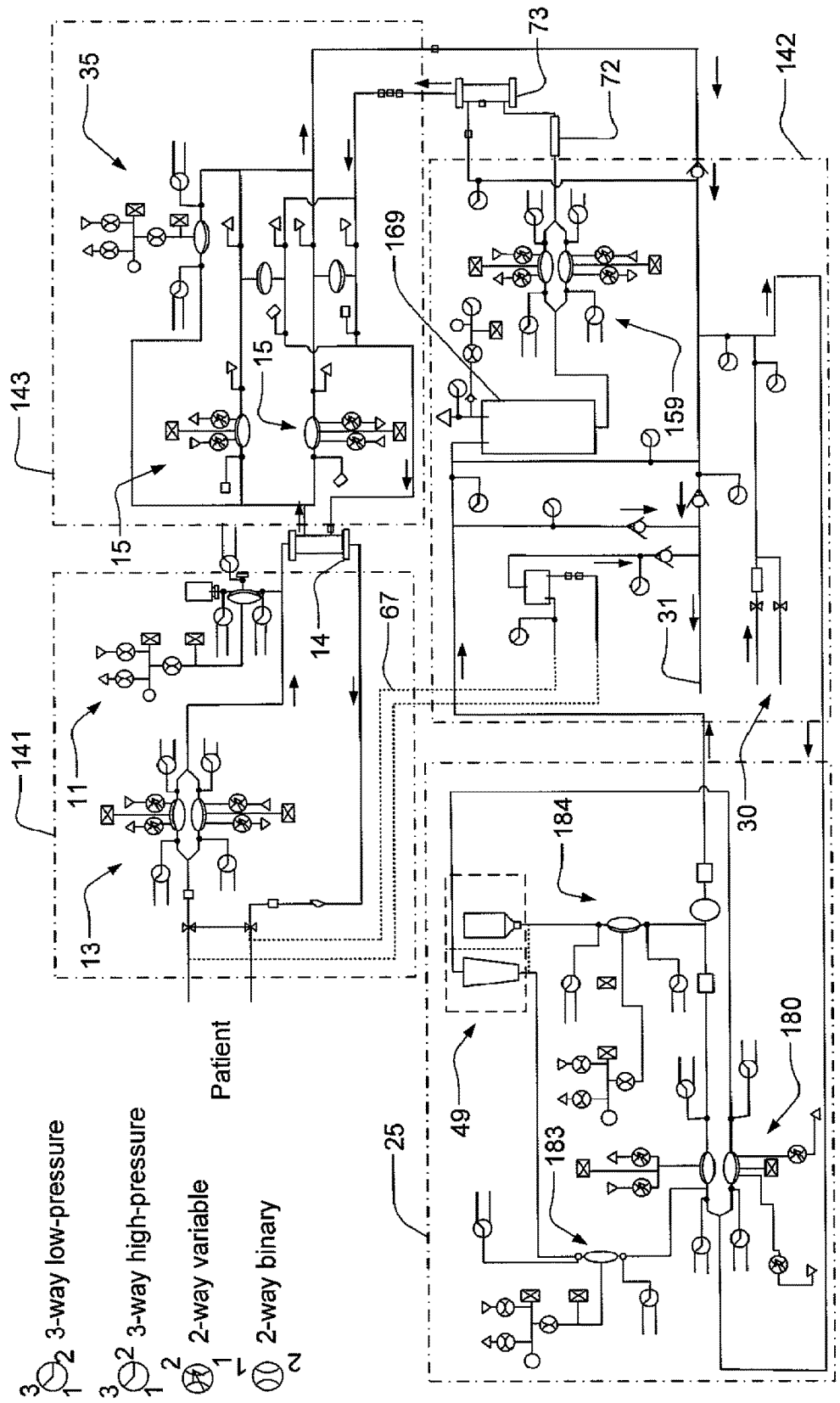
FIGS. 3A-3B are schematics showing an example of a fluid schematic for a dialysis system.

FIG. 3A is a schematic diagram showing a specific embodiment of the general overview shown in FIG. 2A. FIG. 3A shows, in detail, how a blood flow circuit 141, a balancing circuit 143, a directing circuit 142, and a mixing circuit 25 can be implemented on cassettes and made to interrelate with each other and to a dialyzer 14, an ultrafilter 73, and/or a heater 72, in accordance with one embodiment of the invention. It should be understood, of course, that FIG. 3A is only one possible embodiment of the general hemodialysis system of FIG. 2A, and in other embodiments, other fluid circuits, modules, flow paths, layouts, etc. are possible. Examples of such systems are discussed in more detail below, and also can be found in the following, each of which is incorporated herein by reference: U.S. Provisional Patent Application Ser. No. 60/903,582, filed Feb. 27, 2007, entitled "Hemodialysis System and Methods"; U.S. Provisional Patent Application Ser. No. 60/904,024, filed Feb. 27, 2007, entitled "Hemodialysis System and Methods"; U.S. patent application Ser. No. 11/871,680, filed Oct. 12, 2007 and issued as U.S. Pat. No. 8,273,049 on Sep. 25, 2012, entitled "Pumping Cassette"; U.S. patent application Ser. No. 11/871,712, filed Oct. 12, 2007 and issued as U.S. Pat. No. 8,317,492 on Nov. 27, 2012, entitled "Pumping Cassette"; U.S. patent application Ser. No. 11/871,787, filed Oct. 12, 2007, entitled "Pumping Cassette"; U.S. patent application Ser. No. 11/871,793, filed Oct. 12, 2007, entitled "Pumping Cassette"; or U.S. patent application Ser. No. 11/871,803, filed Oct. 12, 2007 and issued as U.S. Pat. No. 7,967,022 on Jun. 28, 2011, entitled "Cassette System Integrated Apparatus."

The components in FIG. 3A will be discussed in detail below. Briefly, blood flow circuit 141 includes an anticoagulant supply 11 and a blood flow pump 13 which pumps blood from a patient to a dialyzer 14. The anticoagulant supply 11, although shown in the path of blood flowing towards the dialyzer, in other embodiments, may be instead located in the path of blood flowing towards the patient, or in another suitable location, such as upstream or downstream of blood flow pump 13. The anticoagulant supply 11 may be placed in any location downstream from blood flow pump 13. Balancing circuit 143 includes two dialysate pumps 15, which also pump dialysate into dialyzer 14, and a bypass pump 35. Directing circuit 142 includes a dialysate pump 159, which pumps dialysate from dialysate tank 169 through heater 72 and/or ultrafilter 73 to the balancing circuit. Directing circuit 142 also takes waste fluid from balancing circuit 143 and directs it to a drain 31. In some cases, the blood flow circuit 141 can be connected via conduits 67 to directing circuit 142, e.g., for disinfection, as discussed below. Dialysate flows into dialysate tank 169 from a dialysate supply. In one embodiment, as is shown in FIG. 3A, the dialysate is produced in mixing circuit 25. Water from water supply 30 flows through directing circuit 142 into mixing circuit 25. Dialysate ingredients 49 (e.g., bicarbonate and acid) are also added into mixing circuit 25, and a series of mixing pumps 180, 183, 184 are used to produce the dialysate, which is then sent to directing circuit 142.

In this example system, one of the fluid circuits is a blood flow circuit, e.g., blood flow circuit 141 in FIG. 3A. In the blood flow circuit, blood from a patient is pumped through a dialyzer and then is returned to the patient. In some cases, blood flow circuit is implemented on a cassette, as discussed below, although it need not be. The flow of blood through the blood flow circuit, in some cases, is balanced with the flow of dialysate flowing through the dialysate flow path, especially through the dialyzer and the balancing circuit.

Figure 4A:
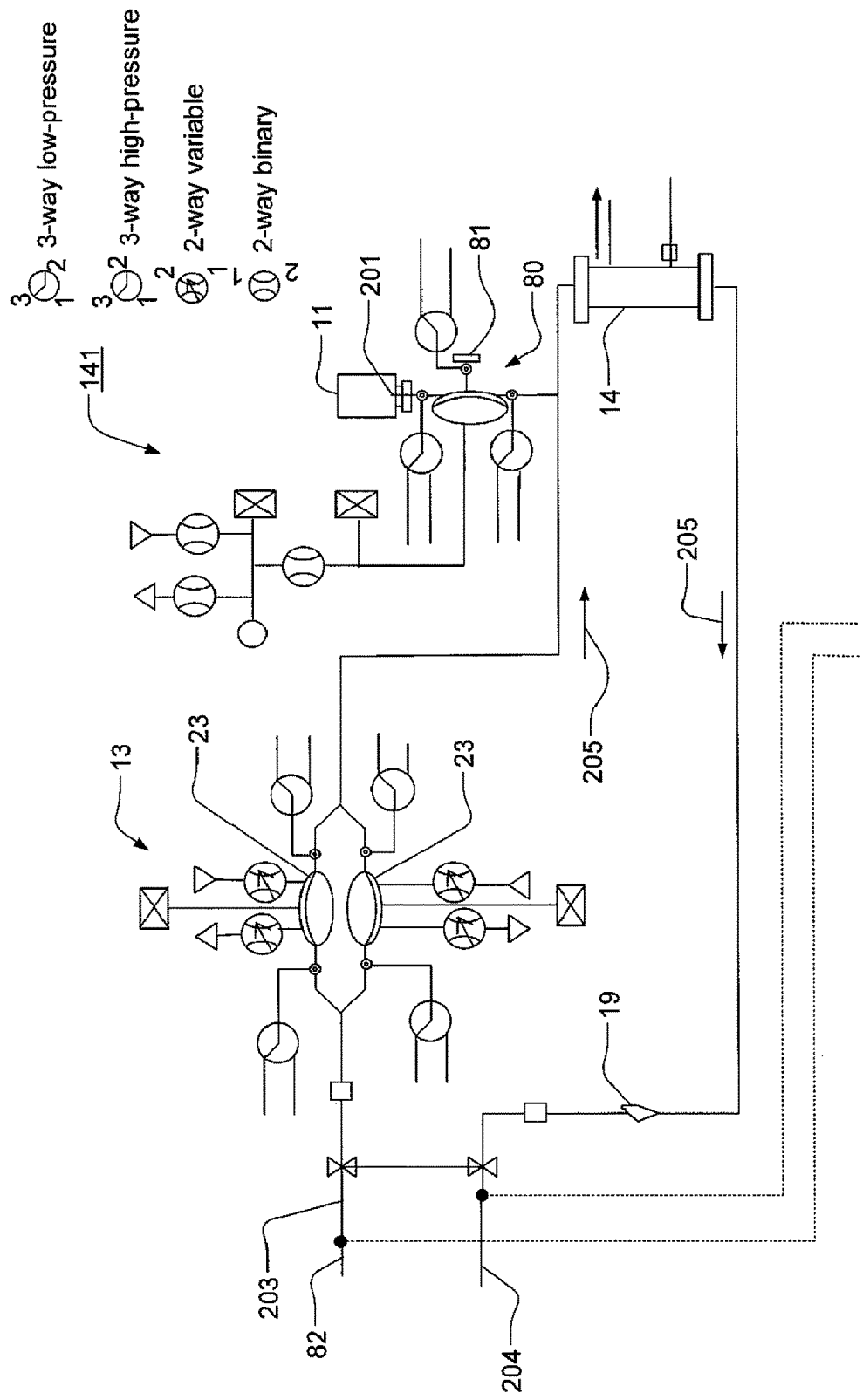
FIGS. 4A-4B are schematic representations of various embodiments of a blood flow circuit that may be used in a hemodialysis system.
Figure 4B:
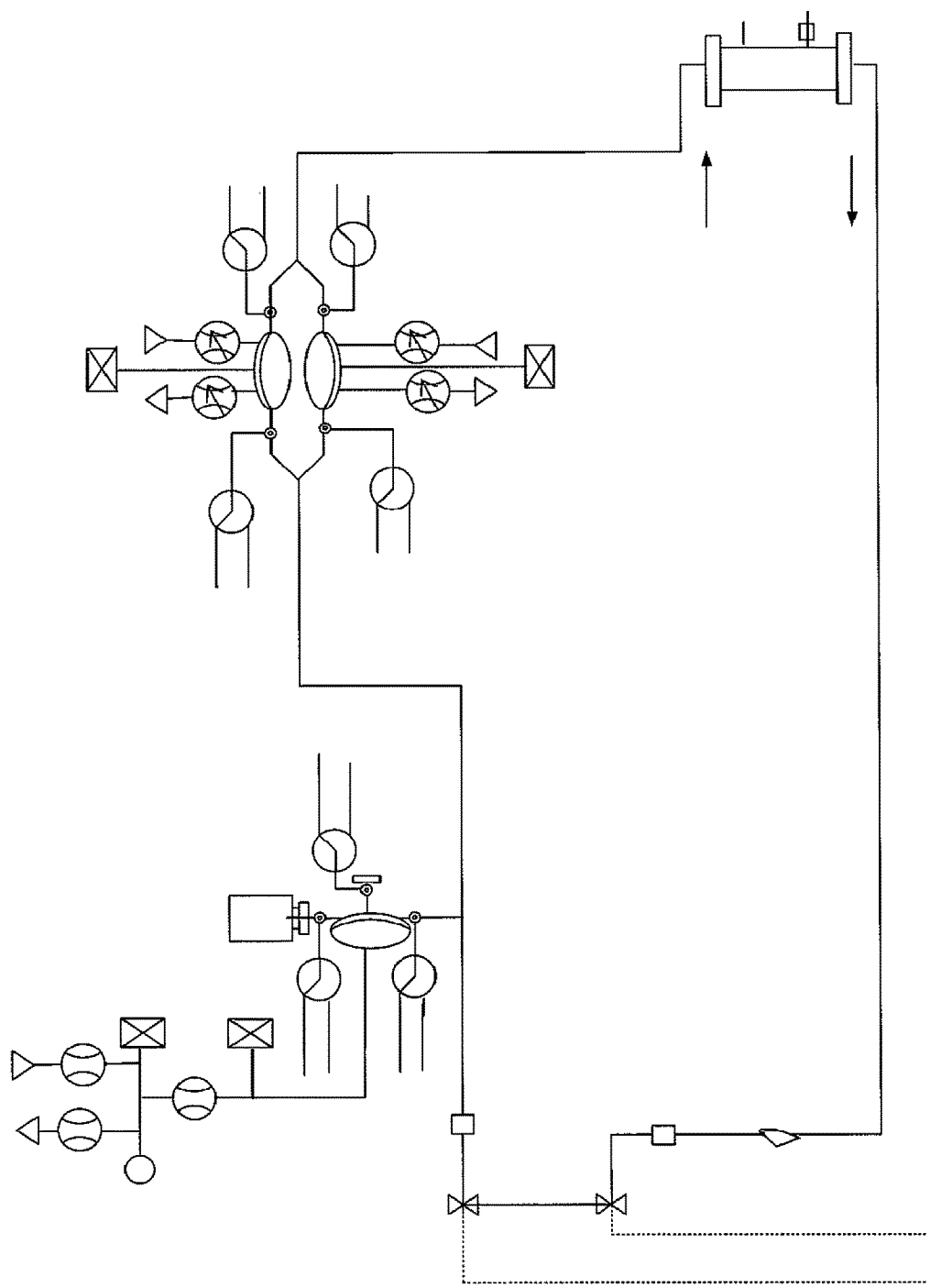

One example of a blood flow circuit is shown in FIG. 4A. Generally, blood flows from a patient through arterial line 203 via blood flow pump 13 to dialyzer 14 (the direction of flow during normal dialysis is indicated by arrows 205; in some modes of operation, however, the flow may be in different directions, as discussed below). Optionally, an anticoagulant may be introduced into the blood via anticoagulant pump 80 from an anticoagulant supply. As shown in FIG. 4A, the anticoagulant can enter the blood flow path after the blood has passed through blood flow pump 13; however, the anticoagulant may be added in any suitable location along the blood flow path in other embodiments. For example, in FIG. 4B, the anticoagulant enters the blood flow path before the blood has passed through blood flow pump 13. This may be useful, for example, if a blood pump cassette of the type shown in FIGS. 30C-33D is used, and blood flow is directed to cause blood to enter at the top of the cassette, and exit at the bottom of the cassette. The blood pump chambers can thus additionally serve to trap air that may be present in the blood before it is pumped to the dialyzer. In other embodiments, anticoagulant supply 11 may be located anywhere downstream from the blood flow pump. After passing through dialyzer 14 and undergoing dialysis, the blood returns to the patient through venous line 204, optionally passing through air trap and/or a blood sample port 19.

As is shown in FIG. 4A, blood flow cassette 141 also includes one or more blood flow pumps 13 for moving blood through the blood flow cassette. The pumps may be, for instance, pumps that are actuated by a control fluid, such as is discussed below. For instance, in one embodiment, pump 13 may comprise two (or more) pod pumps, e.g., pod pumps 23 in FIG. 4A. Each pod pump, in this particular example, may include a rigid chamber with a flexible diaphragm or membrane dividing each chamber into a fluid compartment and control compartment. There are four entry/exit valves on these compartments, two on the fluid compartment and two on the control compartment. The valves on the control compartment of the chambers may be two-way proportional valves, one connected to a first control fluid source (e.g., a high pressure air source), and the other connected to a second control fluid source (e.g., a low pressure air source) or a vacuum sink. The fluid valves on the compartments can be opened and closed to direct fluid flow when the pod pumps are pumping. Non-limiting examples of pod pumps are described in U.S. Provisional Patent Application Ser. No. 60/792,073, filed Apr. 14, 2006, entitled "Extracorporeal Thermal Therapy Systems and Methods"; or in U.S. patent application Ser. No. 11/787,212, filed Apr. 13, 2007 and issued as U.S. Pat. No. 8,292,594 on Oct. 23, 2012, entitled "Fluid Pumping Systems, Devices and Methods," each incorporated herein by reference. Further details of the pod pumps are discussed below. If more than one pod pump is present, the pod pumps may be operated in any suitable fashion, e.g., synchronously, asynchronously, in-phase, out-of-phase, etc.

For instance, in some embodiments, the two-pump pumps can be cycled out of phase to affect the pumping cycle, e.g., one pump chamber fills while the second pump chamber empties. A phase relationship anywhere between 0° (the pod pumps act in the same direction, filling and emptying in unison) and 180° (the pod pumps act in opposite directions, in which one pod pump fills as the other empties) can be selected in order to impart any desired pumping cycle.

Figure 8A:
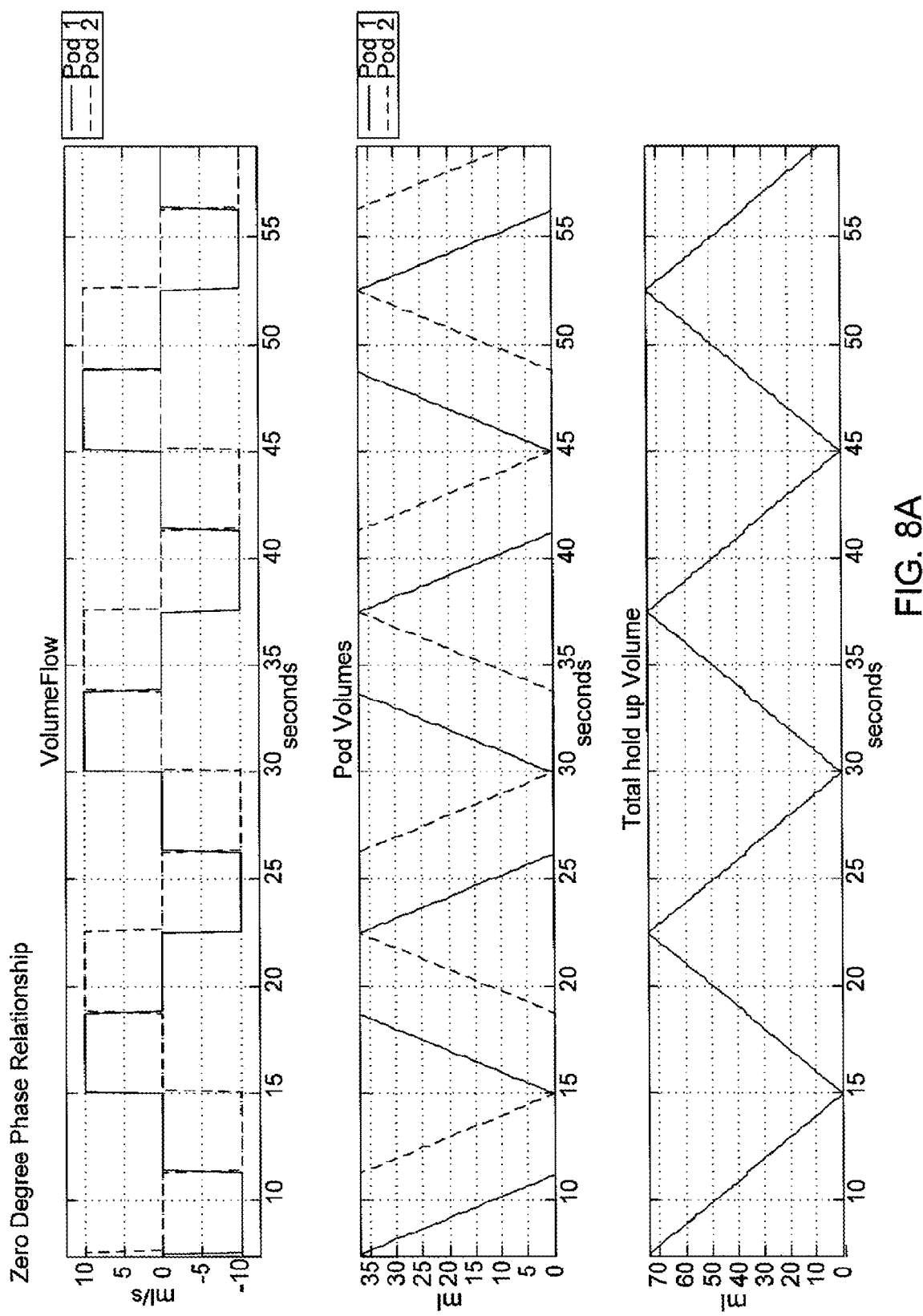
FIGS. 8A-8C are graphical representations of phase relationships.
Figure 8B:
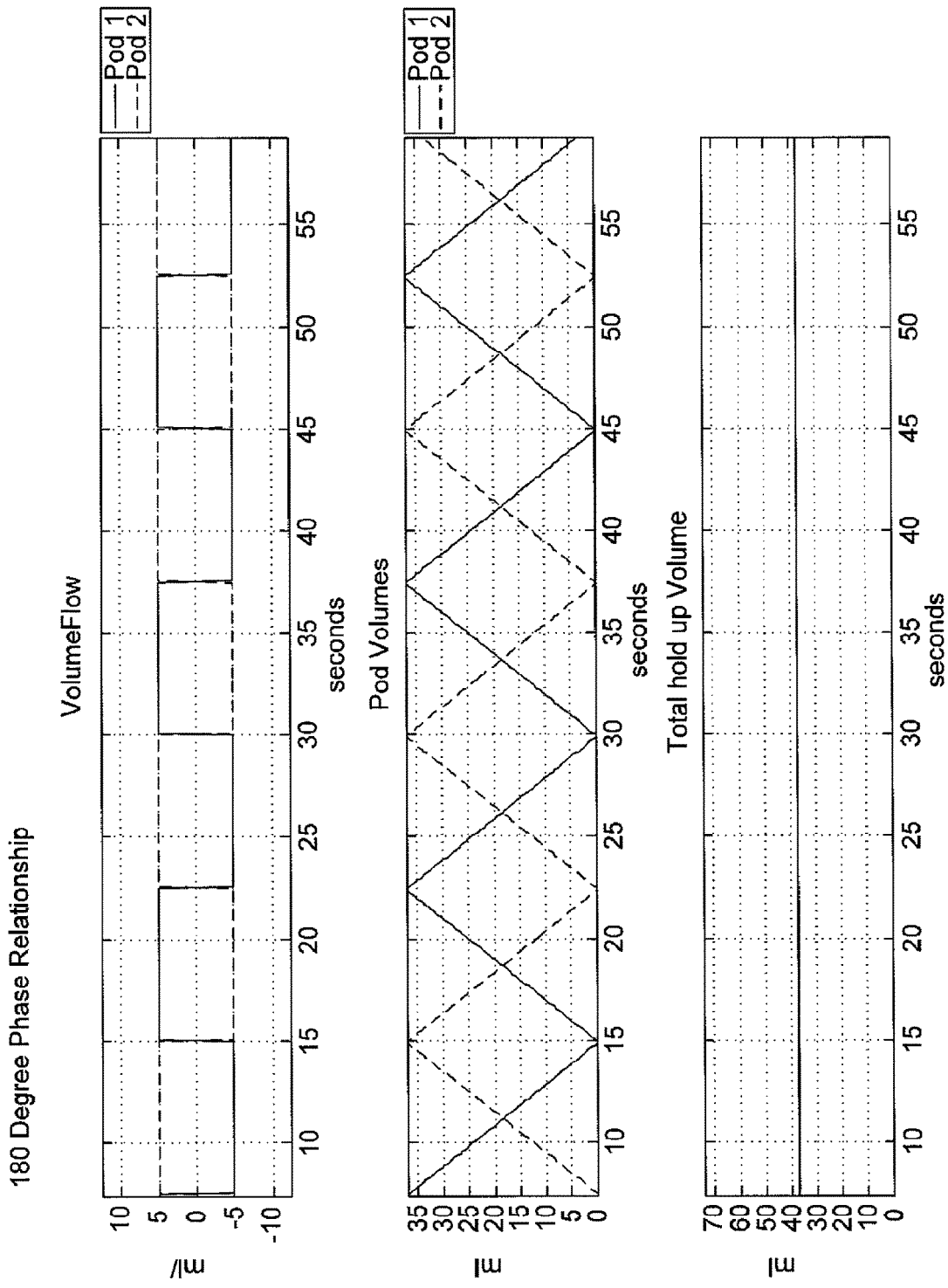
Figure 8C:
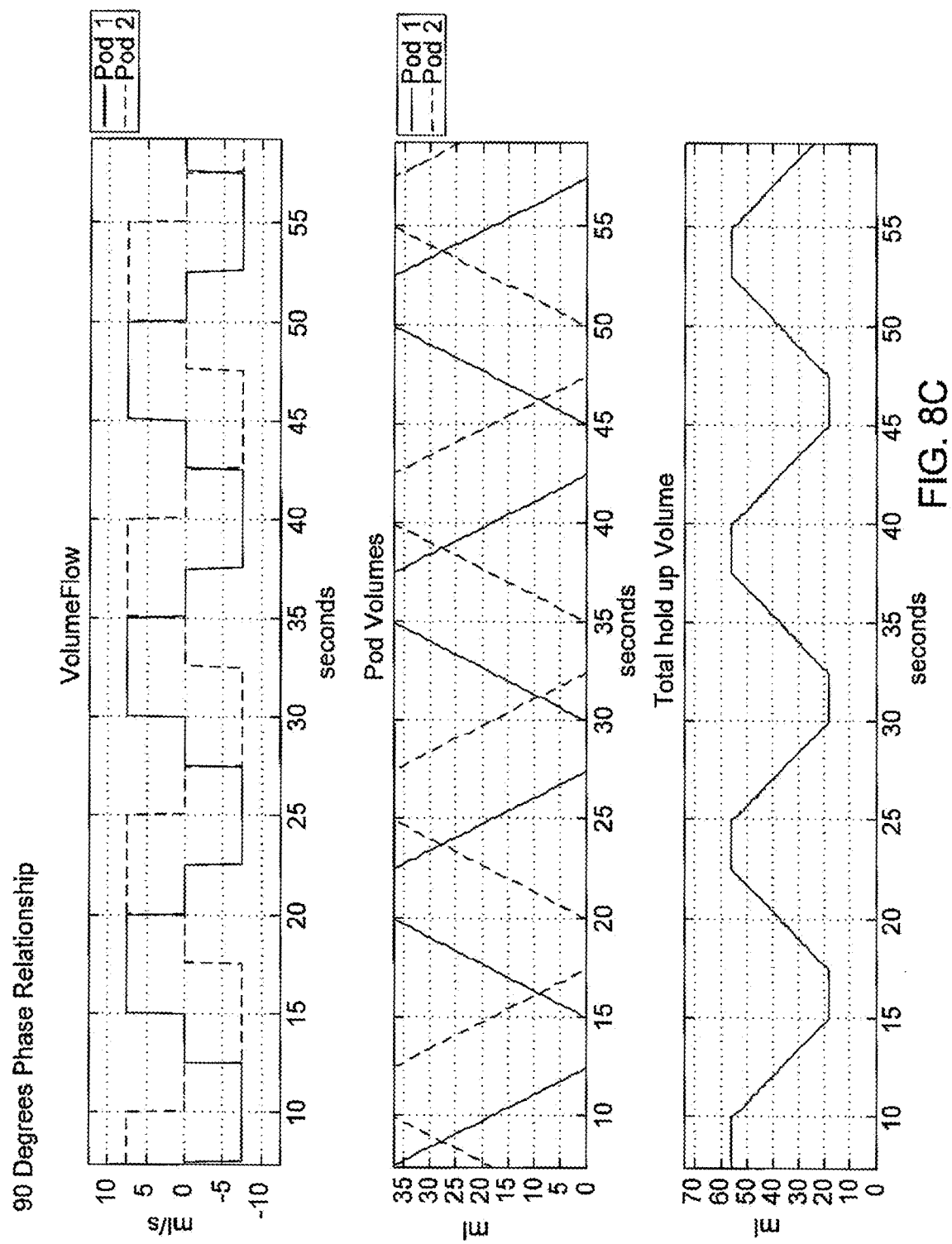

A phase relationship of 180° may yield continuous flow into and out of the pod pump cassette. This is useful, for instance, when continuous flow is desired, e.g., for use with dual needle flow or a "Y" or "T" connection. Setting a phase relationship of 0°, however, may be useful in some cases for single needle flow, in situations in which a "Y" or "T" connection is made with a single needle or single lumen catheter, or in other cases. In a 0° relationship, the pod pumps will first fill from the needle, then deliver blood through the blood flow path and back to the patient using the same needle. In addition, running at phases between 0° and 180° can be used in some cases, to achieve a push/pull relationship (hemodiafiltration or continuous back flush) across the dialyzer. FIGS. 8A-8C are graphical representations of examples of such phase relationships. In these figures, the volume or flow of each pod pump, the volumes of each pod pumps, and the total hold up volume of both pod pumps is shown as a function of time. These times and flow rates are arbitrarily chosen, and are presented here to illustrate the relationships between the pod pumps at different phasings. For instance, at a 180° phase relationship (FIG. 8B), the total hold up volume remains substantially constant.

Figure 14:
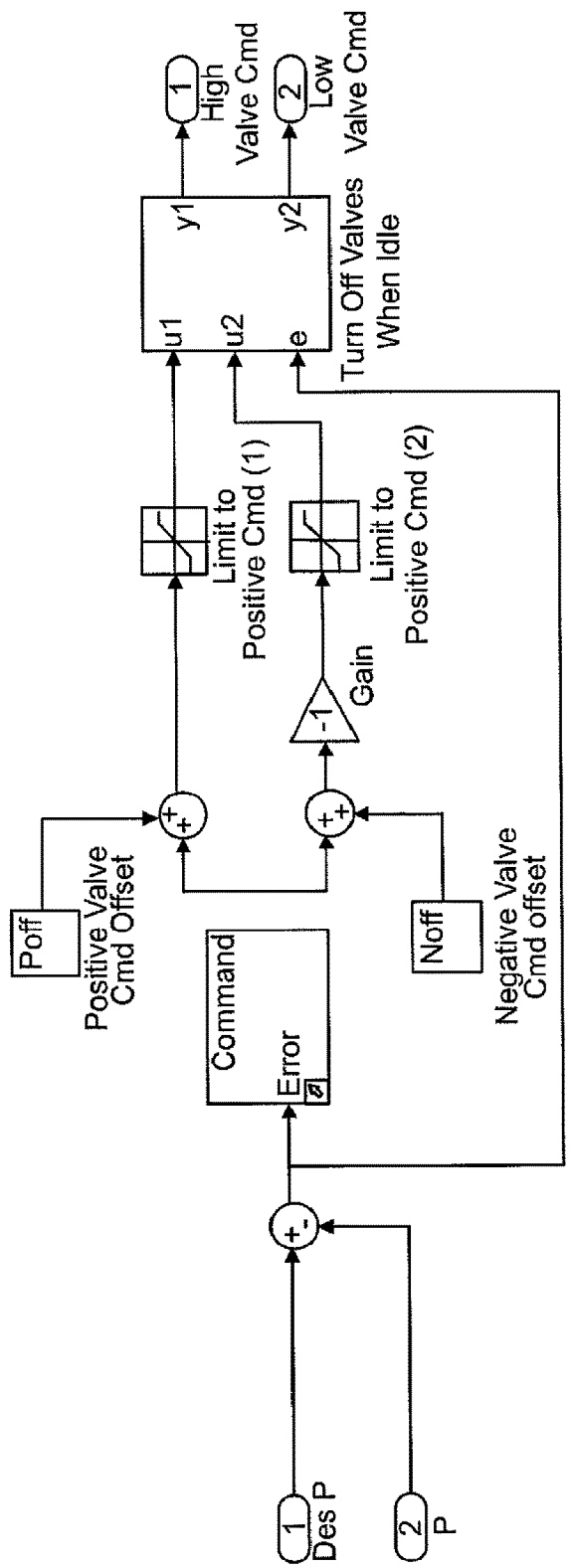
FIG. 14 is a diagram of one embodiment of a control algorithm.

In some cases, an anticoagulant (e.g., heparin, or any other anticoagulant known to those of ordinary skill in the art) may be mixed with the blood within blood flow cassette 141 as is shown in FIG. 14. For instance, the anticoagulant may be contained within a vial 11 (or other anticoagulant supply, such as a tube or a bag), and blood flow cassette 141 may be able to receive the anticoagulant vial with an integrally formed spike 201 (which, in one embodiment, is a needle) that can pierce the seal of the vial. The spike may be formed from plastic, stainless steel, or another suitable material, and may be a sterilizable material in some cases, e.g., the material may be able to withstand sufficiently high temperatures and/or radiation so as to sterilize the material. As an example, as is shown in FIG. 4A, spike 201 may be integrally formed with a blood flow cassette 141, and a vial 11 can be placed onto the spike, piercing the seal of the vial, such that anticoagulant can flow into blood flow cassette to be mixed with the blood in the blood flow path, or in some cases, mixed with dialysate as discussed below.

A third pump 80, which can act as a metering chamber in some cases, in blood flow cassette 141 can be used to control the flow of anticoagulant into the blood within the cassette. Third pump 80 may be of the same or of a different design than pump 13. For instance, third pump 80 may be a pod pump and/or third pump 80 may be actuated by a control fluid, such as air. For example, third pump 80 may be a membrane-based metering pump. For instance, as is shown in FIG. 4A, third pump 80 may include a rigid chamber with a flexible diaphragm dividing the chamber into a fluid compartment and a control compartment. Valves on the control compartment of the chamber may be connected to a first control fluid source (e.g., a high pressure air source), and the other compartment connected to a second control fluid source (e.g., a low pressure air source) or a vacuum sink. Valves on the fluid compartment of the chamber can be opened and closed in response to the control compartment, thus controlling the flow of anticoagulant into the blood. Further details of such a pod pump are discussed below. In one set of embodiments, air may also be introduced into the blood flow path through a filter 81, as discussed below.

Fluid Management System ("FMS") measurements may be used to measure the volume of fluid pumped through a pump chamber during a stroke of the membrane, or to detect air in the pumping chamber. FMS methods are described in U.S. Pat. Nos. 4,808,161; 4,826,482; 4,976,162; 5,088,515;

and 5,350,357, which are hereby incorporated herein by reference in their entireties. In some cases, the volume of liquid delivered by an anticoagulant pump, a dialysate pump, or other membrane-based pump is determined using an FMS algorithm in which changes in chamber pressures are used to calculate a volume measurement at the end of a fill stroke and at the end of a delivery stroke. The difference between the computed volumes at the end of a fill and delivery stroke is the actual stroke volume. This actual stroke volume can be compared to an expected stroke volume for the particular sized chamber. If the actual and expected volumes are significantly different, the stroke has not properly completed and an error message can be generated.

If stroke volumes are collected with a scale, the calculation can be worked backwards to determine a calibration value for the reference chamber. FMS systems can vent to atmosphere for the FMS measurement. Alternatively, the system can vent to a high pressure positive source and a low pressure negative source for the FMS measurement. Doing so provides the following advantages, amongst others: (1) if the high pressure source is a pressure reservoir with a controlled pressure, there is an opportunity to do a cross check on the pressure sensors of the reservoir and chamber to ensure they are similar when the chamber is being vented to the reservoir. This can be used to detect a broken pressure sensor or a failed valve; (2) by using higher/lower pressures to vent, there are larger pressure differences for the FMS measurements so better resolution can be obtained.

Blood flow circuit 141 may also include an air trap 19 incorporated into blood flow circuit 141 in some cases. Air trap 19 may be used to remove air bubbles that may be present within the blood flow path. In some cases, air trap 19 is able to separate any air that may be present from the blood due to gravity. In some cases, air trap 19 may also include a port for sampling blood. Air traps are known to those of ordinary skill in the art.

Figure 4C:
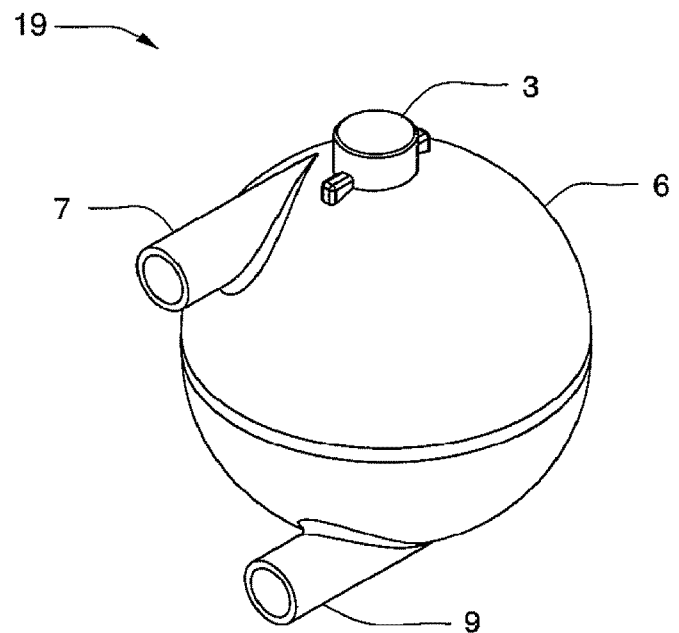
FIGS. 4C-4D are perspective and side views, respectively, of the air trap shown in FIG. 4A.
Figure 4D:
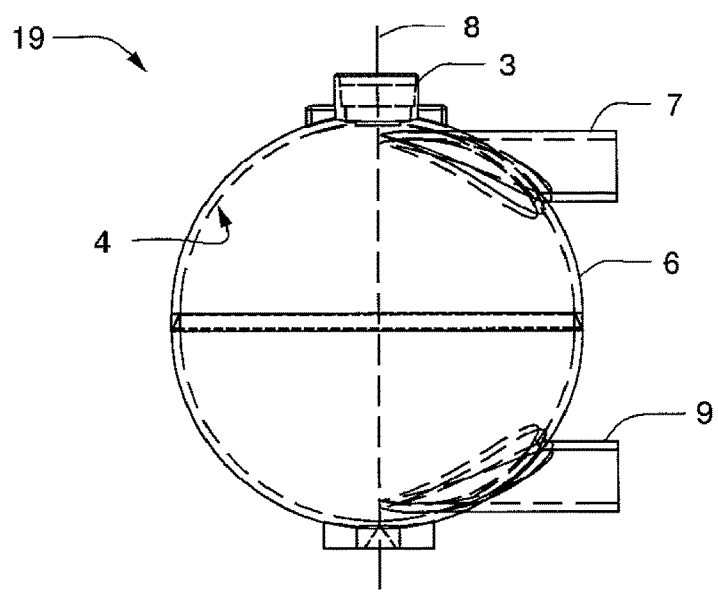

In accordance with another aspect of the invention, the air trap 19 is placed in the blood flow path after the blood exits the dialyzer and before it is returned to the patient. As shown in FIGS. 4C and 4D, air trap 19 may have a spherical or spheroid-shape container 6, and have its inlet port 7 located near the top and offset from the vertical axis of the container, and an outlet 9 at a bottom of the container. The curved shape of the inside wall 4 of the trap can thus direct the blood to circulate along the inside wall as the blood gravitates to the bottom of the container, facilitating the removal of air bubbles from the blood. Air present in the blood exiting the outlet 9 of the dialyzer 14 will enter at the top of the air trap 19 and remain at the top of the container as blood flows out the outlet at the bottom and to the venous blood line 204. By locating the inlet port 7 near the top of trap 19, it is also possible to circulate blood through the trap with minimal or no air present within the container (as a "run-full" air trap). The ability to avoid an air-blood interface for routine circulation of blood in the trap can be advantageous. Placing the inlet port 7 at or near the top of the container also allows most or all of the air present in the trap to be removed from the trap by reversing the flow of fluid through the blood tubing (i.e. from the bottom to the top of the trap 19, exiting through the inlet port of the trap 19). In an embodiment, a self-sealing port 3, such as a self-sealing stopper with a split septum or membrane, or another arrangement, is located at the top of the trap, allowing the withdrawal of air from the container (e.g., by syringe). The blood-side surface of the self-sealing membrane can be situated nearly flush with the top of the interior of the trap, in order to facilitate cleaning of the self-sealing port during disinfection. The self-sealing port 3 can also serve as a blood sampling site, and/or to allow the introduction of liquids, drugs or other compounds into the blood circuit. A sealed rubber-type stopper can be used if access with a needle is contemplated. Using a self-sealing stopper with split septum permits sampling and fluid delivery using a needleless system.

Additional fluid connections 82 may allow blood flow circuit 10 to also be connected to the patient, and/or to a fluid source for priming or disinfecting the system, including blood flow circuit 10. Generally, during disinfection, arterial line 203 and venous line 204 are connected directly to directing circuit 142 via conduits 67, such that a disinfecting fluid (e.g., heated water and in some embodiments, a combination heated water and one or more chemical agent) may be flowed through dialyzer 14 and blood flow circuit 141 back to directing circuit 142 for recirculation, this disinfection is similar to those shown in U.S. Pat. No. 5,651,898 to Kenley, et al., which is incorporated herein by reference. This is also discussed in more detail below.

The pressure within arterial line 203, to draw blood from the patient, may be kept to a pressure below atmospheric pressure in some cases. If a pod pump is used, the pressure within blood flow pump 13 may be inherently limited to the pressures available from the positive and negative pressure reservoirs used to operate the pump. In the event that a pressure reservoir or valve fails, the pump chamber pressure will approach the reservoir pressure. This will increase the fluid pressure to match the reservoir pressure until the diaphragm within the pod pump "bottoms" (i.e., is no longer is able to move, due to contact with a surface), and the fluid pressure will not exceed a safe limit and will equilibrate with a natural body fluid pressure. This failure naturally stops operation of the pod pump without any special intervention.

A specific non-limiting example of a blood flow cassette is shown in FIGS. 30-33. Referring now to FIGS. 30A and 30B, the outer side of the top plate 900 of an exemplary embodiment of the cassette is shown. The top plate 900 includes one half of the pod pumps 820, 828. This half is the liquid half where the source fluid will flow through. The two fluid paths 818, 812 are shown. These fluid paths lead to their respective pod pumps 820, 828.

The pod pumps 820, 828 include a raised flow path 908, 910. The raised flow path 908, 910 allows for the fluid to continue to flow through the pod pumps 820, 828 after the diaphragm (not shown) reaches the end of stroke. Thus, the raised flow path 908, 910 minimizes the diaphragm causing air or fluid to be trapped in the pod pump 820, 828 or the diaphragm blocking the inlet or outlet of the pod pump 820, 828, which would inhibit continuous flow. The raised flow path 908, 910 is shown in one exemplary embodiment having particular dimensions, and in some cases, the dimensions are equivalent to the fluid flow paths 818, 812. However, in alternate embodiments, the raised flow path 908, 910 is narrower, or in still other embodiments, the raised flow path 908, 910 can be any dimensions as the purpose is to control fluid flow so as to achieve a desired flow rate or behavior of the fluid. In some embodiments, the raised flow path 908, 910 and the fluid flow paths 818, 812 have different dimensions. Thus, the dimensions shown and described here with respect to the raised flow path, the pod pumps, the valves or any other aspect are mere exemplary and alternate embodiments. Other embodiments are readily apparent.

In one exemplary embodiment of this cassette, the top plate includes a spike 902 as well as a container perch 904. The spike 902 is hollow in this example, and is fluidly connected to the flow path. In some embodiments, a needle is attached into the spike. In other embodiments, a needle is connected to the container attachment.

Figure 30A:
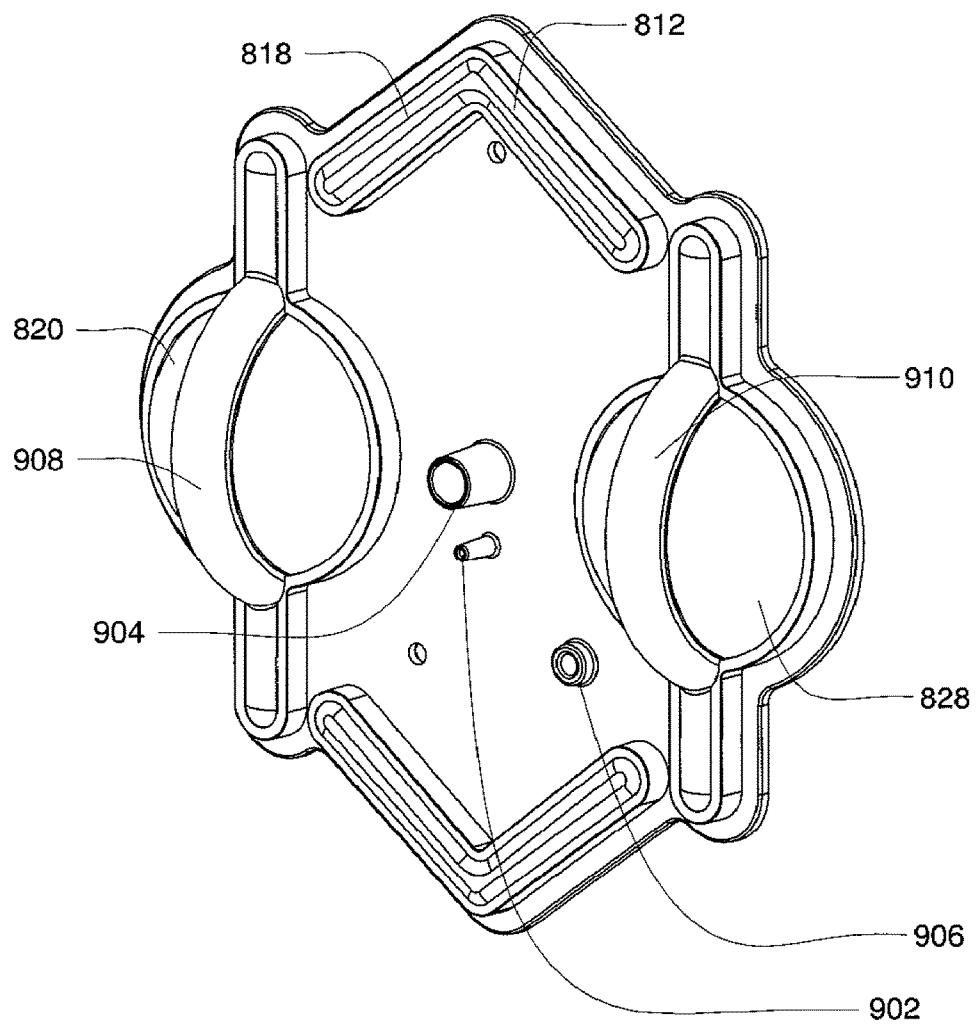
FIGS. 30A and 30B are isometric and top views of an outer top plate of an exemplary embodiment of the cassette.
Figure 30B:
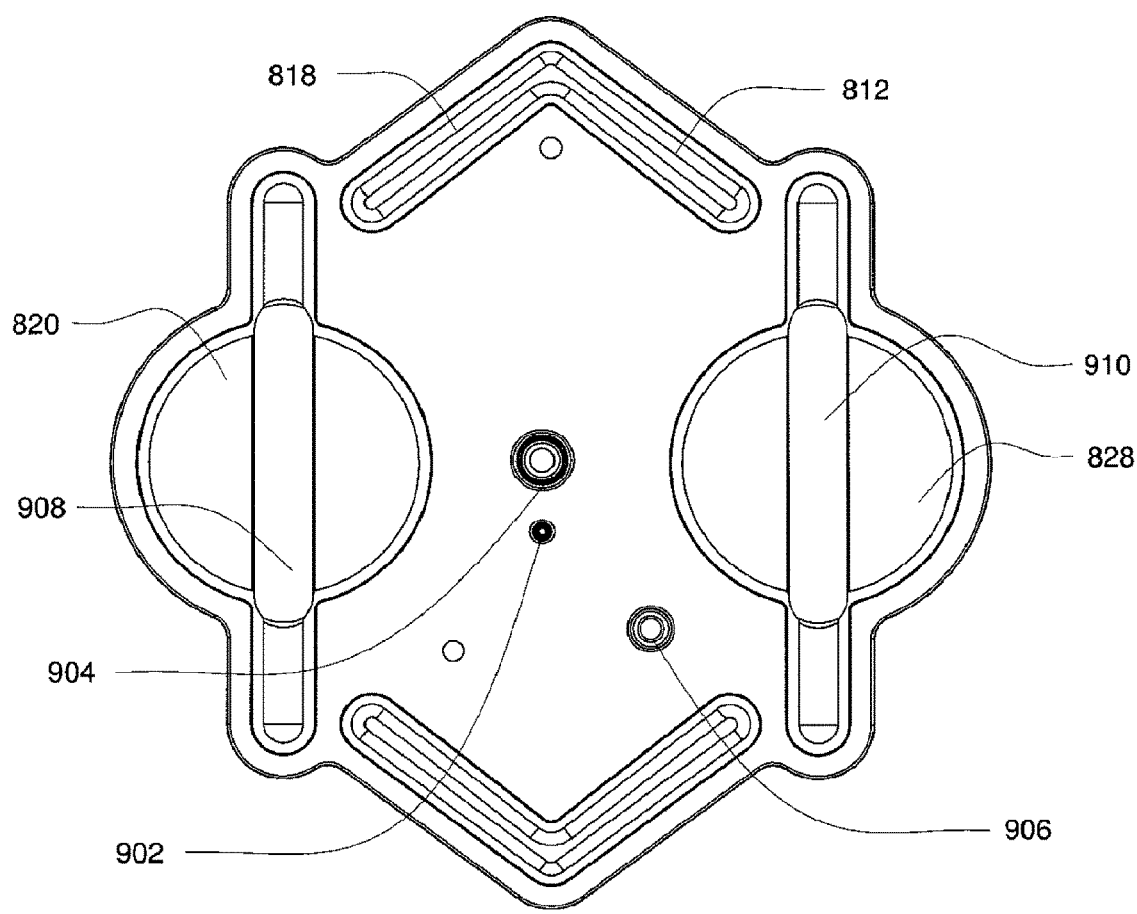
Figure 30C:
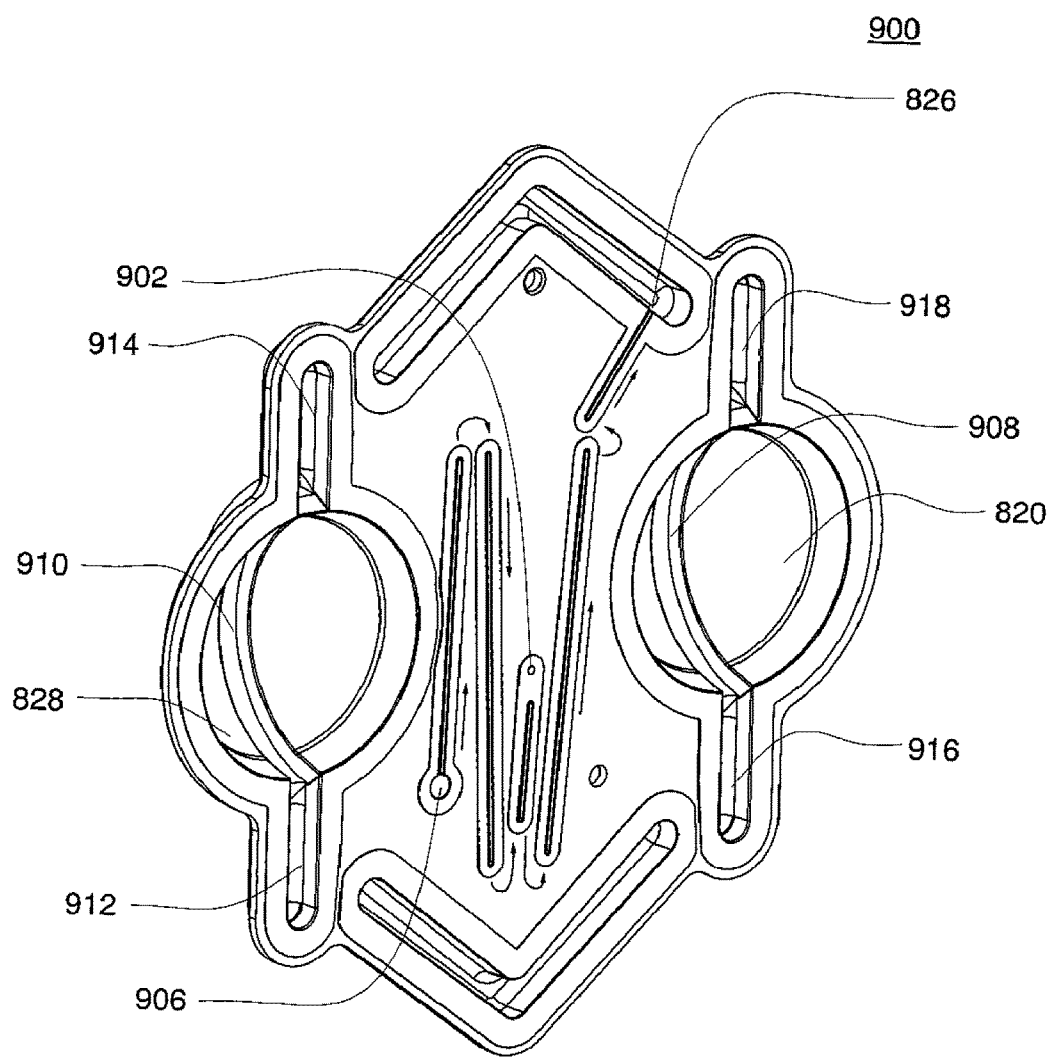
FIGS. 30C and 30D are isometric and top views of an inner top plate of an exemplary embodiment of the cassette.
Figure 30D:
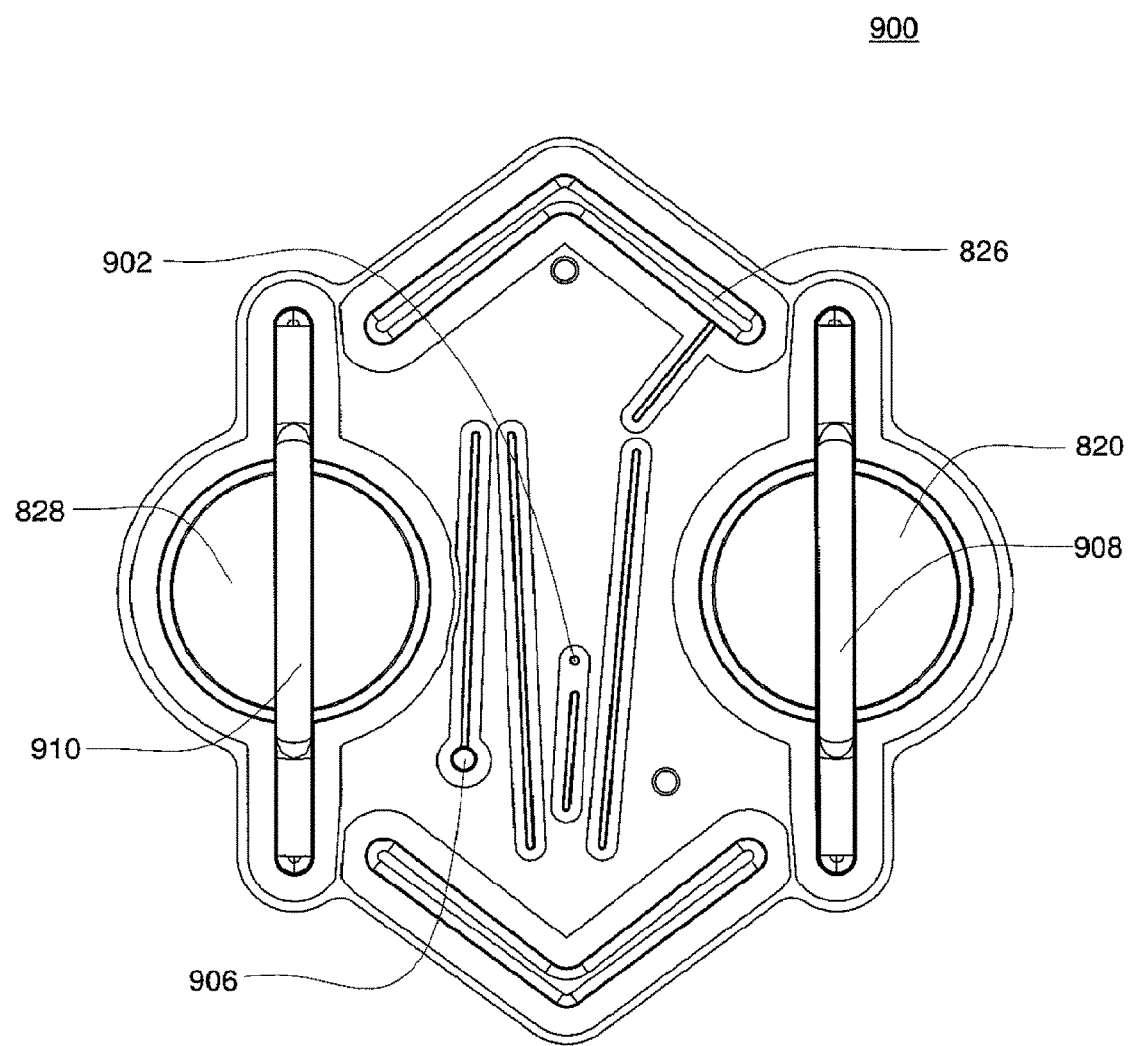
Figure 30E:
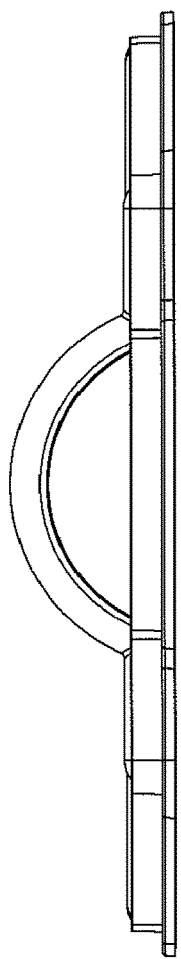
FIG. 30E is a side view of the top plate of an exemplary embodiment of an cassette.

Referring now to FIGS. 30C and 30D, the inside of the top plate 900 is shown. The raised flow paths 908, 910 connects to the inlet flow paths 912, 916 and outlet flow paths 914, 918 of the pod pumps 820, 828. The raised flow paths are described in more detail above.

The metering pump (not shown) includes connection to an air vent 906 as well as connection to the spike's hollow path 902. In one exemplary embodiment, the air vent 906 includes an air filter (not shown). The air filter may be a particle air filter in some cases. In some embodiments, the filter is a somicron hydrophobic air filter. In various embodiments, the size of the filter may vary, in some instances the size will depend on desired outcome. The metering pump works by taking air in through the air vent 906, pumping the air to the container of second fluid (not shown) through the spike's hollow path 902 and then pumping a volume of second fluid out of the container (not shown) through the spike's hollow path 902 and into the fluid line at point 826. This fluid flow path for the metering pump is shown with arrows on FIG. 30C.

Figure 31A:
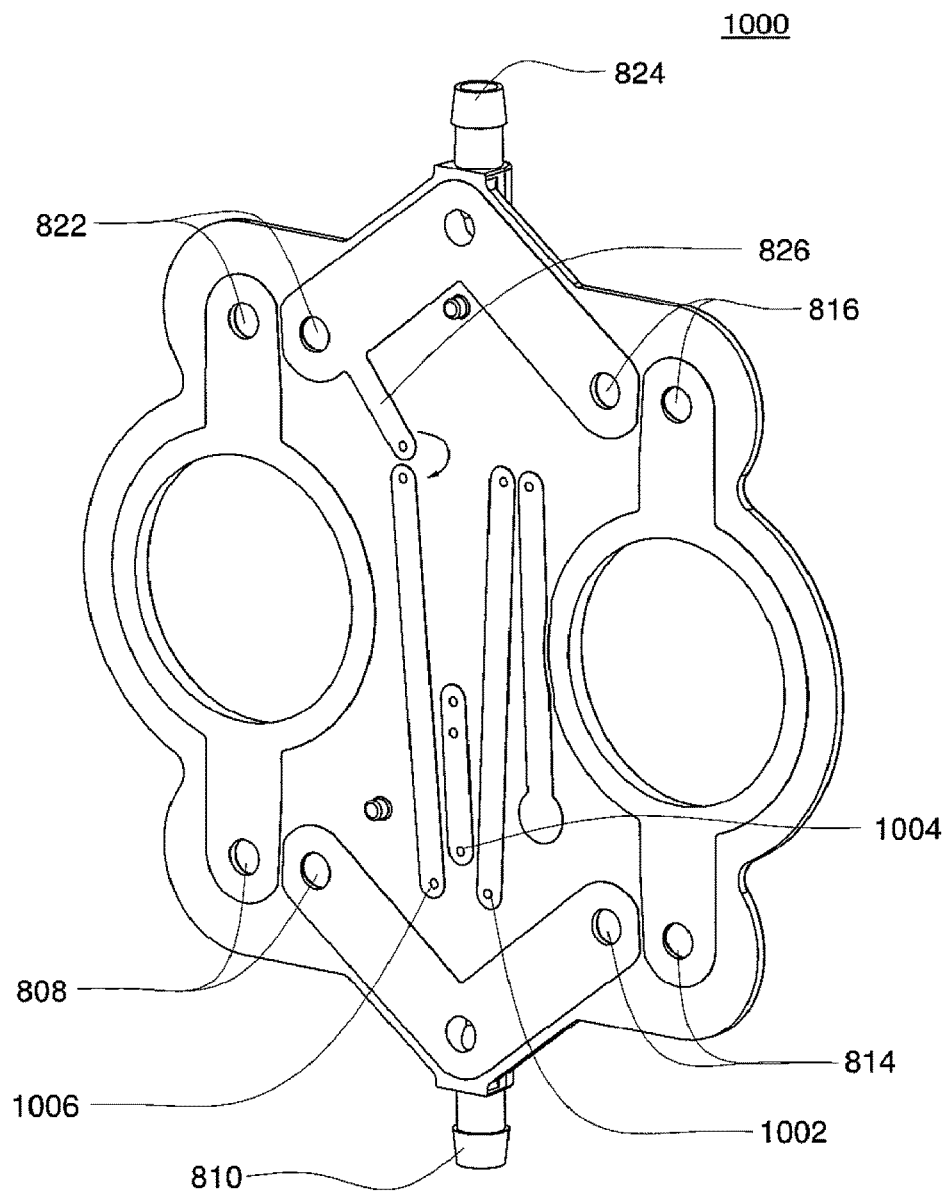
FIGS. 31A and 31B are isometric and top views of the liquid side of a midplate according to an exemplary embodiment of the cassette.
Figure 31B:
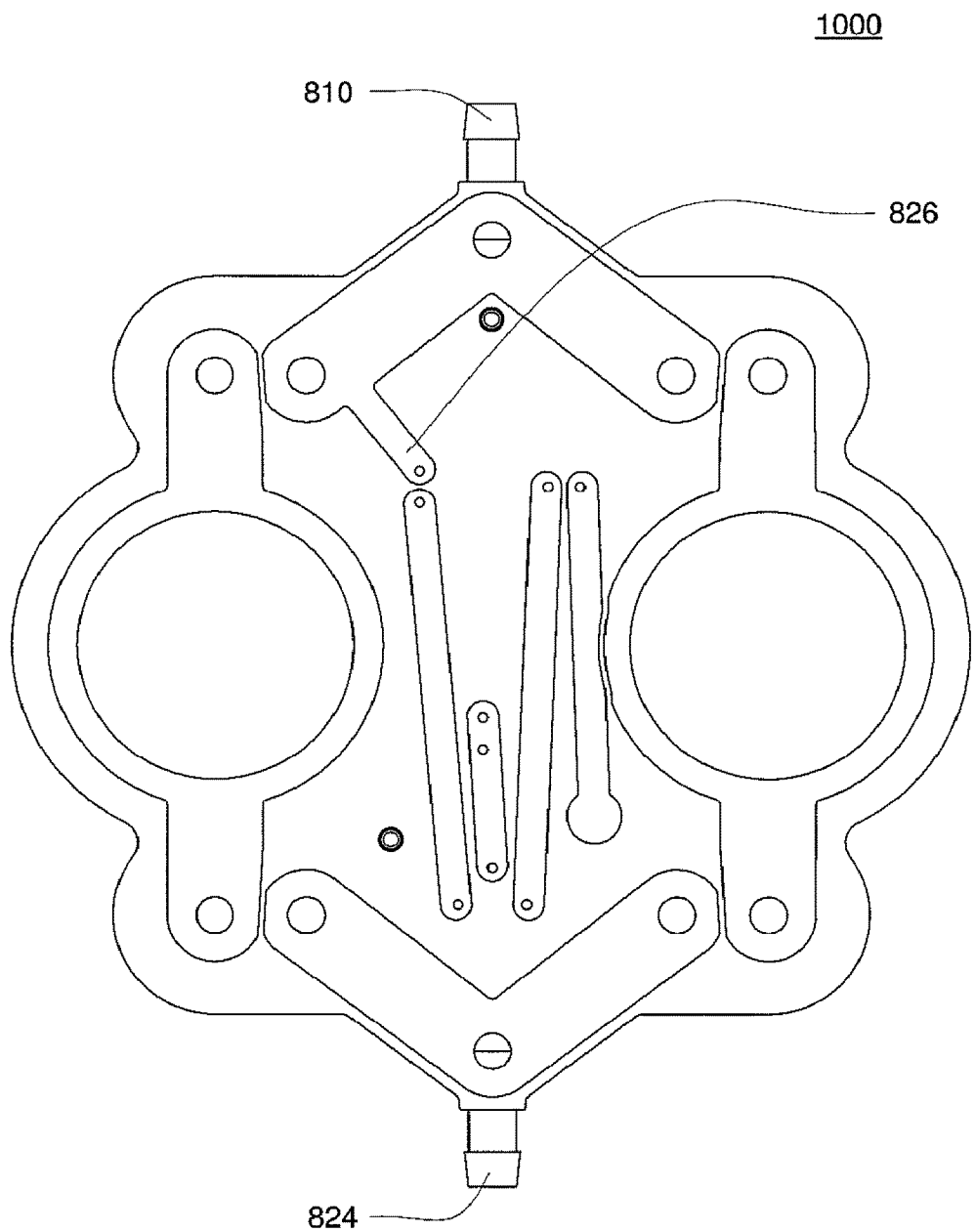

Referring now to FIGS. 31A and 31B, the liquid side of the midplate 1000 is shown. The areas complementary to the fluid paths on the inner top plate are shown. These areas are slightly raised tracks that present a surface finish that is conducive to laser welding, which is the mode of manufacture in one embodiment. The fluid inlet 810 and fluid outlet 824 are also shown in this view.

Figure 31C:
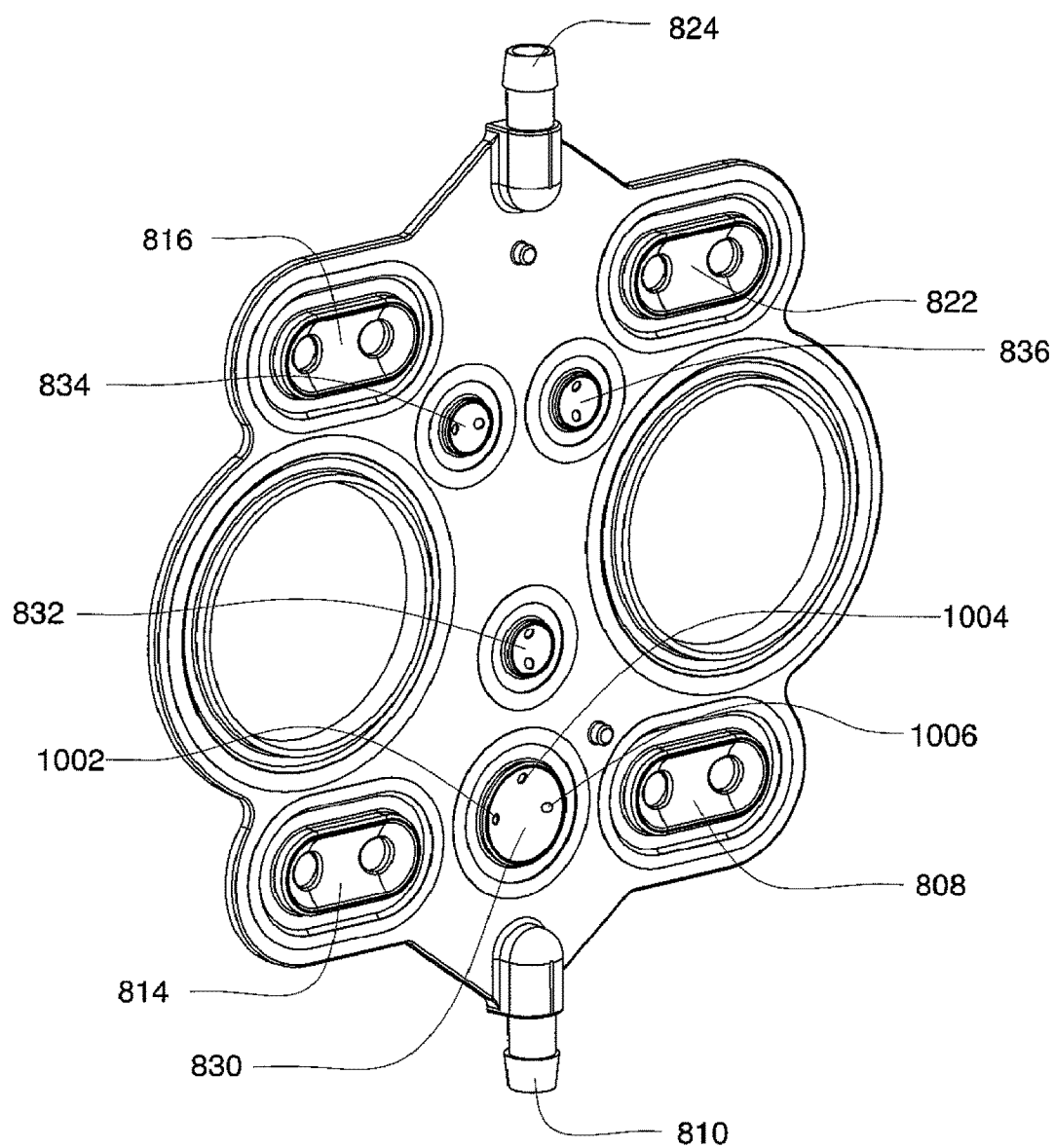
FIGS. 31C and 31D are isometric and top views of the air side of a midplate according to an exemplary embodiment of the cassette.
Figure 31D:
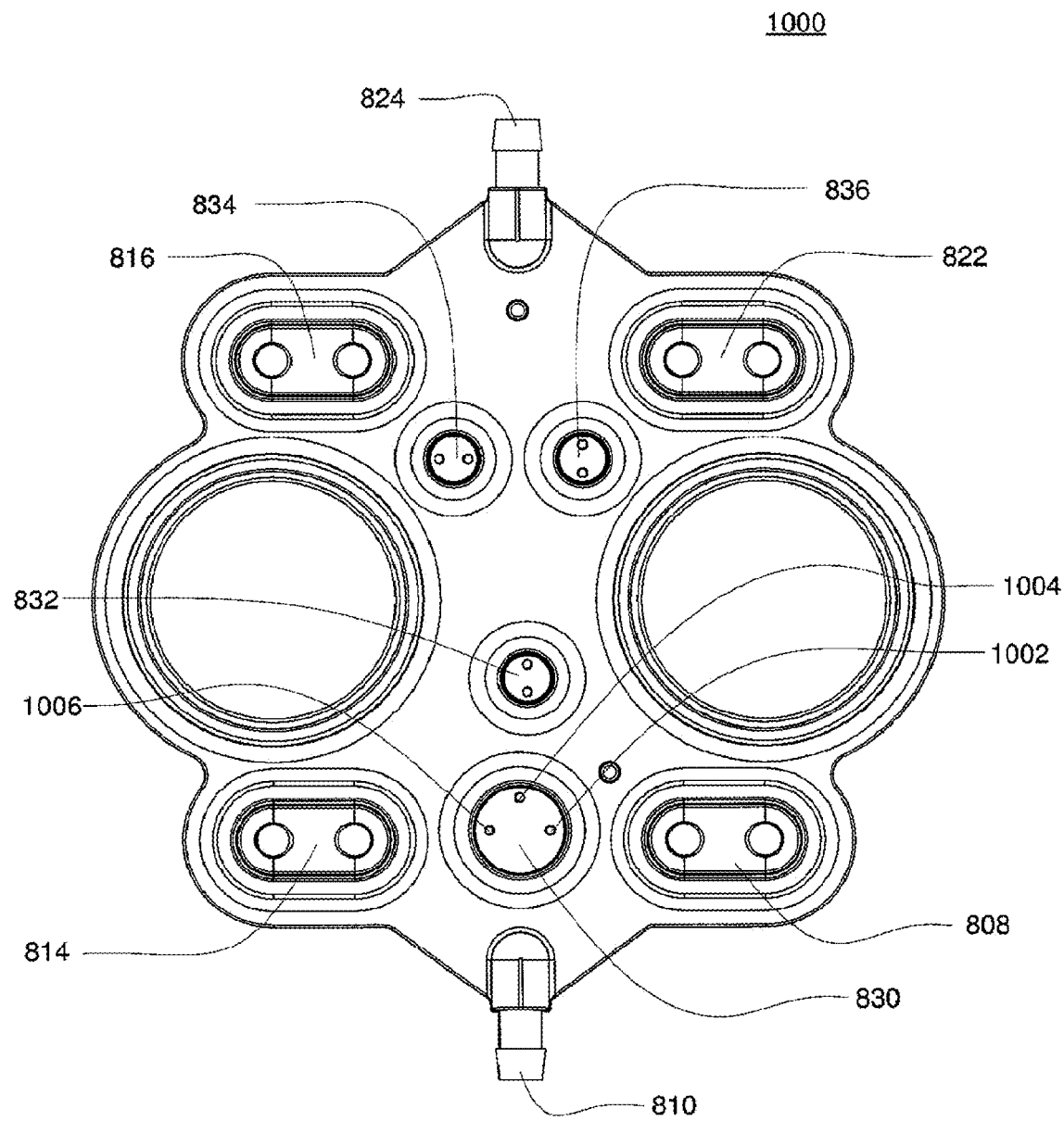

Referring next to FIGS. 31C and 31D, the air side of the midplate 1000 is shown according to one embodiment. The air side of the valve holes 808, 814, 816, 822 correspond to the holes in the fluid side of the midplate (shown in FIG. 31A). As seen in FIGS. 33C and 33D, diaphragms 1220 complete valves 808, 814, 816, 822 while diaphragms 1226 complete pod pumps 820, 828. The metering pump 830 is completed by diaphragm 1224. The valves 808, 814, 816, 822, 832, 834, 836 are actuated pneumatically, and as the diaphragm is pulled away from the holes, liquid is drawn in, and as the diaphragm is pushed toward the holes, liquid is pushed through. The fluid flow is directed by the opening and closing of the valves 808, 814, 816, 822, 832, 834, 836.

Referring to FIGS. 31A and 31C, the metering pump includes three holes, 1002, 1004, 1006. One hole 1002 pulls air into the metering pump, the second hole 1004 pushes air to the spike/source container and also, draws liquid from the source container, and the third hole 1006 pushes the second fluid from the metering pump 830 to the fluid line to point 826.

Valves 832, 834, 836 actuate the second fluid metering pump. Valve 832 is the second fluid/spike valve, valve 834 is the air valve and valve 836 is the valve that controls the flow of fluid to the fluid line to area 826.

Figure 32A:
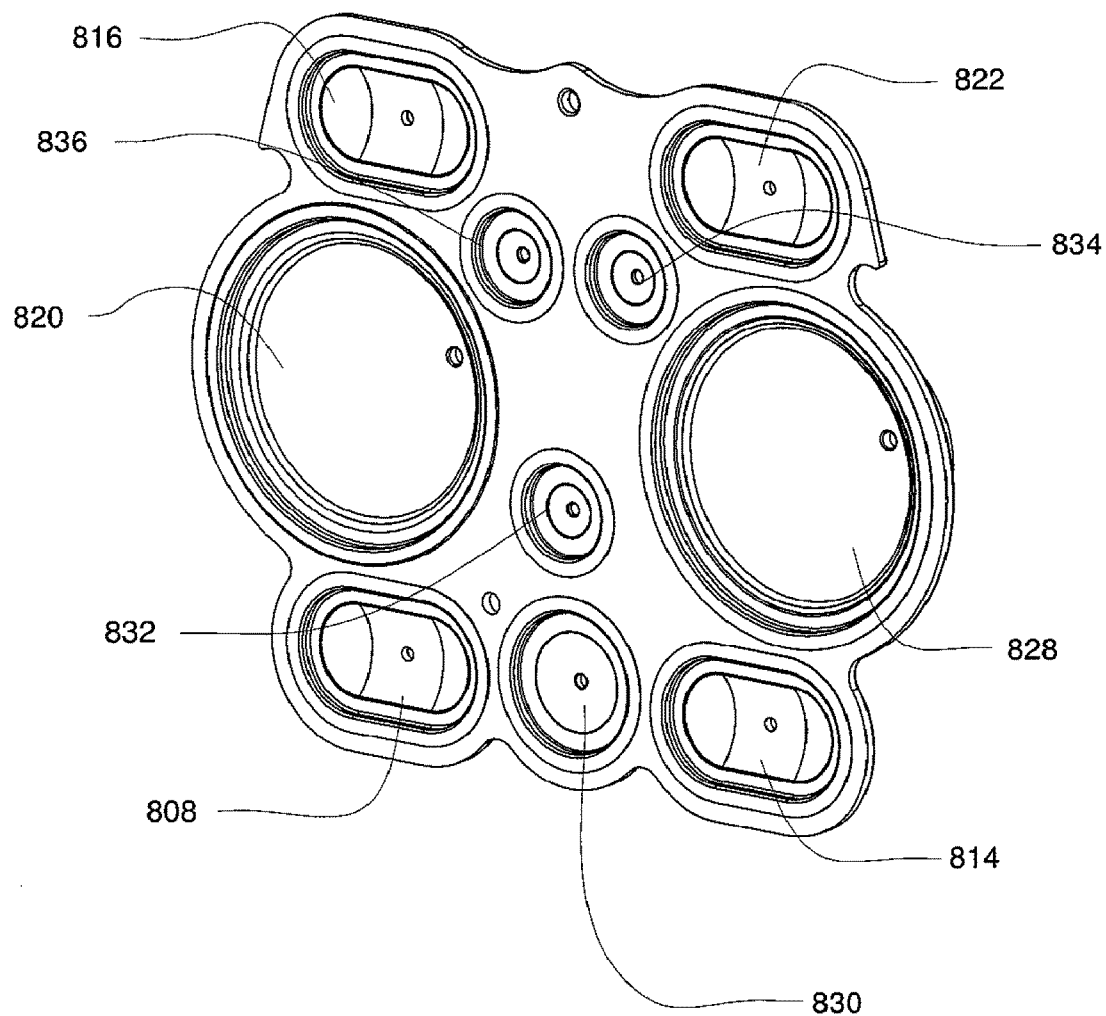
FIGS. 32A and 32B are isometric and top views of the inner side of a bottom plate according to an exemplary embodiment of the cassette.
Figure 32B:
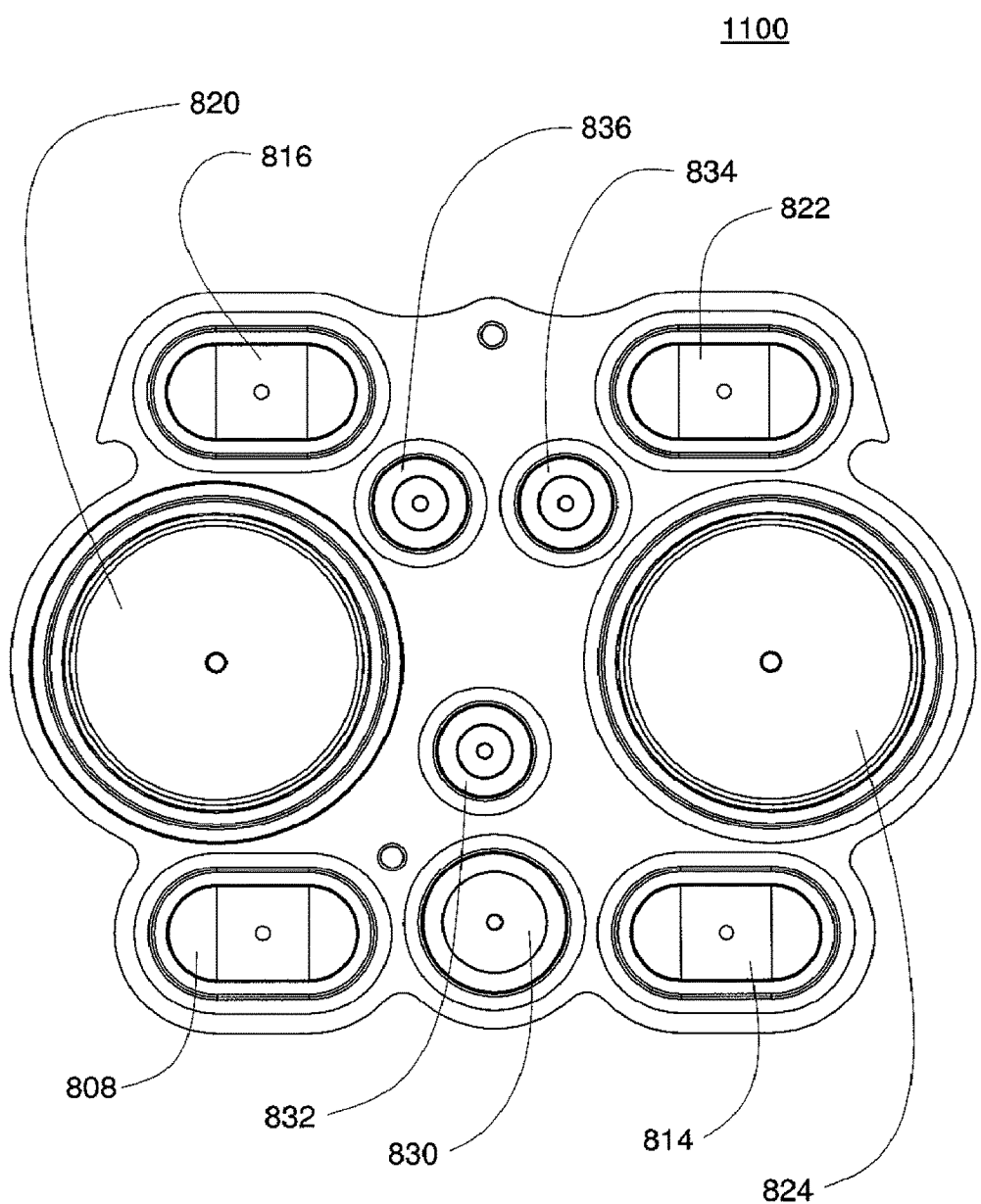
Figure 32C:
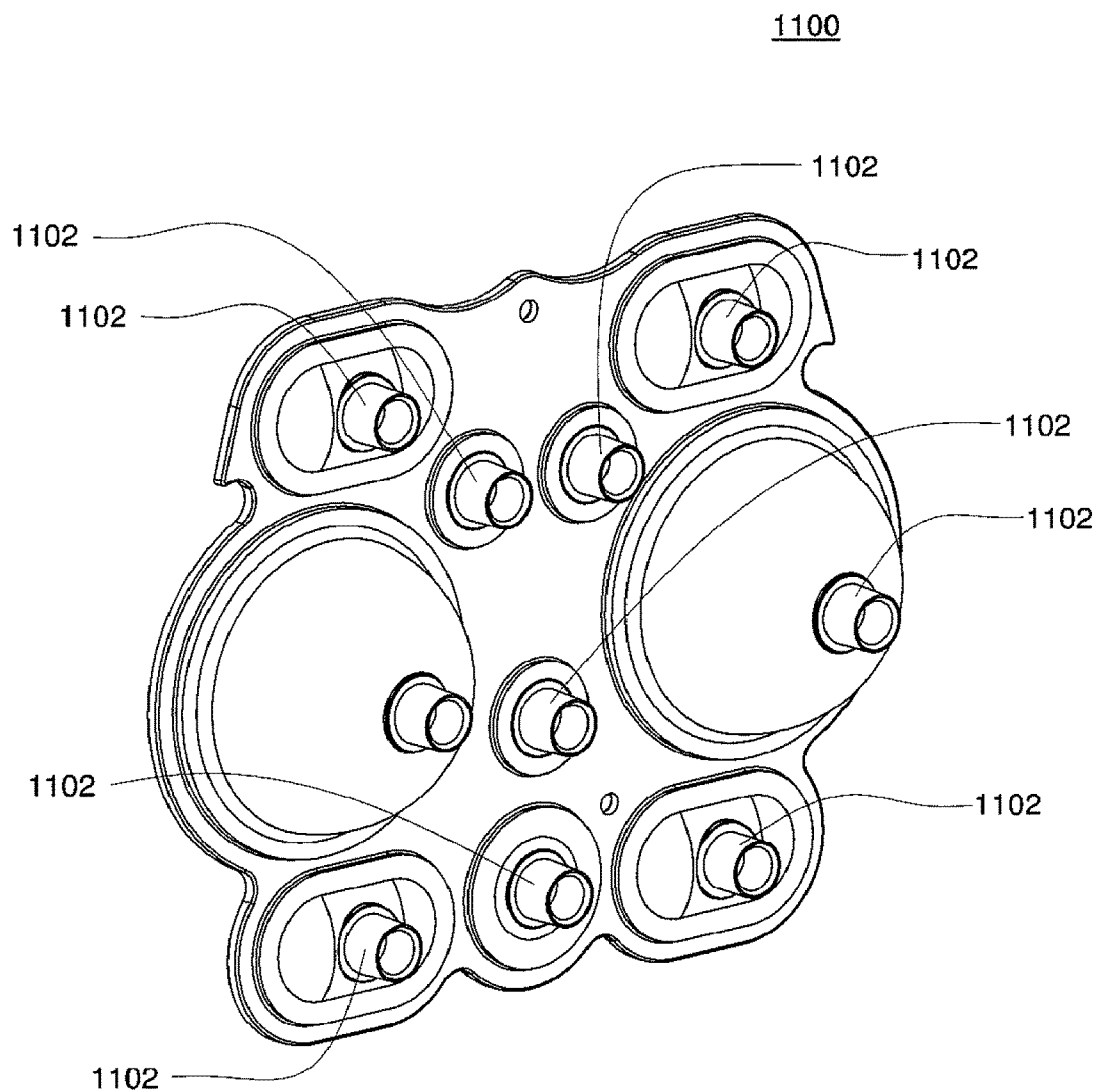
FIGS. 32C and 32D are isometric and top views of the outer side of a bottom plate according to an exemplary embodiment of the cassette.
Figure 32D:
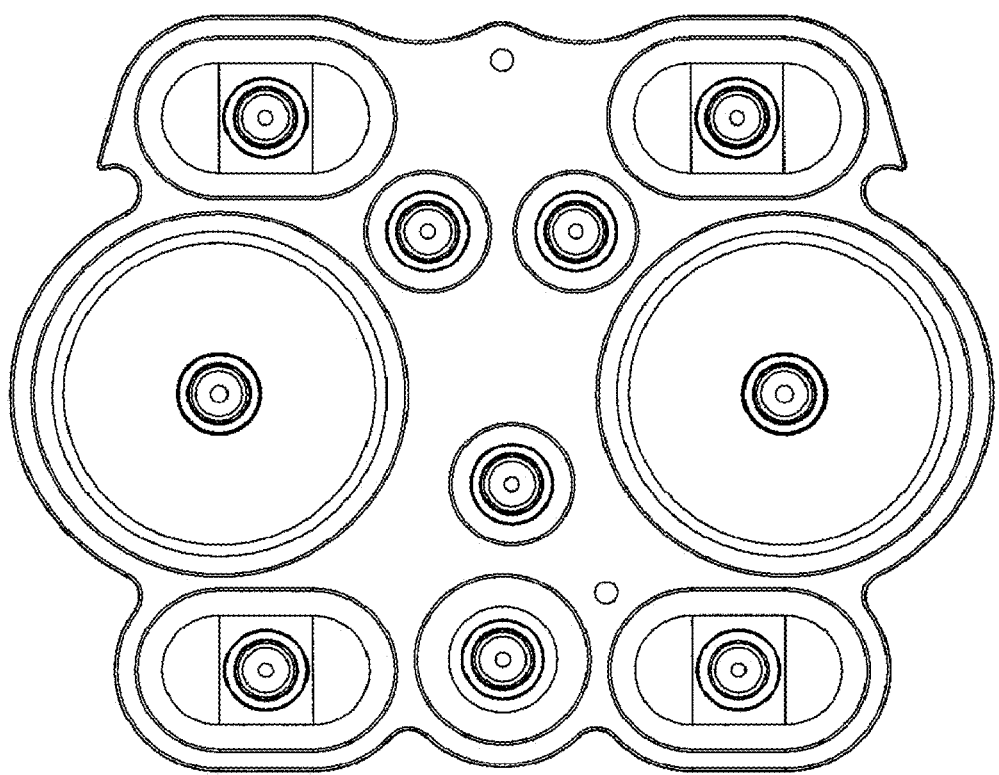
Figure 32E:
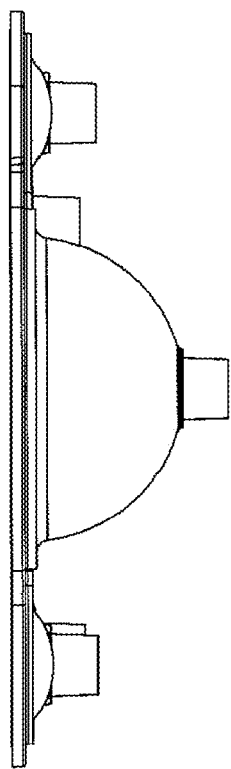
FIG. 32E is a side view of a bottom plate according to an exemplary embodiment of the cassette.

Referring next to FIGS. 32A and 32B, the inner view of the bottom plate 1100 is shown. The inside view of the pod pumps 820, 828, the metering pump 830 and the valves 808, 814, 816, 822, 832, 834, 836 actuation/air chamber is shown. The pod pumps 820, 828, metering pump 830 and the valves 808, 814, 816, 822, 832, 834, 836 are actuated by a pneumatic air source. Referring now to FIGS. 32C and 32D, the outer side of the bottom plate 1100 is shown. The source of air is attached to this side of the cassette. In one embodiment, tubes connect to the features on the valves and pumps 1102. In some embodiments, the valves are ganged, and more than one valve is actuated by the same air line.

Figure 33A:
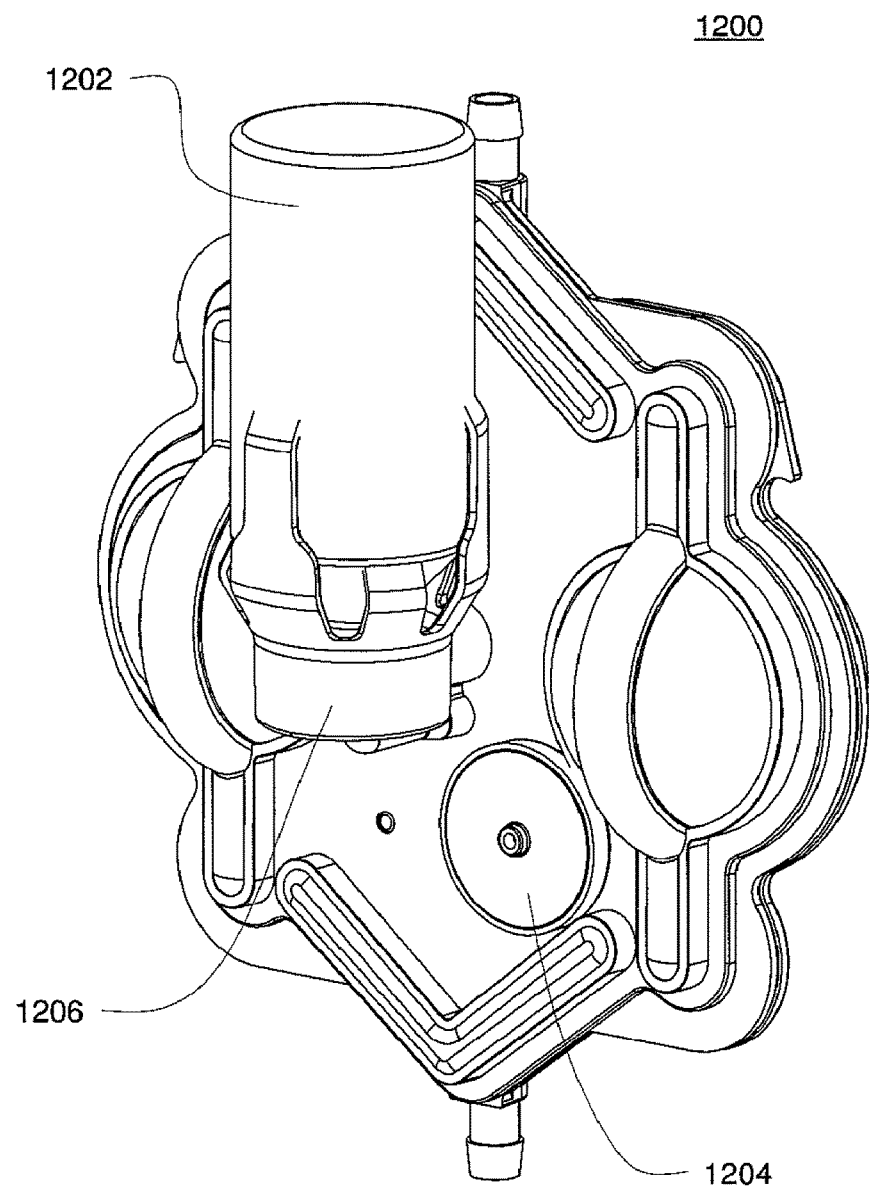
FIG. 33A is a top view of an assembled exemplary embodiment of a cassette with a vial attached.
Figure 33B:
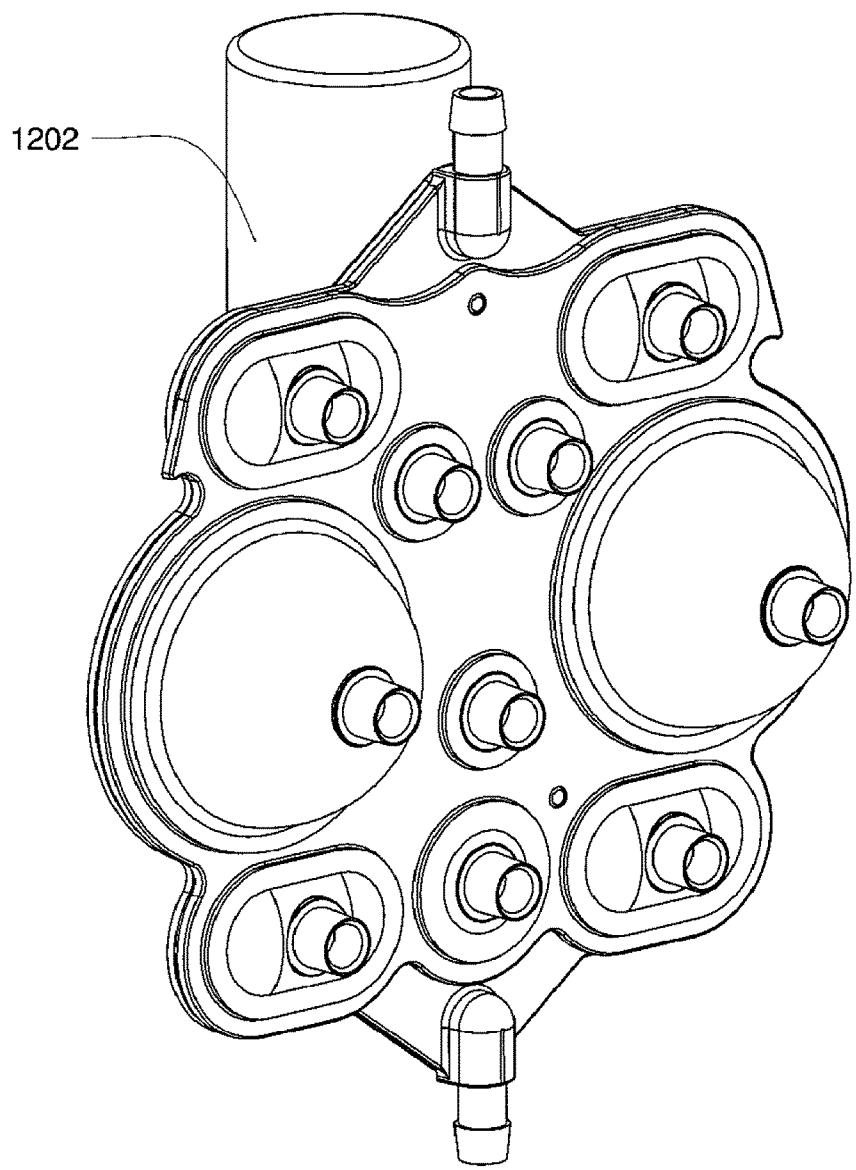
FIG. 33B is a bottom view of an assembled exemplary embodiment of a cassette with a vial attached.
Figure 33C:
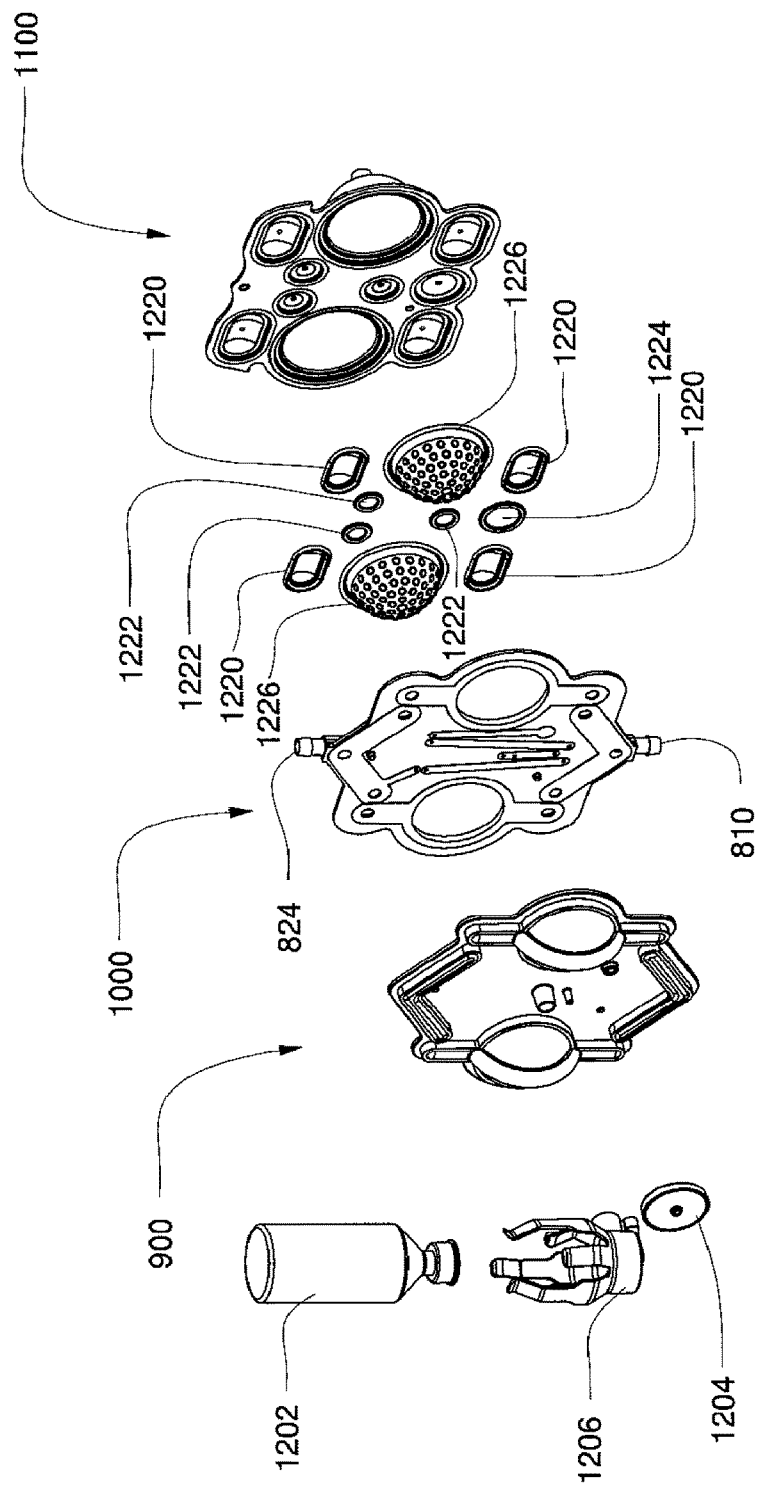
FIG. 33C is an exploded view of an assembled exemplary embodiment of a cassette with a vial.
Figure 33D:
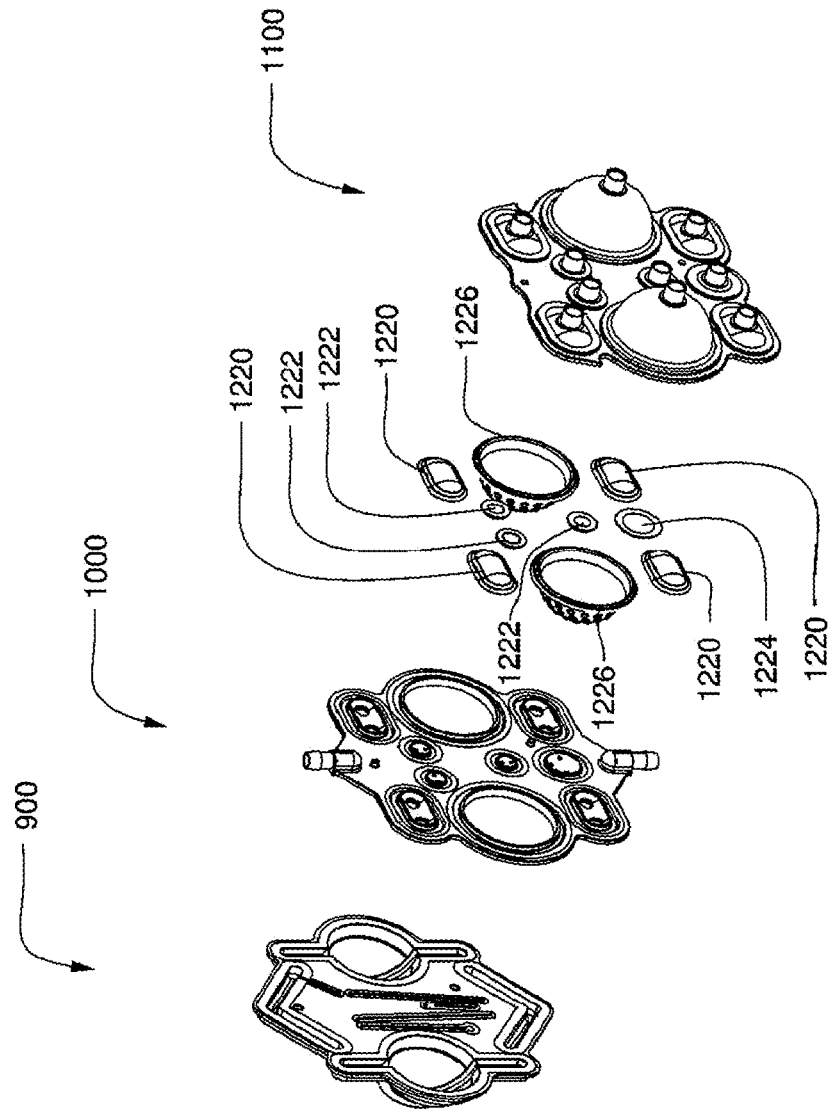
FIG. 33D is an exploded view of an assembled exemplary embodiment of a cassette with a vial.
Figure 33D:
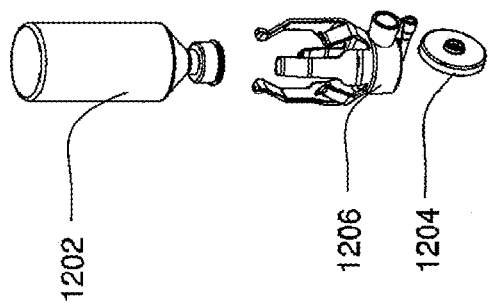
Figure 34A:
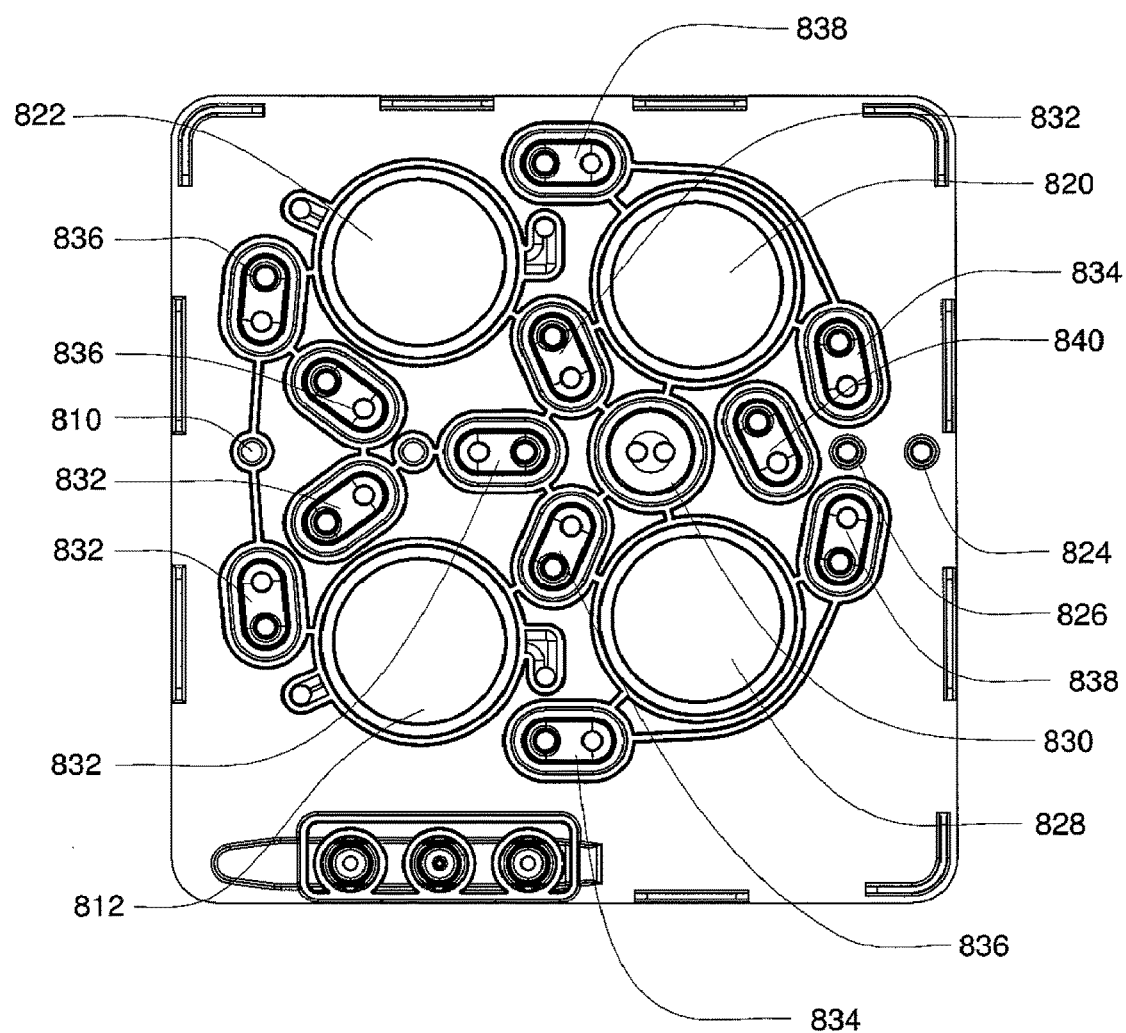
FIG. 34A is an isometric bottom view of an exemplary embodiment of the midplate of an exemplary embodiment of the cassette.
Figure 34B:
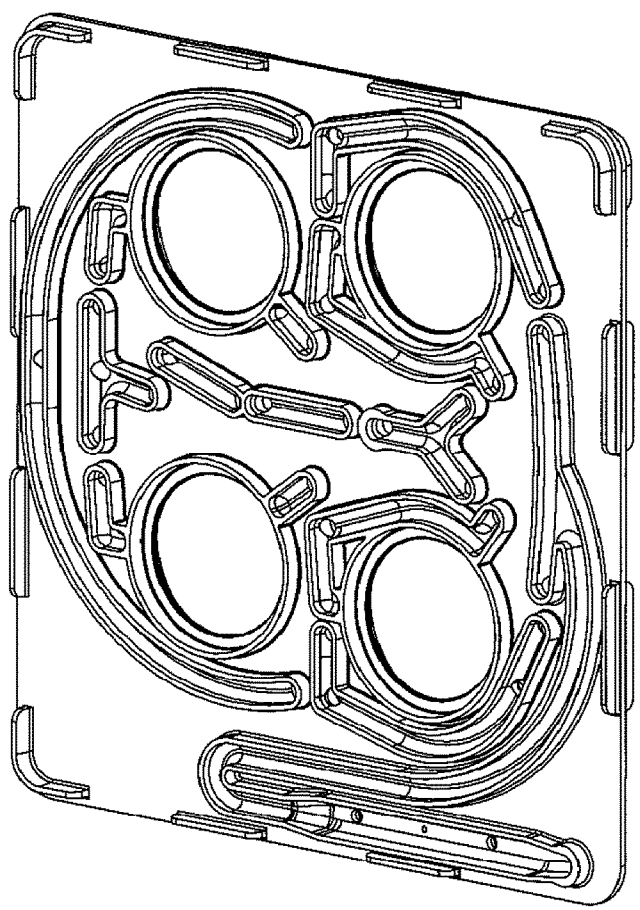
FIG. 34B is an isometric top view of the midplate of an exemplary embodiment of a cassette.
Figure 34C:
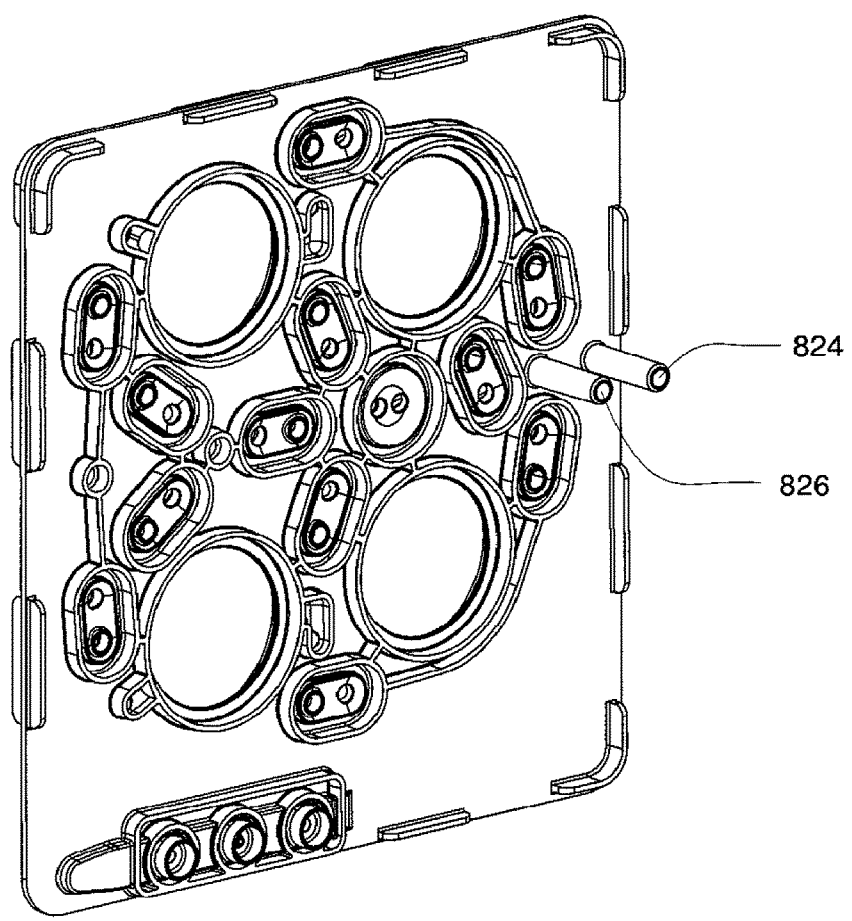
FIG. 34C is an isometric bottom view of an exemplary embodiment of the midplate of a cassette.
Figure 34D:
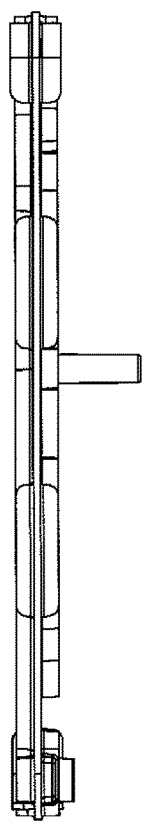
FIG. 34D is a side view of an exemplary embodiment of the midplate of a cassette.

Referring now to FIGS. 33A and 33B, an assembled cassette 1200 with a container (or other source) of a second fluid 1202 is shown, which, in this embodiment, may be an anticoagulant as described above, attached is shown. The container 1202 contains the source of the second fluid and is attached to the spike (not shown) by a container attachment 1206. The air filter 1204 is shown attached to the air vent (not shown, shown in FIG. 30A as 906). Although not visible in FIG. 33A, the container perch (shown in FIG. 30A as 904) is under the container attachment 1206. An exploded view of the assembled cassette 1200 shown in FIGS. 33A and 12B is shown in FIGS. 33C and 33D. In these views, an exemplary embodiment of the pod pump diaphragms 1226 is shown. The gasket of the diaphragm provides a seal between the liquid chamber (in the top plate 900) and the air/actuation chamber (in the bottom plate 1100). The dimpled texture on the dome of diaphragms 1226 provide, amongst other features, additional space for air and liquid to escape the chamber at the end of stroke.

A system of the present invention may also include a balancing circuit, e.g., balancing circuit 143 as shown in FIG. 3A. In some cases, blood flow circuit is implemented on a cassette, although it need not be. Within the balancing circuit, the flow of dialysate that passes in and out of the dialyzer may be balanced in some cases such that essentially the same amount of dialysate comes out of the dialyzer as goes into it (however, this balance can be altered in certain cases, due to the use of a bypass pump, as discussed below).

In addition, in some cases, the flow of dialysate may also be balanced through the dialyzer such that the pressure of dialysate within the dialyzer generally equals the pressure of blood through the blood flow circuit. The flow of blood through the blood flow circuit 141 and dialyzer in some cases is synchronized with the flow of dialysate in the dialysate flow path through the dialyzer. Because of the potential of fluid transfer across the semi-permeable membrane of the dialyzer, and because the pumps of the balancing circuit run at positive pressures, the balancing circuit pumps can be timed to synchronize delivery strokes to the dialyzer with the delivery strokes of the blood pumps, using pressure and control data from the blood flow pumps.

Figure 5:
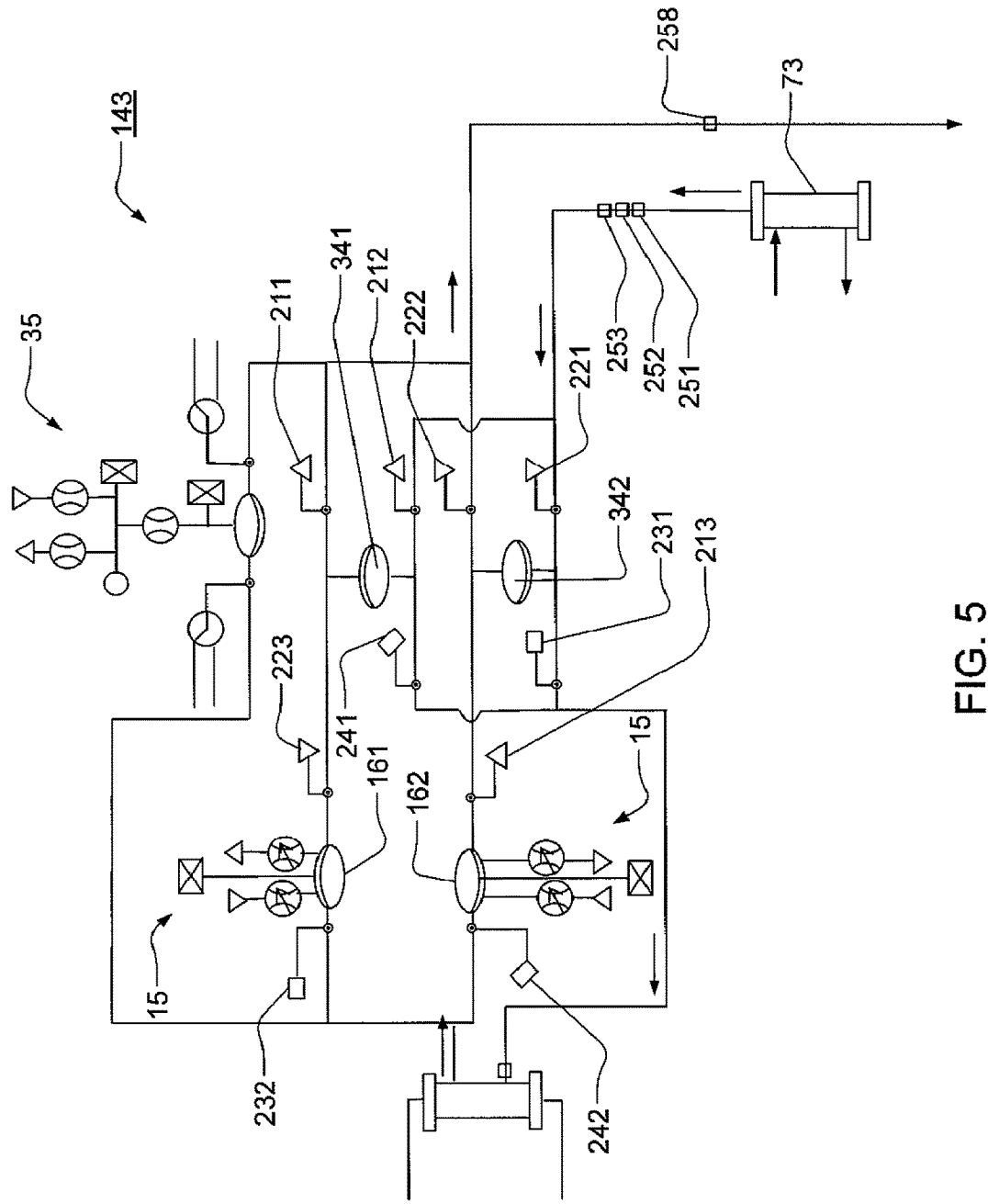
FIG. 5 is a schematic representation of one embodiment of a balancing circuit that may be used in a hemodialysis system.

A non-limiting example of a balancing circuit is shown in FIG. 5. In balancing circuit 143, dialysate flows from optional ultrafilter 73 into one or more dialysate pumps 15 (e.g., two as shown in FIG. 5). The dialysate pumps 15 in this figure include two pod pumps 161, 162, two balancing chambers 341, 342, and pump 35 for bypassing the balancing chambers. The balancing chambers may be constructed such that they are formed from a rigid chamber with a flexible diaphragm dividing the chamber into two separate fluid compartments, so that entry of fluid into one compartment can be used to force fluid out of the other compartment and vice versa. Non-limiting examples of pumps that can be used as pod pumps and/or balancing chambers are described in U.S. Provisional Patent Application Ser. No. 60/792,073, filed Apr. 14, 2006, entitled "Extracorporeal Thermal Therapy Systems and Methods"; or in U.S. patent application Ser. No. 11/787,212, filed Apr. 13, 2007, entitled "Fluid Pumping Systems, Devices and Methods," each incorporated herein by reference. Additional examples of pod pumps are discussed in detail below. As can be seen in the schematic of FIG. 5, many of the valves can be "ganged" or synchronized together in sets, so that all the valves in a set can be opened or closed at the same time.

Figure 18A:
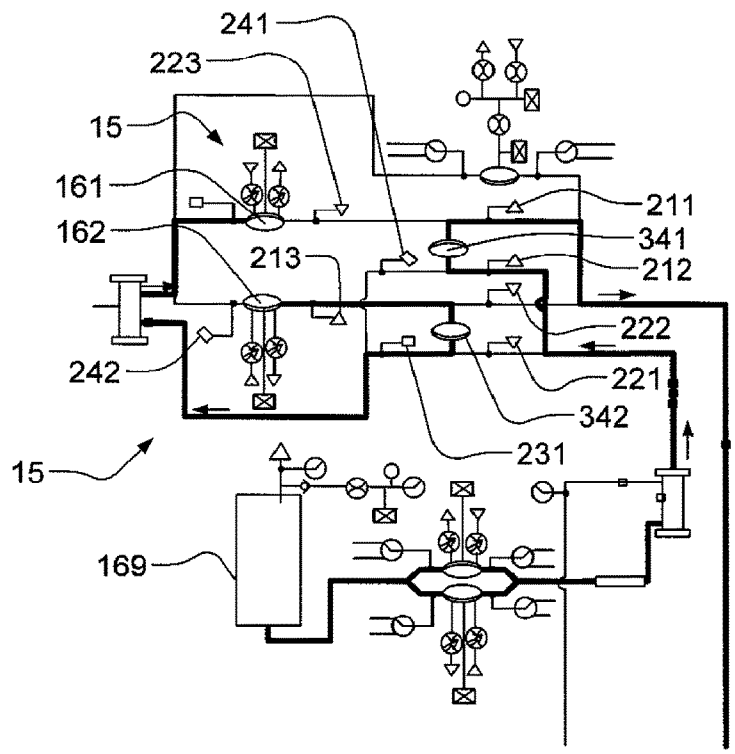
FIGS. 18A-18B illustrate the fluid flow of dialysate from a dialysate tank, through the dialyzer and out to drain in one embodiment of the invention.

More specifically, in one embodiment, balancing of flow works as follows. FIG. 5 includes a first synchronized, controlled together set of valves 211, 212, 213, 241, 242, where valves 211, 212, 213 are ganged and valves 241 and 242 are ganged, as well as a second synchronized, controlled together set of valves 221, 222, 223, 231, 232, where valves 221, 222, 223 are ganged, and valves 231 and 232 are ganged. At a first point of time, the first ganged set of valves 211, 212, 213, 241, 242 is opened while the second ganged set of valves 221, 222, 223, 231, 232 is closed. Fresh dialysate flows into balancing chamber 341 while used dialysate flows from dialyzer 14 into pod pump 161. Fresh dialysate does not flow into balancing chamber 342 since valve 221 is closed. As fresh dialysate flows into balancing chamber 341, used dialysate within balancing chamber 341 is forced out and exits balancing circuit 143 (the used dialysate cannot enter pod pump 161 since valve 223 is closed). Simultaneously, pod pump 162 forces used dialysate present within the pod pump into balancing chamber 342 (through valve 213, which is open; valves 242 and 222 are closed, ensuring that the used dialysate flows into balancing chamber 342). This causes fresh dialysate contained within balancing chamber 342 to exit the balancing circuit 143 into dialyzer 14. Also, pod pump 161 draws in used dialysate from dialyzer 14 into pod pump 161. This is also illustrated in FIG. 18A.

Figure 18B:
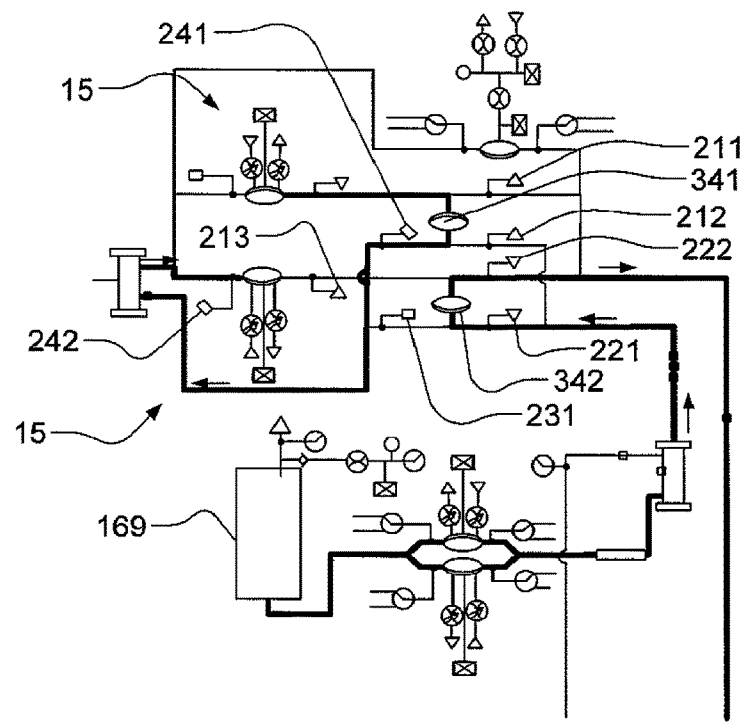

Once pod pump 161 and balancing chamber 341 have filled with dialysate, the first set of valves 211, 212, 213, 241, 242 is closed and the second set of valves 221, 222, 223, 231, 232 is opened. Fresh dialysate flows into balancing chamber 342 instead of balancing chamber 341, as valve 212 is closed while valve 221 is now open. As fresh dialysate flows into balancing chamber 342, used dialysate within the chamber is forced out and exits balancing circuit, since valve 213 is now closed. Also, pod pump 162 now draws used dialysate from the dialyzer into the pod pump, while used dialysate is prevented from flowing into pod pump 161 as valve 232 is now closed and valve 222 is now open. Pod pump 161 forces used dialysate contained within the pod pump (from the previous step) into balancing chamber 341, since valves 232 and 211 are closed and valve 223 is open. This causes fresh dialysate contained within balancing chamber 341 to be directed into the dialyzer (since valve 241 is now open while valve 212 is now closed). At the end of this step, pod pump 162 and balancing chamber 342 have filled with dialysate. This puts the state of the system back into the configuration at the beginning of this description, and the cycle is thus able to repeat, ensuring a constant flow of dialysate to and from the dialyzer. This is also illustrated in FIG. 18B. In an embodiment, the fluid (e.g. pneumatic) pressures on the control side of the balancing chamber valves are monitored to ensure they are functioning properly.

As a specific example, a vacuum (e.g., 4 p.s.i. of vacuum) can be applied to the port for the first ganged set of valves, causing those valves to open, while positive pressure (e.g., 20 p.s.i. of air pressure, 1 p.s.i. is 6.89475 kilopascals) is applied to the second ganged set of valves, causing those valves to close (or vice versa). The pod pumps each urge dialysate into one of the volumes in one of the balancing chambers 341, 342. By forcing dialysate into a volume of a balancing chamber, an equal amount of dialysate is squeezed by the diaphragm out of the other volume in the balancing chamber. In each balancing chamber, one volume is occupied by fresh dialysate heading towards the dialyzer and the other volume is occupied by used dialysate heading from the dialyzer. Thus, the volumes of dialysate entering and leaving the dialyzer are kept substantially equal.

It should be noted that any valve associated with a balancing chamber may be opened and closed under any suitable pressure. However, it may be advantageous to apply a lower or more controlled pressure to initiate and effect valve closure than the pressure ultimately used to keep the valve closed ("holding pressure"). Applying the equivalent of the holding pressure to effectuate valve closure may lead to transient pressure elevations in the fluid line sufficient to cause an already closed downstream valve to leak, adversely affecting the balancing of dialysate flow into and out of the dialyzer. Causing the dialysate pump and balancing chamber inlet and/or outlet valves to close under a lower or more controlled pressure may improve the balancing of dialysate flow into and out of the dialyzer. In an embodiment, this can be achieved, for example, by employing pulse width modulation ("PWM") to the pressure being applied in the fluid control lines of the valves. Without being limited to the following theories, the use of moderate or controlled pressure to 'slow-close' the valves may be effective for example, because:

(1) it is possible that in some cases, the pressure in a balancing chamber can transiently exceed the holding pressure in the closed balancing chamber outlet valve (caused, for example by applying excessive pressure to close the balancing chamber inlet valve against the mass of fluid behind the valve diaphragm). The transient elevation of pressure in the fluid line can overcome the holding pressure of the closed outlet valve, resulting in a leak of fluid and an imbalance of fluid delivery between the two sides of the balancing chamber. (2) Also, the presence of air or gas between the balancing chamber and a balancing chamber valve, coupled with a rapid valve closure, could cause excess fluid to be pushed through the balancing chamber without being balanced by fluid from the opposite side of the balancing chamber.

As the diaphragms approach a wall in the balancing chambers (so that one volume in a balancing chamber approaches a minimum and the other volume approaches a maximum), positive pressure is applied to the port for the first ganged set of valves, causing those valves to close, while a vacuum is applied to the second gangd set of valves, causing those valves to open. The pod pumps then each urge dialysate into one of the volumes in the other of the balancing chambers 341, 342. Again, by forcing dialysate into a volume of a balancing chamber, an equal amount of dialysate is squeezed by the diaphragm out of the other volume in the balancing chamber. Since, in each balancing chamber, one volume is occupied by fresh dialysate heading towards the dialyzer and the other volume is occupied by used dialysate heading from the dialyzer, the volumes of dialysate entering and leaving the dialyzer are kept equal.

Also shown within FIG. 5 is bypass pump 35, which can direct the flow of dialysate from dialyzer 14 through balancing circuit 143 without passing through either of pod pumps 161 or 162. In this figure, bypass pump 35 is a pod pump, similar to those described above, with a rigid chamber and a flexible diaphragm dividing each chamber into a fluid compartment and a control compartment. This pump may be the same or different from the other pod pumps, metering pumps and/or balancing chambers described above. For example, this pump may be a pump as was described in U.S. Provisional Patent Application Ser. No. 60/792,073, filed Apr. 14, 2006, entitled "Extracorporeal Thermal Therapy Systems and Methods"; or in U.S. patent application Ser. No. 11/787,212, filed Apr. 13, 2007 and issued as U.S. Pat. No. 8,292,594 on Oct. 23, 2012, entitled "Fluid Pumping Systems, Devices and Methods," each incorporated herein by reference. Pod pumps are also discussed in detail below.

When control fluid is used to actuate this pump, dialysate may be drawn through the dialyzer in a way that is not balanced with respect to the flow of blood through the dialyzer. The independent action of the bypass pump 35 on the dialysate outlet side of the dialyzer causes an additional net ultrafiltration of fluid from the blood in the dialyzer. This may cause the net flow of liquid away from the patient, through the dialyzer, towards the drain. Such a bypass may be useful, for example, in reducing the amount of fluid a patient has, which is often increased due to the patient's inability to lose fluid (primarily water) through the kidneys. As shown in FIG. 5, bypass pump 35 may be controlled by a control fluid (e.g., air), irrespective of the operation of pod pumps 161 and 162. This configuration may allow for easier control of net fluid removal from a patient, without the need to operate the balancing pumps (inside and outside dialysate pumps) in a way that would allow for such fluid to be withdrawn from the patient. Using this configuration, it is not necessary to operate the inside dialysate pumps either out of balance or out of phase with the blood pumps in order to achieve a net withdrawal of fluid from the patient.

To achieve balanced flow across the dialyzer, the blood flow pump, the pumps of the balancing circuit, and the pumps of the directing circuit (discussed below) may be operated to work together to ensure that flow into the dialyzer is generally equal to flow out of the dialyzer. If ultrafiltration is required, the ultrafiltration pump (if one is present) may be run independently of some or all of the other blood and/or dialysate pumps to achieve the desired ultrafiltration rate.

To prevent outgassing of the dialysate, the pumps of the balancing circuit may be always kept at pressures above atmospheric pressure. In contrast, however, the blood flow pump and the directing circuit pumps use pressures below atmosphere to pull the diaphragm towards the chamber wall for a fill stroke. Because of the potential of fluid transfer across the dialyzer and because the pumps of the balancing circuit run at positive pressures, the balancing circuit pumps may be able to use information from the blood flow pump(s) in order to run in a balanced flow mode. The delivery strokes of the balancing circuit chambers to the dialyzer can thus be synchronized with the delivery strokes of the blood pumps.

In one set of embodiments, when running in such a balanced mode, if there is no delivery pressure from the blood flow pump, the balancing circuit pump diaphragm will push fluid across the dialyzer into the blood and the alternate pod of the balancing circuit will not completely fill. For this reason, the blood flow pump reports when it is actively delivering a stroke. When the blood flow pump is delivering a stroke the balancing pump operates. When the blood flow pump is not delivering blood, the valves that control the flow from the dialyzer to the balancing pumps (and other balancing valves ganged together with these valves, as previously discussed) may be closed to prevent any fluid transfer from the blood side to the dialysate side from occurring. During the time the blood flow pump is not delivering, the balancing pumps are effectively frozen, and the stroke continues once the blood flow pump starts delivering again. The balancing pump fill pressure can be set to a minimal positive value to ensure that the pump operates above atmosphere at minimal impedance. Also, the balancing pump delivery pressure can be set to the blood flow pump pressure to generally match pressures on either side of the dialyzer, minimizing flow across the dialyzer during delivery strokes of the inside pump.

In some cases, it may be advantageous to have the dialysate pump deliver dialysate to the dialyzer at a pressure higher than the delivery pressure of the blood pump to the dialyzer. This can help to ensure, for example, that a full chamber of clean dialysate can get delivered to the dialyzer. In an embodiment, the delivery pressure on the dialysate pump is set sufficiently high to allow the inside pump to finish its stroke, but not so high as to stop the flow of blood in the dialyzer. Conversely, when the dialysate pump is receiving spent dialysate from the dialyzer, in some cases it may also be advantageous to have the pressure in the dialysate pump set lower than the outlet pressure on the blood side of the dialyzer. This can help ensure that the receiving dialysate chamber can always fill, in turn ensuring that there is enough dialysate available to complete a full stroke at the balancing chamber. Flows across the semi-permeable membrane caused by these differential pressures will tend to cancel each other; and the pumping algorithm otherwise attempts to match the average pressures on the dialysate and blood sides of the dialyzer.

Convective flow that does occur across the dialyzer membrane may be beneficial, because a constant and repeated shifting of fluid back and forth across the dialyzer in small increments—resulting in no net ultrafiltration—can nevertheless help to prevent clot formation within the blood tubing and dialyzer, which in turn may allow for a smaller heparin dosage, prolong the useful life of the dialyzer, and facilitate dialyzer cleaning and re-use. Backflushing has the additional benefit of promoting better solute removal through convection. In another embodiment, a form of continuous backflushing across the dialyzer membrane can also be achieved by making small adjustments to the synchronization of the delivery strokes of blood with the delivery strokes of dialysate through the dialyzer.

It is generally beneficial to keep the blood flow as continuous as possible during therapy, as stagnant blood flow can result in blood clots. In addition, when the delivery flow rate on the blood flow pump is discontinuous, the balancing pump must pause its stroke more frequently, which can result in discontinuous and/or low dialysate flow rates.

However, the flow through the blood flow pump can be discontinuous for various reasons. For instance, pressure may be limited within the blood flow pump, e.g., to +600 mmHg and/or −350 mmHg to provide safe pumping pressures for the patient. For instance, during dual needle flow, the two pod pumps of the blood flow pump can be programmed to run 180° out of phase with one another. If there were no limits on pressure, this phasing could always be achieved. However to provide safe blood flow for the patient these pressures are limited. If the impedance is high on the fill stroke (due to a small needle, very viscous blood, poor patient access, etc.), the negative pressure limit may be reached and the fill flow rate will be slower then the desired fill flow rate. Thus the delivery stroke must wait for the previous fill stroke to finish resulting in a pause in the delivery flow rate of the blood flow pump. Similarly, during single needle flow, the blood flow pump may be run at 0° phase, where the two blood flow pump pod pumps are simultaneously emptied and filled. When both pod pumps are filled, the volumes of the two pod pumps are delivered. In an embodiment, the sequence of activation causes a first pod pump and then a second pod pump to fill, followed by the first pod pump emptying and then the second pod pump emptying. Thus the flow in single needle or single lumen arrangement may be discontinuous.

One method to control the pressure saturation limits would be to limit the desired flow rate to the slowest of the fill and deliver strokes. Although this would result in slower blood delivery flow rates, the flow rate would still be known and would always be continuous, which would result in more accurate and continuous dialysate flow rates. Another method to make the blood flow rate more continuous in single needle operation would be to use maximum pressures to fill the pods so the fill time would be minimized. The desired deliver time could then be set to be the total desired stroke time minus the time that the fill stroke took. However, if blood flow rate cannot be made continuous, then dialysate flow rate may have to be adjusted so that when the blood flow rate is delivering the dialysate flow is higher then the programmed value to make up for the time that the dialysate pump is stopped when the blood flow pump is filling. The less continuous the blood flow, the more the dialysate flow rate may have to be adjusted upward during blood delivery to the dialyzer. If this is done with the correct timing, an average dialysate flow rate taken over several strokes can still match the desired dialysate flow rate.

A non-limiting example of a balancing cassette is shown in FIGS. 34-36. In one structure of the cassette shown in FIG. 34A, the valves are ganged such that they are actuated at the same time. In one embodiment, there are four gangs of valves 832, 834, 836, 838. In some cases, the ganged valves are actuated by the same air line. However, in other embodiments, each valve has its own air line. Ganging the valves as shown in the exemplary embodiment creates the fluid-flow described above. In some embodiments, ganging the valves also ensures the appropriate valves are opened and closed to dictate the fluid pathways as desired.

In this embodiment, the fluid valves are volcano valves, as described in more detail herein. Although the fluid flow-path schematic has been described with respect to a particular flow path, in various embodiments, the flow paths may change based on the actuation of the valves and the pumps. Additionally, the terms inlet and outlet as well as first fluid and second fluid are used for description purposes only (for this cassette, and other cassettes described herein as well). In other embodiments, an inlet can be an outlet, as well as, a first and second fluid may be different fluids or the same fluid types or composition.

Figure 35A:
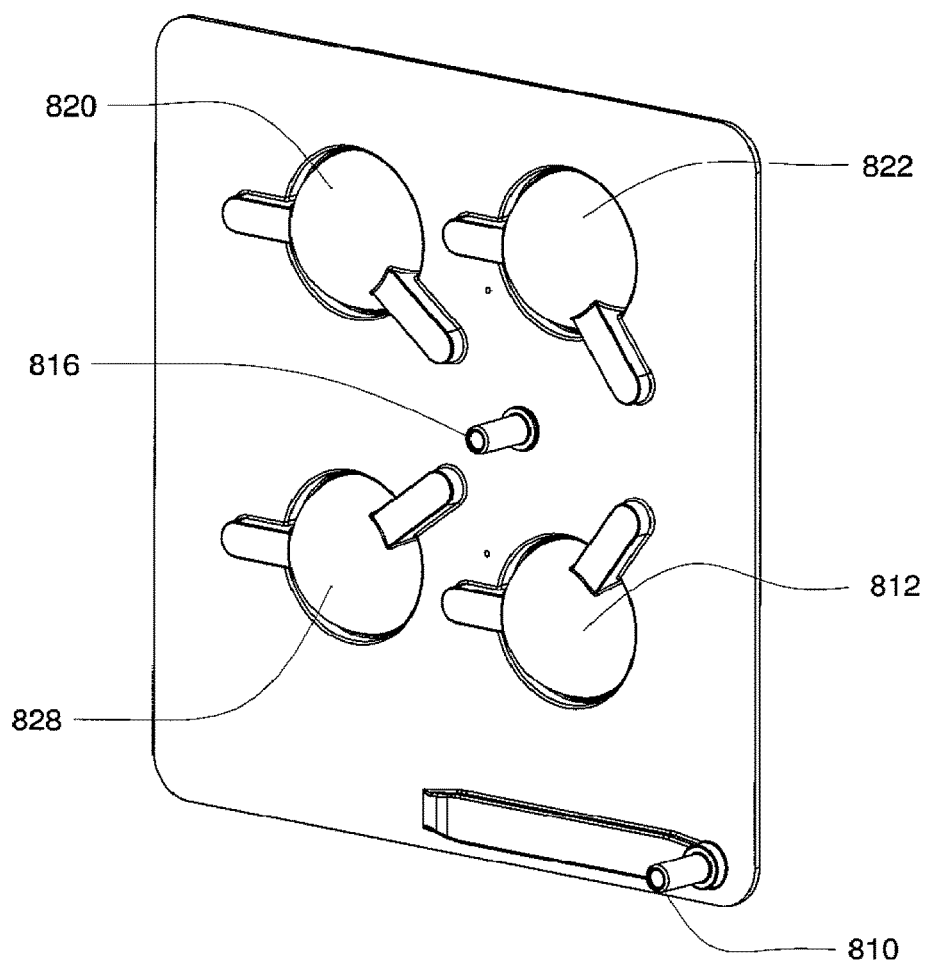
FIGS. 35A-35B are isometric and top views of an exemplary embodiment of the top plate of an exemplary embodiment of the cassette.
Figure 35B:
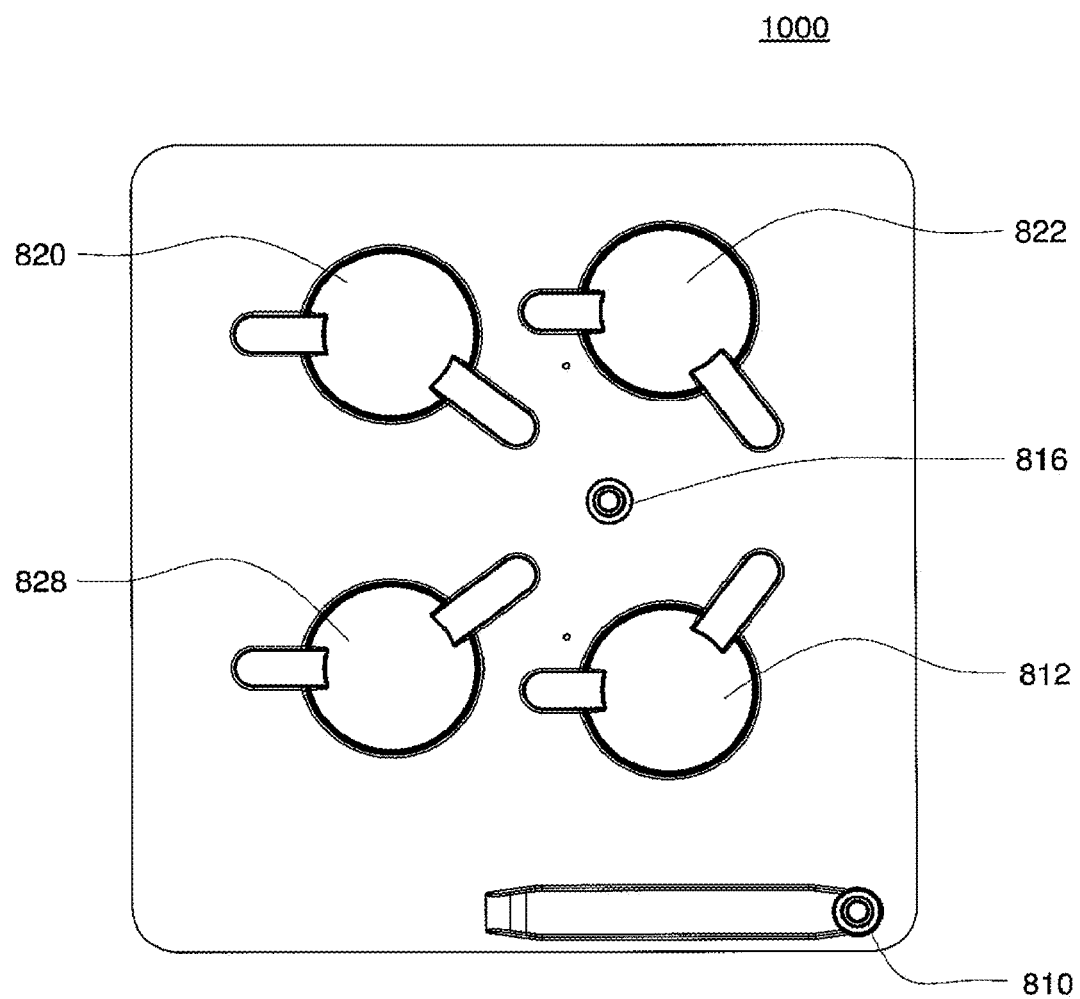

Referring now to FIGS. 35A-35E, the top plate 1000 of an exemplary embodiment of the cassette is shown. Referring first to FIGS. 35A and 35B, the top view of the top plate 1000 is shown. In this exemplary embodiment, the pod pumps 820, 828 and the balancing pods 812, 822 on the top plate, are formed in a similar fashion. In this embodiment, the pod pumps 820, 828 and balancing pods 812, 822, when assembled with the bottom plate, have a total volume of capacity of 38 ml. However, in various embodiments, the total volume capacity can be greater or less than in this embodiment. The first fluid inlet 810 and the second fluid outlet 816 are shown.

Figure 35C:
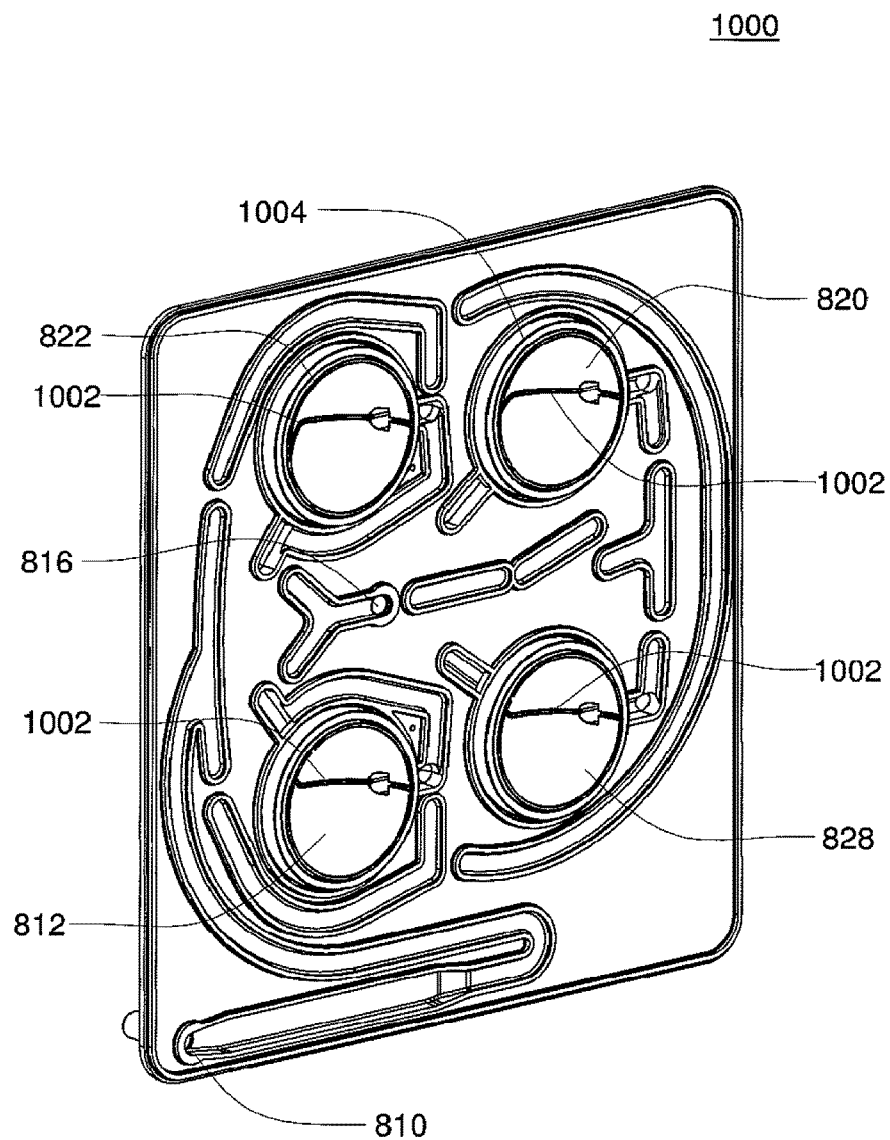
FIGS. 35C-35D are isometric views of an exemplary embodiment of the top plate of an exemplary embodiment of the cassette.
Figure 35D:
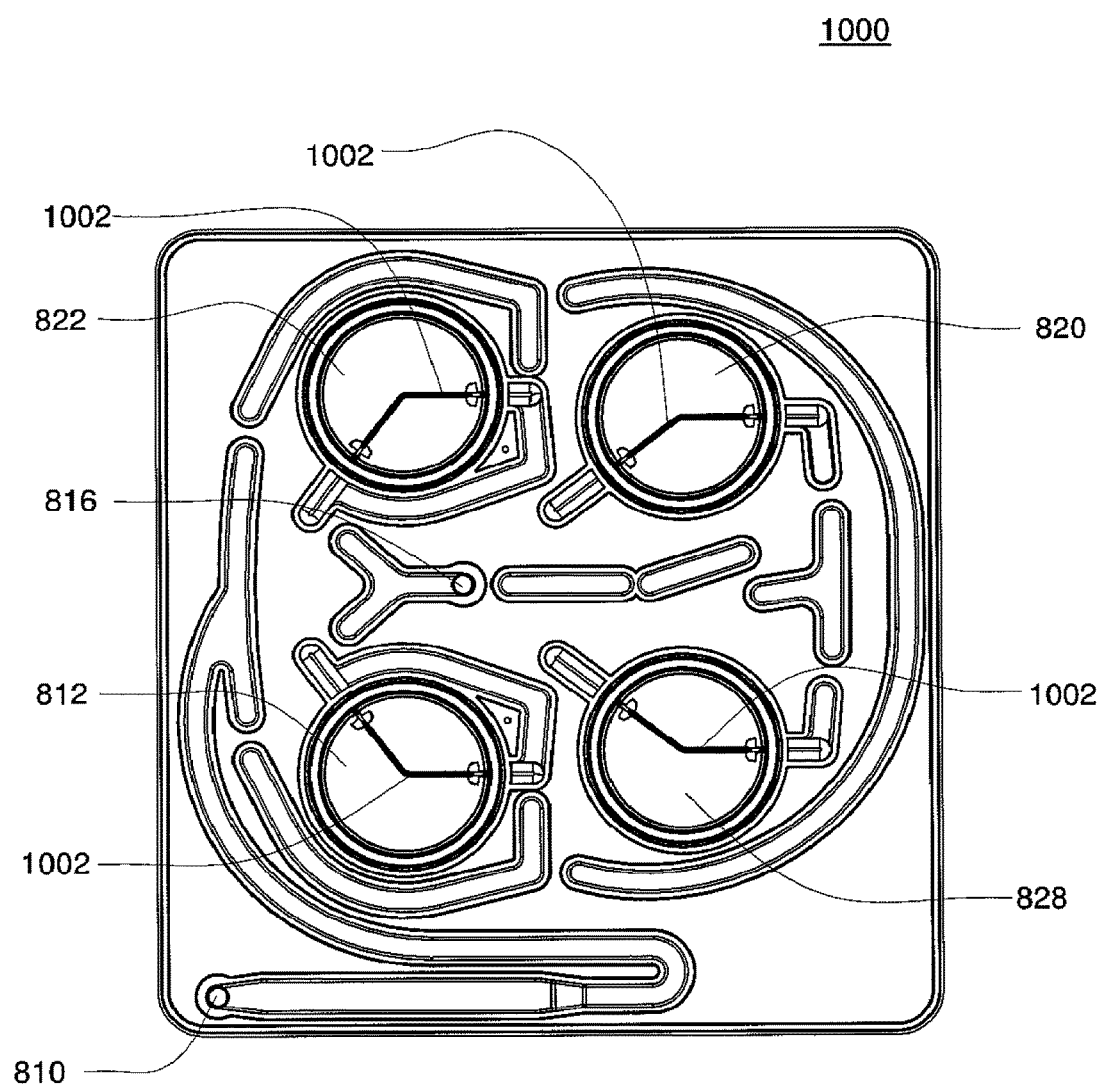

Referring now to FIGS. 35C and 35D, the bottom view of the top plate 1000 is shown. The fluid paths are shown in this view. These fluid paths correspond to the fluid paths shown in FIG. 34B in the midplate 900. The top plate 1000 and the top of the midplate form the liquid or fluid side of the cassette for the pod pumps 820, 828 and for one side of the balancing pods 812, 822. Thus, most of the liquid flow paths are on the top and midplates. The other side of the balancing pods' 812, 822 flow paths are located on the inner side of the bottom plate, not shown here, shown in FIGS. 36A-36B.

Still referring to FIGS. 35C and 35D, the pod pumps 820, 828 and balancing pods 812, 822 include a groove 1002. The groove 1002 is shown having a particular shape, however, in other embodiments, the shape of the groove 1002 can be any shape desirable. The shape shown in FIGS. 35C and 35D is an exemplary embodiment. In some embodiments of the groove 1002, the groove forms a path between the fluid inlet side and the fluid outlet side of the pod pumps 820, 828 and balancing pods 812, 822.

The groove 1002 provides a fluid path whereby when the diaphragm is at the end of stroke, there is still a fluid path between the inlet and outlet such that the pockets of fluid or air do not get trapped in the pod pump or balancing pod. The groove 1002 is included in both the liquid and air sides of the pod pumps 820, 828 and balancing pods 812, 822 (see FIGS. 36A-36B with respect to the air side of the pod pumps 820, 828 and the opposite side of the balancing pods 812, 822).

The liquid side of the pod pumps 820, 828 and balancing pods 812, 822, in one exemplary embodiment, include a feature whereby the inlet and outlet flow paths are continuous while the outer ring 1004 is also continuous. This feature allows for the seal, formed with the diaphragm (not shown) to be maintained.

Figure 35E:
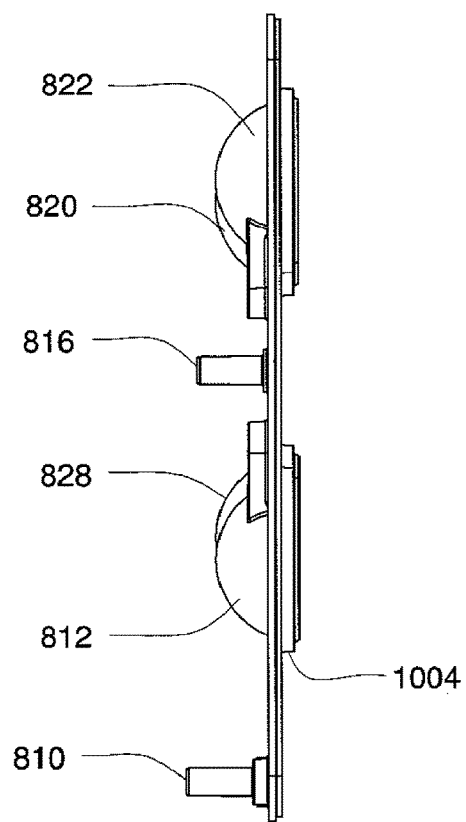
FIG. 35E is a side view of an exemplary embodiment of the top plate of a cassette.

Referring to FIG. 35E, the side view of an exemplary embodiment of the top plate 1000 is shown. The continuous outer ring 1004 of the pod pumps 820, 828 and balancing pods 812, 822 can be seen.

Figure 36A:
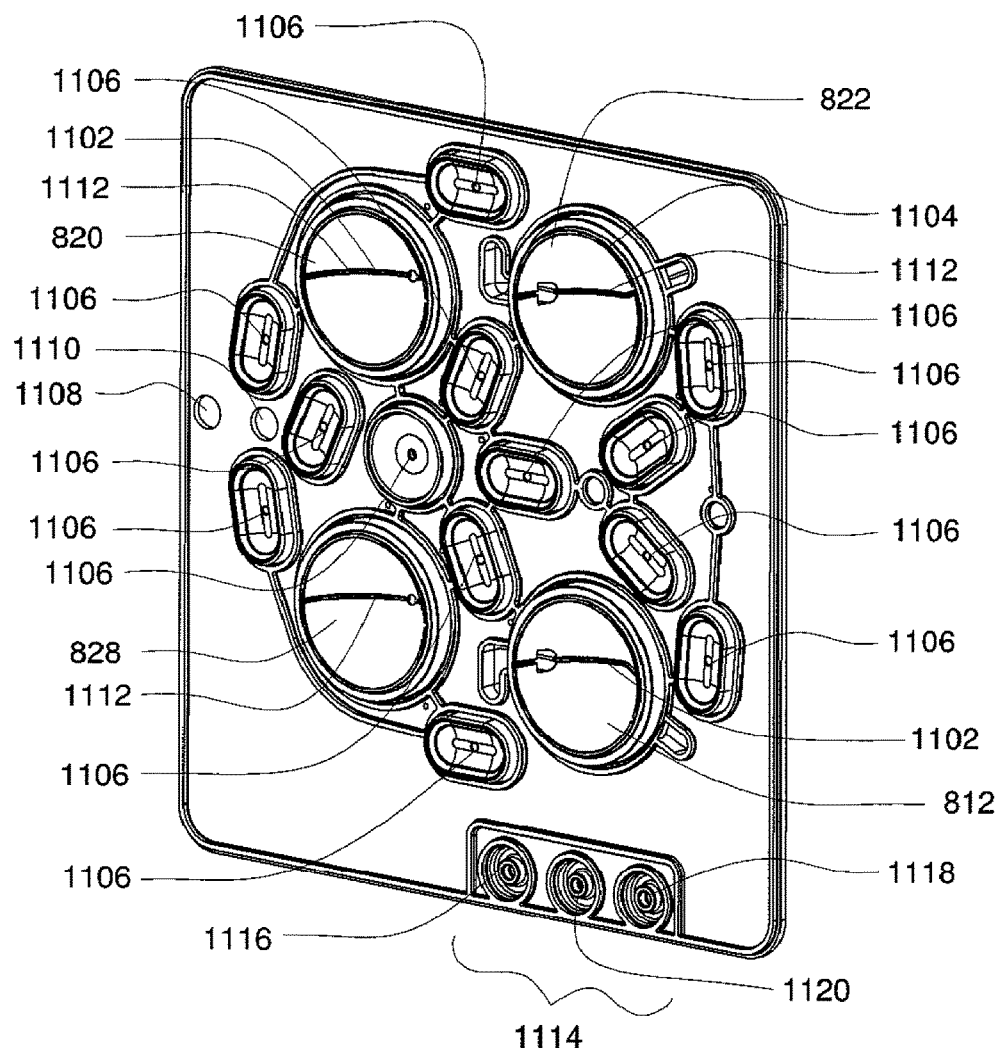
FIGS. 36A and 36B are isometric bottom views of an exemplary embodiment of the bottom plate of an exemplary embodiment of a cassette.
Figure 36B:
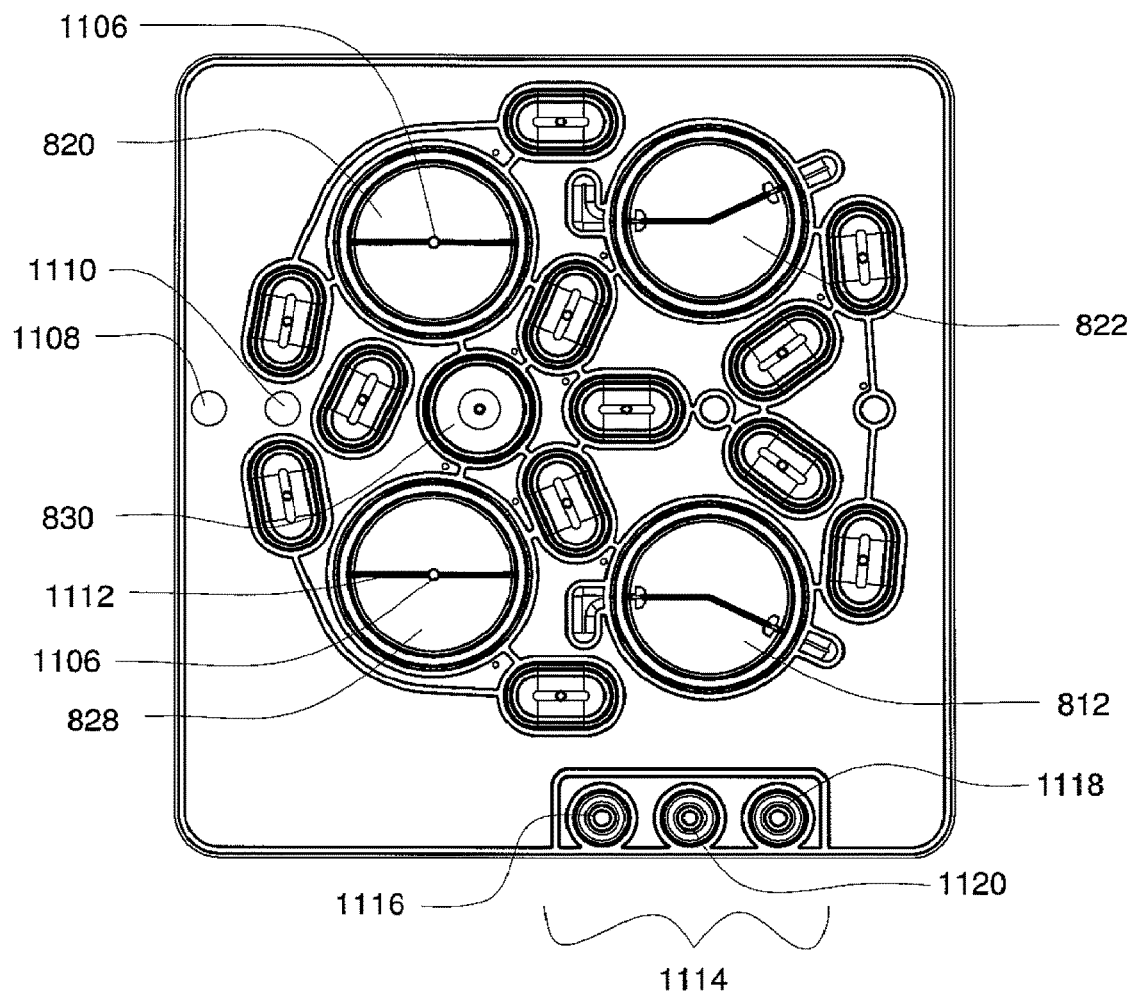

Referring now to FIGS. 36A-36E, the bottom plate 1100 is shown. Referring first to FIGS. 36A and 36B, the inside surface of the bottom plate 1100 is shown. The inside surface is the side that contacts the bottom surface of the midplate (not shown, see FIG. 34E). The bottom plate 1100 attaches to the air lines (not shown). The corresponding entrance holes for the air that actuates the pod pumps 820, 928 and valves (not shown, see FIG. 34E) in the midplate can be seen 1106. Holes 1108, 1110 correspond to the second fluid inlet and second fluid outlet shown in FIG. 34C, 824, 826 respectively. The corresponding halves of the pod pumps 820, 828 and balancing pods 812, 822 are also shown, as are the grooves 1112 for the fluid paths. Unlike the top plate, the bottom plate corresponding halves of the pod pumps 820, 828 and balancing pods 812, 822 make apparent the difference between the pod pumps 820, 828 and balancing pods 812, 822. The pod pumps 820, 828 include an air path on the second half in the bottom plate, while the balancing pods 812, 822 have identical construction to the half in the top plate. Again, the balancing pods 812, 822 balance liquid, thus, both sides of the diaphragm, not shown, will include a liquid fluid path, while the pod pumps 820, 828 are pressure pumps that pump liquid, thus, one side includes a liquid fluid path and the other side, shown in the bottom plate 1100, includes an air actuation chamber or air fluid path.

In one exemplary embodiment of the cassette, sensor elements are incorporated into the cassette so as to discern various properties of the fluid being pumped. In one embodiment, the three sensor elements are included. In one embodiment, the sensor elements are located in the sensor cell 1114. The cell 1114 accommodates three sensor elements in the sensor element housings 1116, 1118, 1120. In an embodiment, two of the sensor housings 1116, 1118 accommodate a conductivity sensor element and the third sensor element housing 1120 accommodates a temperature sensor element. The conductivity sensor elements and temperature sensor elements can be any conductivity or temperature sensor elements in the art. In one embodiment, the conductivity sensor elements are graphite posts. In other embodiments, the conductivity sensor elements are posts made from stainless steel, titanium, platinum or any other metal coated to be corrosion resistant and still be electrically conductive. The conductivity sensor elements can include an electrical lead that transmits the probe information to a controller or other device. In one embodiment, the temperature sensor is a thermistor potted in a stainless steel probe. In alternate embodiments, there are either no sensors in the cassette or only a temperature sensor, only one or more conductivity sensors or one or more of another type of sensor. In some embodiments, the sensor elements are located outside of the cassette, in a separate cassette, and may be connected to the cassette via a fluid line.

Figure 36C:
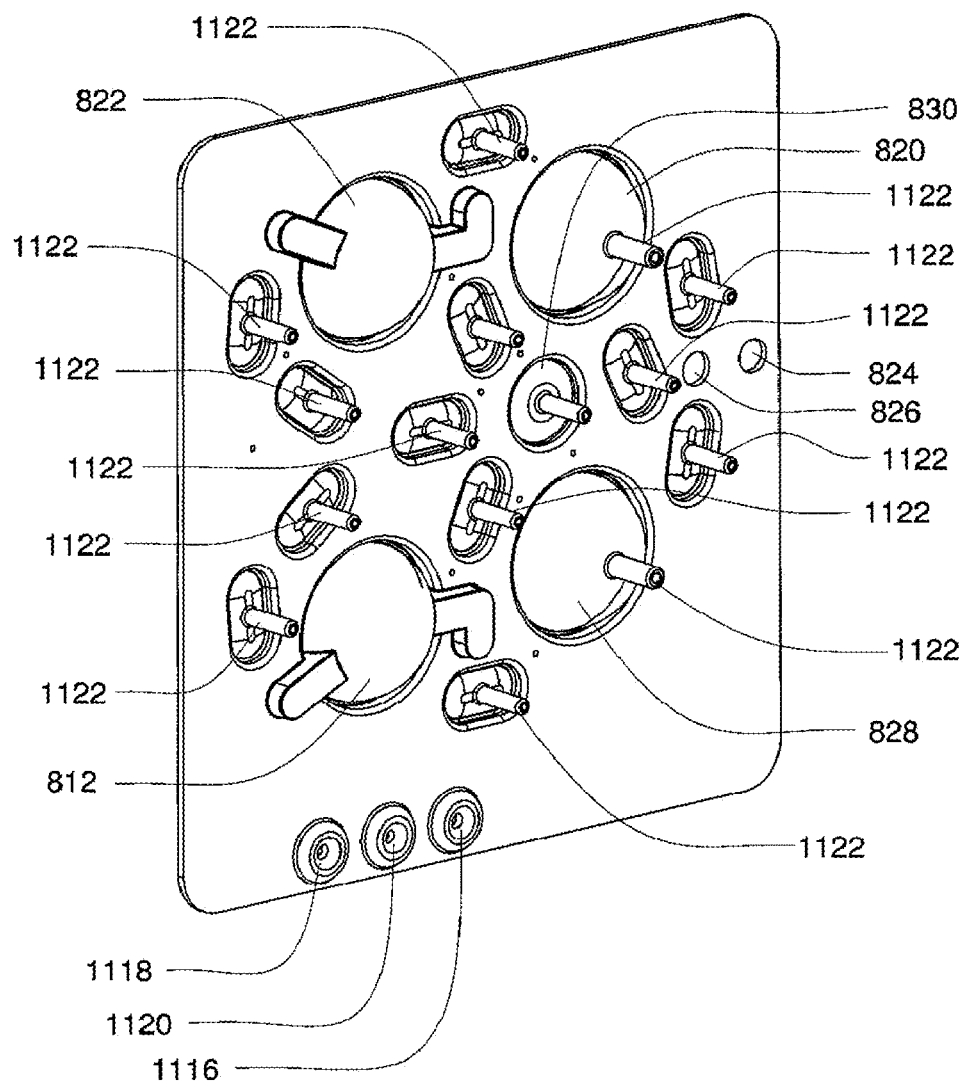
FIGS. 36C and 36D are isometric top views of an exemplary embodiment of the bottom plate of an exemplary embodiment of a cassette.
Figure 36D:
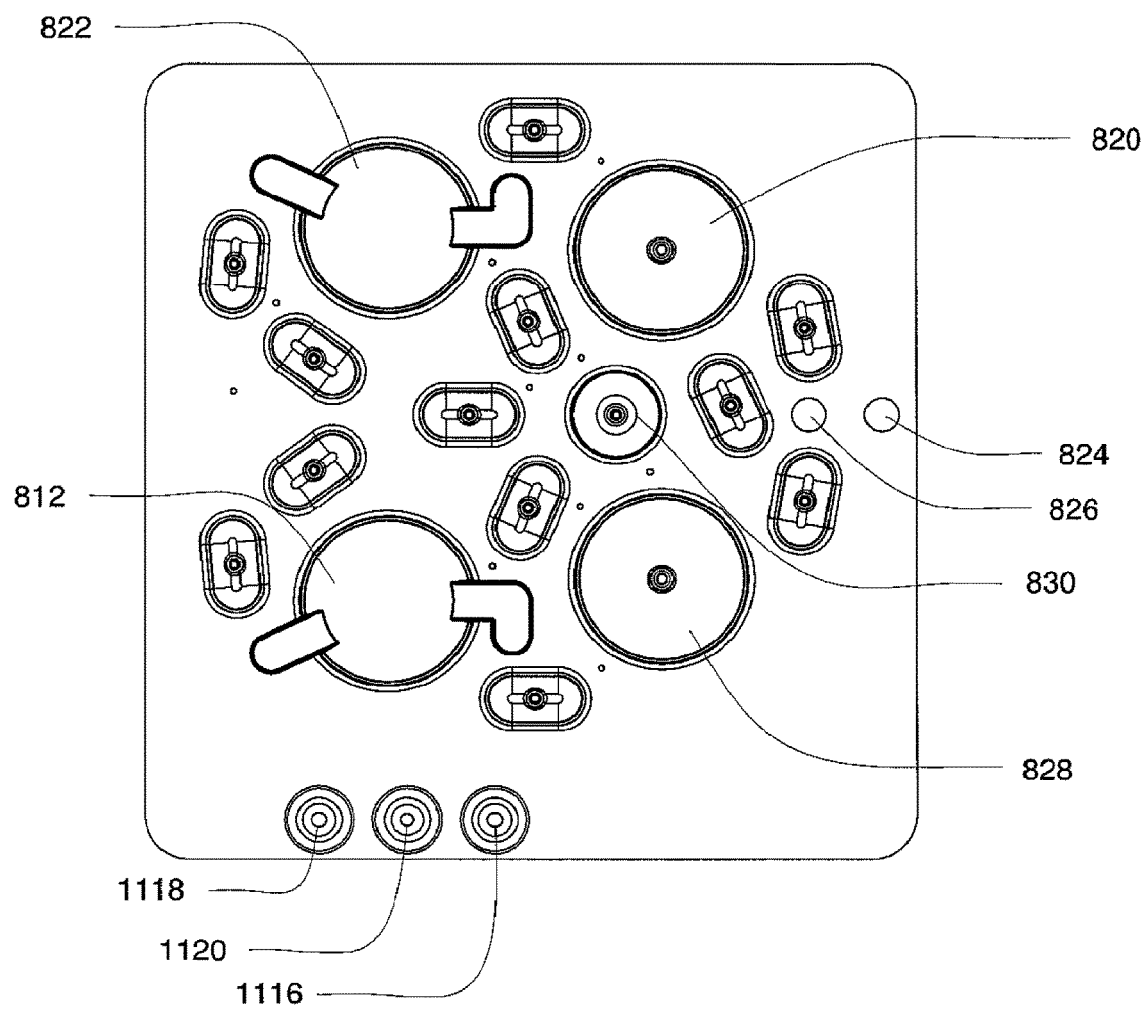

Still referring to FIGS. 36A and 36B, the actuation side of the metering pump 830 is also shown as well as the corresponding air entrance hole 1106 for the air that actuates the pump. Referring now to FIGS. 36C and 36D, the outer side of the bottom plate 1100 is shown. The valve, pod pumps 820, 828 and metering pump 830 air line connection points 1122 are shown. Again, the balancing pods 812, 822 do not have air line connection points as they are not actuated by air. As well, the corresponding openings in the bottom plate 1100 for the second fluid outlet 824 and second fluid inlet 826 are shown.

Figure 36E:
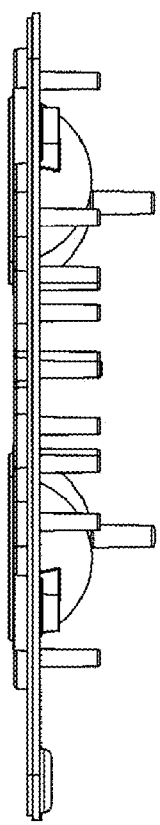
FIG. 36E is a side view of an exemplary embodiment of the bottom plate of an exemplary embodiment of a cassette.

Referring now to FIG. 36E, a side view of the bottom plate 1100 is shown. In the side view, the rim 1124 that surrounds the inner bottom plate 1100 can be seen. The rim 1124 is raised and continuous, providing for a connect point for the diaphragm (not shown). The diaphragm rests on this continuous and raised rim 1124 providing for a seal between the half of the pod pumps 820, 828 and balancing pods 812, 822 in the bottom plate 1100 and the half of the pod pumps 820, 828 and balancing pods 812, 822 in the top plate (not shown, see FIGS. 35A-35D).

As mentioned, dialysate flows from a directing circuit, optionally through a heater and/or through an ultrafilter, to the balancing circuit. In some cases, the directing circuit is implemented on a cassette, although it need not be. An example of a directing circuit can be seen in FIG. 3A as directing circuit 142. Directing circuit 142 is able to perform a number of different functions, in this example. For instance, dialysate flows from a dialysate supply (such as from a mixing circuit, as discussed below) through the directing circuit to a balancing circuit, while used dialysate flows from the balancing circuit to a drain. The dialysate may flow due to the operation of one or more pumps contained within the directing circuit. In some cases, the directing circuit may also contain a dialysate tank, which may contain dialysate prior to passing the dialysate to the balancing circuit. Such a dialysate tank, in certain instances, may allow the rate of production of dialysate to be different than the rate of use of dialysate in the dialyzer within the system. The directing circuit may also direct water from a water supply to the mixing circuit (if one is present). In addition, as previously discussed, the blood flow circuit may be fluidically connected to the directing circuit for some operations, e.g., disinfection.

Thus, in some cases, dialysate may be made as it is needed, so that large volumes of dialysate do not need to be stored. For instance, after the dialysate is prepared, it may be held in a dialysate tank 169. A dialysate valve 17 may control the flow of dialysate from tank 169 into the dialysate circuit 20. The dialysate may be filtered and/or heated before being sent into the dialyzer 14. A waste valve 18 may be used to control the flow of used dialysate out of the dialysate circuit 20.

Figure 6:
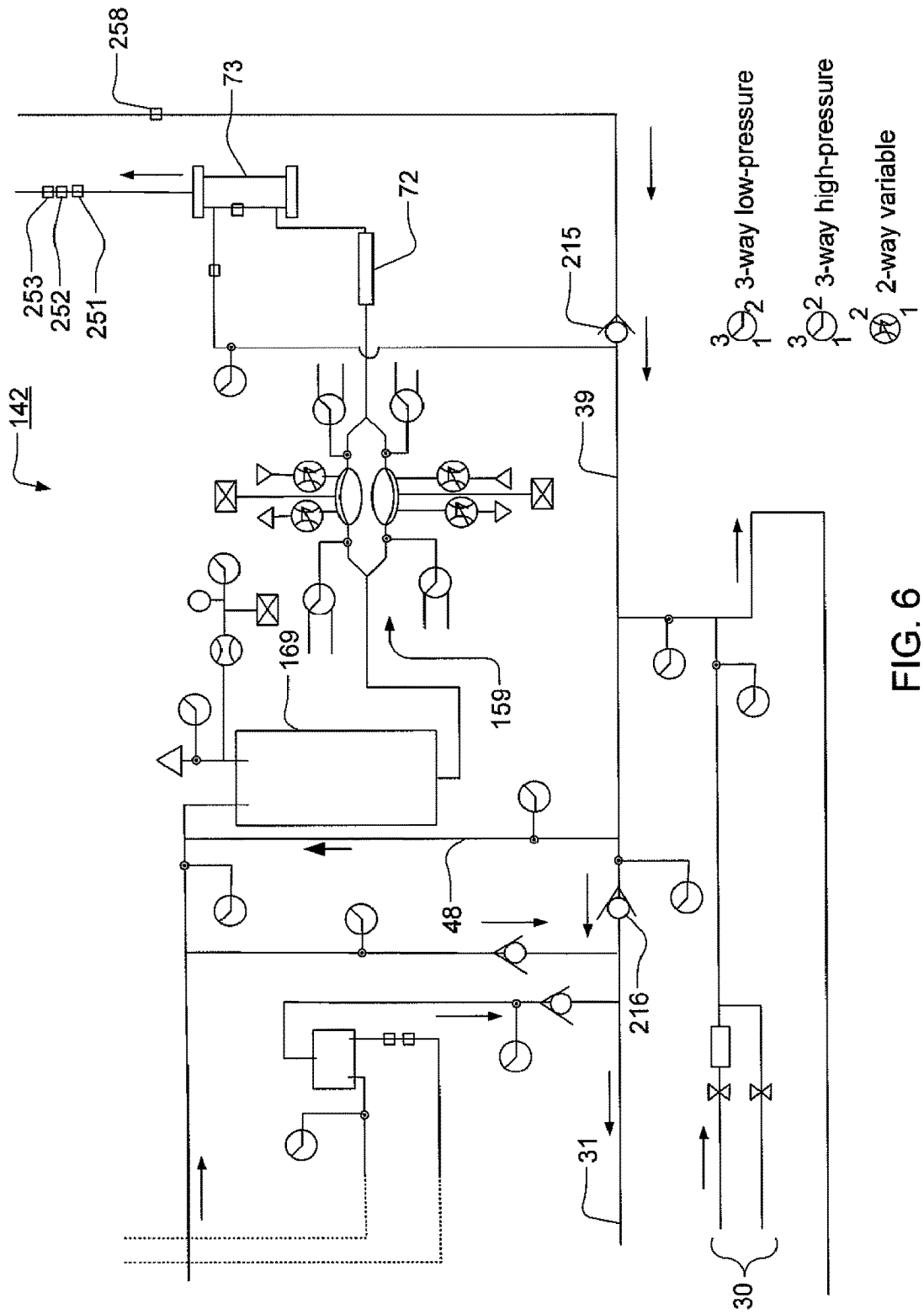
FIG. 6 is a schematic representation of a directing circuit that may be used in a hemodialysis system.

One non-limiting example of a directing circuit is shown in FIG. 6. In this figure, directing circuit 142 fluidically connects dialysate from a dialysate supply to a dialysate tank 169, then through dialysate pump 159, heater 72, and ultrafilter 73, before entering a balancing circuit, as previously discussed. It should be understood that although this figure shows that dialysate in the dialysate flow path flows from the dialysate supply to the dialysate tank, the pump, the heater, and the ultrafilter (in that order), other orderings are also possible in other embodiments. Heater 72 may be used to warm the dialysate to body temperature, and/or a temperature such that the blood in the blood flow circuit is heated by the dialysate, and the blood returning to the patient is at body temperature or higher. Ultrafilter 73 may be used to remove any pathogens, pyrogens, etc. which may be in the dialysate solution, as discussed below. The dialysate solution then flows into the balancing circuit to be directed to the dialyzer.

Dialysate tank 169 may comprise any suitable material and be of any suitable dimension for storing dialysate prior to use. For instance, dialysate tank 169 may comprise plastic, metal, etc. In some cases, dialysate tank may comprise materials similar to those used to form the pod pumps as discussed herein.

The flow of dialysate through directing circuit 142 may be controlled (at least in part) by operation of dialysate pump 159. In addition, dialysate pump 159 may control flow through the balancing circuit. For instance, as discussed above with reference to FIG. 5, fresh dialysate from the directing circuit flows into balancing chambers 341 and 342 on balancing circuit 143; pump 159 may be used as a driving force to cause the fresh dialysate to flow into these balancing chambers. In one set of embodiments, dialysate pump 159 includes a pod pump, similar to those described above. The pod pump may include a rigid chamber with a flexible diaphragm dividing each chamber into a fluid compartment and control compartment. The control compartment may be connected to a control fluid source, such as an air source. Non-limiting examples of pumps that may be used as pod pumps and/or balancing chambers are described in U.S. Provisional Patent Application Ser. No. 60/792,073, filed Apr. 14, 2006, entitled "Extracorporeal Thermal Therapy Systems and Methods"; or in U.S. patent application Ser. No. 11/787,212, filed Apr. 13, 2007 and issued as U.S. Pat. No. 8,292,594 on Oct. 23, 2012, entitled "Fluid Pumping Systems, Devices and Methods," each incorporated herein by reference. Pod pumps are also discussed in detail below.

After passing through pump 159, the dialysate may flow to a heater, e.g., heater 72 in FIG. 6. The heater may be any heating device suitable for heating dialysate, for example, an electrically resistive heater as is known to those of ordinary skill in the art. The heater may be kept separated from the directing circuit (e.g., as is shown in FIG. 3A), or the heater may be incorporated into the directing circuit, or other circuits as well (e.g., the balancing circuit).

In some cases, the dialysate is heated to a temperature such that blood passing through the dialyzer is not significantly chilled. For instance, the temperature of the dialysate may be controlled such that the dialysate is at a temperature at or greater than the temperature of the blood passing through the dialyzer. In such an example, the blood may be heated somewhat, which may be useful in offsetting heat loss caused by the blood passing through the various components of the blood flow circuit, as discussed above. In addition, in some cases as discussed below, the heater may be connected to a control system such that dialysate that is incorrectly heated (i.e., the dialysate is too hot or too cold) may be recycled (e.g., back to the dialysate tank) or sent to drain instead of being passed to the dialyzer, for example, via line 731. The heater may be integrated as part of a fluid circuit, such as a directing circuit and/or a balancing circuit, or, as is shown in FIG. 3A, the heater may be a separate component within the dialysate flow path.

The heater may also be used, in some embodiments, for disinfection or sterilization purposes. For instance, water may be passed through the hemodialysis system and heated using the heater such that the water is heated to a temperature able to cause disinfection or sterilization to occur, e.g., temperatures of at least about 70° C., at least about 80° C., at least about 90° C., at least about 100° C., at least about 110° C., etc. In some cases, as discussed below, the water may be recycled around the various components and/or heat loss within the system may be minimized (e.g., as discussed below) such that the heater is able to heat the water to such disinfection or sterilization temperatures.

The heater may include a control system that is able to control the heater as discussed above (e.g., to bring dialysate up to body temperature for dialyzing a patient, to bring the water temperature up to a disinfection temperatures in order to clean the system, etc.).

A non-limiting example of a heater controller follows. The controller may be selected to be capable of dealing with varying inlet fluid temperatures as well as for pulsatile or varying flow rates. In addition the heater control must function properly when flow is directed through each of the different flow paths (dialyze, disinfect, re-circulate etc). In one embodiment, the heater controller is used on SIP1 boards with an IR (infrared) temperature sensor on the ultra filter and an IR temperature sensor on the tank. In other embodiments, the board is in a box with less heat losses and to uses conductivity sensors for the inlet temperature sensor. Another embodiment of the controller uses a simple proportional controller using both tank (heater inlet) and ultrafilter (heater outlet) temperatures, e.g.:

$$powerHeater = massFlow * ((tankPGain * errorTank) + (UFPGain * errorUF)),$$

where:
PowerHeater=heater duty cycle cmd (0-100%);
MassFlow=the fluid mass flow rate;
TankPGain=proportional gain for the tank or inlet temperature sensor;
ErrorTank=difference between the tank or inlet temperature sensor and the desired temperature;
UFPGain=proportional gain for the ultrafilter or outlet temperature sensor; and
ErrorUF=difference between the of or outlet temperature sensor and the desired temperature.

From the heater duty cycle command (0-100%) a PWM command is generated. In some embodiments, this controller may reduce the mass flow rate if the given temperature is not maintained and the heater is saturated.

It should be understood that the above-described heater control is by way of example only, and that other heater control systems, and other heaters, are also possible in other embodiments of the invention.

The dialysate may also be filtered to remove contaminants, infectious organisms, pathogens, pyrogens, debris, and the like, for instance, using an ultrafilter. The filter may be positioned in any suitable location in the dialysate flow path, for instance, between the directing circuit and the balancing circuit, e.g., as is shown in FIG. 3A, and/or the ultrafilter may be incorporated into the directing circuit or the balancing circuit. If an ultrafilter is used, it may be chosen to have a mesh or pore size chosen to prevent species such as these from through the filter. For instance, the mesh or pore size may be less than about 0.3 micrometers, less than about 0.2 micrometers, less than about 0.1 micrometers, or less than about 0.05 micrometers, etc. Those of ordinary skill in the art will be aware of filters such as ultrafilters, and in many cases, such filters may be readily obtained commercially.

In some cases, the ultrafilter may be operated such that waste from the filter (e.g., the retentate stream) is passed to a waste stream, such as waste line 39 in FIG. 6. In some cases, the amount of dialysate flowing into the retentate stream may be controlled. For instance, if the retentate is too cold (i.e., heater 72 is not working, or heater 72 is not heating the dialysate to a sufficient temperature, the entire dialysate stream (or at least a portion of the dialysate) may be diverted to waste line 39, and optionally, recycled to dialysate tank 169 using line 48. Flow from the filter may also be monitored for several reasons, e.g., using temperature sensors (e.g., sensors 251 and 252), conductivity sensors (for confirming dialysate concentration, e.g., sensor 253), or the like. An example of such sensors is discussed below; further non-limiting examples can be seen in a U.S. patent application Ser. No. 12/038,474, filed on Feb. 27, 2008, published as US PGPub No. 2008/0253427 on Oct. 16, 2008, entitled "Sensor Apparatus Systems, Devices and Methods," incorporated herein by reference.

It should be noted that the ultrafilter and the dialyzer provide redundant screening methods for the removal of contaminants, infectious organisms, pathogens, pyrogens, debris, and the like, in this particular example (although in other cases, the ultrafilter may be absent). Accordingly, for contaminants to reach the patient from the dialysate, the contaminants must pass through both the ultrafilter and the dialyzer. Even in the event that one fails, the other may still be able to provide sterility and prevent contaminants from reaching the patient's blood.

Directing circuit 142 may also be able to route used dialysate coming from a balancing circuit to a drain, e.g., through waste line 39 to drain 31 in FIG. 6. The drain may be, for example, a municipal drain or a separate container for containing the waste (e.g., used dialysate) to be properly disposed of. In some cases, one or more check or "one-way" valves (e.g., check valves 215 and 216) may be used to control flow of waste from the directing circuit and from the system. Also, in certain instances, a blood leak sensor (e.g., sensor 258) may be used to determine if blood is leaking through the dialyzer into the dialysate flow path. In addition, a liquid sensor can be positioned in a collection pan at the bottom of the hemodialysis unit to indicate leakage of either blood or dialysate, or both, from any of the fluid circuits.

In addition, directing circuit 142 may receive water from a water supply 30, e.g., from a container of water such as a bag, and/or from a device able to produce water, e.g., a reverse osmosis device such as those that are commercially available. In some cases, as is known to those of ordinary skill in the art, the water entering the system is set at a certain purity, e.g., having ion concentrations below certain values. The water entering directing circuit 142 may be passed on to various locations, e.g., to a mixing circuit for producing fresh dialysate and/or to waste line 39. In some cases, as discussed below, valves to drain 31, various recycle lines are opened, and conduits 67 may be connected between directing circuit 142 and blood flow circuit 141, such that water is able to flow continuously around the system. If heater 72 is also activated, the water passing through the system will be continuously heated, e.g., to a temperature sufficient to disinfect the system. Such disinfection methods will be discussed in detail below.

A non-limiting example of a balancing cassette is shown in FIGS. 41-45. Referring now to FIGS. 41A and 41B, the outer side of the top plate 900 of one embodiment of the cassette is shown. The top plate 900 includes one half of the pod pumps 820, 828. This half is the fluid/liquid half where the source fluid will flow through. The inlet and outlet pod pump fluid paths are shown. These fluid paths lead to their respective pod pumps 820, 828.

Figure 41A:
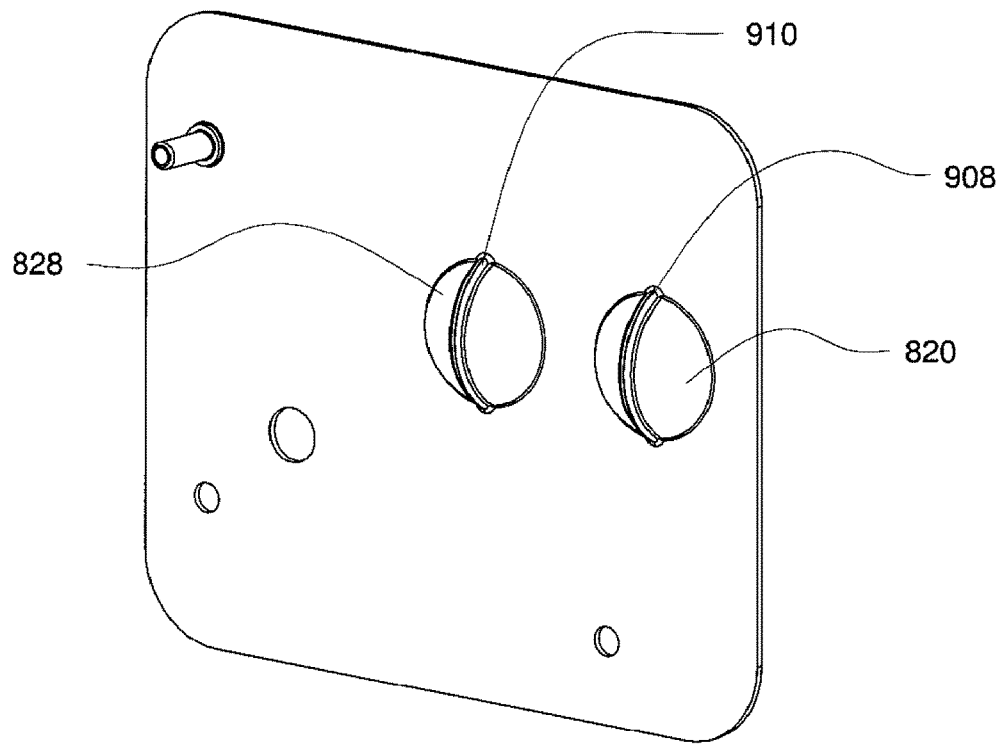
FIGS. 41A and 41B are isometric and front views of an exemplary embodiment of the outer top plate of an exemplary embodiment of a cassette.
Figure 41B:
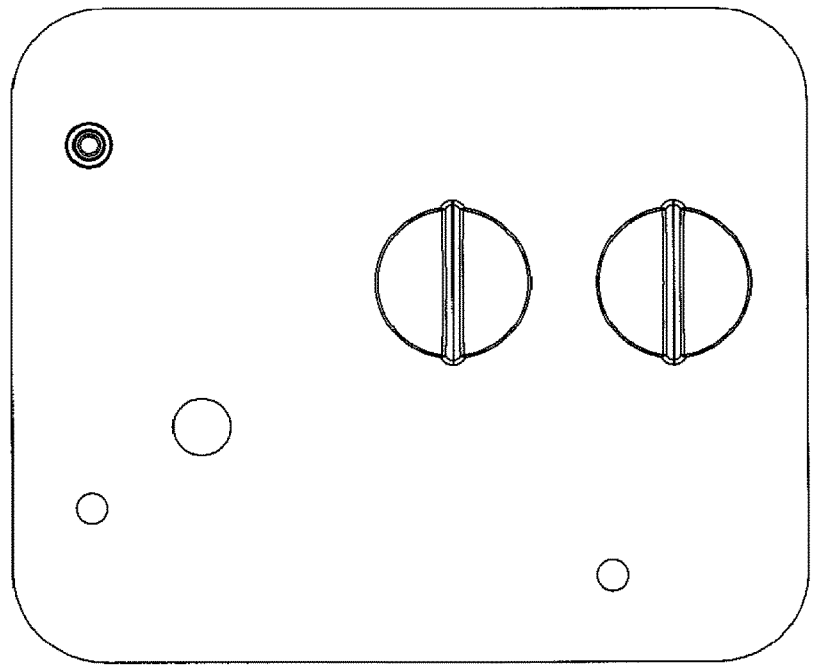
Figure 41C:
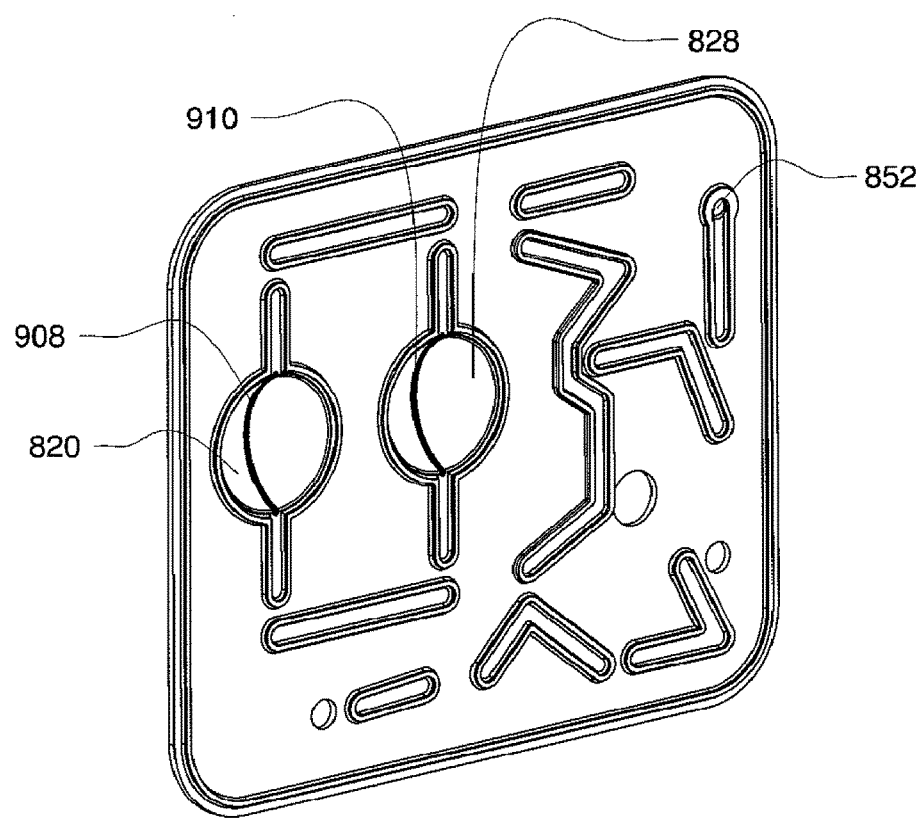
FIGS. 41C and 41D are isometric and front views of an exemplary embodiment of the inner top plate of a cassette.
Figure 41D:
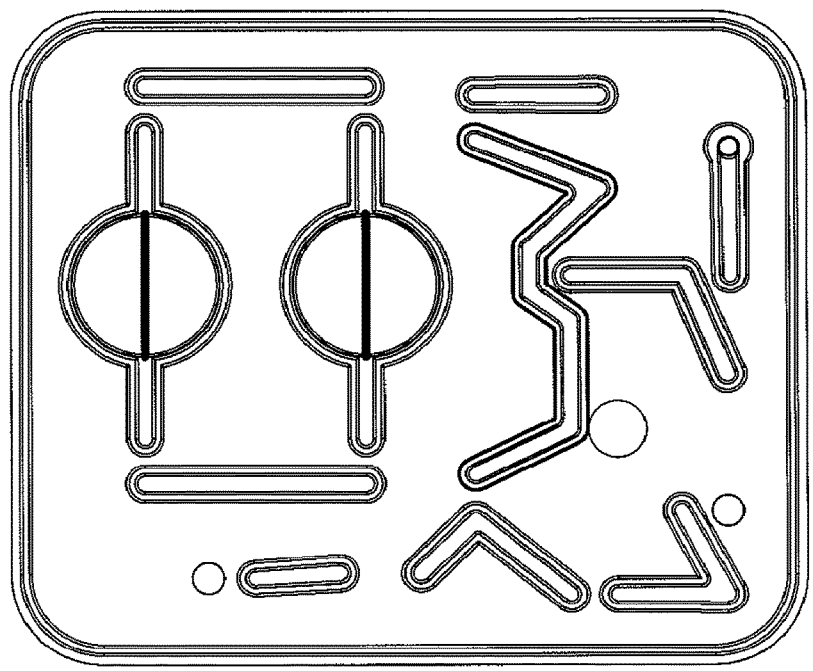
Figure 41E:
FIG. 41E is a side view of the top plate of an exemplary embodiment of a cassette.

The pod pumps 820, 828 can include a raised flow path 908, 910. The raised flow path 908, 910 allows for the fluid to continue to flow through the pod pumps 820, 828 after the diaphragm (not shown) reaches the end of stroke. Thus, the raised flow path 908, 910 minimizes the diaphragm causing air or fluid to be trapped in the pod pump 820, 828 or the diaphragm blocking the inlet or outlet of the pod pump 820, 828, which would inhibit flow. The raised flow path 908, 910 is shown in this embodiment having particular dimensions. In alternate embodiments, the raised flow path 908, 910 is larger or narrower, or in still other embodiments, the raised flow path 908, 910 can be any dimension as the purpose is to control fluid flow so as to achieve a desired flow rate or behavior of the fluid. Thus, the dimensions shown and described here with respect to the raised flow path, the pod pumps, the valves, or any other aspect are mere exemplary and alternate embodiments. Other embodiments are readily apparent. FIGS. 41C and 41D show the inner side of the top plate 900 of this embodiment of the cassette. FIG. 41E shows a side view of the top plate 900.

Figure 42A:
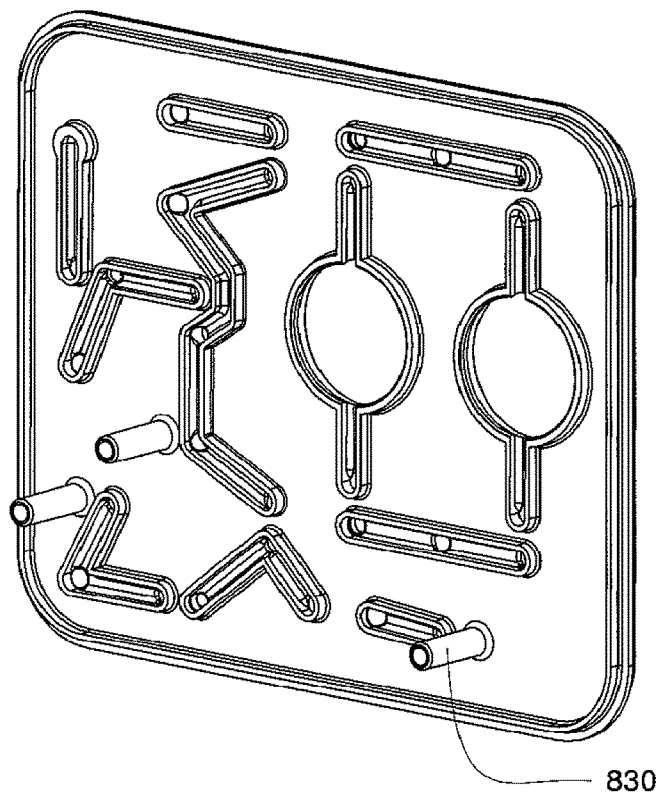
FIGS. 42A and 42B are isometric and front views of an exemplary embodiment of the liquid side of the midplate of a cassette.
Figure 42B:
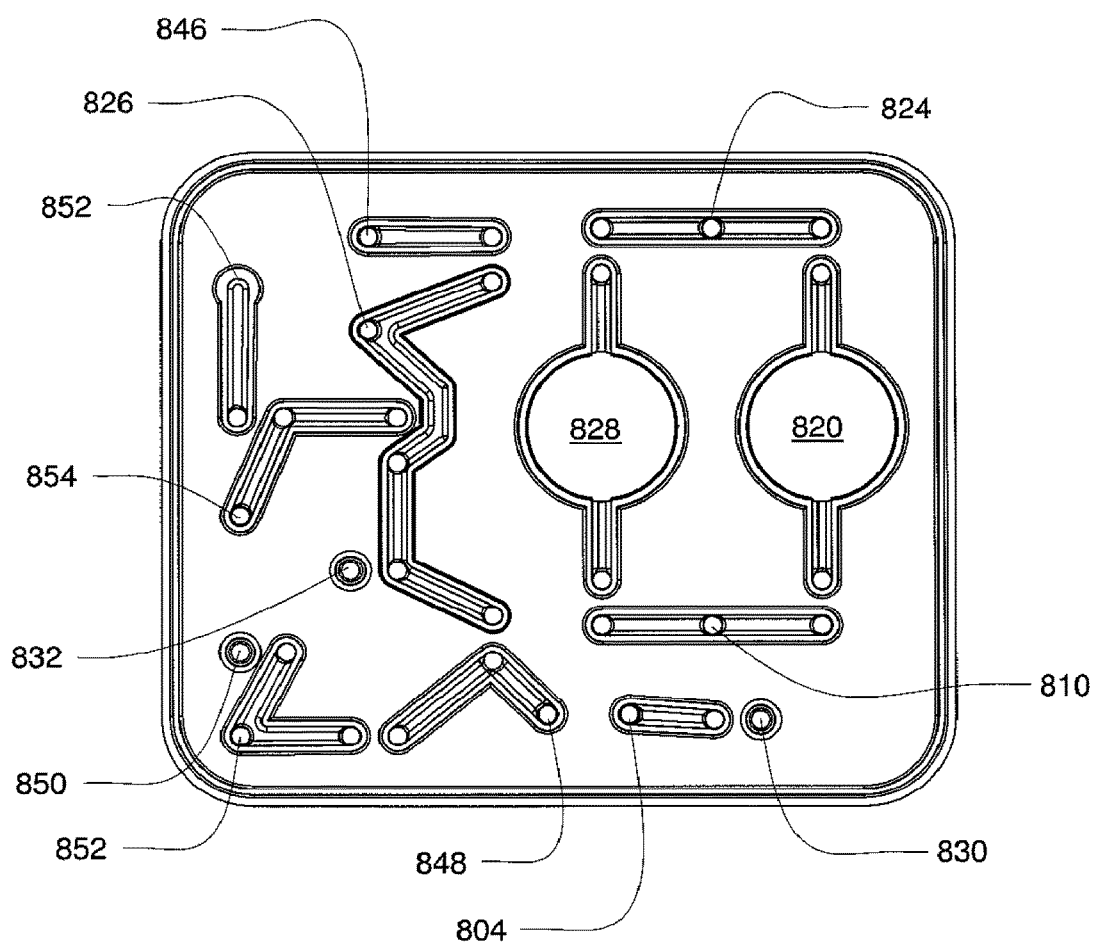

Referring now to FIGS. 42A and 42B, the fluid/liquid side of the midplate 1000 is shown. The areas complementary to the fluid paths on the inner top plate shown in FIGS. 41C and 41D are shown. These areas are slightly raised tracks that present a surface finish that is conducive to laser welding, which is one mode of manufacturing in this embodiment. Other modes of manufacturing the cassette are discussed above.

Figure 42C:
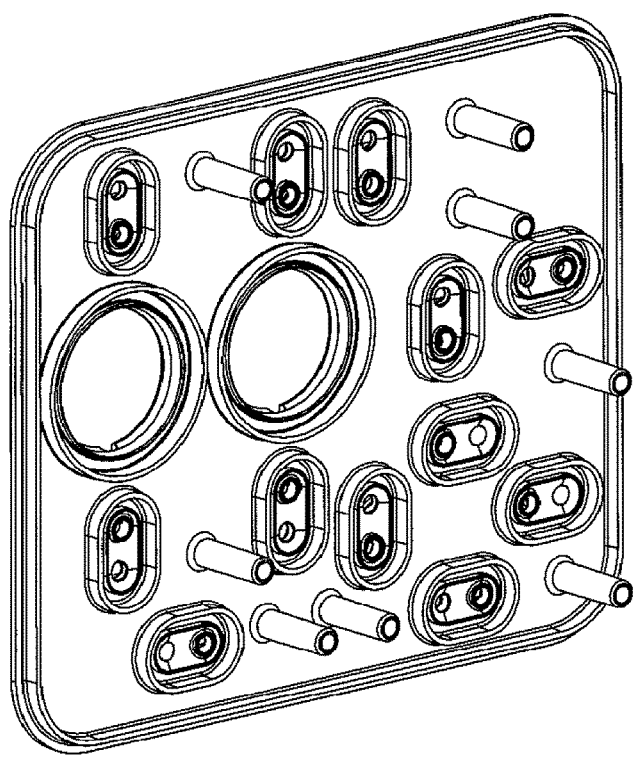
FIGS. 42C and 42D are isometric and front views of an exemplary embodiment of the air side of the midplate of a cassette.
Figure 42D:
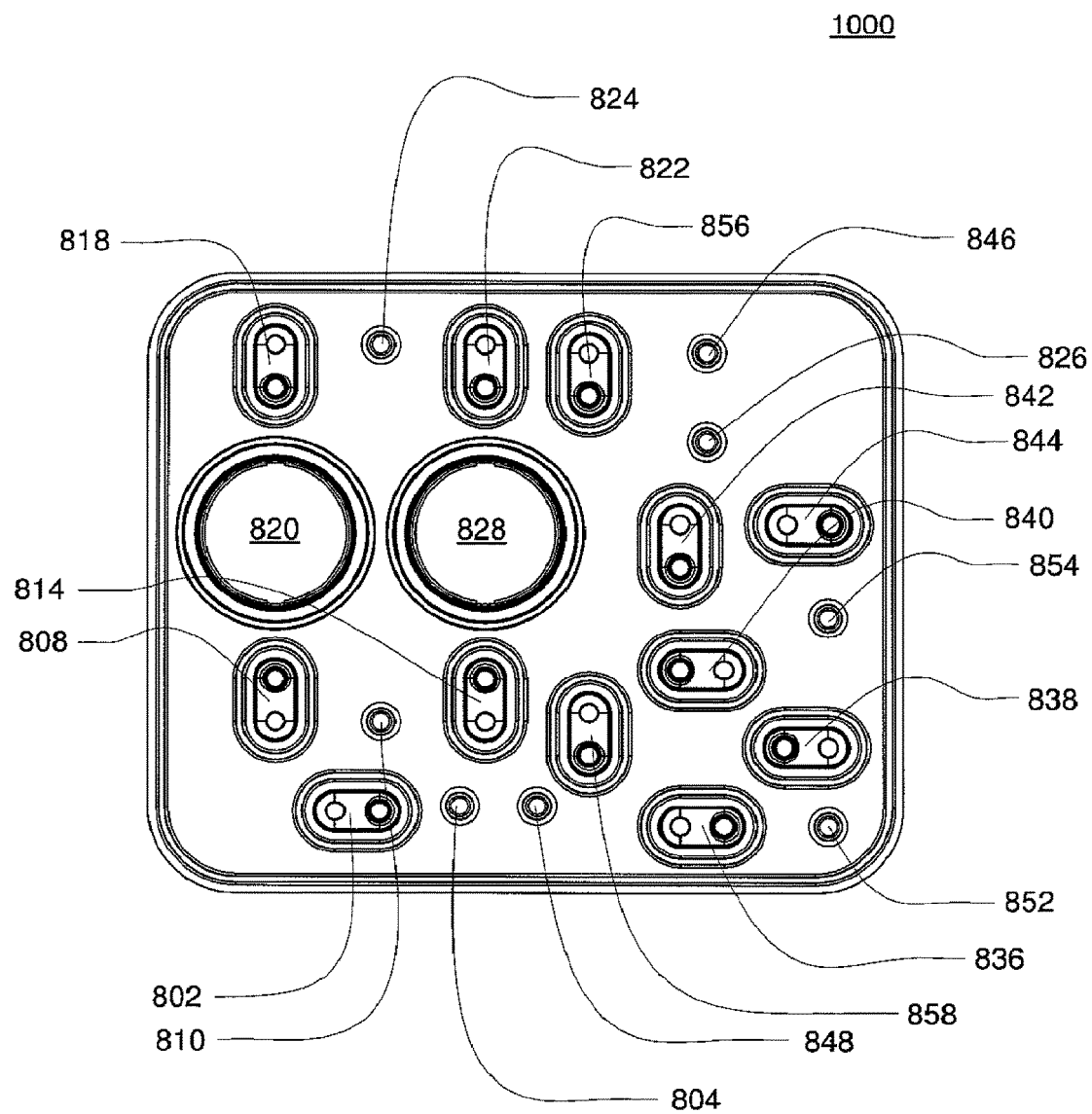
Figure 42E:
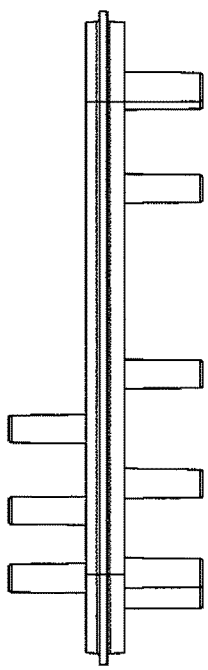
FIG. 42E is a side view of the midplate according to an exemplary embodiment of a cassette.
Figure 43A:
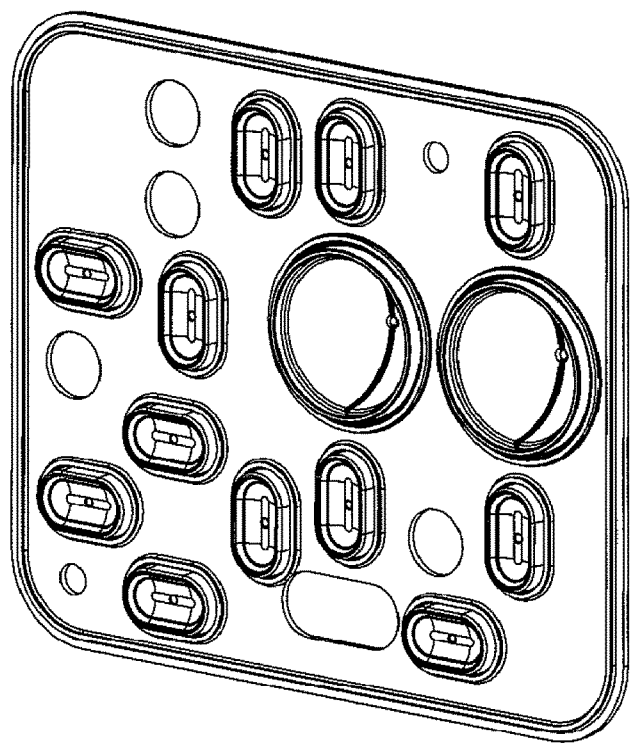
FIGS. 43A and 43B are isometric and front views of the inner side of a bottom plate according to an exemplary embodiment of a cassette.
Figure 43B:
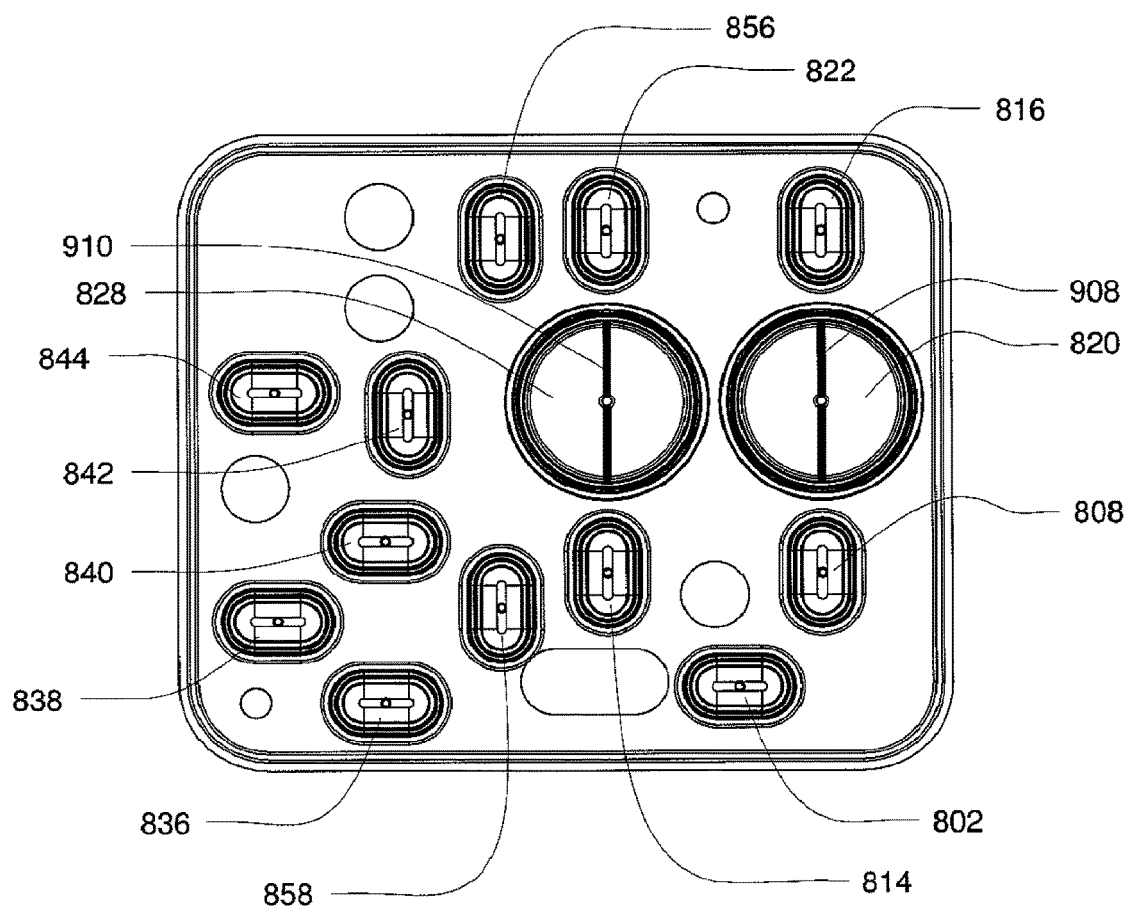
Figure 43C:
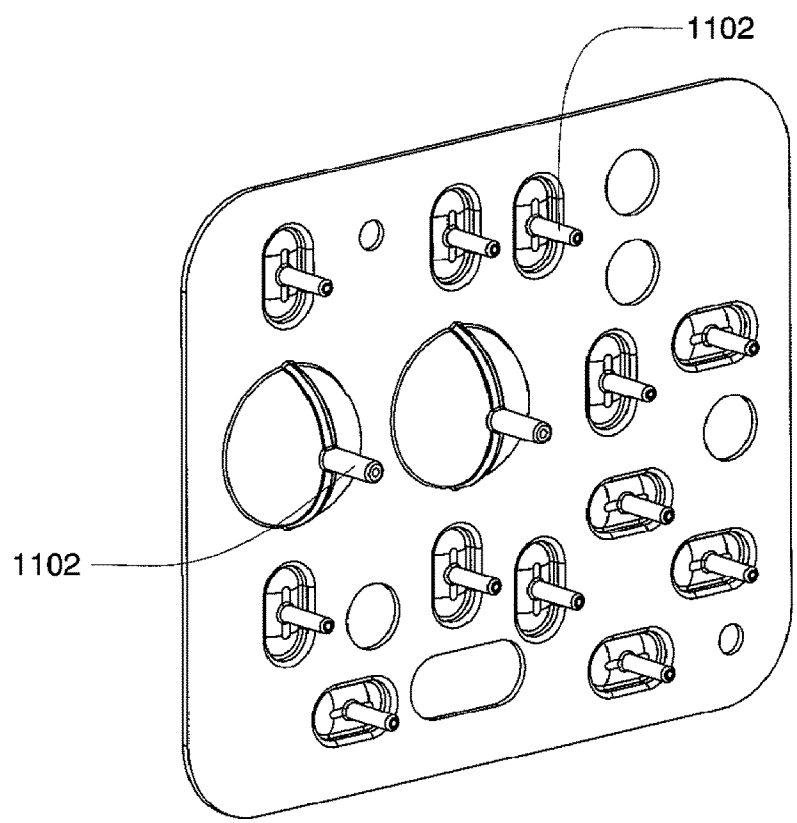
FIGS. 43C and 43D are isometric and front views of an exemplary embodiment of the outer side of the bottom plate of a cassette.
Figure 43D:
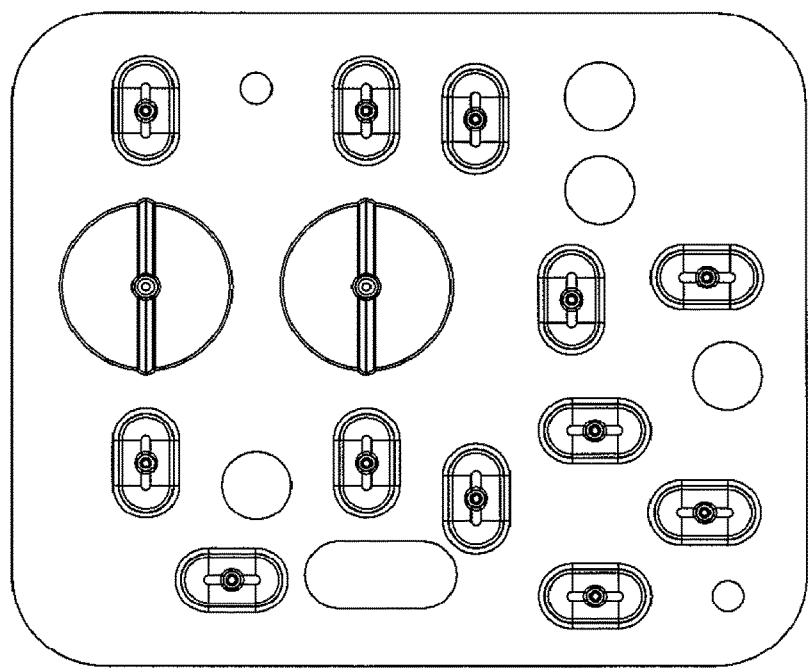
Figure 43E:
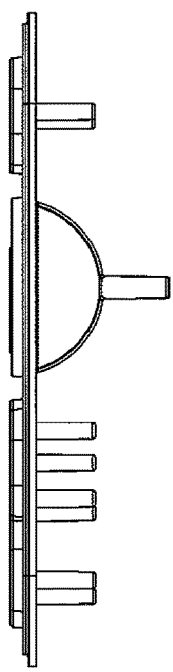
FIG. 43E is a side view of a bottom plate according to an exemplary embodiment of a cassette.

Referring next to FIGS. 42C and 42D, the air side, or side facing the bottom plate (not shown, shown in FIGS. 43A-43E) of the midplate 1000 is shown according to this embodiment. The air side of the valve holes 802, 808, 814, 816, 822, 836, 838, 840, 842, 844, 856 correspond to the holes in the fluid side of the midplate 1000 (shown in FIGS. 42A and 42B). As seen in FIGS. 44C and 44D, diaphragms 1220 complete pod pumps 820, 828 while diaphragms 1222 complete valves 802, 808, 814, 816, 822, 836, 838, 840, 842, 844, 856. The valves 802, 808, 814, 816, 822, 836, 838, 840, 842, 844, 856 are actuated pneumatically, and as the diaphragm is pulled away from the holes, liquid/fluid is allowed to flow. As the diaphragm is pushed toward the holes, fluid flow is inhibited. The fluid flow is directed by the opening and closing of the valves 802, 808, 814, 816, 822, 836, 838, 840, 842, 844, 856. Referring next to FIGS. 43A and 43B, the inner view of the bottom plate 1100 is shown. The inside view of the pod pumps 820, 828, and the valves 802, 808, 814, 816, 822, 836, 838, 840, 842, 844, 856 actuation/air chamber is shown. The pod pumps 820, 828, and the valves 802, 808, 814, 816, 822, 836, 838, 840, 842, 844, 856 are actuated by a pneumatic air source. Referring now to FIGS. 43C and 43D, the outer side of the bottom plate 1100 is shown. The source of air is attached to this side of the cassette. In one embodiment, tubes connect to the tubes on the valves and pumps 1102. In some embodiments, the valves are ganged, and more than one valve is actuated by the same air line.

Figure 44A:
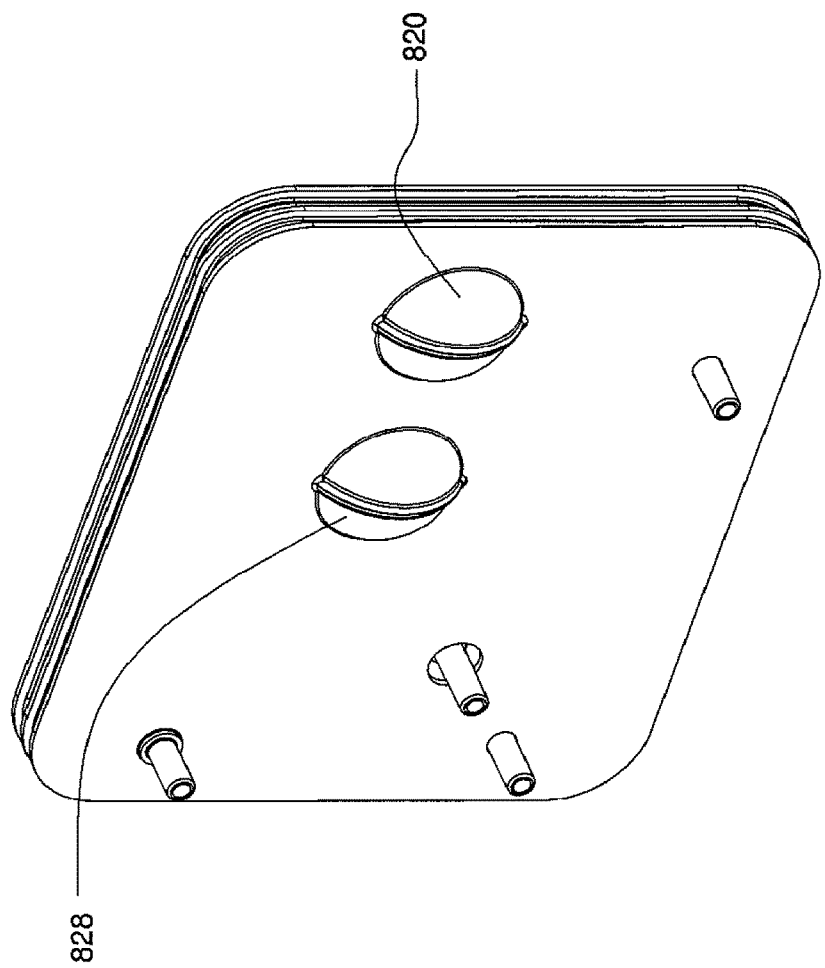
FIG. 44A is a top view of an assembled exemplary embodiment of a cassette.
Figure 44B:
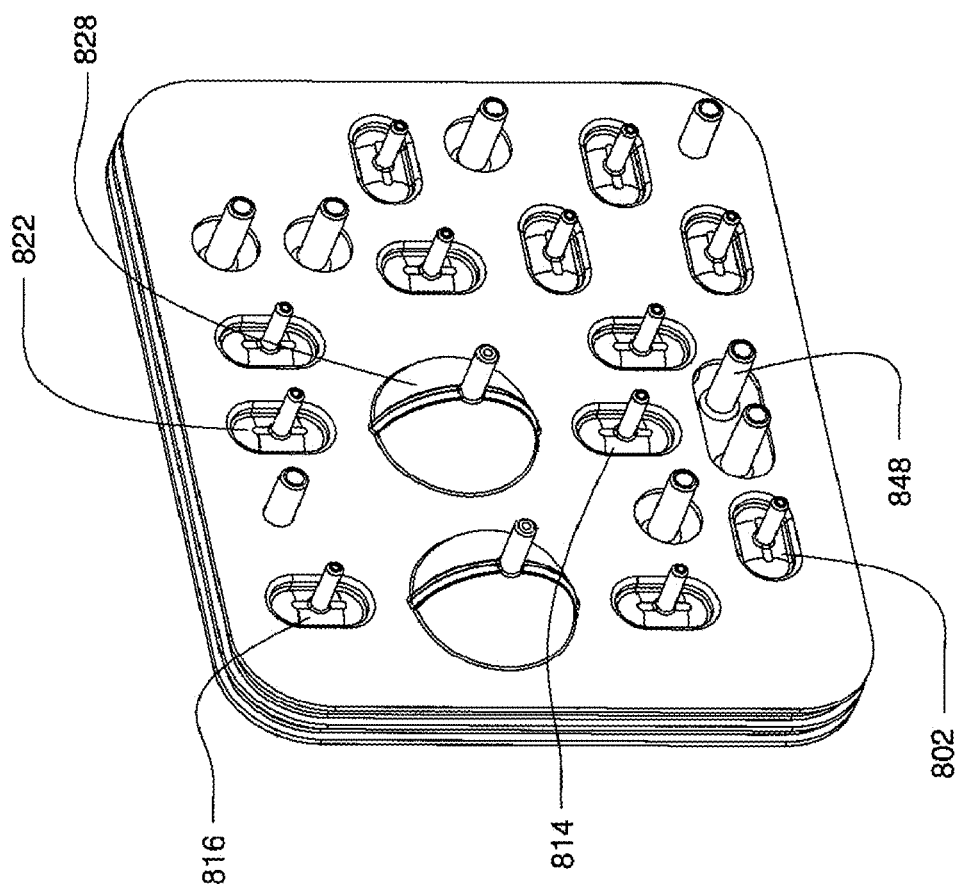
FIG. 44B is a bottom view of an assembled exemplary embodiment of a cassette.
Figure 44C:
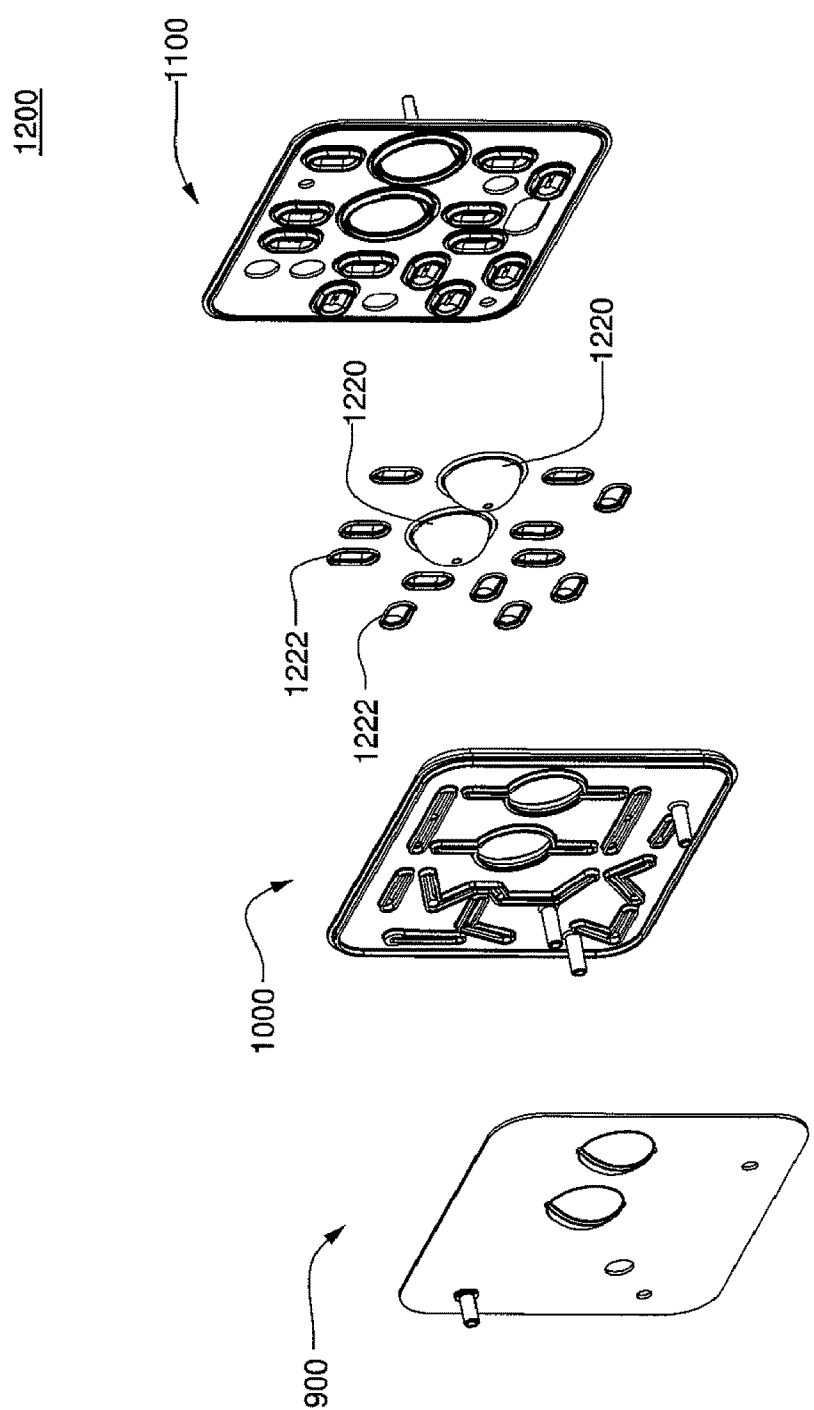
FIG. 44C is an exploded view of an assembled exemplary embodiment of a cassette.
Figure 44D:
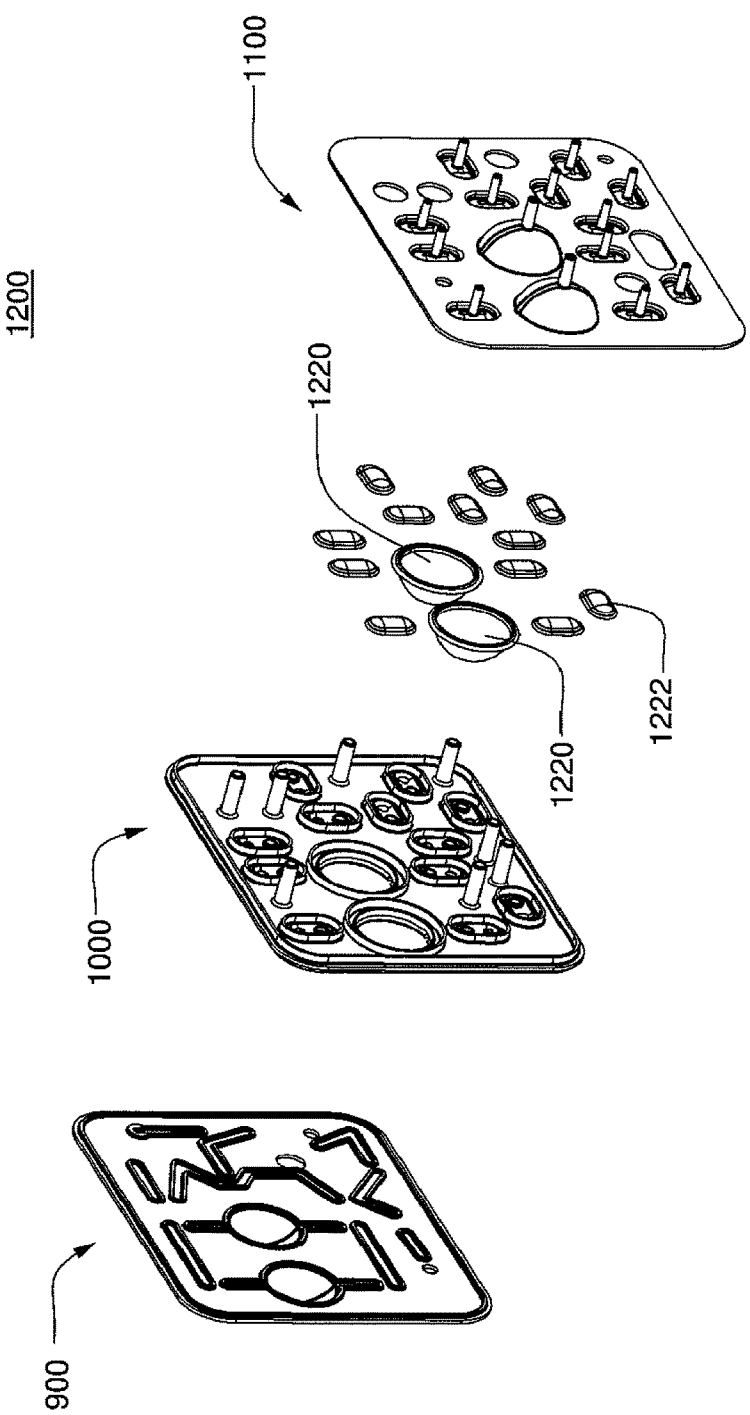
FIG. 44D is an exploded view of an assembled exemplary embodiment of a cassette.

Referring now to FIGS. 44A and 44B, an assembled cassette 1200 is shown. An exploded view of the assembled cassette 1200 shown in FIGS. 44A and 44B is shown in FIGS. 12C and 12D. In these views, the embodiment of the pod pump diaphragms 1220 is shown. The gasket of the diaphragm provides a seal between the liquid chamber (in the top plate 900) and the air/actuation chamber (in the bottom plate 1100). In some embodiment, texture on the dome of the diaphragms 1220 provide, amongst other features, additional space for air and liquid to escape the chamber at the end of stroke. In alternate embodiments of the cassette, the diaphragms may include a double gasket. The double gasket feature would be preferred in embodiments where both sides of the pod pump include liquid or in applications where sealing both chambers' sides is desired. In these embodiments, a rim complementary to the gasket or other feature (not shown) would be added to the inner bottom plate 1100 for the gasket to seal the pod pump chamber in the bottom plate 1100.

Figure 45:
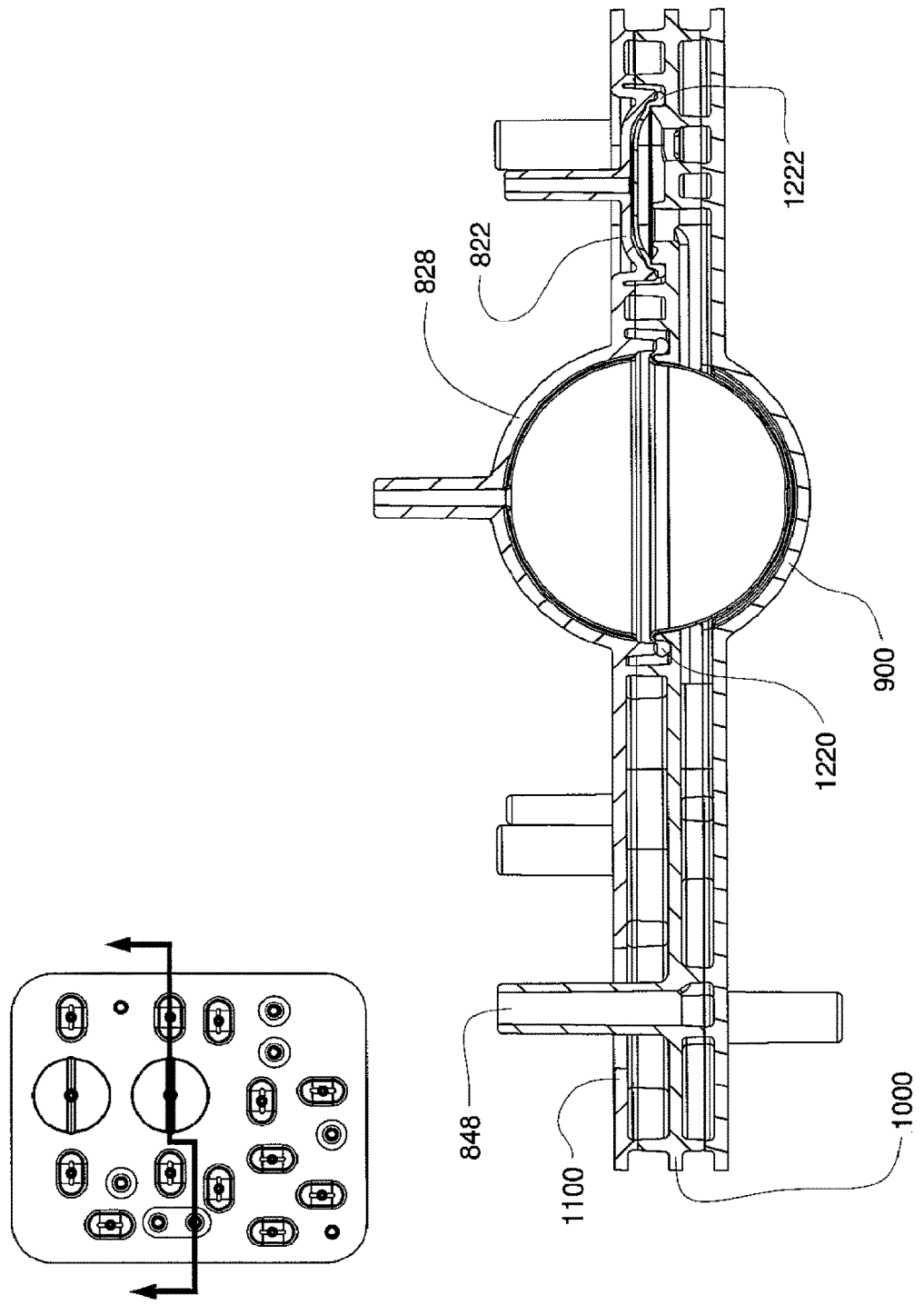
FIG. 45 shows a cross sectional view of an exemplary embodiment of an assembled cassette.

Referring now to FIG. 45, a cross sectional view of the pod pumps 828 in the cassette is shown. The details of the attachment of the diaphragm 1220 can be seen in this view. Again, in this embodiment, the diaphragm 1220 gasket is pinched by the midplate 1000 and the bottom plate 1100. A rim on the midplate 1000 provides a feature for the gasket to seal the pod pump 828 chamber located in the top plate 900.

Referring next to FIG. 45, this cross sectional view shows the valves 834, 836 in the assembled cassette. The diaphragms 1220 are shown assembled and are held in place, in this embodiment, by being sandwiched between the midplate 1000 and the bottom plate 1100. Still referring to FIG. 45, this cross sectional view also shows a valve 822 in the assembled cassette. The diaphragm 1222 is shown held in place by being sandwiched between the midplate 1000 and the bottom plate 1100.

In one set of embodiments, dialysate may be prepared separately and brought to the system for use in the directing circuit. However, in some cases, dialysate may be prepared in a mixing circuit. The mixing circuit may be run to produce dialysate at any suitable time. For instance, dialysate may be produced during dialysis of a patient, and/or prior to dialysis (the dialysate may be stored, for instance, in a dialysate tank. Within the mixing circuit, water (e.g., from a water supply, optionally delivered to the mixing circuit by a directing circuit) may be mixed with various dialysate ingredients to form the dialysate. Those of ordinary skill in the art will know of suitable dialysate ingredients, for instance, sodium bicarbonate, sodium chloride, and/or acid, as previously discussed. The dialysate may be constituted on an as-needed basis, so that large quantities do not need to be stored, although some may be stored within a dialysate tank, in certain cases.

Figure 7A:
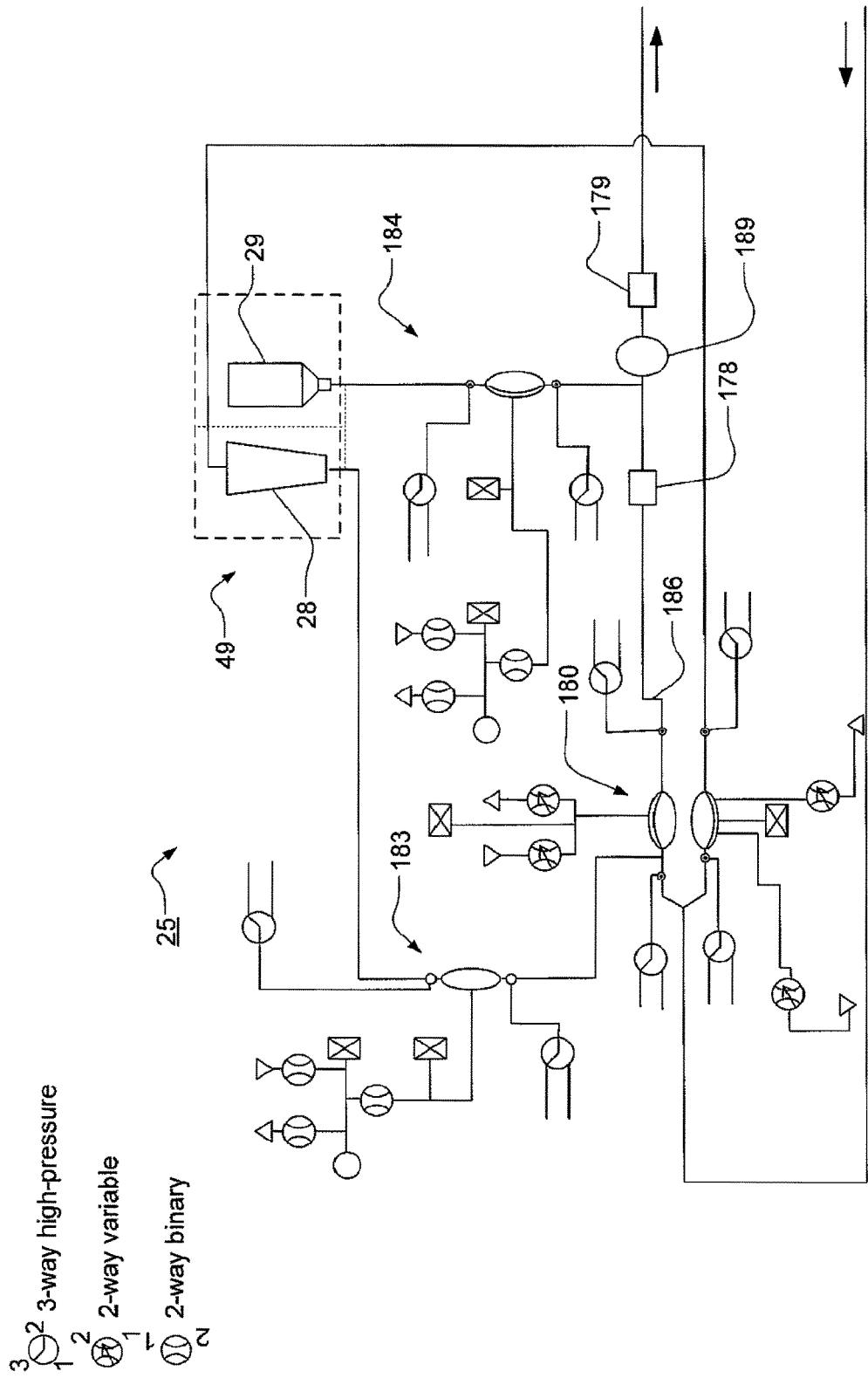
FIGS. 7A-7B are schematic representations of mixing circuits that may be used in a hemodialysis system.

FIG. 7A illustrates a non-limiting example of a mixing circuit, which may be implemented on a cassette in some cases. In FIG. 7A, water from a directing circuit flows into mixing circuit 25 due to action of pump 180. In some cases, a portion of the water is directed to ingredients 49, e.g., for use in transporting the ingredients through the mixing circuit. As shown in FIG. 7A, water is delivered to bicarbonate source 28 (which may also contain sodium chloride in some cases). The sodium chloride and/or the sodium bicarbonate may be provided, in some cases, in a powdered or granular form, which is moved through the action of water. Bicarbonate from bicarbonate source 28 is delivered via bicarbonate pump 183 to a mixing line 186, to which water from the directing circuit also flows. Acid from acid source 29 (which may be in a liquid form) is also pumped via acid pump 184 to mixing line 186. The ingredients (water, bicarbonate, acid, NaCl, etc.) are mixed in mixing chamber 189 to produce dialysate, which then flows out of mixing circuit 25. Conductivity sensors 178 and 179 are positioned along mixing line 186 to ensure that as each ingredient is added to the mixing line, it is added at proper concentrations.

In one set of embodiments, pump 180 comprises one or more pod pumps, similar to those described above. The pod pumps may include a rigid chamber with a flexible diaphragm dividing each chamber into a fluid compartment and control compartment. The control compartment may be connected to a control fluid source, such as an air source. Non-limiting examples of pumps that can be used as pod pumps are described in U.S. Provisional Patent Application Ser. No. 60/792,073, filed Apr. 14, 2006, entitled "Extracorporeal Thermal Therapy Systems and Methods"; or in U.S. patent application Ser. No. 11/787,212, filed Apr. 13, 2007 and issued as U.S. Pat. No. 8,292,594 on Oct. 23, 2012, entitled "Fluid Pumping Systems, Devices and Methods," each incorporated herein by reference. Similarly, in some cases, pumps 183 and/or 184 may each be pod pumps. Additional details of pod pumps are discussed below.

In some cases, one or more of the pumps may have pressure sensors to monitor the pressure in the pump. This pressure sensor may be used to ensure that a pump compartment is filling and delivering completely. For example, ensuring that the pump delivers a full stroke of fluid may be accomplished by (i) filling the compartment, (ii) closing both fluid valves, (iii) applying pressure to the compartment by opening the valve between the positive pneumatic reservoir and the compartment, (iv) closing this positive pressure valve, leaving pressurized air in the path between the valve and the compartment, (v) opening the fluid valve so the fluid can leave the pump compartment, and (vi) monitoring the pressure drop in the compartment as the fluid leaves. The pressure drop corresponding to a full stroke may be consistent, and may depend on the initial pressure, the hold-up volume between the valve and the compartment, and/or the stroke volume. However, in other embodiments of any of the pod pumps described herein, a reference volume compartment may be used, where the volume is determined through pressure and volume data.

The volumes delivered by the water pump and/or the other pumps may be directly related to the conductivity measurements, so the volumetric measurements may be used as a cross-check on the composition of the dialysate that is produced. This may ensure that the dialysate composition remains safe even if a conductivity measurement becomes inaccurate during a therapy.

Figure 7B:
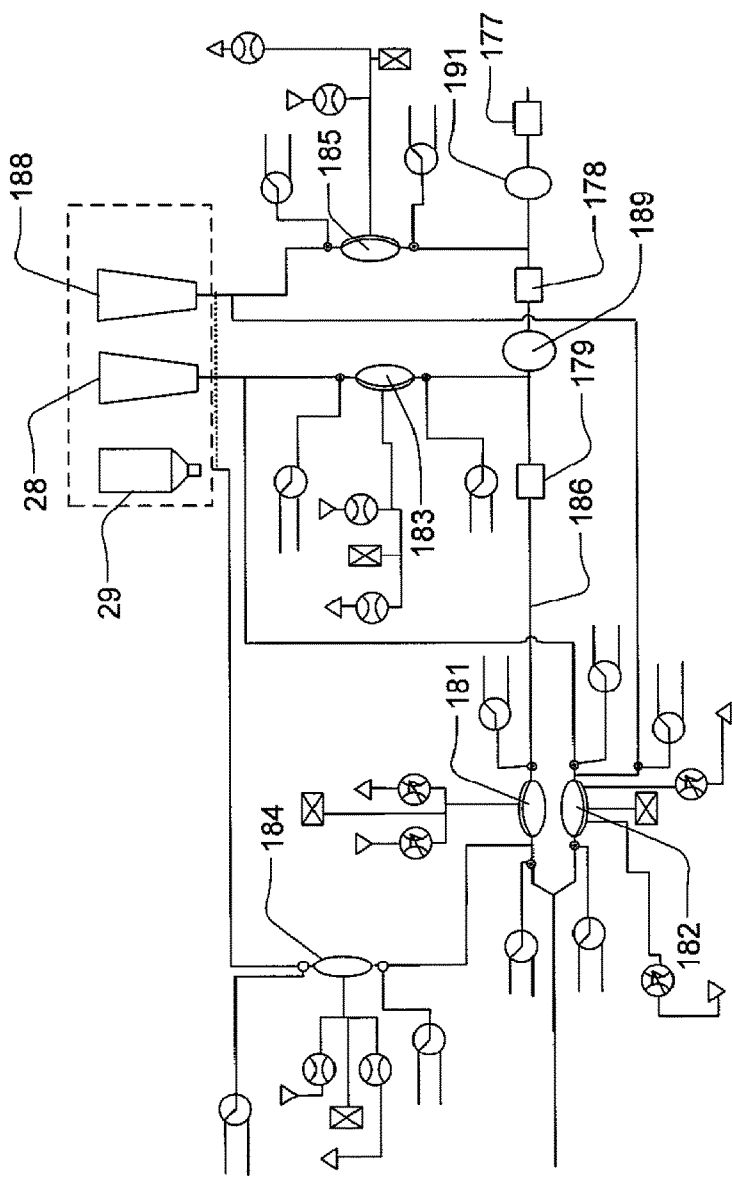

FIG. 7B is a schematic diagram showing another example of a mixing circuit, implementable on a cassette in certain cases. Mixing circuit 25 in this figure includes a pod pump 181 for pumping water from a supply along a line 186 into which the various ingredients for making the dialysate are introduced into the water. Another pump 182 pumps water from a water supply into source 28 holding the sodium bicarbonate (e.g., a container) and/or into source 188 holding the sodium chloride. A third pump 183 introduces the dissolved bicarbonate into mixing line 186 (mixed in mixing chamber 189), while a fourth pump 185 introduces dissolved sodium chloride into line 186 (mixed in mixing chamber 191). A fifth pump 184 introduces acid into the water before it passes through the first pump 181. Mixing is monitored using conductivity sensors 178, 179, and 177, which each measure the conductivity after a specific ingredient has been added to mixing line 186, to ensure that the proper amount and/or concentration of the ingredient has been added. An example of such sensors is discussed below; further non-limiting examples can be seen in a U.S. patent application Ser. No. 12/038,474, filed Feb. 27, 2008, published as US PGPub No. 2008/0253427 on Oct. 16, 2008, entitled "Sensor Apparatus Systems, Devices and Methods," incorporated herein by reference.

Figure 3B:
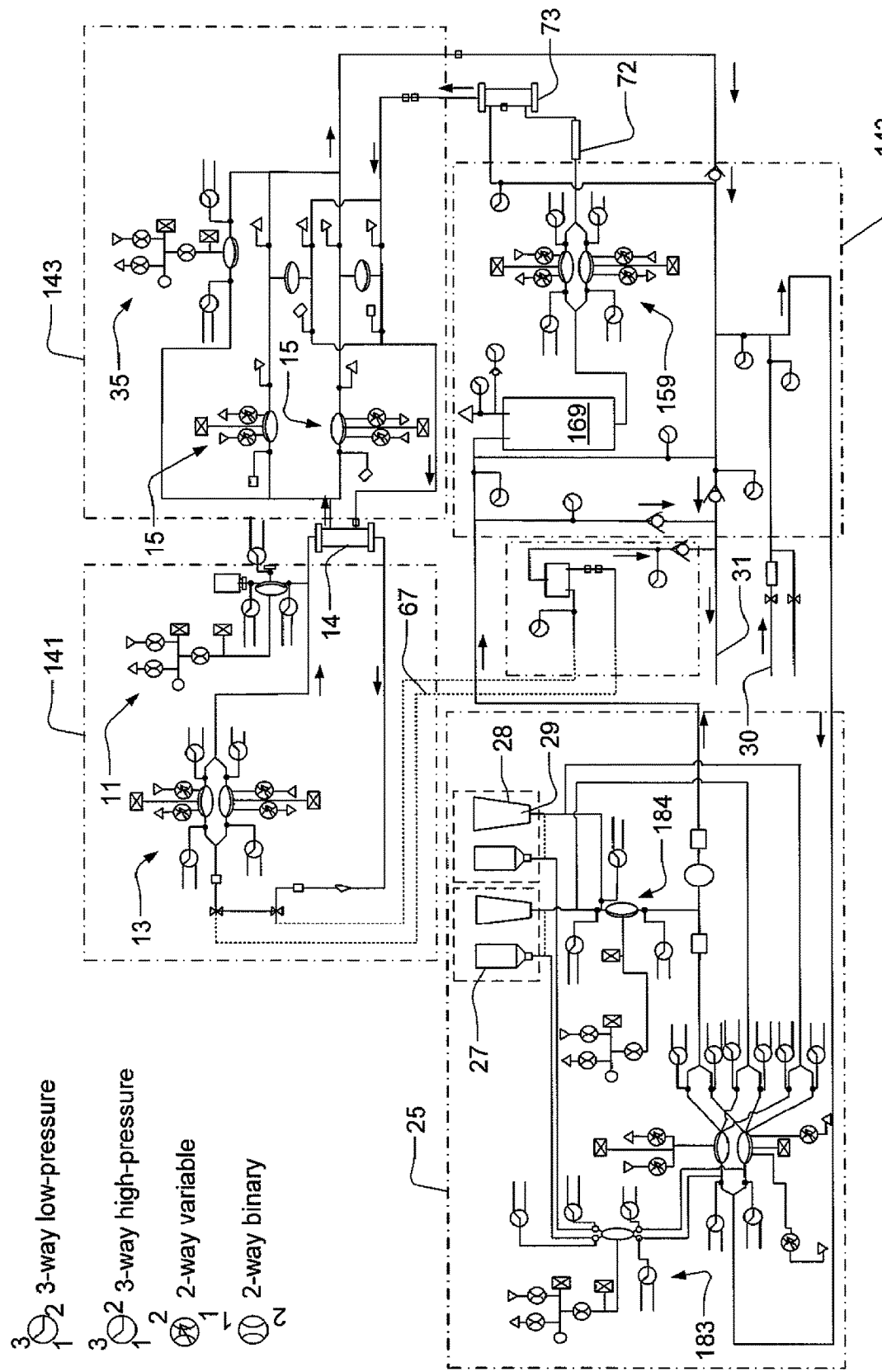

Referring now to FIG. 3B, in this embodiment, mixing circuit 25 constitutes dialysate using two sources: an acid concentrate source 27 and a combined sodium bicarbonate (NaHCO$_3$) and sodium chloride (NaCl) source. As shown in the embodiment shown in FIG. 3B, in some embodiments, the dialysate constituting system 25 may include multiples of each source. In embodiments of the method where the system is run continuously, the redundant dialysate sources allow for continuous function of the system, as one set of sources is depleted, the system uses the redundant source and the first set of sources is replaced. This process is repeated as necessary, e.g., until the system is shut down.

Figure 37:
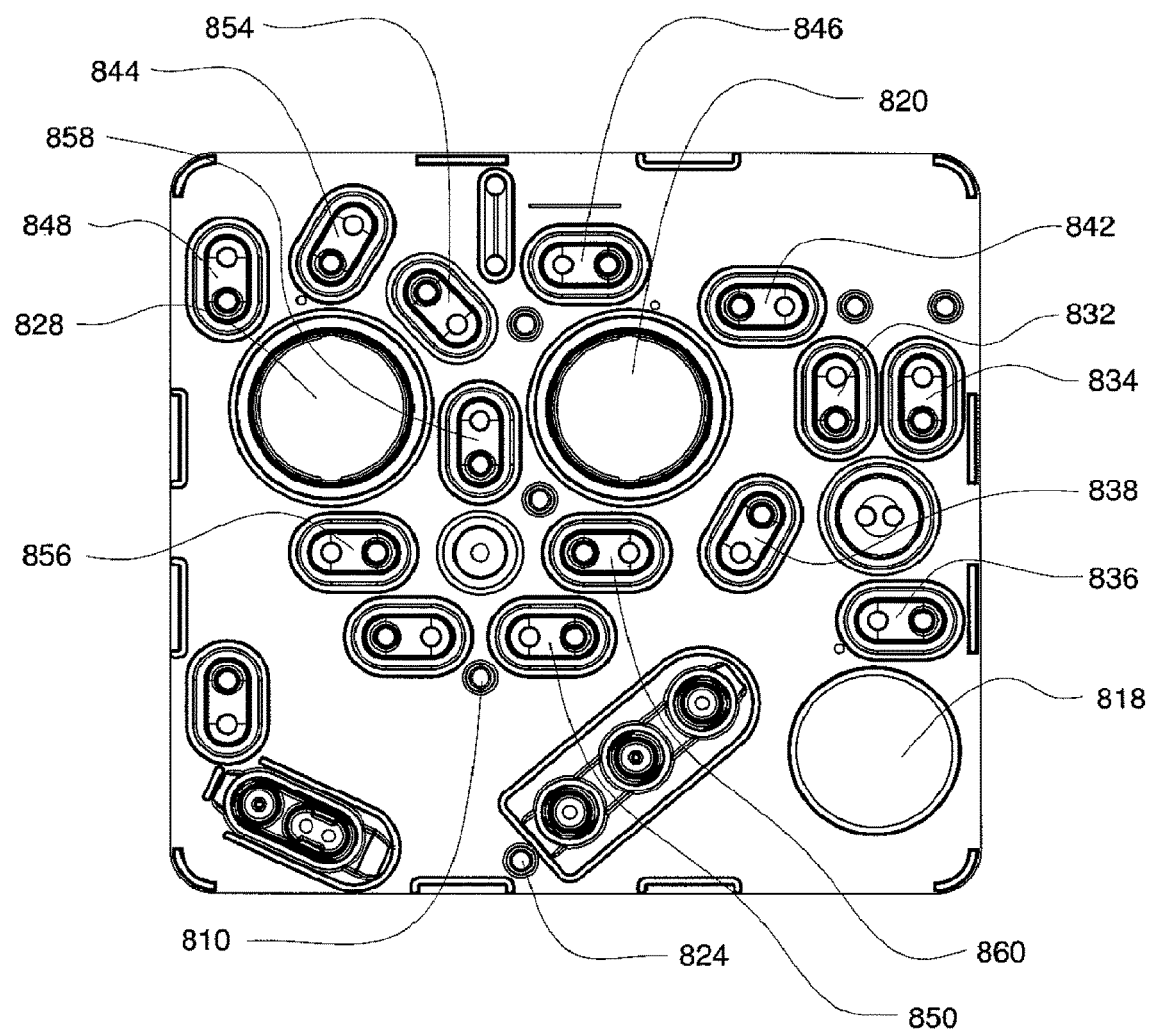
FIG. 37 is an isometric front view of an exemplary embodiment of the actuation side of the midplate of a cassette with the valves indicated corresponding to FIG. 36.

A non-limiting example of a balancing cassette is shown in FIGS. 34-36. In the exemplary fluid flow-path cassette shown in FIG. 37, valves are open individually. In this exemplary embodiment, the valves are pneumatically open. Also, in this embodiment, the fluid valves are volcano valves, as described in more detail elsewhere in this specification.

Figure 38A:
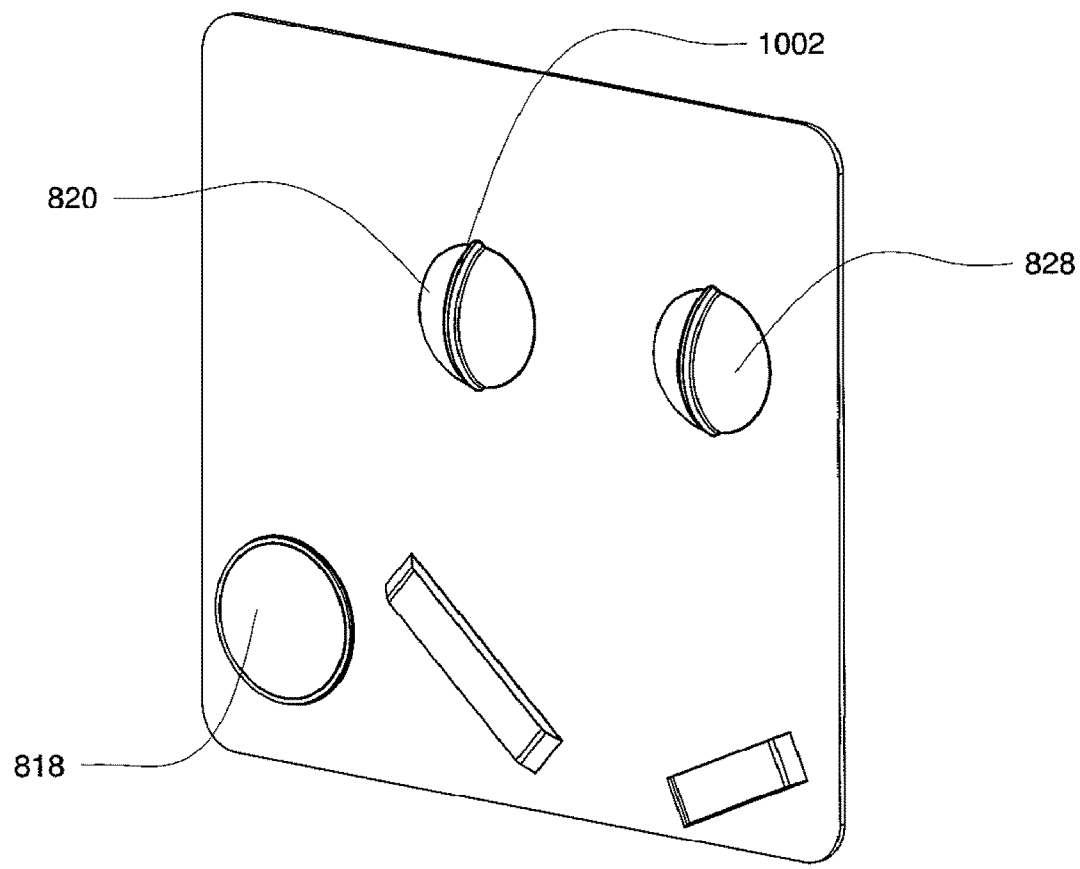
FIG. 38A is a view of an exemplary embodiment of the outer top plate of a cassette.
Figure 38B:
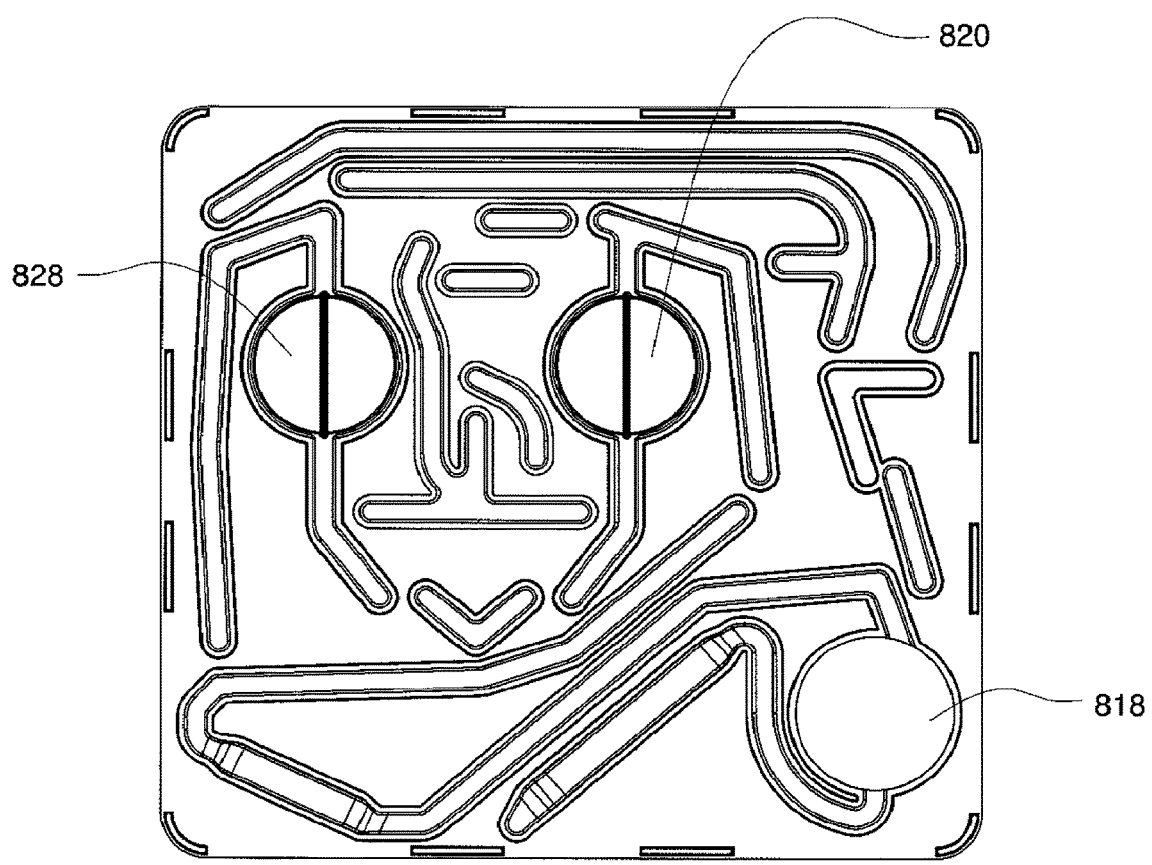
FIG. 38B is a view of an exemplary embodiment of the inner top plate of a cassette.
Figure 38C:
FIG. 38C is a side view of an exemplary embodiment of the top plate of a cassette.

Referring now to FIGS. 38A-38B, the top plate 1100 of one exemplary embodiment of the cassette is shown. In this exemplary embodiment, the pod pumps 820, 828 and the mixing chambers 818 on the top plate 1100, are formed in a similar fashion. In this exemplary embodiment, the pod pumps 820, 828 and mixing chamber 818, when assembled with the bottom plate, have a total volume of capacity of 38 ml. However, in other embodiments, the mixing chamber may have any size volume desired.

Referring now to FIG. 38B, the bottom view of the top plate 1100 is shown. The fluid paths are shown in this view. These fluid paths correspond to the fluid paths shown in FIGS. 39A-39B in the midplate 1200. The top plate 1100 and the top of the midplate 1200 form the liquid or fluid side of the cassette for the pod pumps 820, 828 and for one side of the mixing chamber 818. Thus, most of the liquid flow paths are on the top 1100 and midplates 1200. Referring to FIG. 39B, the first fluid inlet 810 and the first fluid outlet 824 are shown.

Still referring to FIGS. 38A and 38B, the pod pumps 820, 828 include a groove 1002 (in alternate embodiments, this is a groove). The groove 1002 is shown having a particular size and shape, however, in other embodiments, the size and shape of the groove 1002 may be any size or shape desirable. The size and shape shown in FIGS. 38A and 38B is one exemplary embodiment. In all embodiments of the groove 1002, the groove 1002 forms a path between the fluid inlet side and the fluid outlet side of the pod pumps 820, 828. In alternate embodiments, the groove 1002 is a groove in the inner pumping chamber wall of the pod pump.

The groove 1002 provides a fluid path whereby when the diaphragm is at the end-of-stroke there is still a fluid path between the inlet and outlet such that the pockets of fluid or air do not get trapped in the pod pump. The groove 1002 is included in both the liquid/fluid and air/actuation sides of the pod pumps 820, 828. In some embodiments, the groove 1002 may also be included in the mixing chamber 818 (see FIGS. 40A-40B with respect to the actuation/air side of the pod pumps 820, 828 and the opposite side of the mixing chamber 818. In alternate embodiments, the groove 1002 is either not included or on only one side of the pod pumps 820, 828.

In an alternate embodiment of the cassette, the liquid/fluid side of the pod pumps 820, 828 may include a feature (not shown) whereby the inlet and outlet flow paths are continuous and a rigid outer ring (not shown) is molded about the circumference of the pumping chamber is also continuous. This feature allows for the seal, formed with the diaphragm (not shown) to be maintained. Referring to FIG. 38E, the side view of an exemplary embodiment of the top plate 1100 is shown.

Figure 39A:
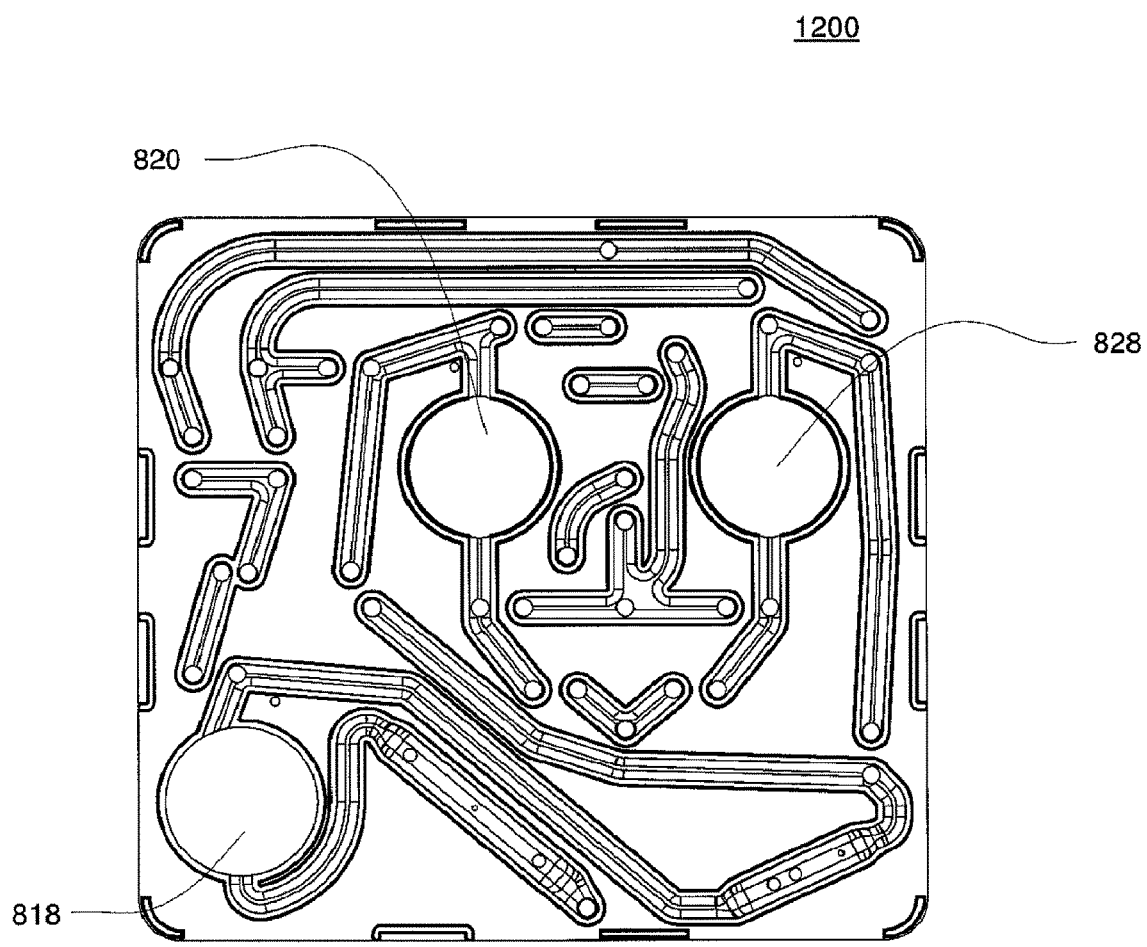
FIG. 39A is a view of an exemplary embodiment of the fluid side of the midplate of a cassette.
Figure 39B:
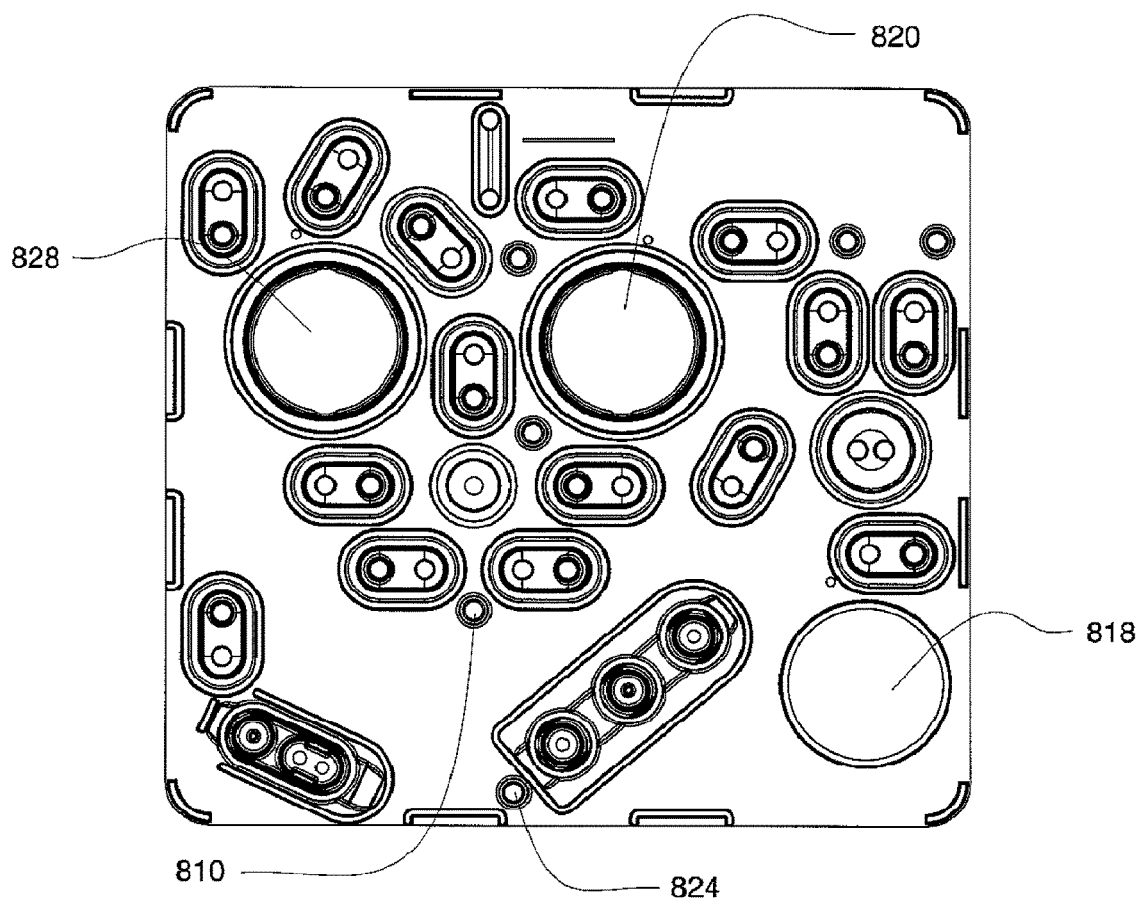
FIG. 39B is a front view of an exemplary embodiment of the air side of the midplate of a cassette.

Referring now to FIGS. 39A-39B, an exemplary embodiment of the midplate 1200 is shown. The midplate 1200 is also shown in FIGS. 37A-37F, where these Figs. correspond with FIGS. 39A-39B. Thus, FIGS. 37A-37F indicate the locations of the various valves and valving paths. The locations of the diaphragms (not shown) for the respective pod pumps 820, 828 as well as the location of the mixing chamber 818 are shown.

Referring now to FIG. 39A, in one exemplary embodiment of the cassette, sensor elements are incorporated into the cassette so as to discern various properties of the fluid being pumped. In one embodiment, three sensor elements are included. However, in this embodiment, six sensor elements (two sets of three) are included. The sensor elements are located in the sensor cell 1314, 1316. In this embodiment, a sensor cell 1314, 1316 is included as an area on the cassette for sensor(s) elements. In one embodiment, the three sensor elements of the two sensor cells 1314, 1316 are housed in respective sensor elements housings 1308, 1310, 1312 and 1318, 1320, 1322. In one embodiment, two of the sensor elements housings 1308, 1312 and 1318, 1320 accommodate conductivity sensor elements and the third sensor elements housing 1310, 1322 accommodates a temperature sensor element. The conductivity sensor elements and temperature sensor elements may be any conductivity or temperature sensor elements in the art. In one embodiment, the conductivity sensors are graphite posts. In other embodiments, the conductivity sensor elements are posts made from stainless steel, titanium, platinum or any other metal coated to be corrosion resistant and still be electrically conductive. The conductivity sensor elements will include an electrical lead that transmits the probe information to a controller or other device. In one embodiment, the temperature sensor is a thermistor potted in a stainless steel probe. However, in alternate embodiments, a combination temperature and conductivity sensor elements is used similar to the one described in a U.S. patent application Ser. No. 11/871,821, published as US PGPub No. 2008/0240929 on Oct. 2, 2008, entitled "Sensor Apparatus Systems, Devices and Methods," filed Oct. 12, 2007.

In alternate embodiments, there are either no sensors in the cassette or only a temperature sensor, only one or more conductivity sensors or one or more of another type of sensor.

Figure 39C:
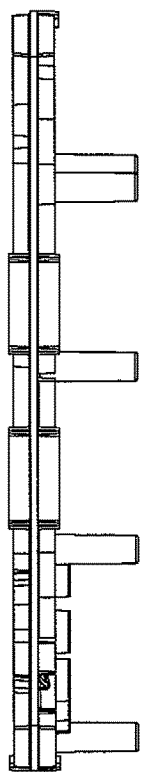
FIG. 39C is a side view of an exemplary embodiment of the midplate of a cassette.
Figure 40A:
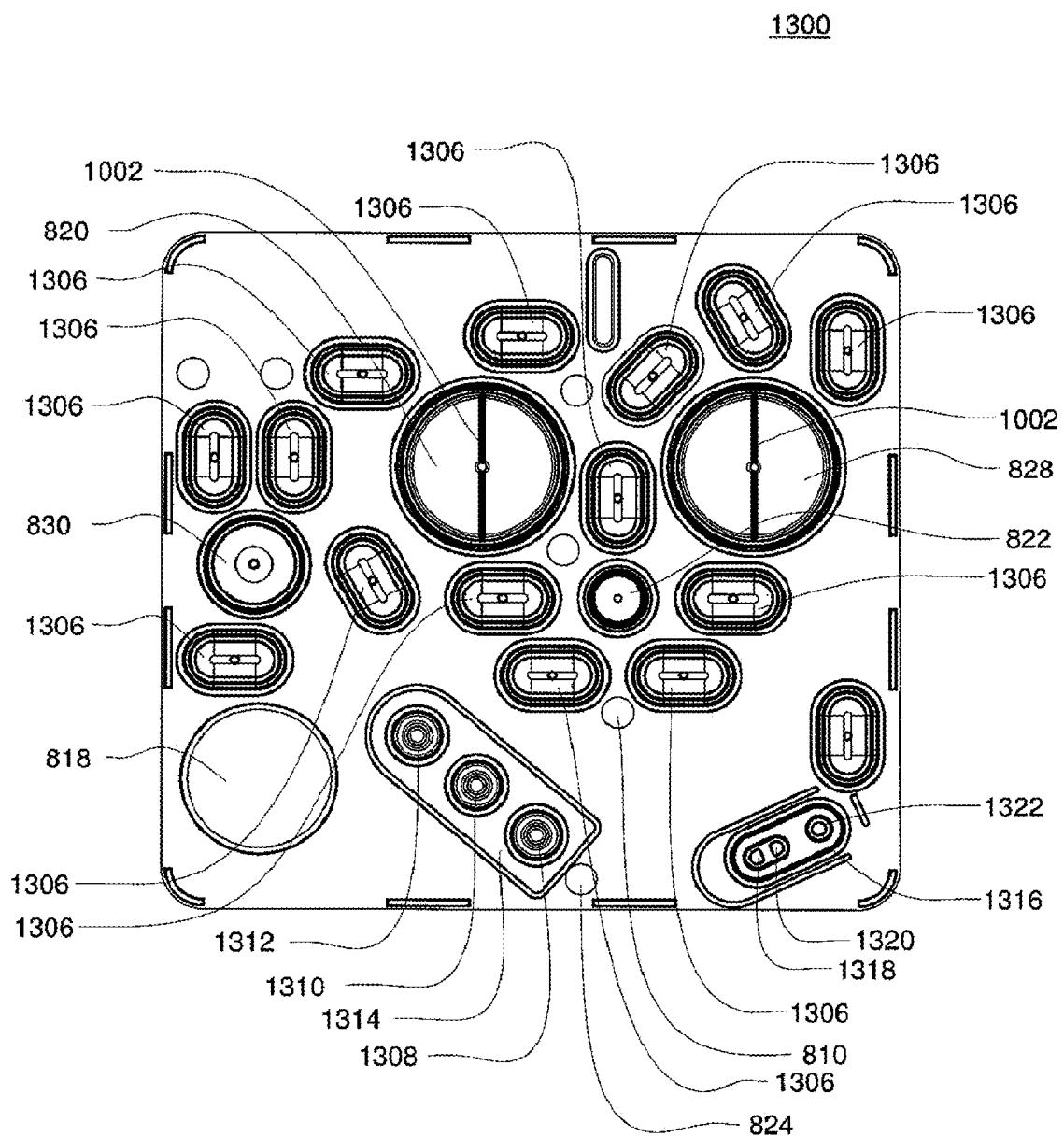
FIG. 40A is a view of an exemplary embodiment of the inner side of the bottom plate of a cassette.
Figure 40B:
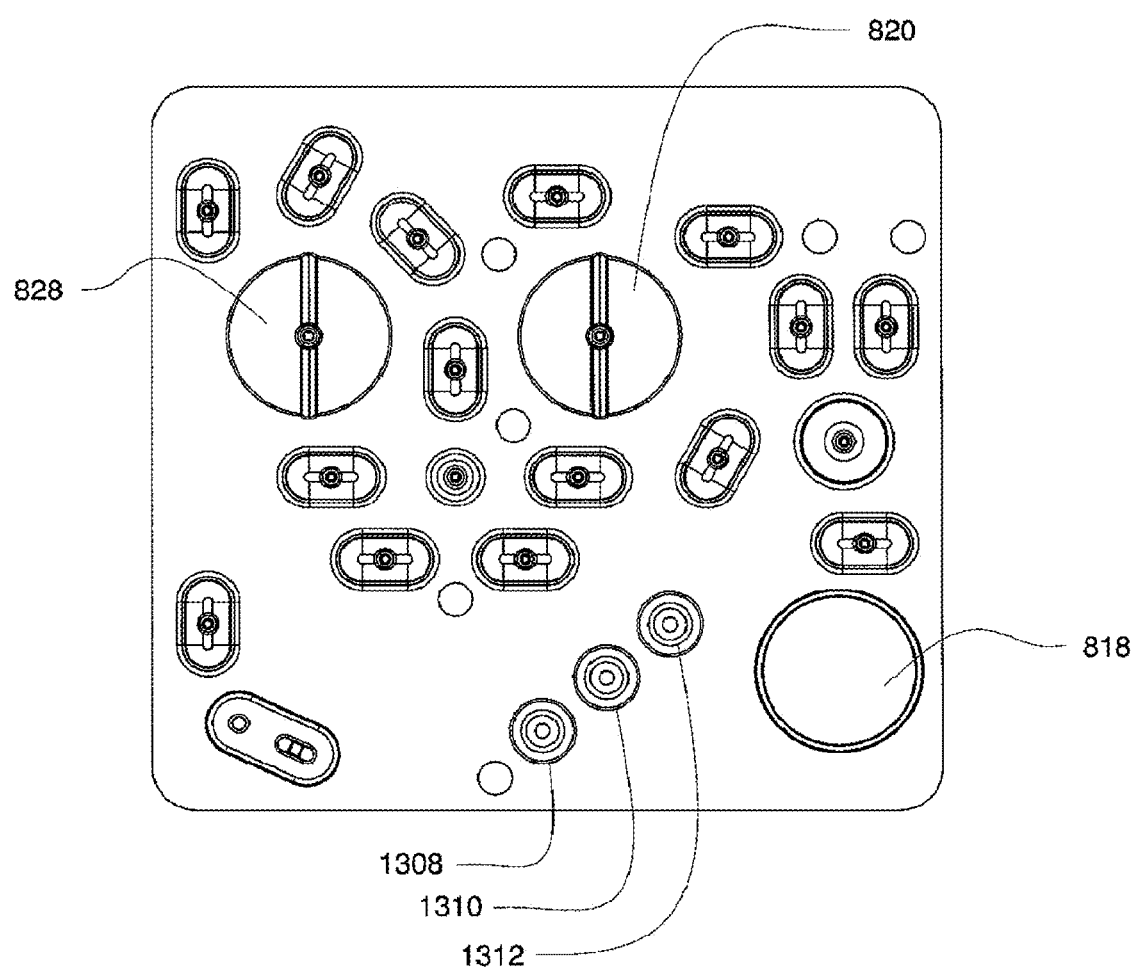
FIG. 40B is a view of an exemplary embodiment of the outer side of the bottom plate of a cassette.

Referring now to FIG. 39C, the side view of an exemplary embodiment of the midplate 1200 is shown. Referring now to FIGS. 40A-40B, the bottom plate 1300 is shown. Referring first to FIG. 40A, the inner or inside surface of the bottom plate 1300 is shown. The inner or inside surface is the side that contacts the bottom surface of the midplate (not shown). The bottom plate 1300 attaches to the air or actuation lines (not shown). The corresponding entrance holes for the air that actuates the pod pumps 820, 828 and valves (not shown, see FIGS. 37A-37F) in the midplate 1300 can be seen. Holes 810, 824 correspond to the first fluid inlet and first fluid outlet shown in FIG. 39B, 810, 824 respectively. The corresponding halves of the pod pumps 820, 828 and mixing chamber 818 are also shown, as are the grooves 1002 for the fluid paths. The actuation holes in the pumps are also shown. Unlike the top plate, the bottom plate 1300 corresponding halves of the pod pumps 820, 828 and mixing chamber 818 make apparent the difference between the pod pumps 820, 828 and mixing chamber 818. The pod pumps 820, 828 include an air/actuation path on the bottom plate 1300, while the mixing chamber 818 has identical construction to the half in the top plate. The mixing chamber 818 mixes liquid and therefore, does not include a diaphragm (not shown) nor an air/actuation path. The sensor cell 1314, 1316 with the three sensor element housings 1308, 1310, 1312 and 1318, 1320, 1322 are also shown.

Figure 40C:
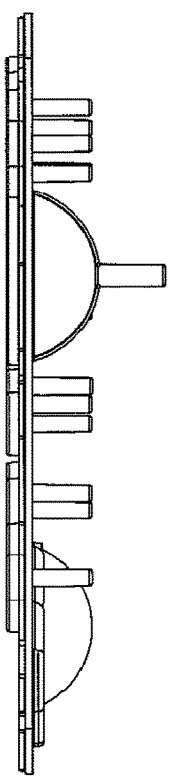
FIG. 40C is a side view of an exemplary embodiment of the midplate of a cassette.

Referring now to FIG. 40B, the actuation ports 1306 are shown on the outside or outer bottom plate 1300. An actuation source is connected to these actuation ports 1306. Again, the mixing chamber 818 does not have an actuation port as it is not actuated by air. Referring to FIG. 40C, a side view of the exemplary embodiment of the bottom plate 1300 is shown.

As described above, in various aspects of the invention, one or more fluid circuits may be implemented on a cassette, such as the blood flow circuit, the balancing circuit, the directing circuit, and/or the mixing circuit, etc. Other cassettes may be present, e.g., a sensing cassette as is disclosed in a U.S. Pat. No. 8,491,184, issued Jul. 23, 2013, entitled "Sensor Apparatus Systems, Devices and Methods," incorporated herein by reference. In some embodiments, some or all of these circuits are combined in a single cassette. In alternate embodiments, these circuits are each defined in respective cassettes. In still other embodiments, two or more of the fluid circuits are included on one cassette. In some cases, two, three, or more cassettes may be immobilized relative to each other, optionally with fluidic connections between the cassettes. For instance, in one embodiment, two cassettes may be connected via a pump, such as a pod pump as previously described. The pod pump may include a rigid chamber with a flexible diaphragm dividing each chamber into a first side and a second side, and the sides may be used for various purposes as noted above.

Non-limiting examples of cassettes that may be used in the present invention include those described in U.S. patent application Ser. No. 11/871,680, filed Oct. 12, 2007 and issued as U.S. Pat. No. 8,273,049 on Sep. 25, 2012, entitled "Pumping Cassette"; U.S. patent application Ser. No. 11/871,712, filed Oct. 12, 2007 and issued as U.S. Pat. No. 8,317,492 on Nov. 27, 2012, entitled "Pumping Cassette"; U.S. patent application Ser. No. 11/871,787, filed Oct. 12, 2007, entitled "Pumping Cassette"; U.S. patent application Ser. No. 11/871,793, filed Oct. 12, 2007, entitled "Pumping Cassette"; U.S. patent application Ser. No. 11/871,803, filed Oct. 12, 2007 and issued as U.S. Pat. No. 7,967,022 on Jun. 28, 2011, entitled "Cassette System Integrated Apparatus"; or in a U.S. patent application Ser. No. 12/038,648, filed Feb. 27, 2008 and issued as U.S. Pat. No. 8,042,563 on Oct. 25, 2011, entitled "Cassette System Integrated Apparatus". Each of these is incorporated by reference herein in their entireties.

A cassette may also include various features, such as pod pumps, fluid lines, valves, or the like. The cassette embodiments shown and described in this description include exemplary and various alternate embodiments. However, any variety of cassettes is contemplated that include a similar functionality. Although the cassette embodiments described herein are implementations of the fluid schematics as shown in the figures, in other embodiments, the cassette may have varying fluid paths and/or valve placement and/or pod pump placements and numbers and thus, is still within the scope of the invention.

In one example embodiment, a cassette may includes a top plate, a midplate and a bottom plate. There are a variety of embodiments for each plate. In general, the top plate includes pump chambers and fluid lines, the midplate includes complementary fluid lines, metering pumps and valves and the bottom plate includes actuation chambers (and in some embodiments, the top plate and the bottom plate include complementary portions of a balancing chamber or a pod pump).

In general, the diaphragms are located between the midplate and the bottom plate, however, with respect to a balancing chamber or a pod pump, a portion of a diaphragm is located between the midplate and the top plate. Some embodiments include where the diaphragm is attached to the cassette, either overmolded, captured, bonded, press fit, welded in or any other process or method for attachment, however, in the exemplary embodiments, the diaphragms are separate from the top plate, midplate and bottom plate until the plates are assembled.

The cassettes may be constructed of a variety of materials. Generally, in the various embodiments, the materials used are solid and non-flexible. In one embodiment, the plates are constructed of polysulfone, but in other embodiments, the cassettes are constructed of any other solid material and in exemplary embodiment, of any thermoplastic or thermoset.

In one exemplary embodiment, the cassettes are formed by placing diaphragms in their correct locations (e.g., for one or more pod pumps, if such pod pumps are present), assembling the plates in order, and connecting the plates. In one embodiment, the plates are connected using a laser welding technique. However, in other embodiments, the plates may be glued, mechanically fastened, strapped together, ultrasonically welded or any other mode of attaching the plates together.

In practice, the cassette may be used to pump any type of fluid from any source to any location. The types of fluid include nutritive, normutritive, inorganic chemicals, organic chemicals, bodily fluids or any other type of fluid. Additionally, fluid in some embodiments include a gas, thus, in some embodiments, the cassette is used to pump a gas.

The cassette serves to pump and direct the fluid from and to the desired locations. In some embodiments, outside pumps pump the fluid into the cassette and the cassette pumps the fluid out. However, in some embodiments, the pod pumps serve to pull the fluid into the cassette and pump the fluid out of the cassette.

As discussed above, depending on the valve locations, control of the fluid paths is imparted. Thus, the valves being in different locations or additional valves are alternate embodiments of this cassette. Additionally, the fluid lines and paths shown in the figures described above are mere examples of fluid lines and paths. Other embodiments may have more, less and/or different fluid paths. In still other embodiments, valves are not present in the cassette.

The number of pod pumps (if pod pumps are present within the cassette) described above may also vary depending on the embodiment. For example, although the various embodiments shown and described above include two pod pumps, in other embodiments, the cassette includes one pod pump. In still other embodiments, the cassette includes more than two pod pumps, or there may be no pod pumps present. The pod pumps may be single pumps or multiple pod pumps may be present that can work in tandem, e.g., to provide a more continuous flow, as discussed above. Either or both may be used in various embodiments of the cassette. However, as noted above, in some cases, there may be pod pumps not present on a cassette, but contained between two or more cassettes. Non-limiting examples of such systems can be seen in a U.S. patent application Ser. No. 12/038,648, filed Feb. 27, 2008 and issued as U.S. Pat. No. 8,042,563 on Oct. 25, 2011, entitled "Cassette System Integrated Apparatus," incorporated by herein reference.

The various fluid inlets and fluid outlets disclosed herein may be fluid ports in some cases. In practice, depending on the valve arrangement and control, a fluid inlet may be a fluid outlet. Thus, the designation of the fluid port as a fluid inlet or a fluid outlet is only for description purposes. The various embodiments have interchangeable fluid ports. The fluid ports are provided to impart particular fluid paths onto the cassette. These fluid ports are not necessarily all used all of the time; instead, the variety of fluid ports provides flexibility of use of the cassette in practice.

Figure 50A:
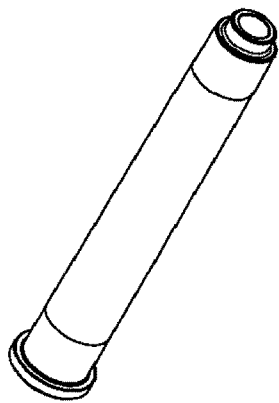
FIG. 50A is an exploded view of one embodiment of a check valve fluid line in the cassette system.
Figure 50A:
Figure 50A:
Figure 50B:
FIG. 50B is an exploded view of one embodiment of a check valve fluid line in the cassette system.
Figure 50B:
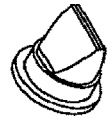
Figure 50B:
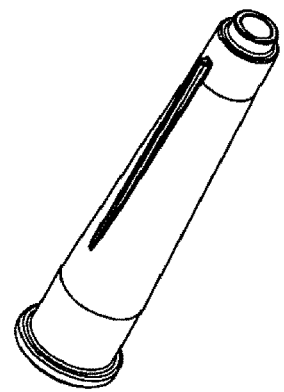
Figure 50C:
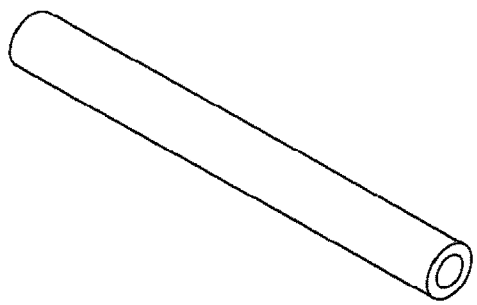
FIG. 50C is an isometric view of an exemplary embodiment of a fluid line in the cassette system.

Another non-limiting example of a cassette is shown with reference to FIG. 46. Referring now to FIG. 46A, the assembled cassette system integrated is shown. The mixing cassette 500, middle cassette 600 and balancing cassette 700 are linked by fluid lines or conduits. The pods are between the cassettes. Referring now to FIGS. 46B and 46C, the various views show the efficiency of the cassette system integrated. The fluid lines or conduits 1200, 1300, 1400 are shown in FIG. 50A, FIG. 50B and FIG. 50C respectively. The fluid flows between the cassettes through these fluid lines or conduits. Referring now to FIGS. 50A and 50B, these fluid lines or conduits represent larger 1300 and smaller 1200 check valve fluid lines. In the exemplary embodiment, the check valves are duck bill valves; however, in other embodiments, any check valve may be used. Referring to FIG. 50C, fluid line or conduit 1400 is a fluid line or conduit that does not contain a check valve. For purposes of this description, the terms "fluid line" and "conduit" are used with respect to 1200, 1300 and 1400 interchangeably.

Figure 46A:
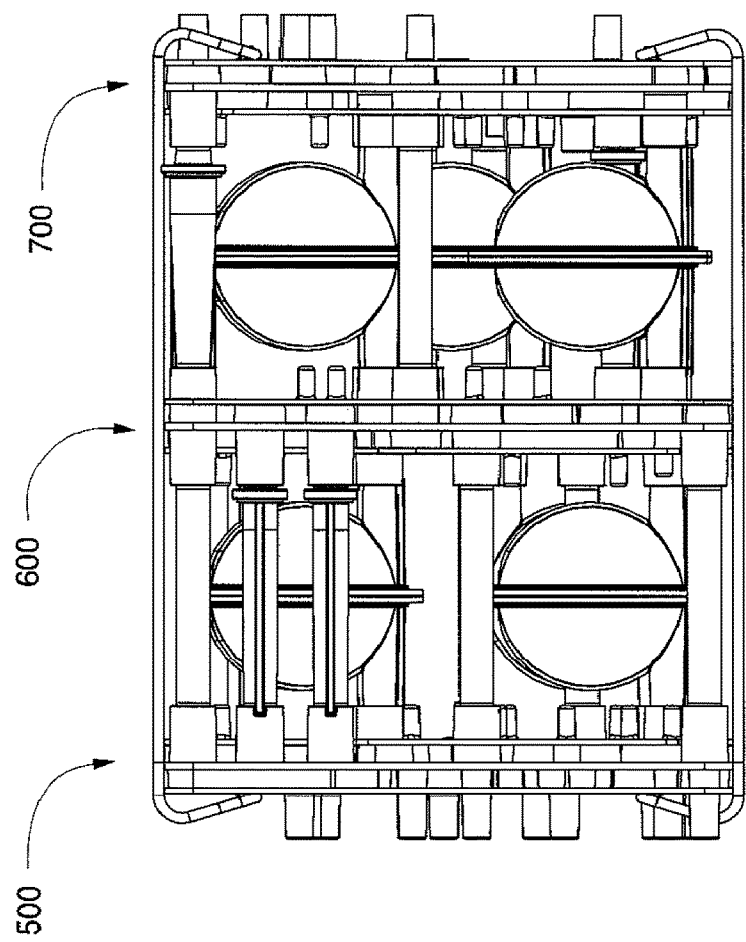
FIG. 46A is a front view of the assembled exemplary embodiment of the cassette system.
Figure 46B:
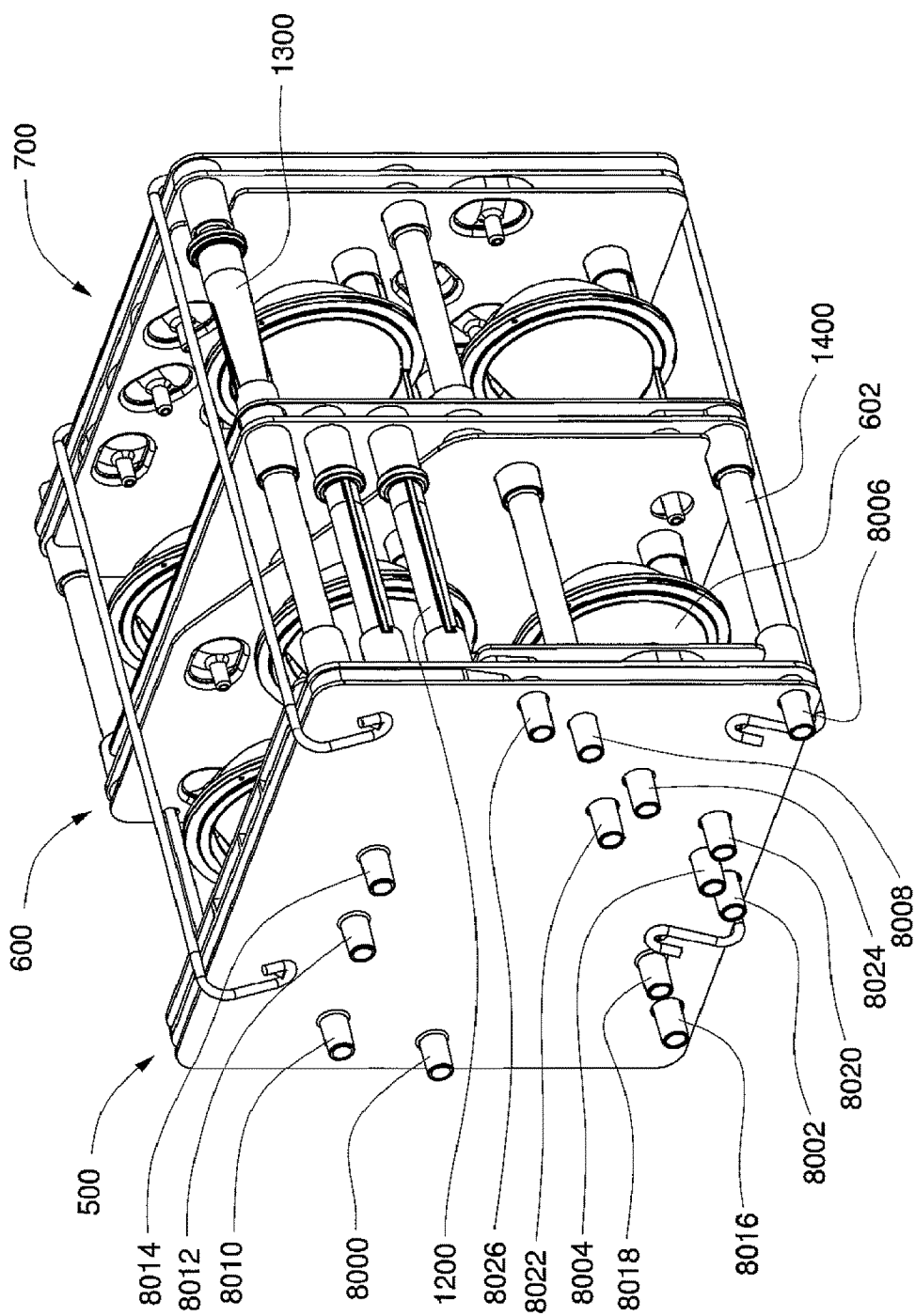
FIG. 46B is an isometric view of the assembled exemplary embodiment of the cassette system.
Figure 46C:
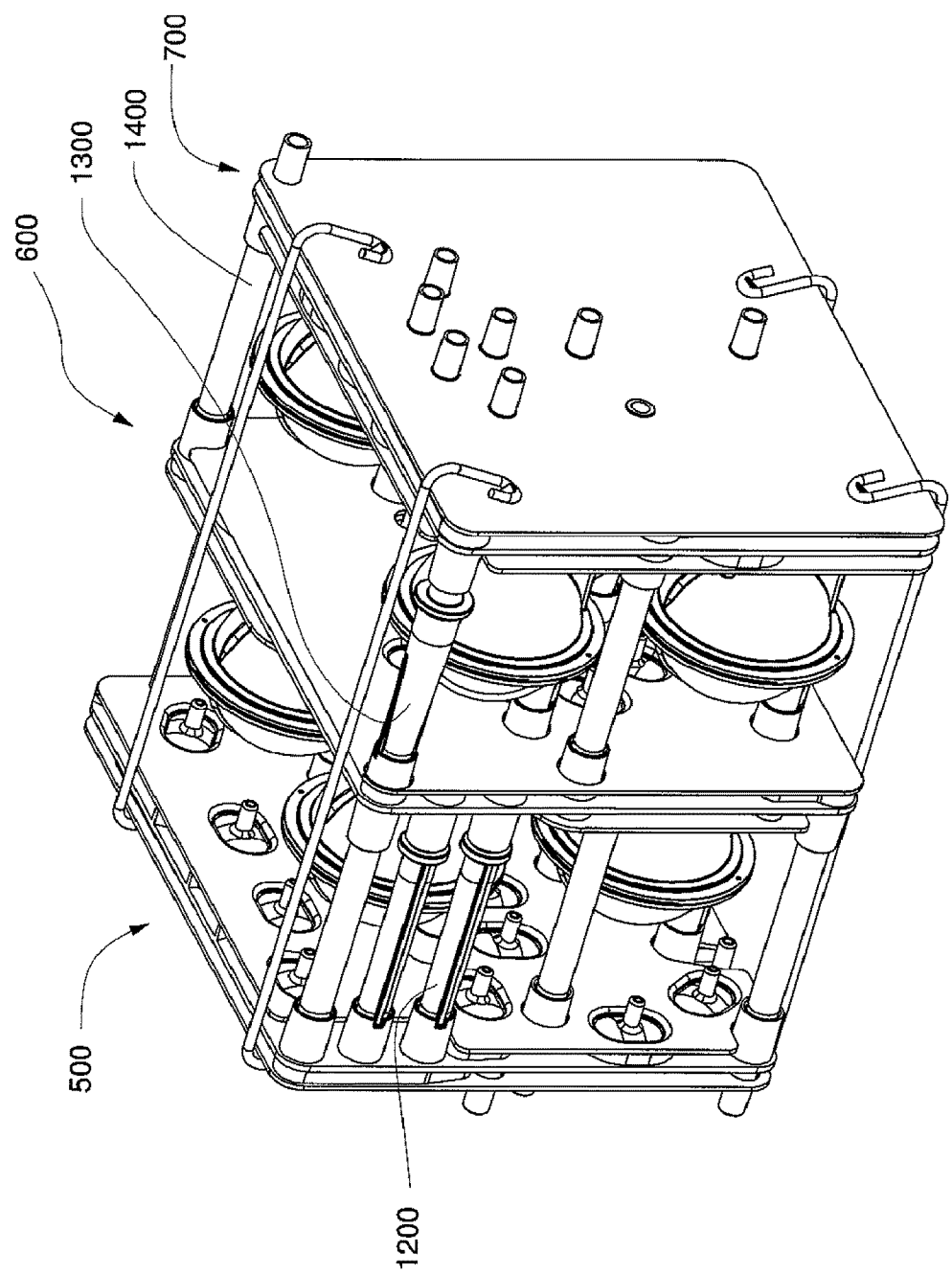
FIG. 46C is an isometric view of the assembled exemplary embodiment of the cassette system.
Figure 51A:
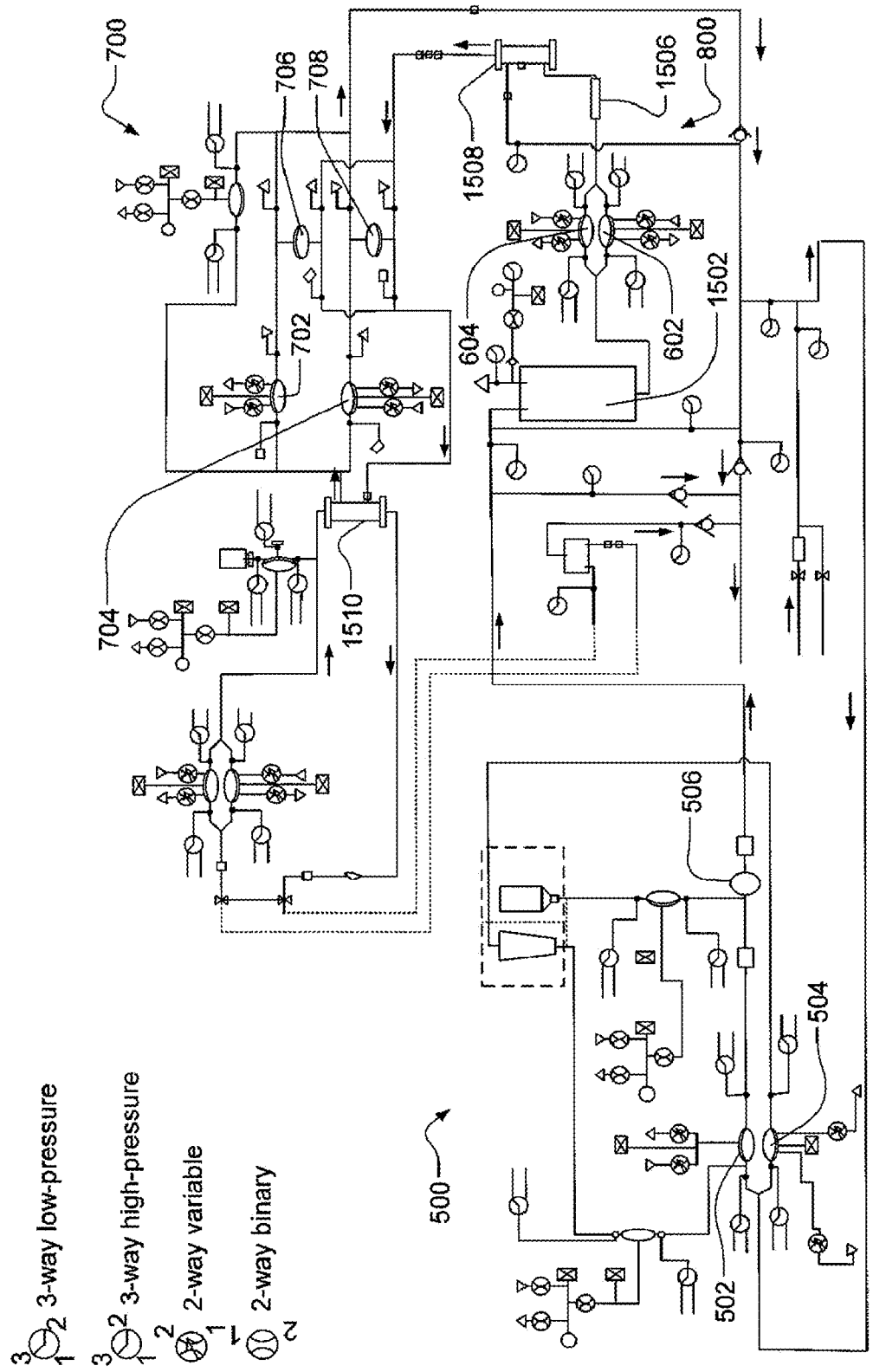
FIG. 51A is one embodiment of the fluid flow-path schematic of the cassette system integrated.

Referring now to FIGS. 46B and 46C, and FIG. 51A, the following is a description of one embodiment of the fluid flow through the various cassettes. For ease of description, the fluid flow will begin with the mixing cassette 500. Referring now to FIG. 46B and FIG. 51A, the fluid side of the mixing cassette 500 is shown. The fluid side includes a plurality of ports 8000, 8002, 8004, 8006, 8008 and 8010-8026 that are either fluid inlets or fluid outlets. In the various embodiments, the fluid inlets and outlets may include one or more fluid inlets for reverse osmosis ("RO") water 8004, bicarbonate, an acid, and a dialysate 8006. Also, one or more fluid outlets, including a drain, acid 8002 and at least one air vent outlet as the vent for the dialysate tank. In one embodiment, a tube (not shown) hangs off the outlet and is the vent (to prevent contamination). Additional outlets for water, bicarbonate and water mixture, dialysate mixture (bicarbonate with acid and water added) are also included.

Figure 46D:
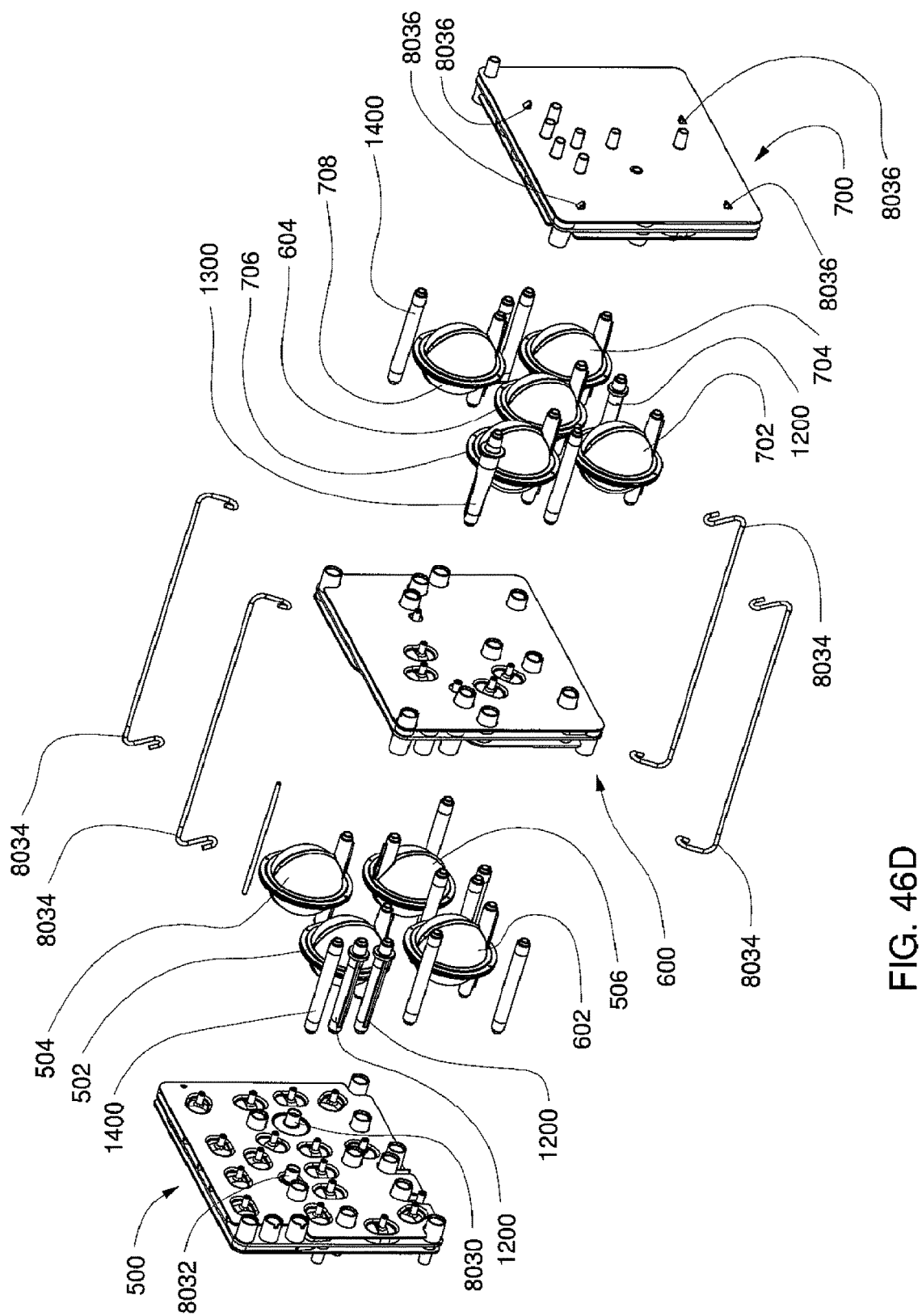
FIG. 46D is an exploded view of the assembled exemplary embodiment of the cassette system.
Figure 46E:
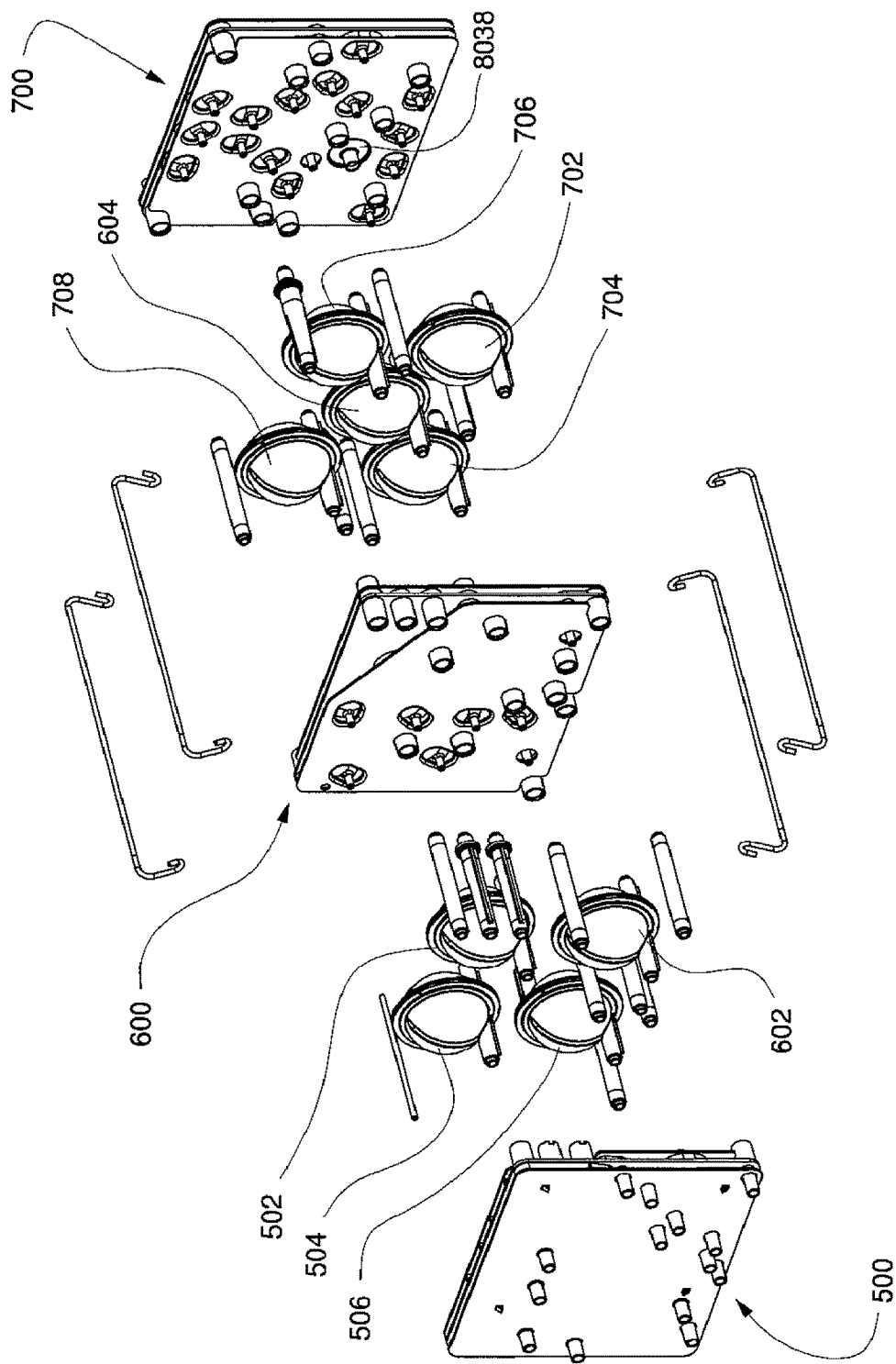
FIG. 46E is an exploded view of the assembled exemplary embodiment of the cassette system.

The dialysate flows out of the mixing cassette 500, to a dialysate tank (not shown, shown as 1502 in FIG. 51A) and then through a conduit to the inner dialysate cassette 700 (pumped by the outer dialysate cassette 600 pod pumps 602 and 604 (604 not shown, shown in FIGS. 46D and 46E). The fluid paths within the cassettes may vary. Thus, the location of the various inlet and outlets may vary with various cassette fluid paths.

Figure 51B:
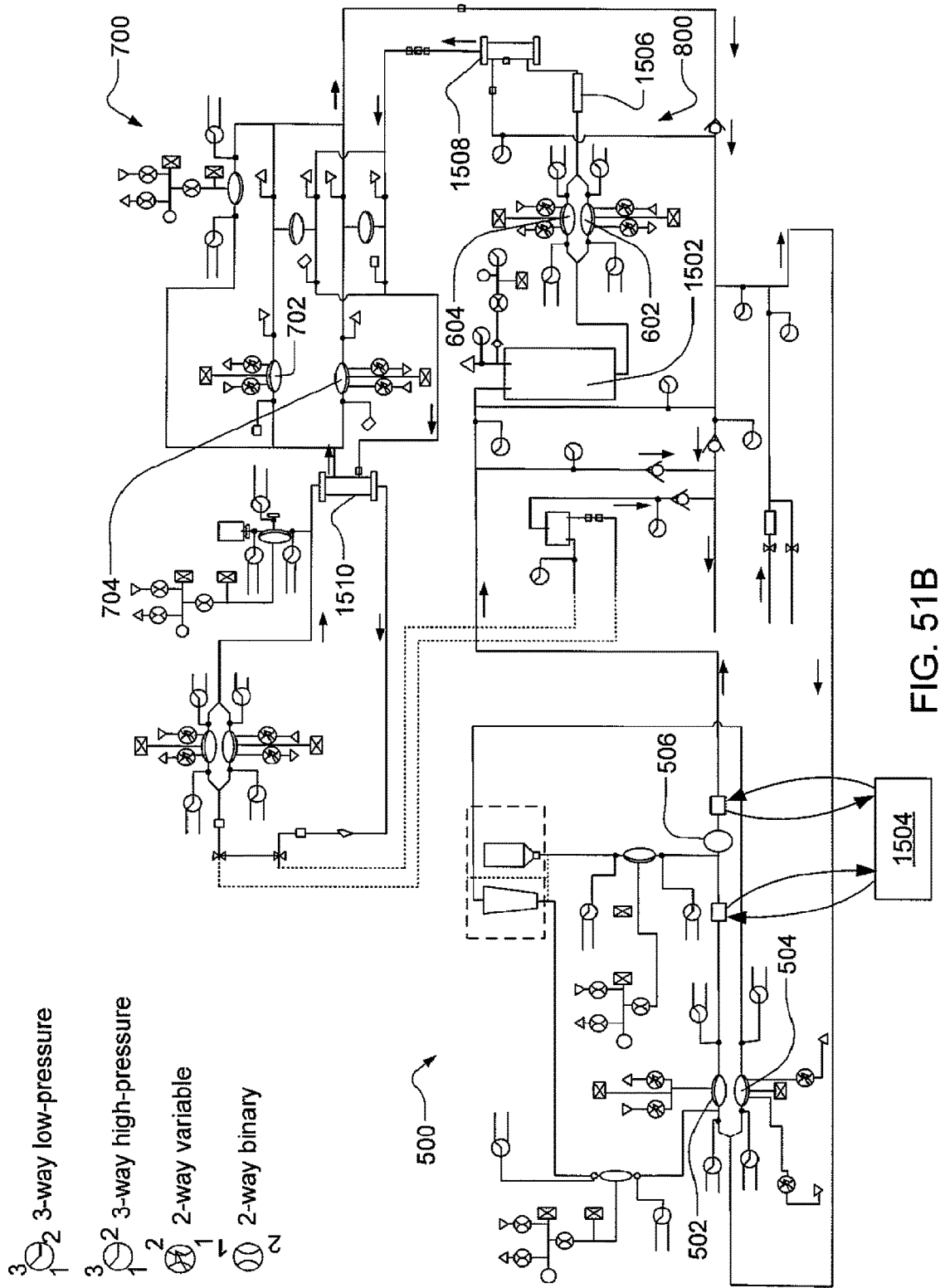
FIG. 51B is one embodiment of the fluid flow-path schematic of the cassette system integrated.
Figure 52C:
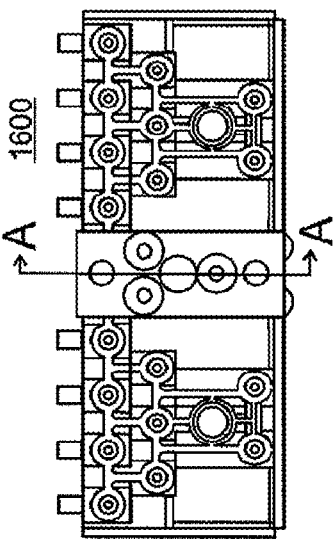
FIGS. 52A-52F are various views of one embodiment of the block for connecting the pneumatic tubes to the manifold according to one embodiment of the present system.
Figure 52F:
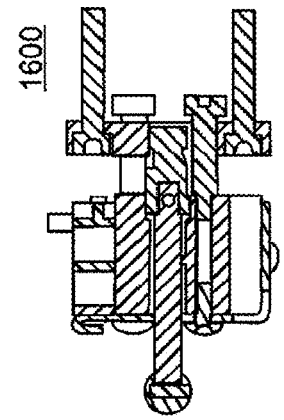
Figure 52B:
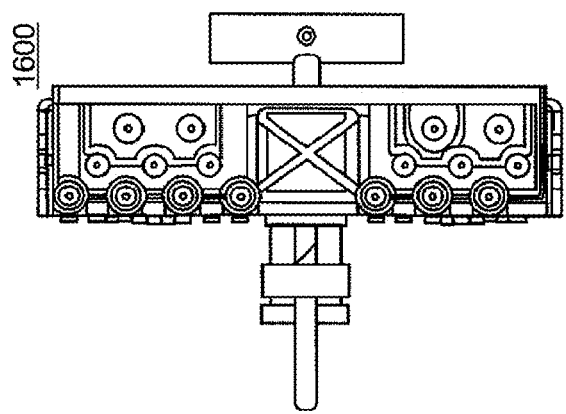
Figure 52E:
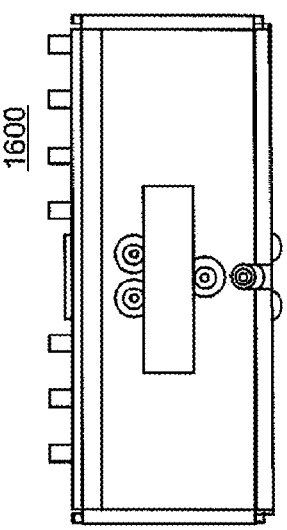
Figure 52A:
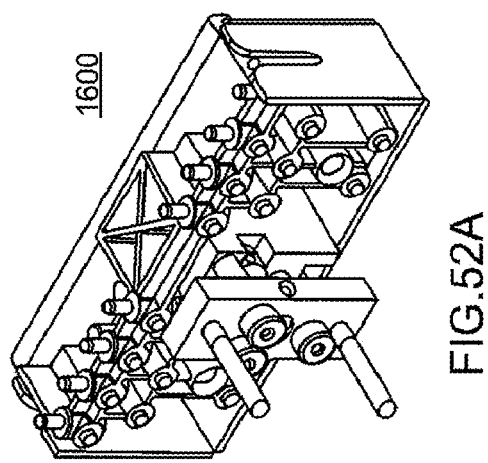
Figure 52D:
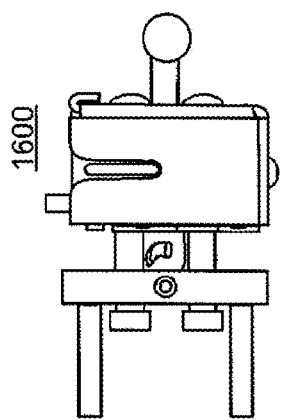

Referring now to FIG. 51B, in one embodiment of the cassette system, the condo cells, conductivity and temperature sensors, are included in a separate cassette 1504 outside of the cassette system shown in FIGS. 46A-46C. This outside sensor cassette 1504 may be one of those described in U.S. Pat. No. 8,491,184, issued Jul. 23, 2013, entitled "Sensor Apparatus Systems, Devices and Methods," and hereby incorporated by reference in its entirety.

The fluid flow-path for this embodiment is shown in FIG. 51B. In this embodiment, during the mixing process for the dialysate, the bicarbonate mixture leaves the mixing cassette 500 and flows to an outside sensor cassette, and then flows back into the mixing cassette 500. If the bicarbonate mixture meets pre-established thresholds, acid is then added to the bicarbonate mixture. Next, once the bicarbonate and acid are mixed in the mixing chamber 506, the dialysate flows out of the cassette into the sensor cassette and then back to the mixing cassette 500.

Referring now to FIG. 46D, the mixing cassette 500 include a pneumatic actuation side. In the block shown as 500, there are a plurality of valves and two pumping chambers 8030, 8032 build into the cassette 500 for pumping or metering the acid or bicarbonate. In some embodiments, additional metering pumps, or less metering pumps, are included. The metering pumps 8030, 8032 can be any size desired. In some embodiments, the pumps are different sizes with respect to one another, however, in other embodiments, the pumps are the same size with respect to one another. For example, in one embodiment, the acid pump is smaller than the bicarbonate pump. This may be more efficient and effective when using a higher concentration acid, as it may be desirable to use a smaller pump for accuracy and also, it may be desirable for control schemes to have a smaller pump so as to use full strokes in the control rather than partial strokes.

The conduits 1200, 1300 include a check-valve. These conduits 1200,1300 allow for one-way flow. In the exemplary embodiment, these conduits 1200, 1300 all lead to drain. Referring to the flow-path schematic FIG. 51A, the locations of these check-valve conduits are apparent. In the embodiment shown, any fluid that is meant for drain flows through the mixing cassette 500. Referring again to FIG. 46B, a fluid drain port 8006 is located on the fluid side of the cassette 500.

Once the dialysate is mixed, and after the dialysate flows to the sensor cassette (1504 in FIG. 51B) and it is determined that the dialysate is not within set parameters/thresholds, then the dialysate will be pumped back into the mixing cassette 500, through a plain conduit 1400 then to the outer dialysate cassette 600, then back through conduit a check valve conduit 1200 and then through the mixing cassette 500 to the drain fluid outlet.

Referring now to FIGS. 46D and 46E, the various pods 502, 504, 506, 602, 604, 702, 704, 706, 708 are shown. Each of the pod housings are constructed identically, however, the inside of the pod housing is different depending on whether the pod is a pod pump 502, 504 602, 604, 702, 704 a balancing chamber pods 706, 708 or a mixing chamber pod 504.

Referring now to FIGS. 46D and 46E, together with FIGS. 51A and 51B, the various pods are shown both in the fluid flow-path and on the cassette system. Pod 502 is the water pod pump and 504 is the bicarbonate water pod pump (sends water to the bicarbonate) of the mixing cassette 500. Pod 506 is the mixing chamber. Once the dialysate is mixed in the mixing chamber 506, and then flows from the mixing cassette 500 to the sensor cassette 1504, and it is determined that the dialysate qualifies as acceptable, then the dialysate flows to the dialysate tank 1502 through the mixing cassette dialysate tank outlet. However, if the dialysate is rendered unacceptable, then the fluid is pumped back into the cassette 500, then through a 1400 conduit, to the outer dialysate cassette 600 and then pumped through a 1200 check valve conduit, through the mixing cassette 500 and out the drain outlet.

Referring to FIGS. 46A-46C, together with FIGS. 51A-B, the outer dialysate cassette is shown 600 between the mixing cassette 500 and the inner dialysate cassette 700. Pod pumps 602, 604, pump the dialysate from the dialysate tank 1502 and send it to the balancing chambers 706,708 in the inner dialysate cassette 700 (driving force for the dialysate solution). The outer dialysate cassette 600 pushes the dialysate into the inner dialysate cassette (i.e., the pumps in the inner dialysate cassette 700 do not draw the dialysate in). Thus, from the outer dialysate cassette 600, the dialysate is pumped from the dialysate tank 1502, through a heater 1506 and through an ultrafilter 1508, and then into the inner dialysate cassette 700.

Still referring now to FIGS. 46D and 46E, together with FIGS. 51A-B, the inner dialysate cassette 700 includes a metering pod 8038 (i.e., an ultra filtration metering pod) and includes balancing pods 706, 708 and pod pumps 702, 704. The inner dialysate cassette 700 also includes fluid outlets and inlets. These inlets and outlets include the outlet to the dialyzer 1510, the inlet from the dialyzer 1510, and a dialysate inlet (the ultrafilter 1508 connects to a port of the inner dialysate cassette). Fluid inlets and outlets are also included for the DCA and DCV connections during priming and disinfection. Various conduits (1200,1300,1400) serve as fluid connections between the cassettes 500, 600, 700 and are used for dialysate fluid flow as well as fluid to pass through in order to drain through the mixing cassette 500. The largest check valve 1300 (also shown in FIG. 50B) is the largest checkvalve, and is used during disinfection. This tube is larger in order to accommodate, in the preferred embodiment, blood clots and other contaminants that flow through the conduits during disinfection.

The valves and pumps of the cassette system are pneumatically actuated in the exemplary embodiment. The pneumatics attach to the cassettes via individual tubes. Thus, each pump, balancing pod, or valve includes an individual tube connection to a pneumatic actuation manifold (not shown). Referring now to FIGS. 52A-F, the tubes are connected, in the exemplary embodiment, to at least one block, 1600. In some embodiments, more than one block is used to connect the various tubes. The block 1600 is dropped into the manifold and then connected to the pneumatics actuators appropriately. This allows for easy connection of the pneumatic tubes to the manifold.

Referring again to FIG. 46D, the cassette system includes springs 8034, in one embodiment, to aid in holding the system together. The springs 8034 hook onto the mixing cassette 500 and inner dialysate cassette 700 via catches 8036. However, in other embodiments, any other means or apparatus to assist in maintaining the system in appropriate orientation may be used including, but not limited to, latching means or elastic means, for example.

Figure 47A:
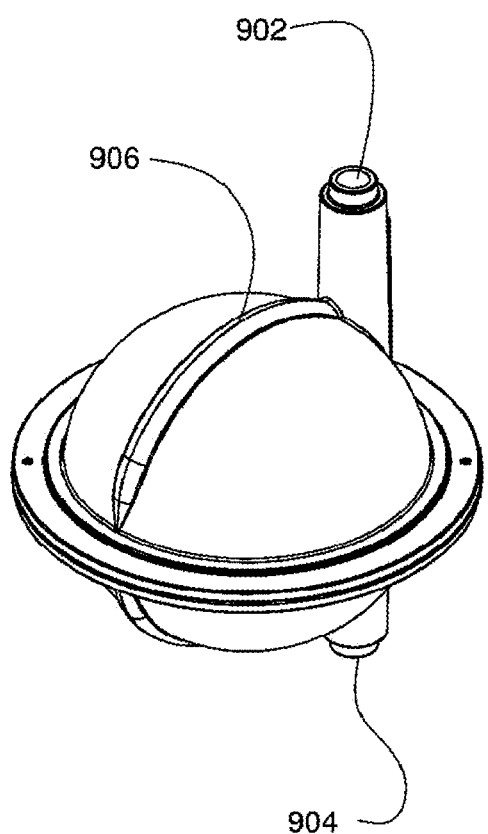
FIG. 47A is an isometric view of an exemplary embodiment of the pod of the cassette system.
Figure 47B:
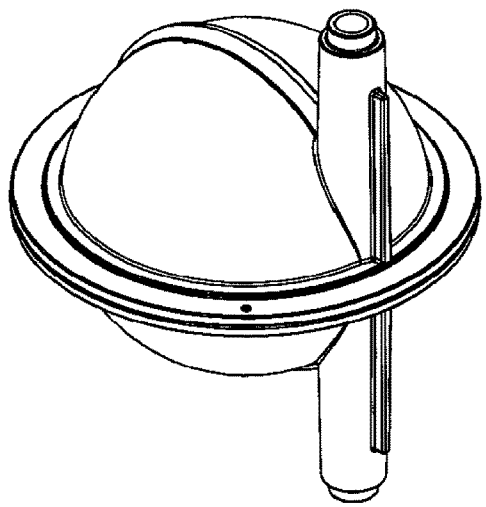
FIG. 47B is an isometric view of an exemplary embodiment of the pod of the cassette system.
Figure 47C:
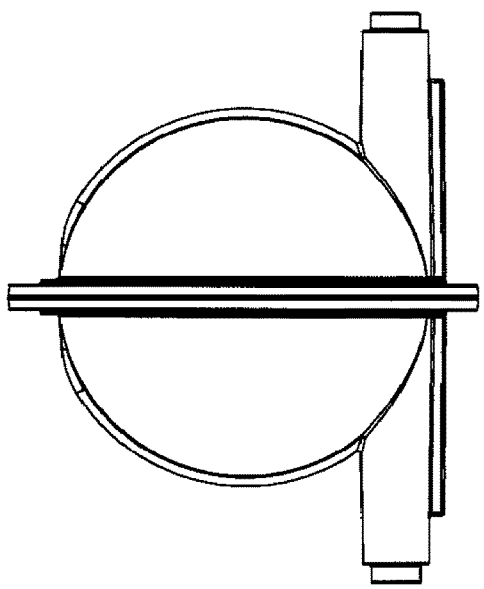
FIG. 47C is a side view of an exemplary embodiment of the pod of the cassette system.

Referring now to FIGS. 47A-47C, the exemplary embodiment of the pod is shown. The pod includes two fluid ports 902, 904 (an inlet and an outlet) and the pod may be constructed differently in the various embodiments. A variety of embodiments of construction are described in pending U.S. Pat. No. 8,292,594, issued Oct. 23, 2012 and entitled "Fluid Pumping Systems, Devices and Methods," which is hereby incorporated herein by reference in its entirety.

Figure 47D:
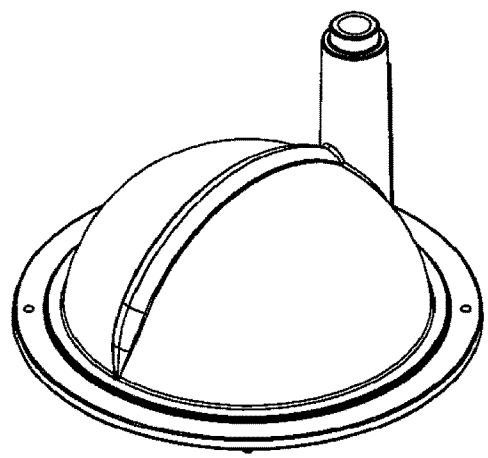
FIG. 47D is an isometric view of an exemplary embodiment of one half of the pod of the cassette system.
Figure 47E:
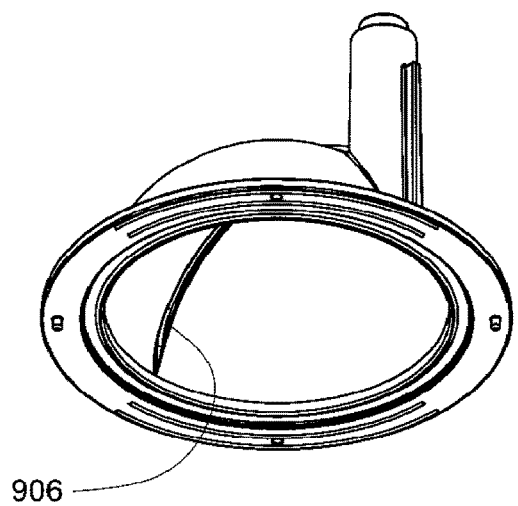
FIG. 47E is an isometric view of an exemplary embodiment of one half of the pod of the cassette system.

Referring now to FIGS. 47A, 47D and 47E the groove 906 in the chamber is shown. A groove 906 is included on each half of the pod housing. In other embodiments, a groove is not included and in some embodiments, a groove is only included on one half of the pod.

Figure 48A:
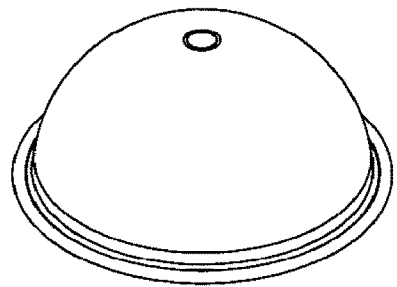
FIG. 48A is a pictorial view of the exemplary embodiment of the pod membrane of the cassette system.
Figure 48B:
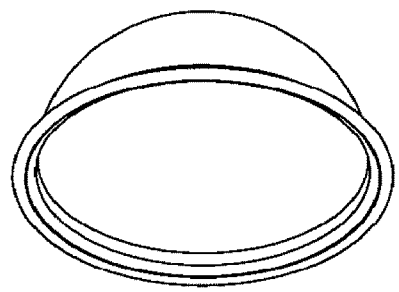
FIG. 48B is a pictorial view of the exemplary embodiment of the pod membrane of the cassette system.
Figure 49:
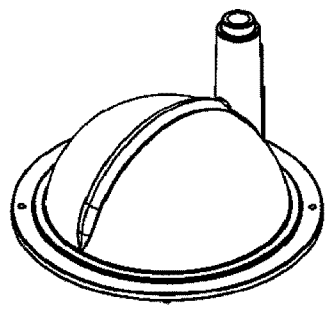
FIG. 49 is an exploded view of an exemplary embodiment of the pod of the cassette system.
Figure 49:
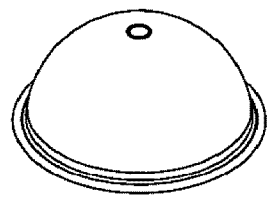
Figure 49:
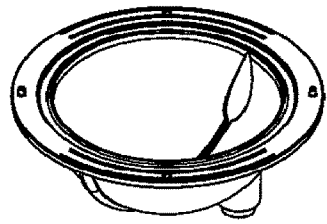

Referring now to FIGS. 48A and 48B, the exemplary embodiment of the membrane used in the pod pumps 502, 504 602, 604, 702, 704 is shown. This membrane is shown and described above with respect to FIG. 5A. In other embodiments, any of the membranes shown in FIGS. 5B-5D may be used. An exploded view of a pod pump according to the exemplary embodiment is shown FIG. 49.

Various aspects of the invention include one or more "pod pumps," used for various purposes. The structure of a general pod pump will now be described, although, as noted above, this structure may be modified for various uses, e.g., as a pump, a balancing chamber, a mixing chamber, or the like. In addition, a pod pump may be positioned anywhere in the system, for instance, on a cassette or between two or more cassettes, etc.

Generally, a pod pump includes a rigid chamber (which may have any suitable shape, e.g., spherical, ellipsoid, etc.), and the pod pump may include a flexible diaphragm dividing each chamber into a first half and a second half. In some cases, the rigid chamber is a spheroid. As used herein, "spheroid" means any three-dimensional shape that generally corresponds to a oval rotated about one of its principal axes, major or minor, and includes three-dimensional egg shapes, oblate and prolate spheroids, spheres, and substantially equivalent shapes.

Each half of the pod pump may have at least one entry valve, and often (but not always) has at least one exit valve (in some cases, the same port may be used for both entry and exit). The valves may be, for instance, open/closing valves or two-way proportional valves. For instance, valves on one side of a chamber may be two-way proportional valves, one connected to a high pressure source, the other connected to a low pressure (or vacuum) sink, while the valves on the other half may be opened and closed to direct fluid flow.

In some embodiments, the diaphragm has a variable cross-sectional thickness. Thinner, thicker or variable thickness diaphragms may be used to accommodate the strength, flexural and other properties of the chosen diaphragm materials. Thinner, thicker or variable diaphragm wall thickness may also be used to manage the diaphragm thereby encouraging it to flex more easily in some areas than in other areas, thereby aiding in the management of pumping action and flow of subject fluid in the pump chamber. In this embodiment, the diaphragm is shown having its thickest cross-sectional area closest to its center. However in other embodiments having a diaphragm with a varying cross-sectional, the thickest and thinnest areas may be in any location on the diaphragm. Thus, for example, the thinner cross-section may be located near the center and the thicker cross-sections located closer to the perimeter of the diaphragm. In one embodiment of the diaphragm, the diaphragm has a tangential slope in at least one section, but in other embodiments, the diaphragm is completely smooth or substantially smooth.

The diaphragm may be made of any flexible material having a desired durability and compatibility with the subject fluid. The diaphragm may be made from any material that may flex in response to fluid, liquid or gas pressure or vacuum applied to the actuation chamber. The diaphragm material may also be chosen for particular bio-compatibility, temperature compatibility or compatibility with various subject fluids that may be pumped by the diaphragm or introduced to the chambers to facilitate movement of the diaphragm. In the exemplary embodiment, the diaphragm is made from high elongation silicone. However, in other embodiments, the diaphragm is made from any elastomer or rubber, including, but not limited to, silicone, urethane, nitrile, EPDM or any other rubber, elastomer or flexible material.

The shape of the diaphragm is dependent on multiple variables. These variables include, but are not limited to: the shape of the chamber; the size of the chamber; the subject fluid characteristics; the volume of subject fluid pumped per stroke; and the means or mode of attachment of the diaphragm to the housing. The size of the diaphragm is dependent on multiple variables. These variables include, but are not limited to: the shape of the chamber; the size of the chamber; the subject fluid characteristics; the volume of subject fluid pumped per stroke; and the means or mode of attachment of the diaphragm to the housing. Thus, depending on these or other variables, the shape and size of the diaphragm may vary in various embodiments.

The diaphragm may have any thickness. However, in some embodiments, the range of thickness is between 0.002 inches to 0.125 inches (1 inch=2.54 cm). Depending on the material used for the diaphragm, the desired thickness may vary. In one embodiment, high elongation silicone is used in a thickness ranging from 0.015 inches to 0.050 inches. However in other embodiments, the thickness may vary.

In the exemplary embodiment, the diaphragm is preformed to include a substantially dome-shape in at least part of the area of the diaphragm. Again, the dimensions of the dome may vary based on some or more of the variables described above. However, in other embodiments, the diaphragm may not include a pre-formed dome shape.

In the exemplary embodiment, the diaphragm dome is formed using liquid injection molding. However, in other embodiments, the dome may be formed by using compression molding. In alternate embodiments, the diaphragm is substantially flat. In other embodiments, the dome size, width or height may vary.

In various embodiments, the diaphragm may be held in place by various means and methods. In one embodiment, the diaphragm is clamped between the portions of the cassette, and in some of these embodiments, the rim of the cassette may include features to grab the diaphragm. In others of this embodiment, the diaphragm is clamped to the cassette using at least one bolt or another device. In another embodiment, the diaphragm is over-molded with a piece of plastic and then the plastic is welded or otherwise attached to the cassette. In another embodiment, the diaphragm is pinched between a mid plate and a bottom plate. Although some embodiments for attachment of the diaphragm to the cassette are described, any method or means for attaching the diaphragm to the cassette may be used. The diaphragm, in one alternate embodiment, is attached directly to one portion of the cassette. In some embodiments, the diaphragm is thicker at the edge, where the diaphragm is pinched by the plates, than in other areas of the diaphragm. In some embodiments, this thicker area is a gasket, in some embodiments an O-ring, ring or any other shaped gasket.

In some embodiments of the gasket, the gasket is contiguous with the diaphragm. However, in other embodiments, the gasket is a separate part of the diaphragm. In some embodiments, the gasket is made from the same material as the diaphragm. However, in other embodiments, the gasket is made of a material different from the diaphragm. In some embodiments, the gasket is formed by over-molding a ring around the diaphragm. The gasket may be any shape ring or seal desired so as to complement the pod pump housing embodiment. In some embodiments, the gasket is a compression type gasket.

Due to the rigid chamber, the pod pump has a generally constant volume. However, within the pod pump, the first and second compartments may have differing volumes depending on the position of the flexible diaphragm dividing the chamber. Forcing fluid into one compartment may thus cause the fluid within the other compartment of the chamber to be expelled. However, the fluids are typically not able to come into direct contact with each other within the pod pump due to the presence of the flexible diaphragm.

Accordingly, in one embodiment, a pod pump used for pumping is constructed to receive a control fluid in a first compartment and a fluid to be pumped in a second compartment. The control fluid may be any fluid, and may be a liquid or a gas. In one embodiment, the control fluid is air. Drawing control fluid away from the pod pump (e.g., through a vacuum, or at least a pressure lower than the pressure within the pod pump) causes the pod pump to draw in fluid (e.g., blood, dialysate, etc.) into the other compartment of the pod pump. Similarly, forcing control fluid into the pod pump (e.g., from a high pressure source) causes the pod pump to expel fluid. By also controlling the valves of the second compartment, fluid may be brought in through a first valve and then expelled through a second valve due to action of the control fluid.

As another example, a pod pump may be used for fluid balancing, e.g., of dialysate as discussed above. In such cases, instead of a control fluid, a fluid may be directed to each compartment of the pod pump. As mentioned, the volume of the pod pump remains generally constant due to the rigid chamber. Accordingly, when a first volume of fluid is drawn into a first compartment of a balancing pod, an equal volume of fluid is expelled from the second compartment of the balancing pod (assuming the fluids to be generally incompressible under conditions in which the pod is operated). Thus, using such balancing pods, equal volumes of fluid can be moved. For instance, in FIG. 5, a balancing pod may allow fresh dialysate to enter a first compartment and used dialysate to enter a second compartment; the volumetric flows of fresh dialysate and used dialysate can be balanced against each other.

In some cases, a pod pump is used that does not contain a flexible diaphragm dividing the chamber. In such instances, the pod pump can be used as a mixing chamber. For instance, mixing chamber 189 in FIG. 7A may be such a pod pump.

Figure 9:
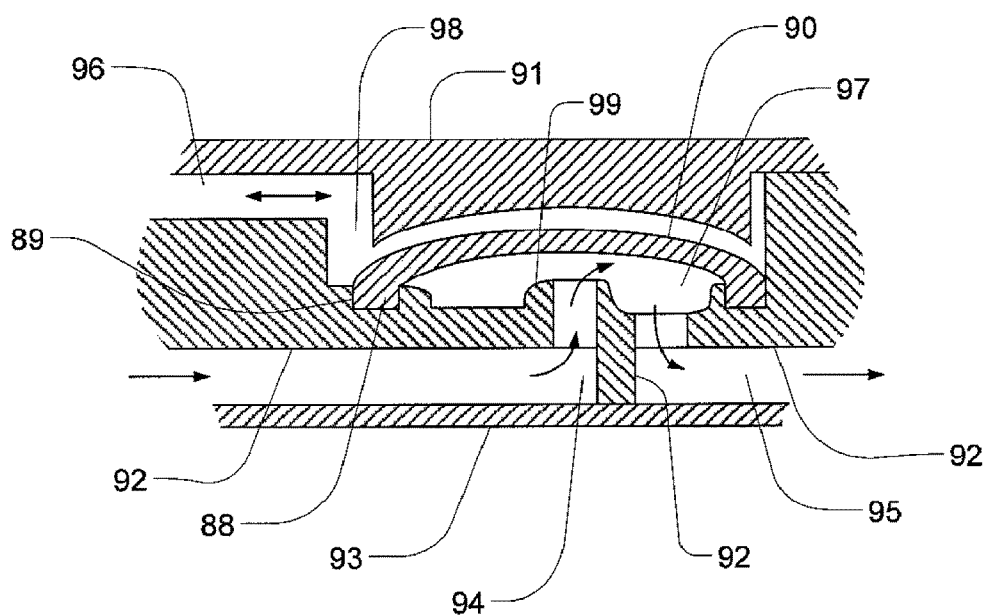
FIG. 9 is a sectional view of a valve that may be incorporated into embodiments of the fluid-control cassettes.

A non-limiting example of a pod pump is shown in FIG. 9. This figure is a sectional view of a pneumatically controlled valve that may be used in embodiments of the cassettes.

"Pneumatic," as used herein, means using air or other gas to move a flexible diaphragm or other member. (It should be noted that air is used by way of example only, and in other embodiments, other control fluids, such as nitrogen ($N_2$), $CO_2$, water, an oil, etc. may be used). Three rigid pieces are used, a "top" plate 91, a middle plate 92, and a "bottom" plate. (The terms "top" and "bottom" only refer to the orientation shown in FIG. 9. The valve may be oriented in any direction in actual use.) The top and bottom plates 91, 93 may be flat on both sides, while the middle plate 92 is provided with channels, indentations and holes to define the various fluid paths, chamber and ports. A diaphragm 90, along with the middle plate 92, defines a valving chamber 97. Pneumatic pressure is provided through a pneumatic port 96 to either force, with positive gas pressure, the diaphragm 90 against a valve seat 99 to close the valve, or to draw, with negative gas pressure, the diaphragm away from the valve seat to open the valve. A control gas chamber 98 is defined by the diaphragm 90, the top plate 91, and the middle plate 92. The middle plate 92 has an indentation formed on it, into which the diaphragm 90 is placed so as to form the control gas chamber 98 on one side of the diaphragm and the valving chamber 97 on the other side.

The pneumatic port 96 is defined by a channel formed on the "top" surface of the middle plate 92, along with the top plate 91. By providing fluid communication between several valving chambers in a cassette, valves may be ganged together so that all the valves ganged together may be opened or closed at the same time by a single source of pneumatic pressure. Channels formed on the "bottom" surface of the middle plate 92, along with the bottom plate, define the valve inlet 94 and the valve outlet 95. Holes formed through the middle plate 92 provide communication between the inlet 94 and the valving chamber 97 (through the valve seat 99) and between the valving chamber and the outlet 95.

The diaphragm 90 is provided with a thickened rim 88, which fits tightly in a groove 89 in the middle plate 92. Thus, the diaphragm 90 may be placed in and held by the groove 88 before the top plate 91 is ultrasonically welded to the middle plate 92, so the diaphragm will not interfere with the ultrasonic welding of the two plates together, and so that the diaphragm does not depend on the two plates being ultrasonically welded together in just the right way to be held in place. Thus, this valve may be manufactured easily without relying on ultrasonic welding to be done to very tight tolerances. As shown in FIG. 9, the top plate 91 may include additional material extending into control gas chamber 98 so as to prevent the diaphragm 90 from being urged too much in a direction away from the groove 89, so as to prevent the diaphragm's thickened rim 88 from popping out of the groove 89.

Pressure sensors may be used to monitor pressure in the pods. For instance by alternating applied air pressure to the pneumatic side of the chamber, the diaphragm is cycled back and forth across the total chamber volume. With each cycle, fluid is drawn through the upstream valve of the inlet fluid port when the pneumatics pull a vacuum on the pods. The fluid is then subsequently expelled through the outlet port and the downstream valve when the pneumatics deliver positive pressure to the pods.

Figure 10:
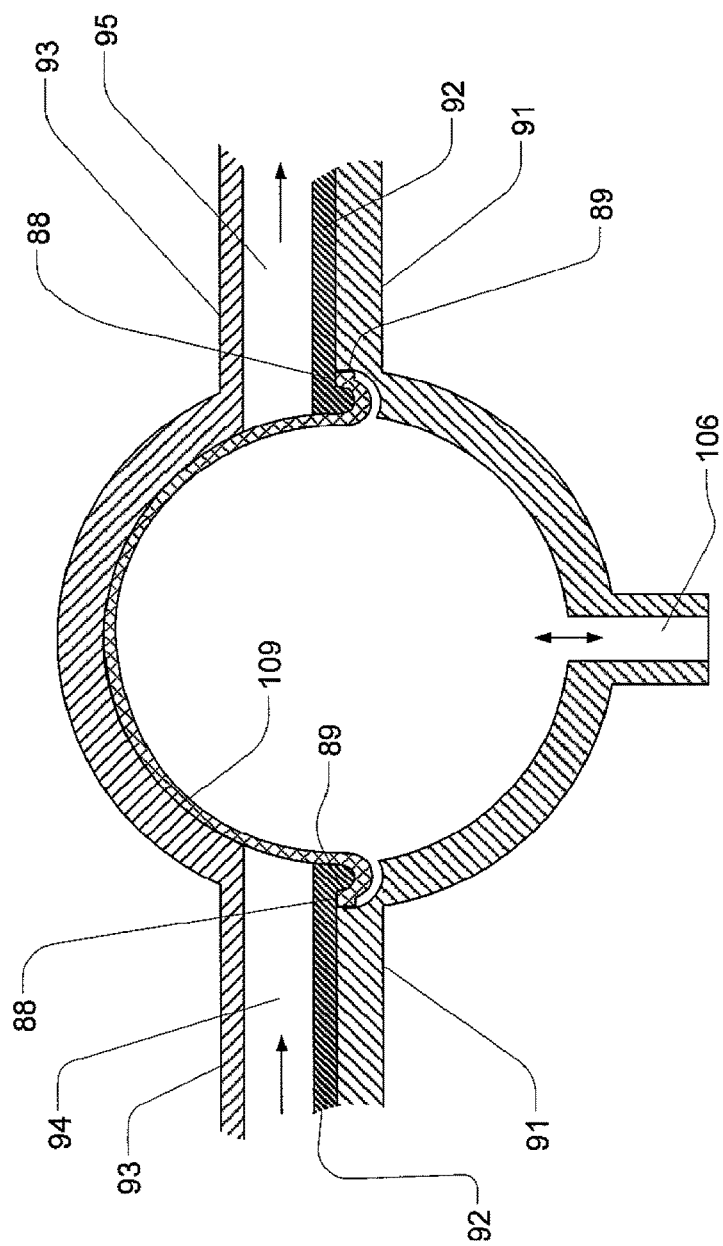
FIG. 10 is a sectional view of a pod-pump that may be incorporated into embodiments of the fluid-control cassettes.

FIG. 10 is a sectional view of one embodiment of a pod pump that may be incorporated into embodiments of the fluid-control cassettes. In some embodiments, the cassette would incorporate several pod pumps and several valves made in accordance with the construction techniques shown in FIGS. 9 and 10. In such embodiments, the pod pump of FIG. 10 is made from different portions of the same three rigid pieces used to make the valve of FIG. 9. These rigid pieces are the "top" plate 91, the middle plate 92, and the "bottom" plate. (As noted above, the terms "top" and "bottom" only refer to the orientation shown in FIG. 9.) To form the pod pump, the top and bottom plates 91, 93 may include generally hemispheroid portions that together define a hemispheroid pod pump.

A diaphragm 109 separates the central cavity of the pod pump into a chamber (the pumping chamber) that receives the fluid to be pumped and another chamber (the actuation chamber) for receiving the control gas that pneumatically actuates the pump. An inlet 94 allows fluid to enter the pumping chamber, and an outlet allows fluid to exit the pumping chamber. The inlet 94 and the outlet 95 may be formed between middle plate 92 and the bottom plate 93. Pneumatic pressure is provided through a pneumatic port 106 to either force, with positive gas pressure, the diaphragm 109 against one wall of pod pump's cavity to minimize the pumping chamber's volume (as shown in FIG. 10), or to draw, with negative gas pressure, the diaphragm towards the other wall of the pod pump's cavity to maximize the pumping chamber's volume.

In some embodiments of the pod pump, various configurations, including grooving on one or more plates exposed to the cavity of the pod pump, are used. Amongst other benefits, grooving can prevent the diaphragm from blocking the inlet or outlet (or both) flow path for fluid or air (or both).

The diaphragm 109 may be provided with a thickened rim 88, which is held tightly in a groove 89 in the middle plate 92. Thus, like in the valving chamber of FIG. 9, the diaphragm 109 may be placed in and held by the groove 89 before the top plate 91 is ultrasonically welded to the middle plate 92, so the diaphragm will not interfere with the ultrasonic welding of the two plates together, and so that the diaphragm does not depend on the two plates being ultrasonically welded together in just the right way to be held in place. Thus, this pod pump can be manufactured easily without relying on ultrasonic welding to be done to very tight tolerances.

Figure 11A:
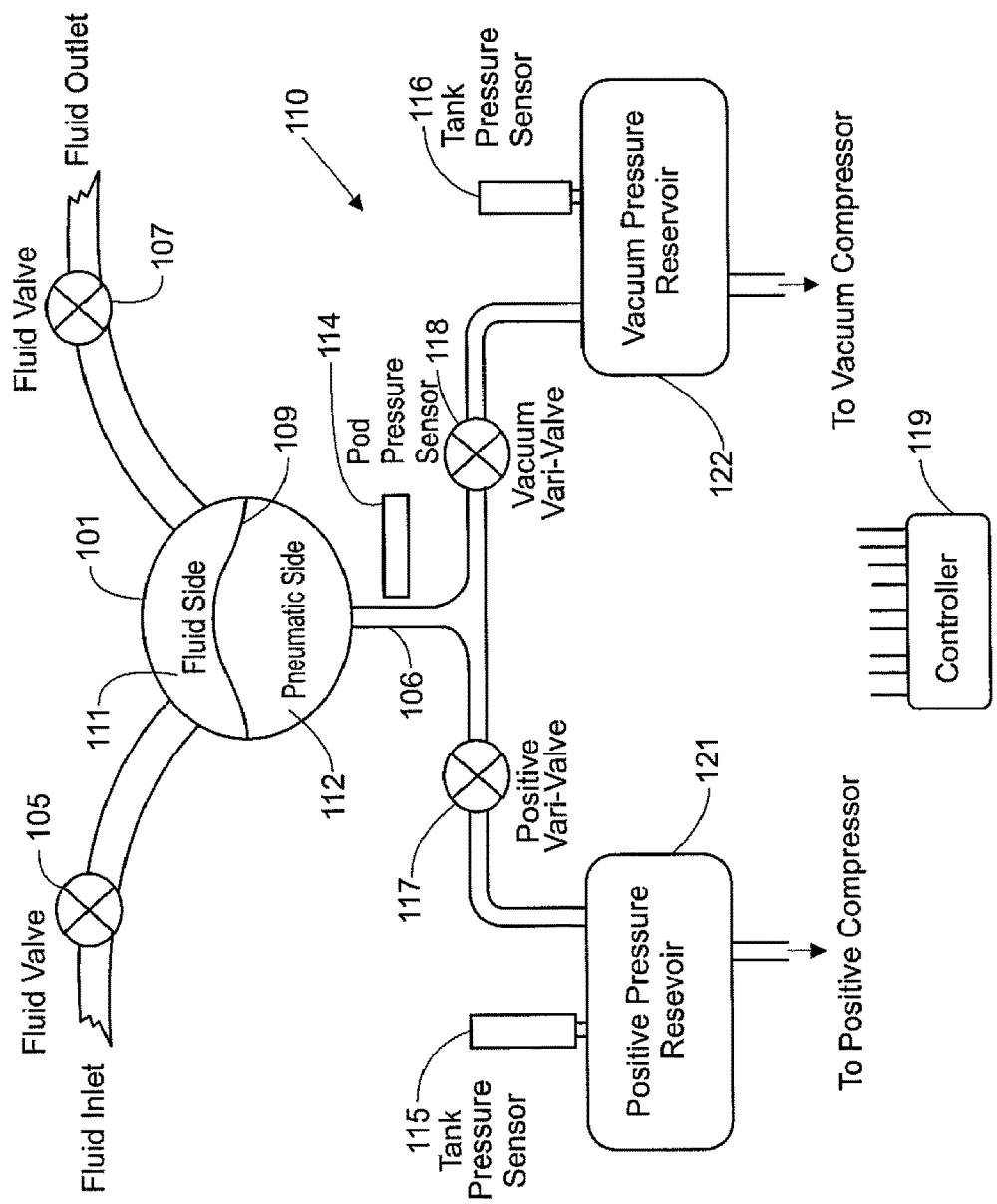
FIGS. 11A-11B are schematic views of various pneumatic control system for a pod pump.

FIG. 11A is a schematic view showing an embodiment of a pressure actuation system 110 for a pod pump, such as that shown in FIG. 10. In this example, air is used as a control fluid (e.g., such that the pump is pneumatically driven). As mentioned, other fluids (e.g., water) may also be used as control fluids in other embodiments.

In FIG. 11A, pressure actuation system 110 alternately provides positive and negative pressurizations to the gas in the actuation chamber 112 of the pod pump 101. The pneumatic actuation system 110 includes an actuation-chamber pressure transducer 114, a variable positive-supply valve 117, a variable negative-supply valve 118, a positive-pressure gas reservoir 121, a negative-pressure gas reservoir 122, a positive-pressure-reservoir pressure transducer 115, a negative-pressure-reservoir pressure transducer 116, as well as an electronic controller 119.

The positive-pressure reservoir 121 provides to the actuation chamber 112 the positive pressurization of a control gas to urge the diaphragm 109 towards a position where the pumping chamber 111 is at its minimum volume (i.e., the position where the diaphragm is against the rigid pumping-chamber wall). The negative-pressure reservoir 122 provides to the actuation chamber 112 the negative pressurization of the control gas to urge the diaphragm 109 in the opposite direction, towards a position where the pumping chamber 111 is at its maximum volume (i.e., the position where the diaphragm is against the rigid actuation-chamber wall).

A valving mechanism is used in this example to control fluid communication between each of these reservoirs 121, 122 and the actuation chamber 112. In FIG. 11A, a separate valve is used for each of the reservoirs; a positive-supply valve 117 controls fluid communication between the positive-pressure reservoir 121 and the actuation chamber 112, and a negative-supply valve 118 controls fluid communication between the negative-pressure reservoir 122 and the actuation chamber 112. These two valves are controlled by an electronic controller 119. (Alternatively, a single three-way valve may be used in lieu of the two separate valves 117, 118.) In some cases, the positive-supply valve 117 and the negative-supply valve 118 are variable-restriction valves, as opposed to binary on-off valves. An advantage of using variable valves is discussed below.

The controller 119 also receives pressure information from the three pressure transducers shown in FIG. 11A: an actuation-chamber pressure transducer 114, a positive-pressure-reservoir pressure transducer 115, and a negative-pressure-reservoir pressure transducer 116. As their names suggest, these transducers respectively measure the pressure in the actuation chamber 112, the positive-pressure reservoir 121, and the negative-pressure reservoir 122. The controller 119 monitors the pressure in the two reservoirs 121, 122 to ensure they are properly pressurized (either positively or negatively). A compressor-type pump or pumps may be used to attain the desired pressures in these reservoirs 121, 122.

In one embodiment, the pressure provided by the positive-pressure reservoir 121 is strong enough, under normal conditions, to urge the diaphragm 109 all the way against the rigid pumping-chamber wall. Similarly, the negative pressure (i.e., the vacuum) provided by the negative-pressure reservoir 122 is preferably strong enough, under normal conditions, to urge the diaphragm all the way against the rigid actuation-chamber wall. In some embodiments, however, these positive and negative pressures provided by the reservoirs 121, 122 are within safe enough limits that even with either the positive-supply valve 117 or the negative-supply valve 118 open all the way the positive or negative pressure applied against the diaphragm 109 is not so strong as to harm the patient.

In one embodiment, the controller 119 monitors the pressure information from the actuation-chamber-pressure transducer 114 and, based on this information, controls the valving mechanism (valves 117, 118) to urge the diaphragm 109 all the way to its minimum-pumping-chamber-volume position and then after this position is reached to pull the diaphragm 109 all the way back to its maximum-pumping-chamber-volume position.

The pressure actuation system (including the actuation-chamber pressure transducer 114, the positive-pressure-reservoir pressure transducer 115, the negative-pressure-reservoir pressure transducer 116, the variable positive-supply valve 117, the variable negative-supply valve 118, the controller 119, the positive-pressure gas reservoir 121, and the negative-pressure gas reservoir 122) is located entirely or mostly outside the insulated volume (item 61 of FIG. 6). The components that come into contact with blood or dialysate (namely, pod pump 101, the inlet valve 105 and the outlet valve 107) may be located, in some cases, in the insulated volume so that they can be more easily disinfected.

Figure 11B:
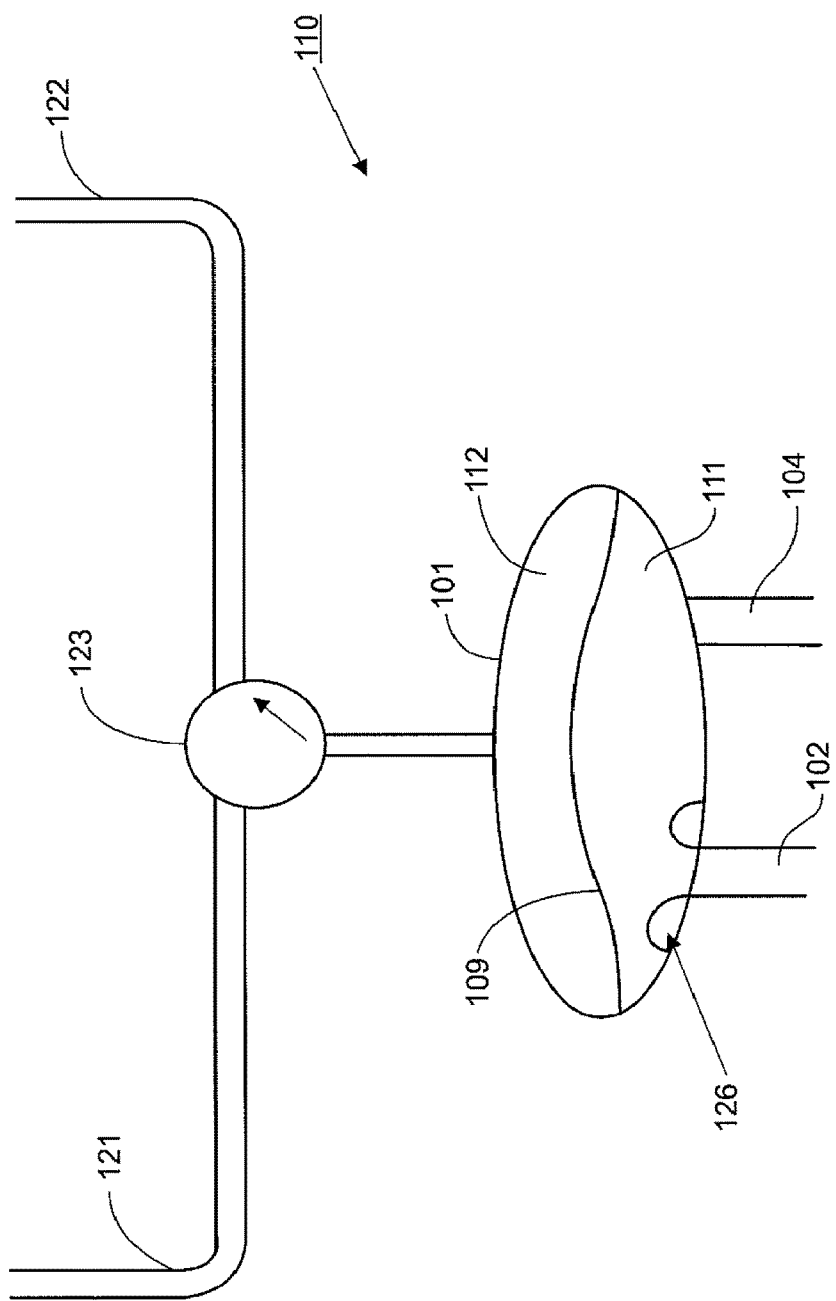

Another example of a pressure actuation system 110 for a pod pump is illustrated in FIG. 11B. In this example, pod pump 101 includes a pumping chamber 111, an actuation chamber 112, and a diaphragm 109 separating the two sides. Fluid ports 102 and 104 allow access of fluid in and out of pumping chamber 111, e.g., through the use of fluid valves (not shown). Within pod pump 101, however, fluid ports 102 and 104 include a "volcano" port 126, generally having a raised shape, such that when diaphragm 109 contacts the port, the diaphragm is able to form a tight seal against the port. Also shown in FIG. 11B is a 3-way valve connecting pressure reservoirs 121, 122. The 3-way valve 123 is in fluid communication with actuation chamber 112 by a single port in this example.

It will be appreciated that other types of actuation systems may be used to move the diaphragm back and forth instead of the two-reservoir pneumatic actuation system shown in FIGS. 11A-11B.

As noted above, the positive-supply valve 117 and the negative-supply valve 118 in the pneumatic actuation system 110 of FIG. 11A are preferably variable-restriction valves, as opposed to binary on-off valves. By using variable valves, the pressure applied to the actuation chamber 112 and the diaphragm 109 can be more easily controlled to be just a fraction of the pressure in reservoir 121, 122, instead of applying the full reservoir pressure to the diaphragm. Thus, the same reservoir or set of reservoirs may be used for different pod pumps, even though the pressures for operating the pod pumps may differ from pod pump to pod pump. Of course, the reservoir pressure needs to be greater than the desired pressures to be applied to various pod pump's diaphragms, but one pod pump may be operated at, say, half of the reservoir pressure, and another pod pump may be actuated with the same reservoir but at, say, a quarter of the reservoir pressure. Thus, even though different pod pumps in the dialysis system are designed to operate at different pressures, these pod pumps may all share the same reservoir or set of reservoirs but still be actuated at different pressures, through the use of variable valves. The pressures used in a pod pump may be changed to address conditions that may arise or change during a dialysis procedure. For example, if flow through the system's tubing becomes constricted because the tubes get twisted, one or both of the positive or negative pressures used in the pod pump may be increased in order to over compensate for the increased restriction.

Figure 12:
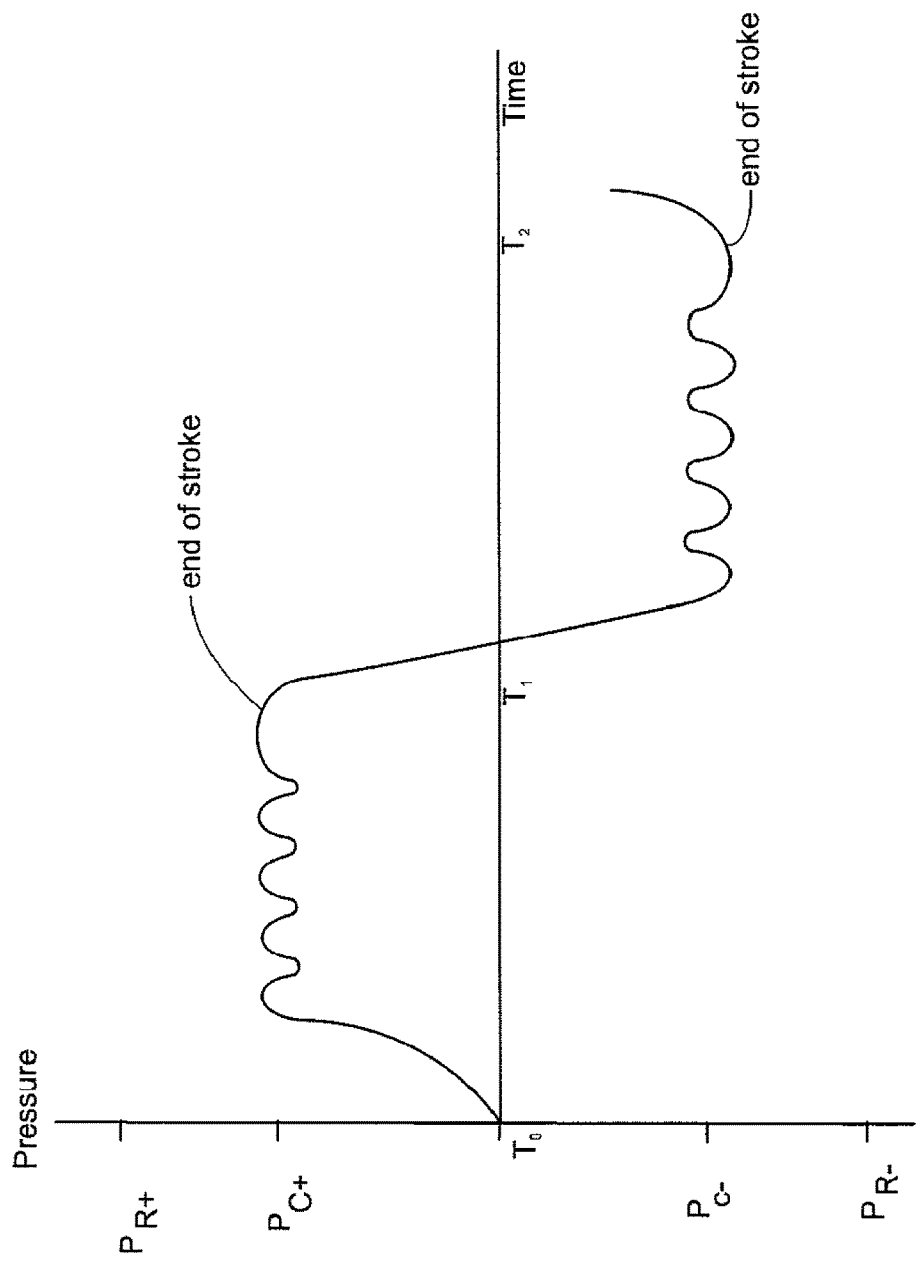
FIG. 12 is a graph showing how pressures applied to a pod pump may be controlled.

FIG. 12 is a graph showing how pressures applied to a pod pump may be controlled using variable valves. The vertical axis represents pressure with $P_{R+}$ and $P_{R-}$ representing respectively the pressures in the positive and negative reservoirs (items 121 and 122 in FIG. 11A), and $P_{C+}$ and $P_{C-}$ representing respectively the positive and negative control pressures acting on the pod pump's diaphragm. As can be seen in FIG. 12, from time $T_0$ to about time $T_1$, a positive pressure is applied to the actuation chamber (so as to force fluid out of the pumping chamber). By repeatedly reducing and increasing the flow restriction caused by the positive variable valve (item 117 in FIG. 11A), the pressure being applied to the actuation chamber can be held at about the desired positive control pressure, $P_{C+}$. The pressure varies, in a sinusoidal manner, around the desired control pressure. An actuation-chamber pressure transducer (item 114 in FIG. 11A) in communication with the actuation chamber measures the pressure in the actuation chamber and passes the pressure-measurement information to the controller (item 119 in FIG. 11A), which in turn controls the variable valve so as to cause the actuation chamber's pressure to vary around the desired control pressure, $P_{C+}$. If there are no fault conditions, the diaphragm is pushed against a rigid wall of the pumping chamber, thereby ending the stroke. The controller determines that the end of stroke has been reached when the pressure measured in the actuation chamber no longer drops off even though the restriction created by the variable valve is reduced. In FIG. 12, the end of the expelling stroke occurs around time $T_1$. When the end of stroke is sensed, the controller causes the variable valve to close completely so that the actuation chamber's pressure does not increase much beyond the desired control pressure, $P_{C+}$.

After the positive variable valve is closed, the negative variable valve (item 118 in FIG. 11A) is partially opened to allow the negative pressure reservoir to draw gas from the actuation chamber, and thus draw fluid into the pumping chamber. As can be seen in FIG. 12, from a time shortly after $T_1$ to about time $T_2$, a negative pressure is applied to the actuation chamber). As with the expelling (positive pressure), stroke described above, repeatedly reducing and increasing the flow restriction caused by the negative variable valve can cause the pressure being applied to the actuation chamber can be held at about the desired negative control pressure, $P_{C-}$ (which is weaker than the pressure in the negative pressure reservoir). The pressure varies, in a sinusoidal manner, around the desired control pressure. The actuation-chamber pressure transducer passes pressure-measurement information to the controller, which in turn controls the variable valve so as to cause the actuation chamber's pressure to vary around the desired control pressure, $P_{C-}$. If there are no fault conditions, the diaphragm is pulled against a rigid wall of the actuation chamber, thereby ending the draw (negative pressure) stroke. As described above, the controller determines that the end of stroke has been reached when the partial vacuum measured in the actuation chamber no longer drops off even though the restriction created by the variable valve is reduced. In FIG. 12, the end of the draw stroke occurs around time $T_2$. When the end of stroke is sensed, the controller causes the variable valve to close completely so that the actuation chamber's vacuum does not increase much beyond the desired negative control pressure, $P_{C-}$. Once the draw stroke has ended, the positive variable valve can be partially opened to begin a new expelling stroke with positive pressure.

Thus, each pod pump in this example uses the two variable-orifice valves to throttle the flow from the positive-pressure source and into the negative-pressure. The pressure in the actuation chamber is monitored and a controller uses this pressure measurement to determine the appropriate commands to both valves to achieve the desired pressure in the actuation chamber. Some advantages of this arrangement are that the filling and delivering pressure may be precisely controlled to achieve the desired flow rate while respecting pressure limits, and that the pressure may be varied with a small sinusoidal signature command. This signature may be monitored to determine when the pump reaches the end of a stroke.

Another advantage of using variable valves in this way, instead of binary valves, is that by only partially opening and closing the variable valves the valves are subject to less wear and tear. The repeated "banging" of binary valves all the way opened and all the way closed can reduce the life of the valve.

Figure 13A:
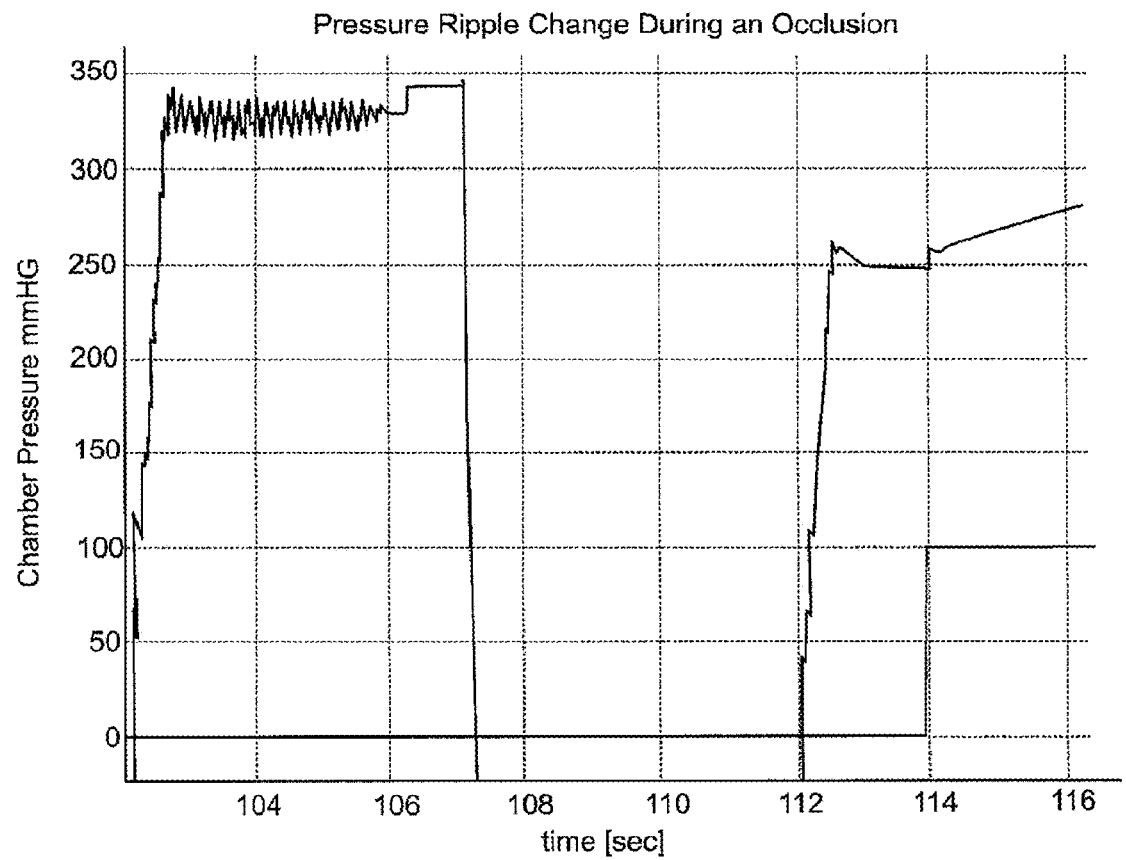
FIGS. 13A-13B are graphical representations of occlusion detection.
Figure 13B:
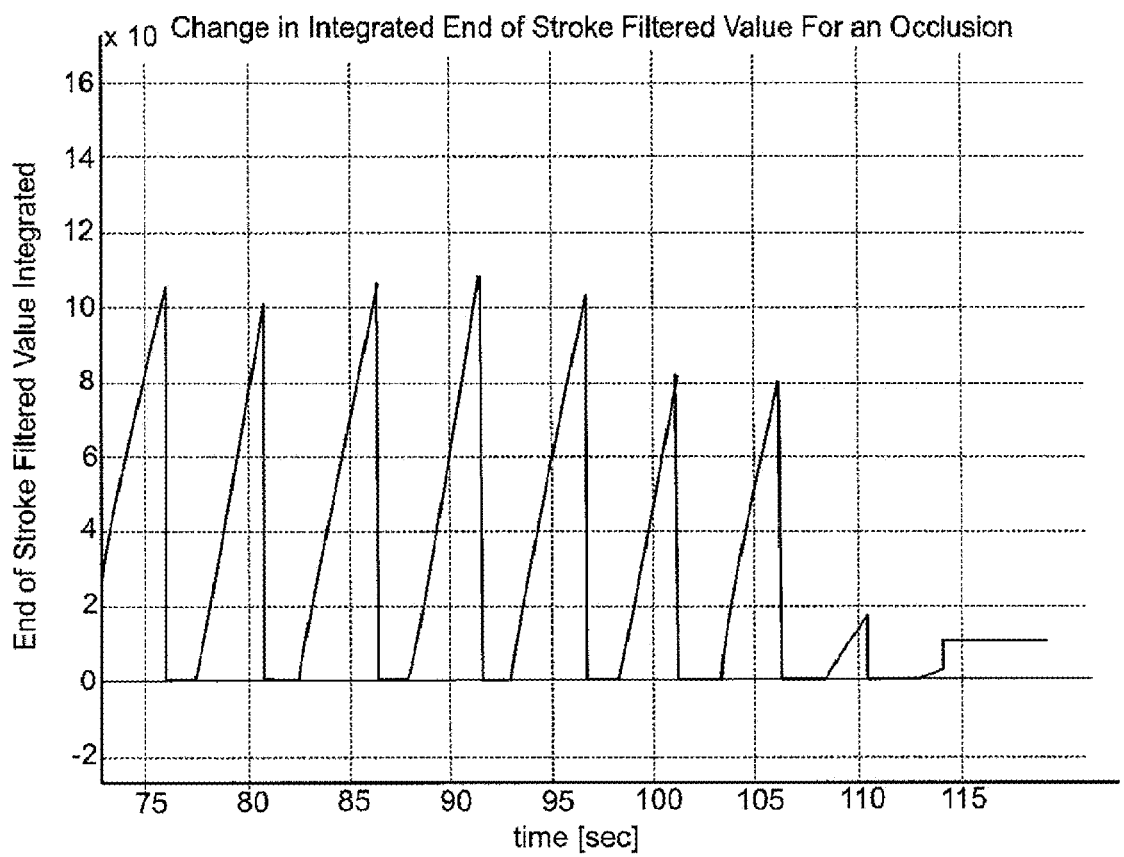

If the end of stroke is detected and the integrated value of the correlation function is very small, this may be an indication that the stroke occluded and did not complete properly. It may be possible to distinguish upstream occlusions from downstream occlusions by looking at whether the occlusion occurred on a fill or a delivery stroke (this may be difficult for occlusions that occur close to the end of a stroke when the diaphragm is near the chamber wall). FIGS. 13A-13B depict occlusion detection (the chamber pressure drops to 0 when an occlusion is detected).

Under normal operation, the integrated value of the correlation function increases as the stroke progresses. If this value remains small or does not increase the stroke is either very short (as in the case of a very low impedance flow or an occlusion) or the actual pressure may not be tracking the desired sinusoidal pressure due to a bad valve or pressure signals. Lack of correlation can be detected and used for error handling in these cases.

Under normal circumstances when the flow controller is running, the control loop will adjust the pressure for any changes in flow rate. If the impedance in the circuit increases dramatically and the pressure limits are saturated before the flow has a chance to reach the target rate, the flow controller will not be capable of adjusting the pressures higher to reach the desired flow rate. These situations may arise if a line is partially occluded, such as when a blood clot has formed in the circuit. Pressure saturation when the flow has not reached the target flow rate can be detected and used in error handling.

If there are problems with the valves or the pneumatics such as a leaking fluid valve or a noisy pressure signal, ripple may continue on the stroke indefinitely and the end of stroke algorithm may not see enough of a change in the pressure ripple to detect end of stroke. For this reason a safety check is added to detect if the time to complete a stroke is excessive. This information can be used for error handling.

In a dual pump, such as pump 13 in FIG. 3A, the two pump chambers may be cycled in opposite directions to affect the pumping cycle. A phase relationship from 0° (both chambers act in the same direction) to 180° (chambers act in opposite directions) can be selected. Phase movement may be modified somewhat in certain cases because it may not be possible to move both chambers in the same direction simultaneously; doing so could have both input or output valves open and end of stroke will not be detected properly.

Selecting a phase relationship of 180° yields continuous flow into and out of the pod. This is the nominal pumping mode when continuous flow is desired. Setting a phase relationship of 0° is useful for single needle flow. The pods will first fill from the needle and then deliver to the same needle. Running at phases between 0 and 180 degrees can be used to achieve a push/pull relationship (hemodiafiltration/continuous back flush) across the dialyzer. FIGS. 8A-8C are graphical representations of such phase relationships.

The pod pumps may control flow of fluid through the various subsystems. For instance, a sinusoidal pressure waveform may be added to a DC pressure command to make up the commanded pressure signal for the pod pumps. When the diaphragm is moving, the pressure in the pods tracks the sinusoidal command. When the diaphragm comes in contact with the chamber wall and is no longer moving, the pressure in the pod remains constant and does not track the sinusoidal input command. This difference in the pressure signal command following of the pods is used to detect the end of a stroke. From the end of stroke information, the time for each stroke is calculated. Knowing the volume of the pods and the time to complete a stroke, a flow rate for each pod can be determined. The flow rate is fed back in a PI loop in order to calculate the required DC pressure for the next stroke.

The amplitude of the sinusoidal input may be selected such it is large enough for the actual pressure to reasonably track the command and small enough such that when it is subtracted from the minimum DC pump pressure and applied to the pod, the pressure is sufficient to cause the diaphragm to move under expected operating conditions of fluid viscosity, head height and fluid circuit resistance. The frequency of the sinusoidal input was selected empirically such that it is possible to reliably detect end of stroke. The more cycles of the sine wave per stroke, the more accurate the end of stroke detection algorithm.

To detect the change in the command following of the pod pressure, the pressure signal in the pods is sent through a cross correlation filter. The size of the sampling window for the cross correlation filter is equivalent to the period of the input sine wave. For every sample in the window the commanded pressure signal is multiplied by the previous sample of the actual pressure and added to the previous correlation value. The window is then shifted by one frame and the process is repeated. The resulting product is then differentiated and passed through a second order filter with a corner frequency the same as the input sine wave frequency and a damping ratio of one. The effect of this filter is to act as a band pass filter, isolating correlated signals at the input sinusoidal frequency. The absolute value of the output of this filter is then passed through a second order low pass filter with the same frequency of the sinusoidal frequency and a damping ratio of 3.0. This second filter is used integrate the differentiated signal to and to reduce noise in the resulting signal. If the two signals are correlated, the resulting filtered value will be large. If the two signals are not correlated (for example at end of stroke), the resulting filtered value will be small. The end of stroke can be detected when the filtered cross correlation signal drops below a particular threshold, or when the signal drops off a by a percentage of its maximum value through out the stroke. To tune performance for a particular pumping scenario, this threshold or percent drop can be varied as a function of pressure or flow rate.

Since the end of stroke algorithm typically takes about one cycle of the sinusoidal ripple to detect end of stroke, minimizing this cycle time (maximizing the sine wave frequency) reduces the delay at the end of stroke. Low pressure, high frequency flows are not well tracked by the controller. Lower pressure strokes tend to have lower flow rates and thus the delay at the end of stroke is a lesser percentage of the total stroke time. For this reason, the frequency can be lower for low pressure strokes. Frequency of the sine wave can be adjusted as a linear function of the delivery pressures. This insures minimum delays when the strokes are the shortest. When the frequency of the sine wave for the desired pressure is changed, the filters for the cross correlation function must also be adjusted. Filters are set up to continuously calculate the filter coefficients based on this changing frequency.

Pressure in the pod chambers may also be controlled using two variable solenoid valves; one connecting the plenum to a higher pressure source, the second connecting the plenum to lower pressure (or vacuum) sink. Solenoid valves tend to have a large dead band region so a non-linear offset term is added to the controller to compensate.

A diagram of an example control algorithm is shown in FIG. 14. The controller in this example is a standard discrete PI controller. The output of the PI controller is split into two paths; one for the source valve, one to the sink valve. An offset term is added to each of these paths to compensate for the valve dead band. The resulting command is then limited to valves greater than zero (after being inverted in the case of the sink valve).

The offset term is positive in the case of the source valve, and negative in the case of the sink valve. As a result, both valves will be active even as the error goes to zero. These offsets do improve the trajectory following and disturbance rejection ability of the controller, but can also result in leakage from both valves at steady state if the command offsets are slightly larger than the actual valve dead band. If this is the case, the valves will have equal and opposite leakage mass flows at steady state.

To eliminate this leakage mass flow when the control system is idle, a "power save" block can be added to turn off the valves if the absolute value of the error term remains small for a period of time. This is analogous to using mechanical brakes on a servomotor.

Figure 15:
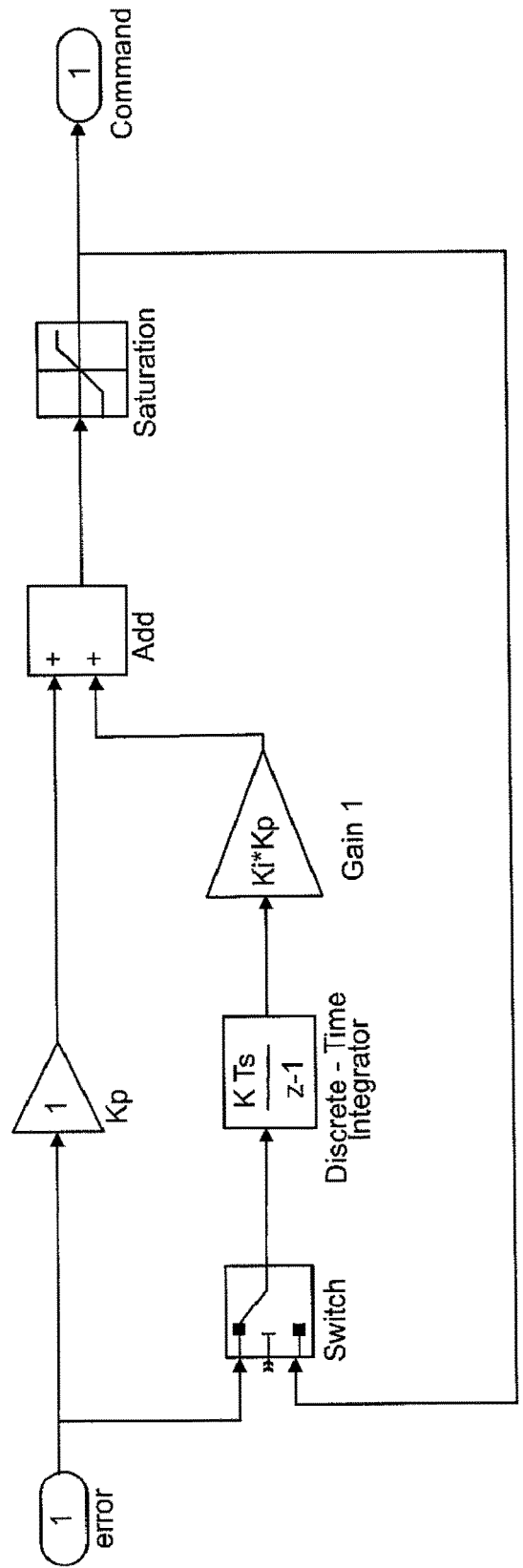
FIG. 15 is a diagram of one embodiment of the controller's standard discrete PI regulator.

Referring now to FIG. 15, the controller in this example uses a standard discrete PI regulator; a diagram of the PI regulator is shown. The integrator can be limited to prevent wind up when the commands are saturated. The integrator will always be capable of unwinding. Because there are different amounts of air in the pod for a fill and a deliver stroke, the response of the pod can be very different for a fill and deliver stroke. The proportional gain is adjusted differently for a fill and deliver stroke to better tune for the different pod responses.

The saturation limits chosen for the PI regulator should take into account the offset that will be added to the result. For example, if the valve saturates at 12V and a 5V fixed offset will be added after the PI loop, the saturation limit in the PI loop should be set to 7V. This positive and negative saturation limits will likely be different due to the different dead band in the source and sink valves.

During a fill stroke, the upstream fluid valve is closed and the down stream fluid valve is opened to allow fluid flow into the chamber. During a delivery stroke the upstream fluid valve is opened and the downstream fluid valve is closed to allow fluid flow out of the chamber. At the end of stroke, and until the next stroke starts, both fluid valves are closed.

As discussed, in certain aspects, a pod pump may be operated through action of a control fluid, for example, air, nitrogen, water, an oil, etc. The control fluid may be chosen to be relatively incompressible, and in some cases, chosen to be relatively inexpensive and/or non-toxic. The control fluid may be directed into the system towards the pumps using a series of tubes or other suitable conduits. A controller may control flow of control fluid through each of the tubes or conduits. In some cases, the control fluid may be held at different pressures within the various tubes or conduits. For instance, some of the control fluid may be held at positive pressure (i.e., greater than atmospheric pressure), while some of the control fluid may be held at negative pressures (less than atmospheric pressure) or even zero pressure (i.e., vacuum). As a specific, non-limiting example, a pod pump such as the one illustrated in FIG. 11A may be controlled through operation of the control fluid by the controller. As previously discussed, the controller (119) may open and close valves (e.g., valves 117 and 118) to expose the pneumatic side of the pod pump to a positive pressure (121) or a vacuum pressure (122) at different points during a pumping cycle.

In addition, in certain embodiments, the controller (typically electronic) may also be kept separate from the various fluid circuits, such that there is no electronic contact between the controller and the various fluid circuits, although the control fluid (e.g., air) is able to pass between the controller and the various pumps. This configuration has a number of advantages, including ease of maintenance (the controller and the various circuits can be repaired independently of each other). In one embodiment, the fluid circuits may be heated to disinfection temperatures and/or exposed to relatively high temperatures or other harsh conditions (e.g., radiation) to effect disinfection, while the electronic controller (which is typically more delicate) is not exposed to such harsh conditions, and may even be kept separate by an insulating wall (e.g., a "firewall") or the like.

Thus, in some embodiments, the system may include a "cold" section (which is not heated), and a "hot" section, portions of which may be heated, e.g., for disinfection purposes. The cold section may be insulated from the hot section through insulation. In one embodiment, the insulation may be molded foam insulation, but in other embodiments can be any type of insulation, including but not limited to a spray insulation or an insulation cut from sheets.

In some cases, the "hot" section may be heated to relatively high temperatures, e.g., the "hot" section may be heated to temperatures sufficient to sterilize components within the "hot" section. As many electronics can not go above 50° C. without failing or other adverse consequences, it may be advantageous in some embodiments to separate the electronics from other components that may be disinfected. Thus, in some cases, the components that may need to be disinfected are kept in the "hot" section, while components that cannot be heated to such temperatures are kept in the "cold" section. In one embodiment, the cold section includes a circulation system, e.g., a fan and/or a grid to allow air to flow in and out of the cold box.

All, or a portion of, the "hot" section may be encased in insulation. In some cases, the insulation may be extended to cover access points to the "hot" section, e.g., doors, ports, gaskets, and the like. For instance, when the "hot" section is sealed, the insulation may completely surround the "hot" section in some cases.

Non-limiting examples of components that may be present within the "cold" section include power supplies, electronics, power cables, pneumatic controls, or the like. In some cases, at least some of the fluids going to and from the "hot" section may pass through the "cold" section; however, in other cases, the fluids may pass to the "hot" section without passing through the "cold" section.

Non-limiting examples of components that may be present within the "hot" section include cassettes (if present), fluid lines, or the like. In some cases, some electrical components may also be included in the "hot" section. These include, but are not limited to, a heater. In one embodiment, the heater can be used to heat the hot box itself, in addition to fluid (see, e.g., heater 72 of FIG. 3A). In some embodiments, the heater heats the entire "hot" section to reach a desired temperature.

In one embodiment, the "hot" section includes some or all of the fluidic lines. In addition, in some cases, the "hot" section may include, but is not limited to, temperature and conductivity sensors, blood leak sensors, heaters, other sensors, switches, emergency lights, or the like.

In some cases, a manifold may transition from the "cold" section to the "hot" section, e.g., a manifold for air or another control fluid.

Separating the components into "hot" and "cold" sections may offer several advantages; those include, but are not limited to: longevity of electrical components, reliability, or efficiency. For example, by separating the components into hot and cold, the entire hot box may be heated. This may allows for more efficient use of heat which leads to a more energy efficient system. This also may allow for the use of standard, off the shelf electronics which leads to lower cost.

In some embodiments, the control fluid used for controlling the pumps, valves, etc. is air, and the air may be brought into the system through the operation of one or more air compressors. In some cases, the air compressor may be kept separate from the blood flow path and the dialysate flow path systems within the system, and air from the air compressor may be brought to the various pumps through various tubes, conduits, pipes, or the like. For example, in one embodiment, a pneumatic interface is used to direct air from the air compressor to a series of tubes or conduits fluidically connected with the various pumps or chambers.

Figure 16:
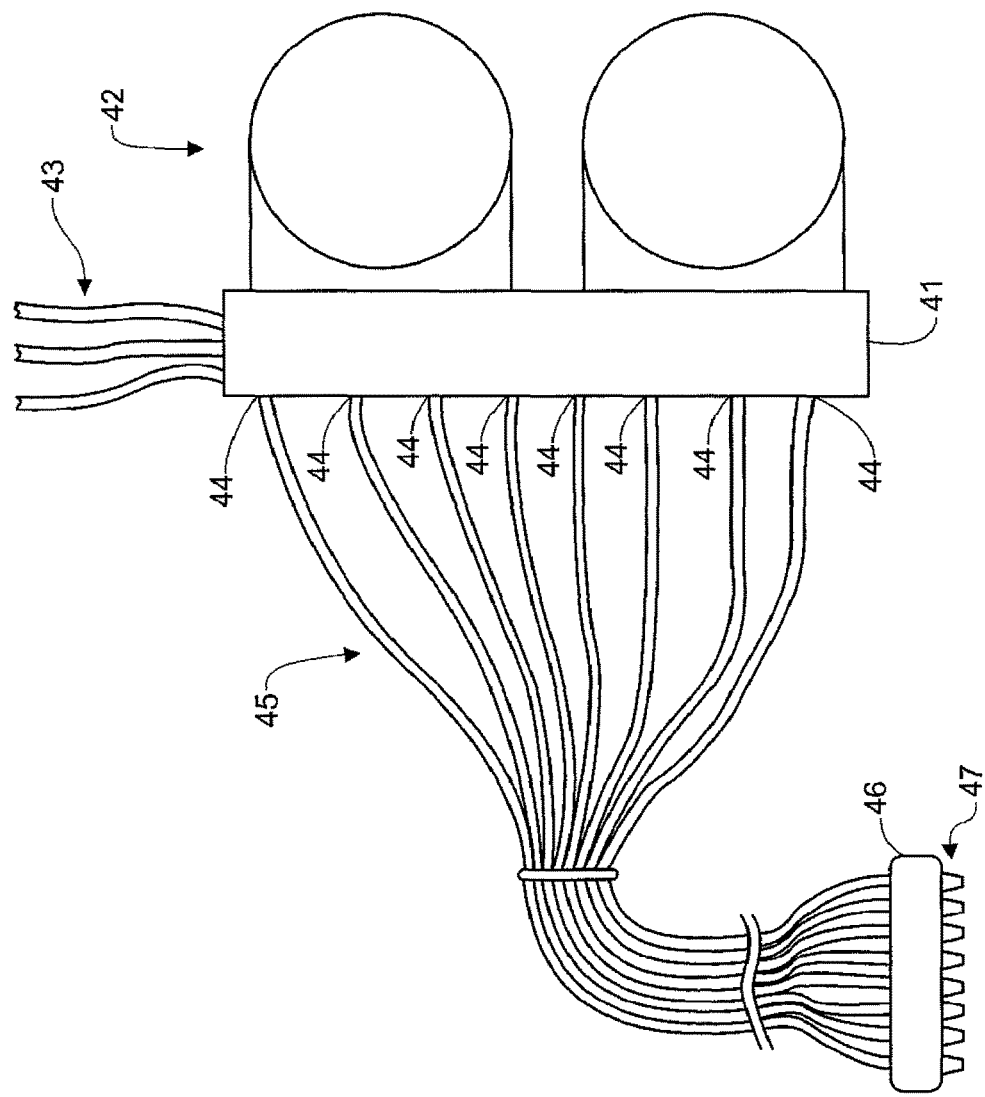
FIG. 16 is a schematic representation of a dual-housing cassette arrangement according to one embodiment.

A non-limiting example can be seen in FIG. 16, which shows a schematic representation of a dual-housing arrangement according to one embodiment. This arrangement may be advantageously used with cassettes that include many pneumatically actuated pumps and/or valves. If the number of pneumatically actuated pumps and/or valves in a cassette is large enough, the cassette containing these pumps and valves can become so large, and the pressures involved can become so great, that it may become difficult to properly seal and position all of the pumps and valves. This difficulty may be alleviated by using two or more different housings. The valves and pumps (such as pod pumps 42) are placed in a main housing 41, from which connecting tubes 45 lead from pneumatic ports 44. The main housing 41 also has inlet and outlet tubes 43, which allow liquid to flow into and out of the main housing. The connecting tubes 45 provide pneumatic communication between valves and pumps in the main housing 41 and a smaller, secondary tube-support housing 46, which is provided with a pneumatic interface 47 for each of the tubes. The proper positioning and sealing of all the pneumatic interfaces 47 against receptacles in the base unit can be accomplished more easily with the smaller tube-support housing 46 than it would be if the pneumatic actuation was applied to the larger main housing directly.

The control fluid (e.g., air) may be supplied to the system with one or more supply tanks or other pressure sources, in one set of embodiments. For instance, if two tanks are used, one supply tank may be a positive pressure reservoir, and in one embodiment, has a set point of 750 mmHg (gauge pressure) (1 mmHg is about 133.3 pascals). The other supply tank can be a vacuum or negative pressure reservoir, and in one embodiment, has a set point of −450 mmHg (gauge pressure). This pressure difference may be used, for instance, between the supply tanks and the required pod pressure to allow for accurate control of the variable valves to the pod pumps. The supply pressure limits can be set based on maximum pressures that can be set for the patient blood flow pump plus some margin to provide enough of a pressure difference for control of the variable valves. Thus, in some cases, the two tanks may be used to supply pressures and control fluids for the entire system.

In one embodiment, two independent compressors service the supply tanks. Pressure in the tanks can be controlled using any suitable technique, for instance, with a simple bang-bang controller (a controller that exists in two states, i.e., in an on or open state, and an off or closed state), or with more sophisticated control mechanisms, depending on the embodiment. As an example of a bang-bang controller, for the positive tank, if the actual pressure is less then the desired pressure minus a hysteresis, the compressor servicing the positive tank is turned on. If the actual pressure is greater then the desired pressure plus a hysteresis, the compressor servicing the positive tank is turned off. The same logic may be applied to the vacuum tank and control of the vacuum compressor with the exception that the sign of the hysteresis term is reversed. If the pressure tanks are not being regulated, the compressor is turned off and the valves are closed.

Tighter control of the pressure tanks can be achieved by reducing the size of the hysteresis band, however this will result in higher cycling frequencies of the compressor. If very tight control of these reservoirs is required, the bang-bang controller could be replaced with a PID controller and using PWM signals on the compressors. Other methods of control are also possible.

However, other pressure sources may be used in other embodiments, and in some cases, more than one positive pressure source and/or more than one negative pressure source may be used. For instance, more than one positive pressure source may be used that provides different positive pressures (e.g., 1000 mmHg and 700 mmHg), which may be used to minimize leakage. For example, high positive pressure can be used to control valves, whereas lower positive pressures can be used to control pumps. This limits the amount of pressure that can potentially be sent to the dialyzer or to the patient, and helps to keep actuation of the pumps from overcoming the pressures applied to adjacent valves. A non-limiting example of a negative pressure is −400 mmHg. In some cases, the negative pressure source may be a vacuum pump, while the positive pressure pump may be an air compressor.

Certain aspects of the invention include various sensors; for instance, in various embodiments of the inventions described herein, systems and methods for fluid handling may be utilized that comprise sensor apparatus systems comprising a sensor manifold. Examples of such embodiments may include systems and methods for the diagnosis, treatment, or amelioration of various medical conditions, including embodiments of systems and methods involving the pumping, metering, measuring, controlling, and/or analysis of various biological fluids and/or therapeutic agents, such as various forms of dialysis, cardiac bypass, and other types of extracorporeal treatments and therapies. Further examples include fluid treatment and preparation systems, including water treatment systems, water distillation systems, and systems for the preparation of fluids, including fluids utilized diagnosis, treatment, or amelioration of various medical conditions, such as dialysate.

Examples of embodiments of the inventions described herein may include dialysis systems and methods. More specifically, examples of embodiments of the inventions described herein may include hemodialysis systems and methods of the types described in U.S. patent application Ser. No. 11/871,680, filed Oct. 12, 2007 and issued as U.S. Pat. No. 8,273,049 on Sep. 25, 2012, entitled "Pumping Cassette"; or U.S. patent application Ser. No. 12/038,648, filed Feb. 27, 2008 and issued as U.S. Pat. No. 8,042,563 on Oct. 25, 2011, entitled "Cassette System Integrated Apparatus," each incorporated herein by reference.

In such systems and methods, the utilization of one or more sensor manifolds may allow subject media to be moved from one environment to another environment that is more conducive to obtaining sensor readings. For example, the cassette manifold may be contained in an area that is less subject to various types of environment conditions, such as temperature and/or humidity, which would not be preferable for sensor apparatus such as a sensing probe. Alternatively, sensing apparatus and sensing apparatus system may be delicate and may be more prone to malfunctions than other components of a system. Separating the sensor apparatus and the sensor apparatus systems from other components of the system by use of a sensor manifold may allow the sensing apparatus and sensing apparatus systems to be checked, calibrated, repaired or replaced with minimal impact to other components in the system. The ability to check, calibrate, repair or replace the sensor manifold with minimal impact to the remainder of the system may be advantageous when utilized in connection with the integrated cassette systems and methods described in a U.S. patent application Ser. No. 12/038,648, filed Feb. 27, 2008 and issued as U.S. Pat. No. 8,042,563 on Oct. 25, 2011, entitled "Cassette System Integrated Apparatus". Alternatively, the sensor manifold may be replaced either more or less frequently than other components of the system.

With reference to FIGS. 53-58, various embodiments of an exemplary sensor manifold are shown. One or more subject media, e.g., a liquid in these exemplary embodiments, may be contained in or flow through cassette manifold 4100. For example, one subject media may enter cassette manifold 4100 via pre-molded tube connector 4101 and exit the cassette manifold via pre-molded tube connector 4102. Between tube connector 4101 and 4102, there is a fluid path though the cassette (best shown as fluid path 4225 in FIG. 54). Likewise, fluid paths (shown as fluid paths 4223, 4220, 4222, 4224, and 4221 respectively in FIG. 54) extend between sets of tube connectors 4103 and 4104; 4105 and 4106; 4107, 4108, and 4109; 4110 and 4111; and 4112 and 4113. In certain embodiments, each fluid path may contain subject media of different composition or characteristics. In other embodiments, one or more fluid paths may contain the same or similar subject media. In certain embodiments, the same subject media may be flowed through more than one flow path at the same time to check and/or calibrate the sensor apparatus systems associated with such fluid paths.

Figure 54:
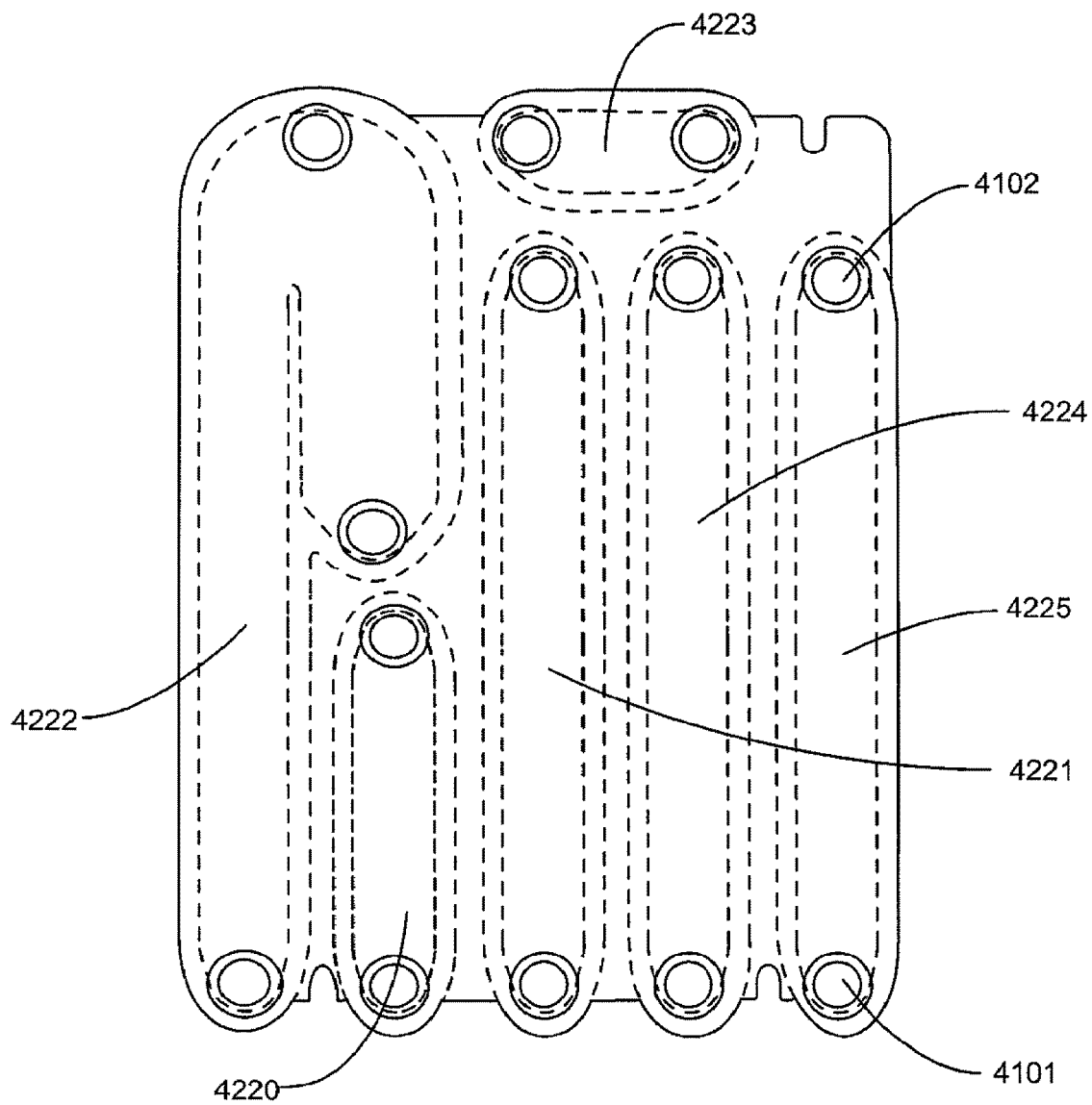
FIG. 54 is a view of the fluid paths within the exemplary sensor manifold shown in FIG. 53.
Figure 55:
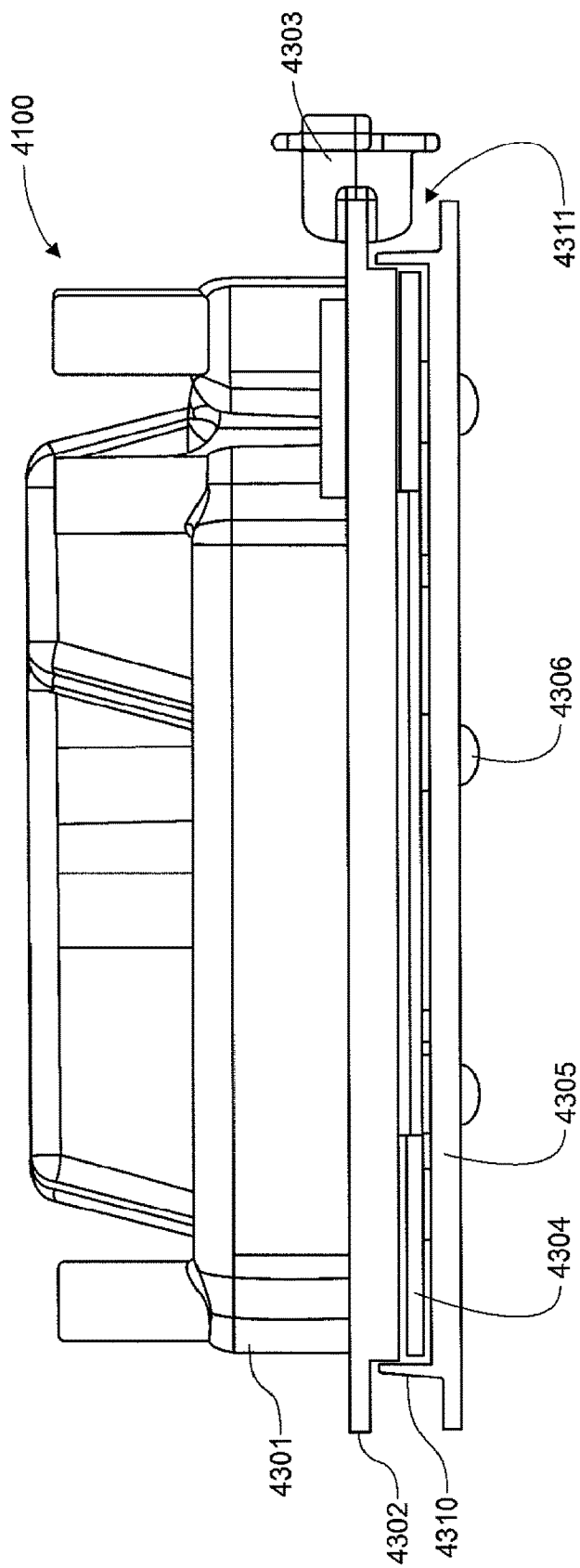
FIG. 55 is a side view of the exemplary sensor manifold shown in FIG. 53.

Referring now to FIG. 55, in these exemplary embodiments of sensor manifold 4100 that may be used in conjunction with the sensor apparatus and sensor apparatus systems described herein, the cassette includes a top plate 4302 and a base 4301. Fluid paths, such as the fluid path 4225 (as shown in FIG. 54) extending between tube connectors 4101 and 4102 extend between the base and top plate. The cassettes may be constructed from a variety of materials. Generally, in the various exemplary embodiment, the materials used are solid and non flexible. In the preferred embodiment, the plates are constructed of polysulfone, but in other embodiments, the cassettes are constructed of any other solid material and in exemplary embodiments, of any thermoplastic. Some embodiments of sensor manifold 4100 may be fabricated utilizing the systems and methods described in U.S. patent application Ser. No. 12/038,648, filed Feb. 27, 2008 and issued as U.S. Pat. No. 8,042,563 on Oct. 25, 2011, entitled "Cassette System Integrated Apparatus".

Referring again to FIG. 55, in these exemplary embodiments of sensor manifolds that may be used in conjunction with the sensor apparatus and sensor apparatus systems described herein, the sensor manifold 4100 may also include printed circuit board (PCB) 4304 and a PCB cover 4305. Various embodiments may also include connector 4303 (also shown in FIGS. 53 and 56B) which may be utilized to mechanically connect the cassette manifold 4100 to the system, such as a hemodialysis system. Cassette manifold 4100 may also utilize various methods to hold the layers of sensor manifold 4100 together as a unit. In various embodiments, as shown in FIG. 43, connectors 4306 (also shown in FIG. 56B), which in one embodiment is a screw, but in other embodiments may be any means for connection, are utilized, but any means known to one of skill in the art, such as other types of screws, welds, clips, clamps, and other types of chemical and mechanical bonds may be utilized.

Figure 56A:
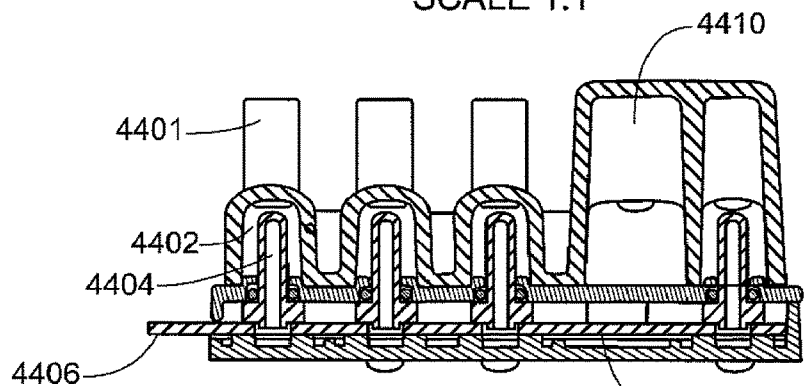
FIG. 56A is a cross sectional view of the exemplary sensor manifold shown in FIG. 53 at cross section A-A of FIG. 56B.

Referring now to FIG. 56A, in exemplary embodiments of the sensor manifold 4100, tube connectors, such as tube connector 4401, is utilized to bring subject media into or remove subject media from fluid path 4402. Sensing probes, such as sensing probe 4404 extending into fluid path 4402, are incorporated into sensor manifold 4100 so as to determine various properties of the subject media contained in or flowing through the particular fluid path in the sensor manifold. In various embodiments one sensing probe may be utilized to sense temperature and/or other properties of the subject media. In another embodiment, two sensing probes may be utilized to sense temperature and/or conductivity and/or other properties of the subject media. In yet further embodiments, three or more sensing probes may be included. In some embodiments, one or more combination temperature and conductivity sensing probes of the types generally described herein may be utilized. In other embodiments, the conductivity sensors and temperature sensor can be any conductivity or temperature sensor in the art. In one embodiment, the conductivity sensor elements (or sensor leads) are graphite posts. In other embodiments, the conductivity sensors elements are posts made from stainless steel, titanium, or any other material of the type typically used for (or capable of being used for) conductivity measurements. In certain embodiments, the conductivity sensors will include an electrical connection that transmits signals from the sensor lead to a sensor mechanism, controller or other device. In various embodiments, the temperature sensor can be any of the temperature sensors commonly used (or capable of being used) to sense temperature.

Figure 53:
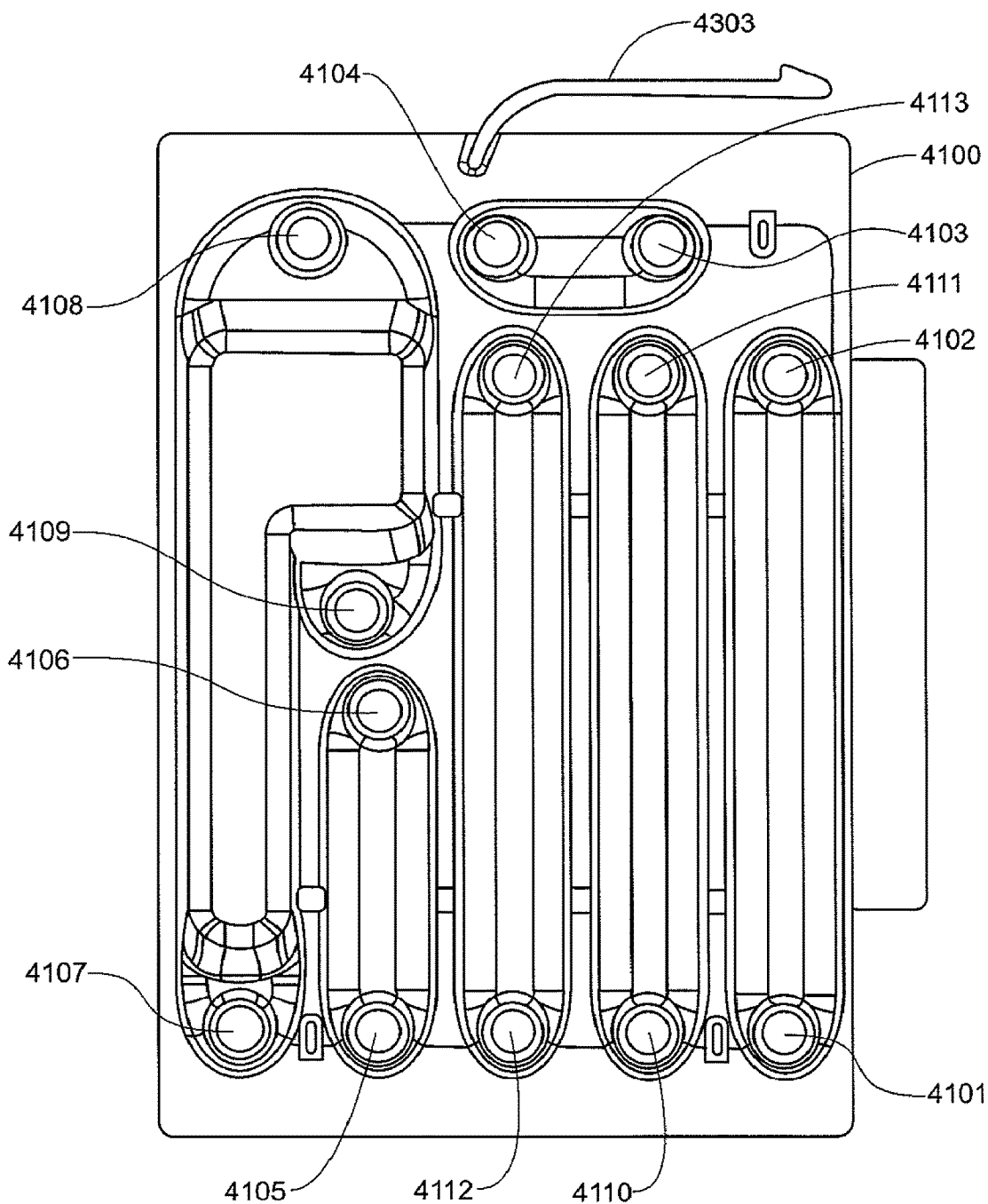
FIG. 53 is a view of another exemplary sensor manifold.

Referring again to FIG. 56A, sensing probe 4404 is electrically connected to PCB 4405. In certain embodiments, an electrically conductive epoxy is utilized between sensor element 4404 and PCB 4405 to ensure appropriate electrical connection, although other methods known to those of skill in the art may be used to obtain an appropriate electrical connection between sensor element 4404 and PCB 4405. PCB 4405 is shown with edge connector 4406. In various embodiments, edge connector 4406 may be used to transmit sensor information from cassette manifold 4100 to the main system. Edge connector 4406 may be connected to a media edge connector (such as media edge connector 4601 shown in FIG. 58). In various embodiments, media edge connector 4601 may be installed in a hemodialysis machine (not shown). In such embodiments, guide tracks 4310 and 4311 (as shown in FIG. 55) may be utilized to assist in the connection of edge connector 4406 and media edge connector 4601. Various embodiments may also include connector 4303 (as shown in FIGS. 53, 55 and 56B) which may be utilized to mechanically connect the cassette manifold 4100 to the system, such as a hemodialysis system.

Referring again to FIG. 56A, air trap 4410 is shown. In certain embodiments, an air trap, such as air trap 4410, may be utilized to trap and purge air in the system. As may be best shown in FIG. 54, subject media may flow through fluid path 4222 between tube connectors 4107 and 4109 in sensor manifold 4100. As the flow of the subject media is slowed around the turn in fluid path 4222 (near tube connector 4108), air may be removed from the subject media through connector 4108.

Figure 56B:
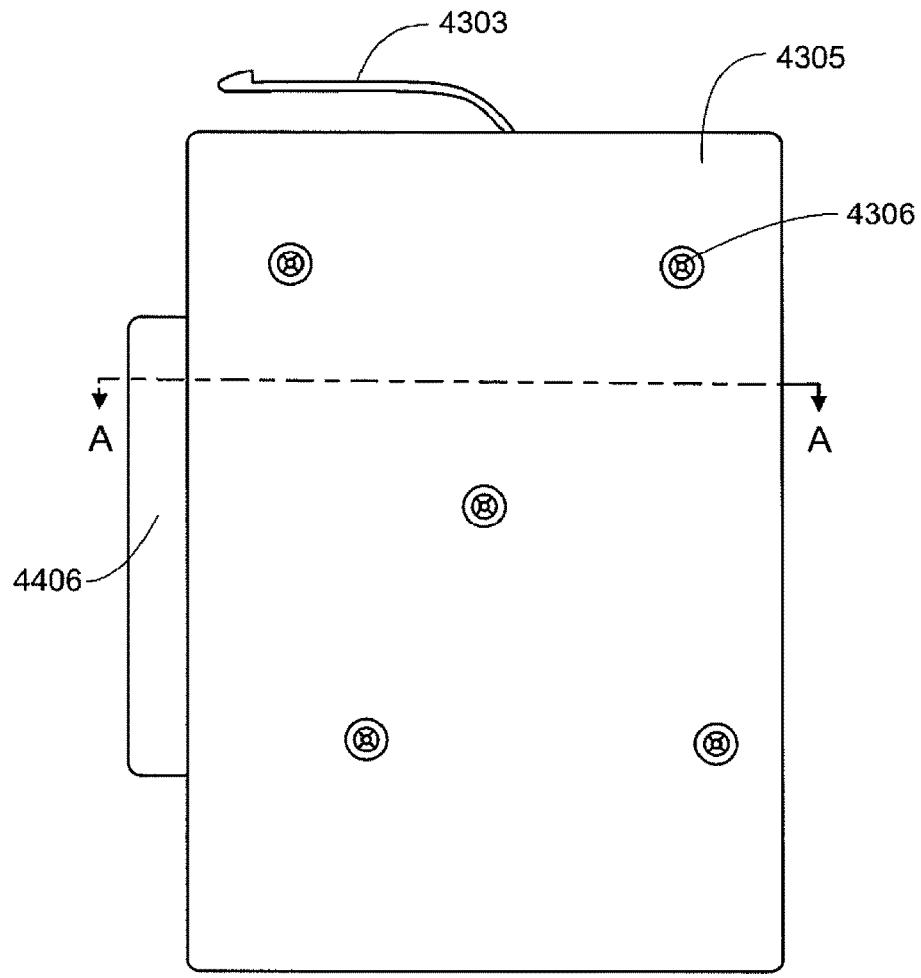
FIG. 56B is a front view of the exemplary sensor manifold shown in FIG. 53.

Referring now to FIG. 56B, PCB cover 4305 is shown. PCB cover 4305 may be connected to sensor manifold 4100 by connectors 4306. Edge connector 4406 is also shown.

In accordance with certain embodiments, sensor manifold 4100 is passive with respect to control of the fluid flow. In such embodiments, sensor manifold 4100 does not contain valves or pumping mechanisms to control the flow of the subject media. In such embodiments, the flow of the subject media may be controlled by fluid control apparatus external to sensor manifold 4100. In other embodiments, the sensor manifold may include one or more mechanical valves, pneumatic valves or other type of valve generally used by those of skill in the art. In such embodiments, the sensor manifold may include one or more pumping mechanisms, including pneumatic pumping mechanisms, mechanical pumping mechanisms, or other type of pumping mechanisms generally used by those of skill in the art. Examples of such valves and pumping mechanisms may include the valves and pumping mechanisms described in U.S. patent application Ser. No. 11/871,680, filed Oct. 12, 2007 and issued as U.S. Pat. No. 8,273,049 on Sep. 25, 2012, entitled "Pumping Cassette"; or U.S. patent application Ser. No. 12/038,648, filed Feb. 27, 2008 and issued as U.S. Pat. No. 8,042,563 on Oct. 25, 2011, entitled "Cassette System Integrated Apparatus".

Figure 57:
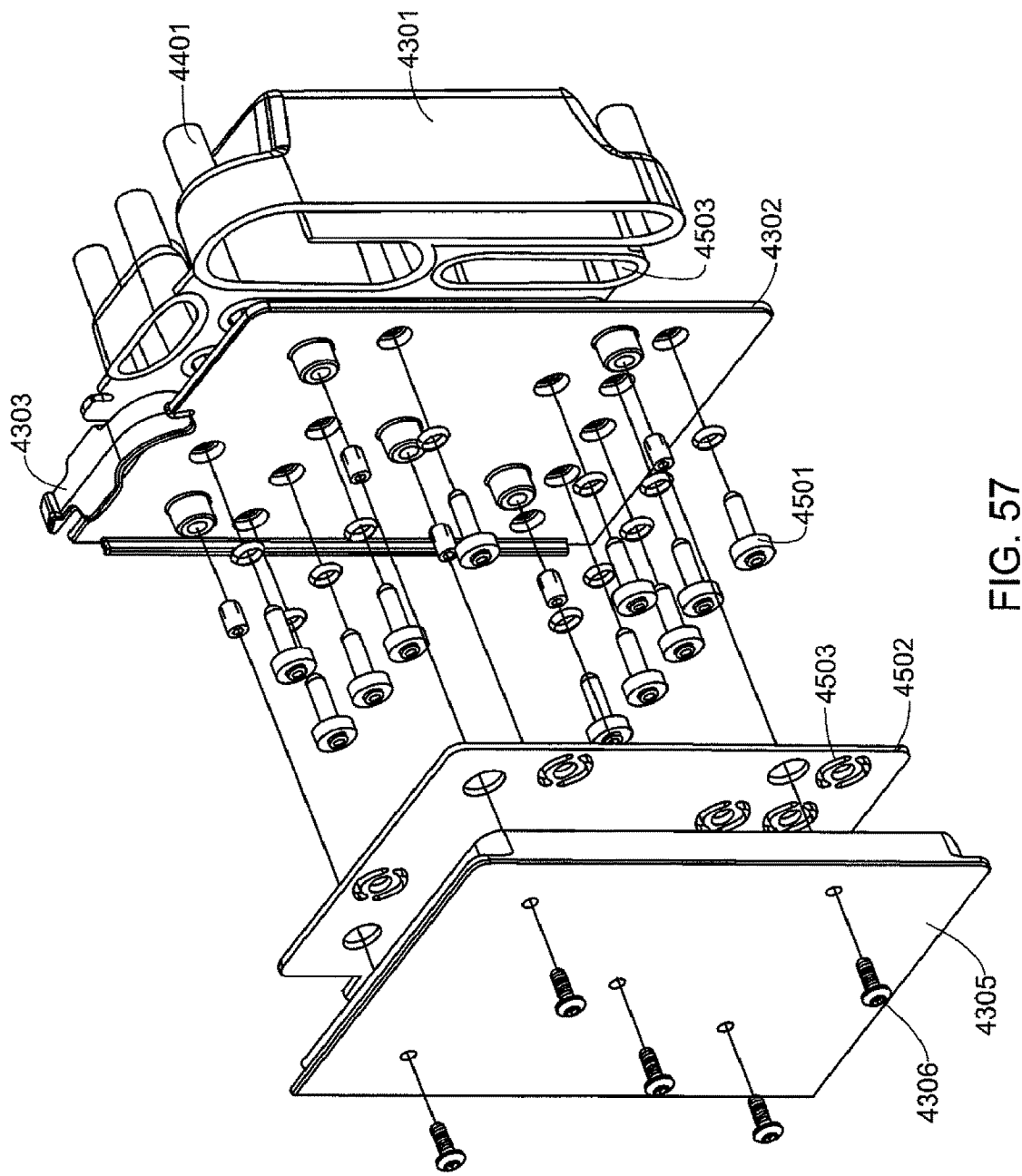
FIG. 57 is an exploded view of the exemplary sensor manifold shown in FIG. 53.
Figure 58:
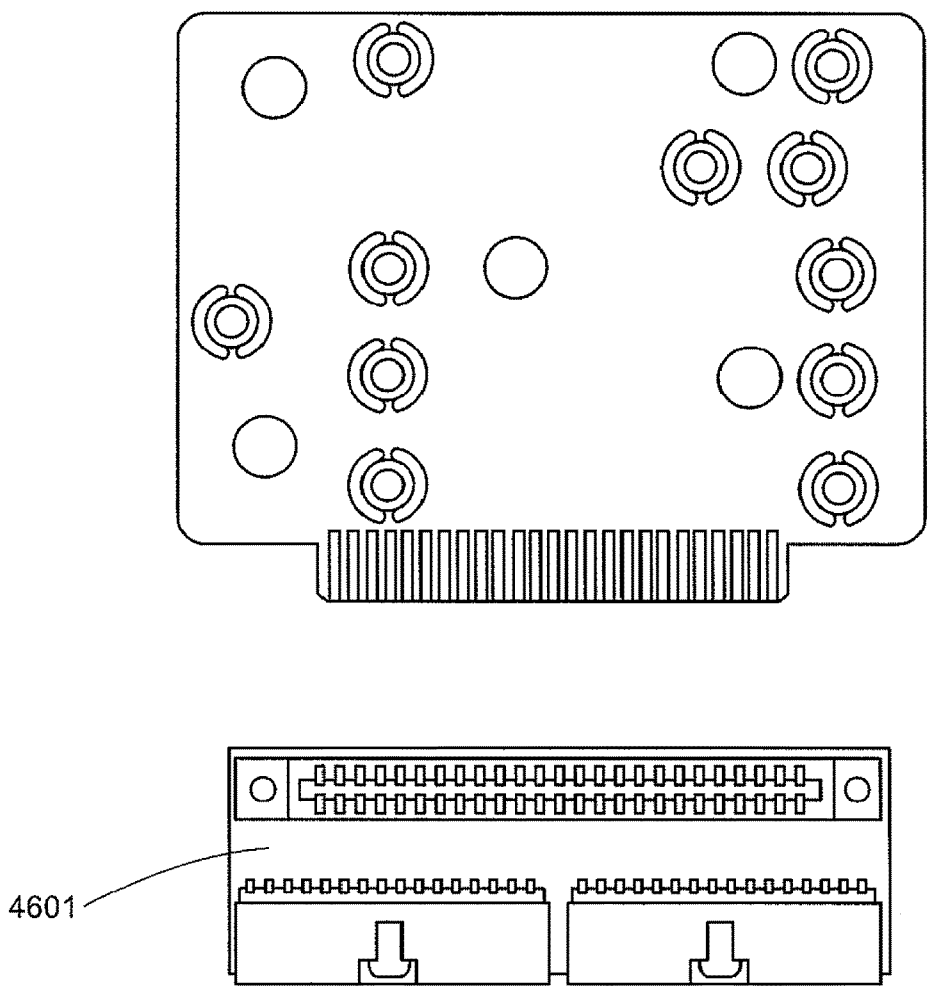
FIG. 58 is a view of a printed circuit board and media edge connector in accordance with the exemplary sensor manifold shown in FIG. 53.

Referring now to FIG. 57, tube connector 4401 is shown in base 4301. Top plate 4302 is shown, along with connector 4303. Sensing probes, such as sensing probe 4501, extend through top plate 4302 into fluid path 4503. Sensing probe 4501 may be various types of sensors, including the embodiments of sensing probes generally discussed herein.

The sensing probes, such as sensing probe 4501, may be all the same, may be individually selected from various sensors based on the type of function to be performed, or the same probe may be individually modified based on the type of function to be performed. Similarly, the configuration of the fluid paths, such as the length of the fluid path and the shape of the fluid path, may be selected based on the function to be performed. By way of example, to detect the temperature of the subject media in a fluid path, a temperature sensor, such as a thermistor, may be used. Again, by way of example, to measure the conductivity of the subject media, one sensing probe configured to measure temperature and conductivity, and one sensing probe configured only to measure conductivity may be utilized. In other embodiments, two or more sensing probes configured to measure both temperature and conductivity may be utilized. In various embodiments of such configurations, by way of example, the second temperature sensor may be present but not utilized in normal operation, or the second temperature may be utilized for redundant temperature measurements, or the or the second temperature may be utilized for redundant temperature measurements.

Referring again to FIG. 57, PCB 4502 is shown with electrical connection 4503. As further shown in FIG. 58, PCB 4602 is shown with electrical connection 4603 for connection to a sensing probe (shown as 4501 in FIG. 45). PCB 4602 also contains opening 4604 for attachment to top plate (shown as 4305 in FIG. 57). In certain embodiments, electrical connection 4603 is mounted onto, or manufactured with, PCB 4602 with air gap 4606. In such embodiments, air gap 4606 may be utilized to provide protection to the electrical connection between sensing probe 4501 and PCB 4602 by allowing shrinking and expansion of the various components of sensor manifold 4100 with lesser impact to PCB 4602.

Referring again to FIG. 58, PCB 4602 is also shown with edge connector 4605. As described herein, edge connector 4605 may interface with edge connector receiver 4601, which may be connected to the system, such as the hemodialysis system, to which sensor manifold 4100 interfaces.

Figure 59:
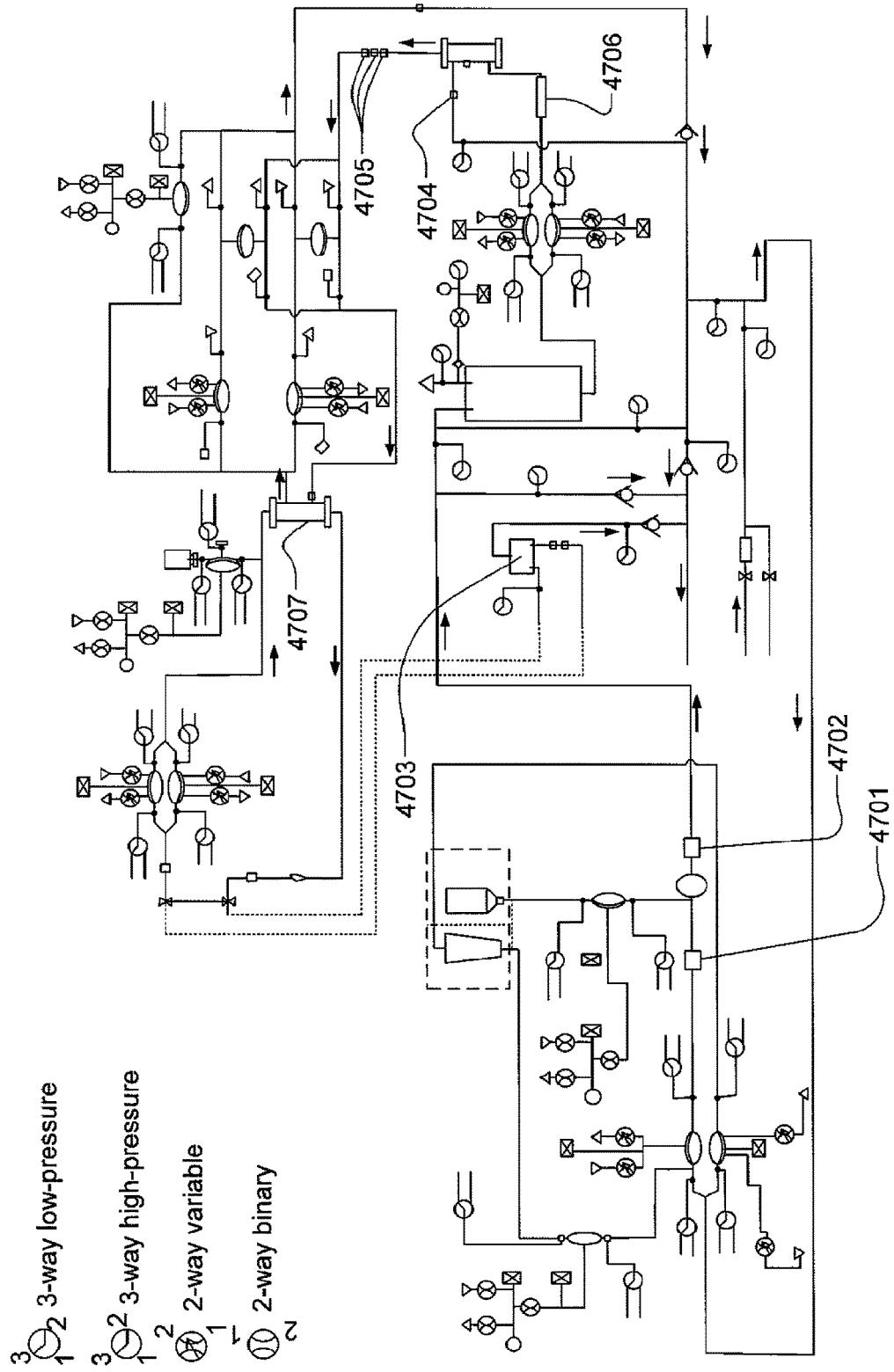
FIG. 59 is an exemplary fluid schematic of a hemodialysis system.

Various embodiments of exemplary sensor manifold 4100 shown in FIG. 53-58 may be utilized in conjunction with hemodialysis systems and methods described in U.S. patent application Ser. No. 11/871,680, filed Oct. 12, 2007 and issued as U.S. Pat. No. 8,273,049 on Sep. 25, 2012, entitled "Pumping Cassette"; or U.S. patent application Ser. No. 12/038,648, filed Feb. 27, 2008 and issued as U.S. Pat. No. 8,042,563 on Oct. 25, 2011, entitled "Cassette System Integrated Apparatus". In certain embodiments, sensor manifold 4100 contains all of the temperature and conductivity sensors shown in FIG. 59. FIG. 59 depicts a fluid schematic in accordance with one embodiment of the inventions described in the patent applications reference above.

By way of example, in various embodiments, the temperature and conductivity of the subject media at position 4701 as shown in FIG. 59 may be determined utilizing sensor manifold 4100. In such embodiments, subject media flows into tube connector 4105 (as shown in FIG. 53) through fluid path 4220 (as shown in FIG. 54) and exits at tube connector 4106 (as shown in FIG. 53). The conductivity of the subject media is measured by two sensing probes (not shown) extending into fluid path 4220, at least one of which has been configured to include a temperature sensing element, such as a thermistor. The conductivity measurement or the temperature measurement of the subject media may be utilized to determine and/or correlate a variety of information of utility to the hemodialysis system. For example, in various embodiments at position 4701 in FIG. 59, the subject media may be comprised of water to which a bicarbonate-based solution has been added. Conductivity of the subject media at position 4701 may be utilized to determine if the appropriate amount of the bicarbonate based solution has been added prior to position 4701. In certain embodiments, if the conductivity measurement deviates from a predetermined range or deviates from a predetermined measurement by more than a predetermined amount, then the subject media may not contain the appropriate concentration of the bicarbonate based solution. In such instances, in certain embodiments, the hemodialysis system may be alerted.

Again, by way of example, in various embodiments, the conductivity of the subject media at position 4702 as shown in FIG. 59 may be determined utilizing sensor manifold 4100. In such embodiments, subject media flows into tube connector 4112 (as shown in FIG. 41) through fluid path 4221 (as shown in FIG. 54) and exits at tube connector 4113 (as shown in FIG. 53). The conductivity of the subject media is measured by two sensing probes (not shown) extending into fluid path 4221, at least one of which has been configured to include a temperature sensing element, such as a thermistor. The conductivity measurement or the temperature measurement of the subject media may be utilized to determine and/or correlate a variety of information of utility to the hemodialysis system. For example, in various embodiments at position 4702 in FIG. 59, the subject media may be comprised of water to which a bicarbonate-based solution and then an acid based solution has been added. Conductivity of the subject media at position 4702 may be utilized to determine if the appropriate amount of the acid based solution (and the bicarbonate based solution in a previous step) has been added prior to position 4702. In certain embodiments, if the conductivity measurement deviates from a predetermined range or deviates from a predetermined measurement by more than a predetermined amount, then the subject media may not contain the appropriate concentration of the acid based solution and the bicarbonate based solution. In such instances, in certain embodiments, the hemodialysis system may be alerted.

By way of further example, in various embodiments, the temperature and to conductivity of the subject media at position 4703 as shown in FIG. 59 may be determined utilizing sensor manifold 4100. In such embodiments, subject media may flow into or out of tube connector 4107 (as shown in FIG. 53) through fluid path 4222 (as shown in FIG. 54) and may flow into or out of tube connector 4109 (as shown in FIG. 53). As described herein, air may be removed from the subject media as it moves past the turn in fluid path 4222. In such instances, a portion of the subject media may be removed through tube connector 4108 to the drain, bringing with it air from the air trap. The conductivity of the subject media is measured by two sensing probes (not shown) extending into fluid path 4222, at least one of which has been configured to include a temperature sensing element, such as a thermistor. The conductivity measurement or the temperature measurement of the subject media may be utilized to determine and/or correlate a variety of information of utility to the hemodialysis system. For example, in various embodiments, the conductivity measurement at position 4703 in FIG. 59 may be utilized to correlate to the clearance of the dialyzer. In such instances, in certain embodiments, this information may then be sent to the hemodialysis system.

Again, by way of further example, in various embodiments, the temperature of the subject media at position 4704 as shown in FIG. 59 may be determined utilizing sensor manifold 4100. In such embodiments, subject media flows into tube connector 4103 (as shown in FIG. 53) through fluid path 4223 (as shown in FIG. 54) and exits at tube connector 4104 (as shown in FIG. 53). The temperature of the subject media is measured by one or more sensing probes (not shown) extending into fluid path 4223. The temperature measurement of the subject media at position 4704 may be utilized to determine and/or correlate a variety of information of utility to the hemodialysis system. For example, in various embodiments at position 4704 in FIG. 59, the temperature of the subject media is determined down stream of a heating apparatus 4706. If the temperature deviates from a predetermined range or deviates from a predetermined measurement by more than a predetermined amount, then the hemodialysis system may be alerted. For example in certain embodiments, the subject media may be re-circulated through the heating apparatus 4706 until the temperature of the subject media is within a predetermined range.

Again, by way of further example, in various embodiments, the temperature and conductivity of the subject media at position 4705 as shown in FIG. 59 may be determined utilizing sensor manifold 4100. In such embodiments, subject media flows into tube connector 4110 (as shown in FIG. 53) through fluid path 4224 (as shown in FIG. 54) and exits at tube connector 4111 (as shown in FIG. 53). The conductivity of the subject media is measured by two sensing probes (not shown) extending into fluid path 4224, at least one of which has been configured to include a temperature sensing element, such as a thermistor. The conductivity measurement or the temperature measurement of the subject media may be utilized to determine and/or correlate a variety of information of utility to the hemodialysis system. For example, the temperature and conductivity measurement at position 4705 may be used as a further safety check to determine if the temperature, conductivity, and, by correlation, the composition of, the subject media is within acceptable ranges prior to the subject media reaching the dialyzer 4707 and, thus, the patient. In certain embodiments, if the temperature and/or conductivity measurement deviates from a predetermined range or deviates from a predetermined measurement by more than a predetermined amount, then the hemodialysis system may be alerted.

For the various embodiments described herein, the cassette may be made of any material, including plastic and metal. The plastic may be flexible plastic, rigid plastic, semi-flexible plastic, semi-rigid plastic, or a combination of any of these. In some of these embodiments the cassette includes one or more thermal wells. In some embodiments one or more sensing probes and/or one or more other devices for transferring information regarding one or more characteristics of such subject media are in direct contact with the subject media. In some embodiments, the cassette is designed to hold fluid having a flow rate or pressure. In other embodiments, one or more compartments of the cassette is designed to hold mostly stagnant media or media held in the conduit even if the media has flow.

In some embodiments, the sensor apparatus may be used based on a need to separate the subject media from the sensing probe. However, in other embodiments, the sensing probe is used for temperature, conductivity, and/or other sensing directly with subject media.

Another aspect of the invention is generally directed to methods and operations of the systems as discussed herein. For instance, a hemodialysis system may be primed, flow-balanced, emptied, purged with air, disinfected, or the like.

Figure 17A:
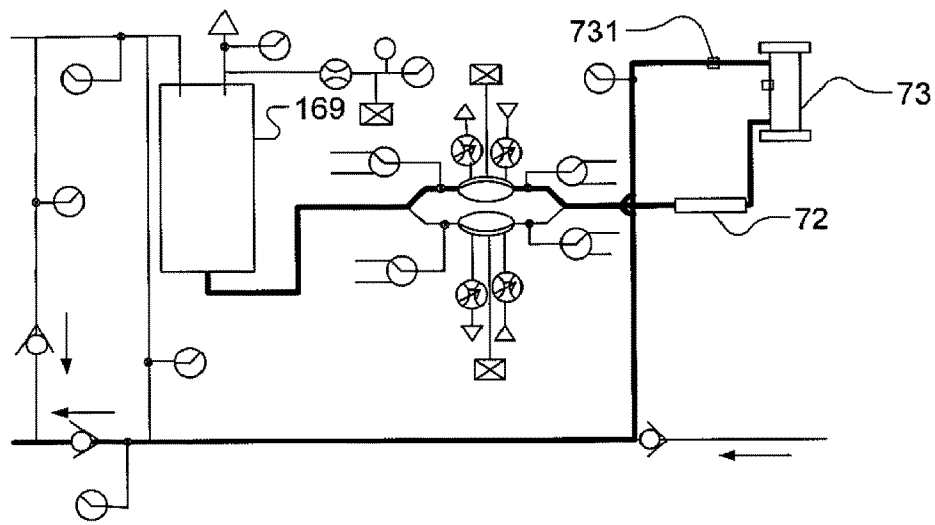
FIGS. 17A-17C are schematics relating to the priming of a portion of a system, in one embodiment of the invention.

One set of embodiments is generally directed to priming of the system with a fluid. The fluid to be primed is first directed to a dialysate tank (e.g. dialysate tank 169). Ultrafilter 73 is then first primed by pushing fluid from dialysate tank 169 to ultrafilter 73, and caused to exit line 731 through waste line 39 to the drain, as is shown by the heavy black lines in FIG. 17A. Any air present in ultrafilter 73 naturally rises to the priming port and is flushed to the drain.

Figure 17B:
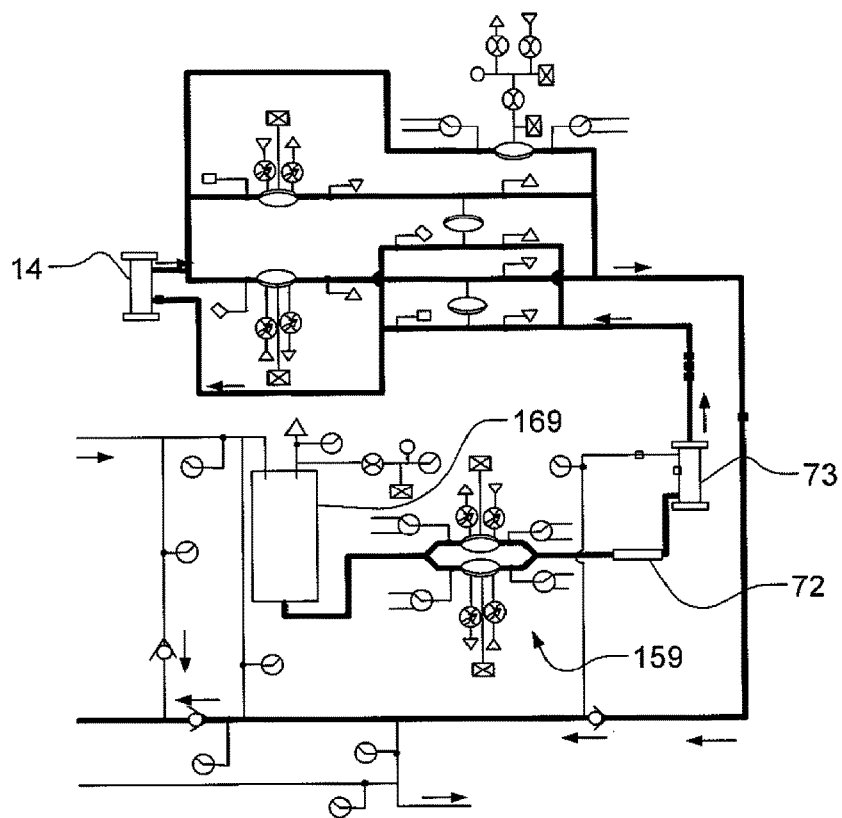

Next, as is shown in FIG. 17B, the balancing circuit and pump 159 of the directing circuit are primed by pushing fluid through the ultrafilter 73, through the balancing circuit, and out to the drain. Pump 159 is primed by running fluid forwards (through the ultrafilter to the drain). Air entering dialyzer 14 bubbles to the top of the dialyzer and leaves through the dialyzer exit to the drain.

Figure 17C:
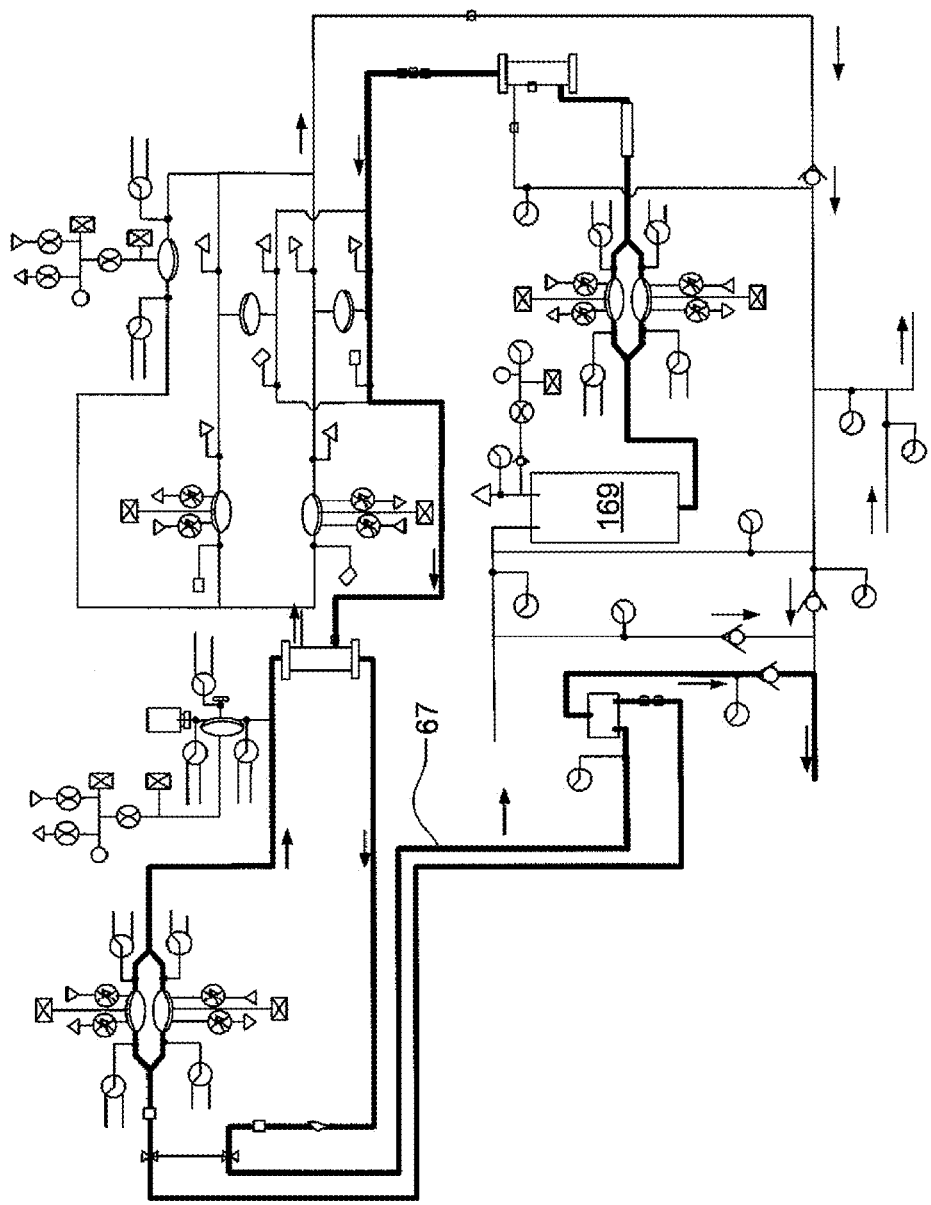

Next, the blood flow pump and tubing are primed by circulating fluid through the blood flow circuit and the air trap back to the directing circuit via conduit 67. As can be seen in FIG. 17C, fluid passes through the ultrafilter and dialyzer, forcing flow through the air trap and down the drain. The air trap traps air circulating in the blood flow circuit and sends it to the drain. Priming can be stopped when the air sensors stop detecting air (and some additional fluid has been passed through the system, as a safety margin).

Figure 19:
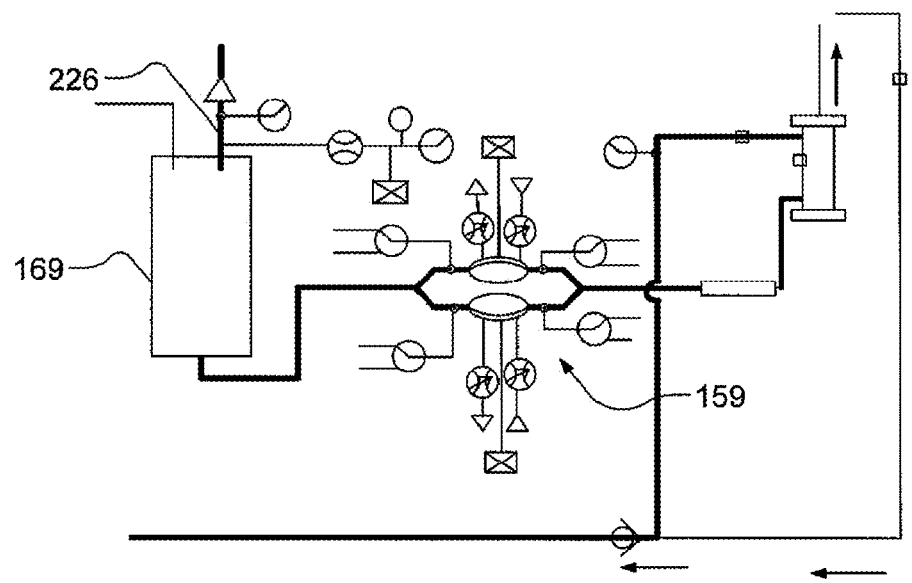
FIG. 19 illustrates emptying of a dialysate tank, in another embodiment of the invention.

Another set of embodiments is directed to adding air to the system, e.g., to empty the system of various fluids. For example, in one operation the dialysate tank is emptied. Vent 226 on dialysate tank 169 is opened, and pump 159 is used to pump fluid from the dialysate tank to the drain until air is detected in pump 159 (discussed below). This is shown in FIG. 19.

Figure 20:
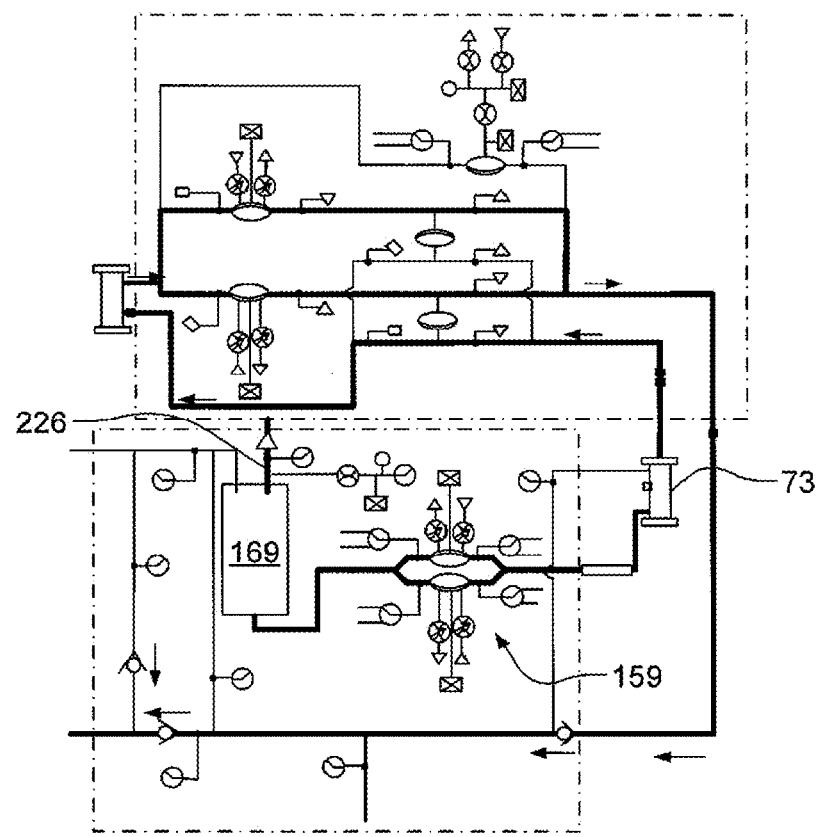
FIG. 20 illustrates the purging of the system with air at the end of treatment according to one embodiment of the invention.

Air may also be pumped into the balancing circuit in certain embodiments. This is shown in FIG. 20. Vent 226 on dialysate 16 is opened so that air may enter the dialysate tank. Pump 159 is used to pump air through the outside of ultrafilter 73. This air pressure displaces fluid outside the ultrafilter to the inside, then it flows through the dialyzer and down the drain. During this operation, pump 159 and the outside of the ultrafilter will fill with air.

Figure 21A:
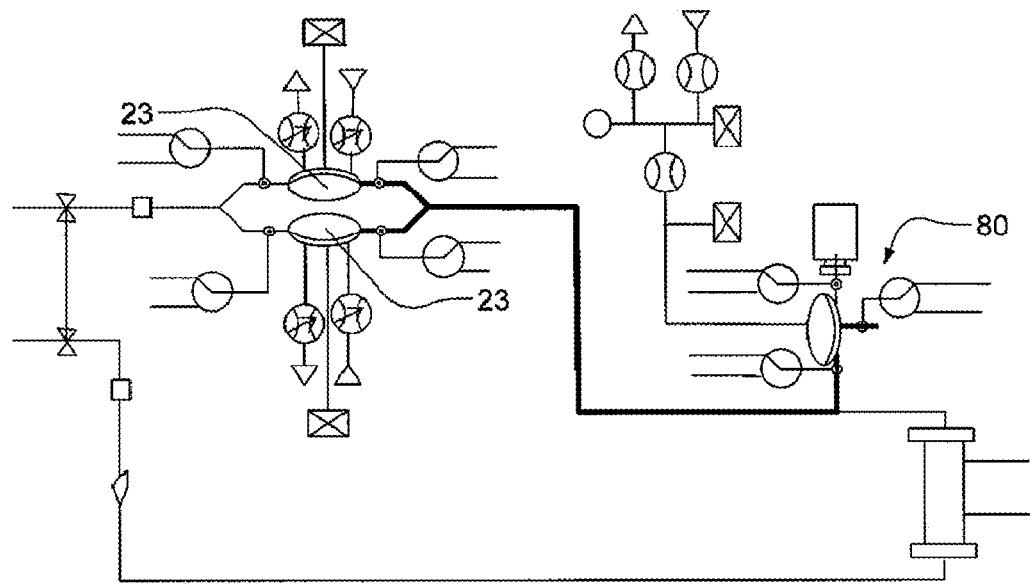
FIGS. 21A-21C illustrate the drawing of air in an anticoagulant pump, in still another embodiment of the invention.
Figure 21B:
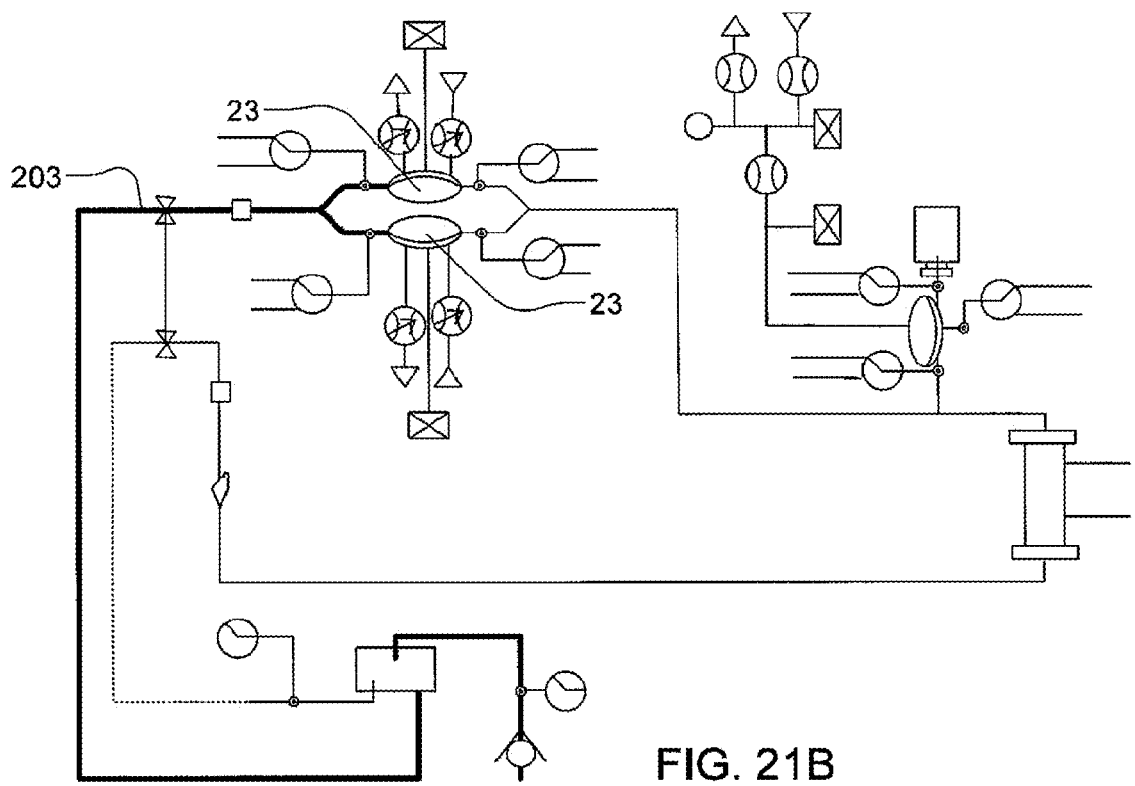
Figure 21C:
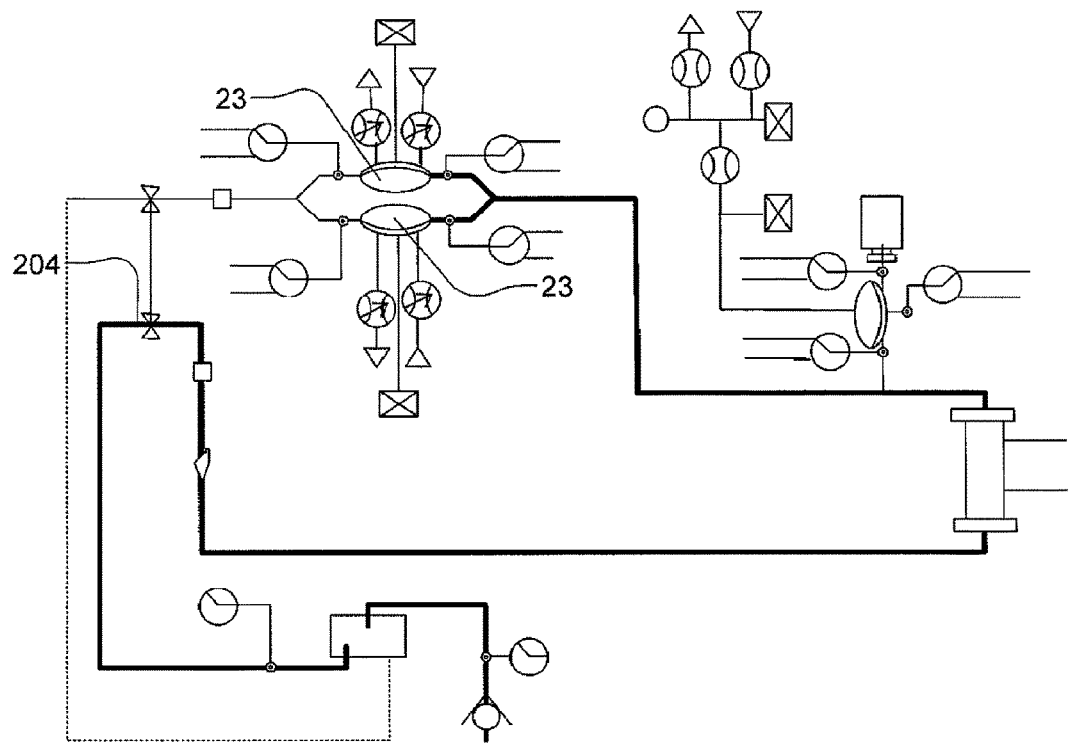

In addition, air can be drawn in through the anticoagulant pump 80 into the blood flow circuit, as is shown in FIG. 21A. The air is first brought into pod pumps 23 (FIG. 21A), then may be directed from the pod pumps to the arterial line 203 and down the drain (FIG. 21B), or to the venous line 204 (through dialyzer 14) and down the drain (FIG. 21C).

In one set of embodiments, integrity tests are conducted. As the ultrafilter and the dialyzer may be constructed with membrane material that will not readily pass air when wet, an integrity test may be conducted by priming the filter with water, then applying pressurized air to one side of the filter. In one embodiment, an air outlet is included on one of the blood flow pumps and thus, the pumping chamber may be used to pump air for use in the integrity test. This embodiment uses the advantage of a larger pump. The air pressure pushes all of the water through the filter, and the air flow stops once the water has been displaced. However, if the air flow continues, the membrane is ruptured and must be replaced. Accordingly, the system is primed with water. First, the mixing circuit is primed first to eliminate air prior to the dialysate tank. Then the outside of the ultrafilter is primed next, as the ultrafilter will not pass water to the balancing circuit until the outside is primed. The balancing circuit and the dialyzer are primed next. Finally, water is pushed across the dialyzer to prime the blood flow circuit.

Figure 22A:
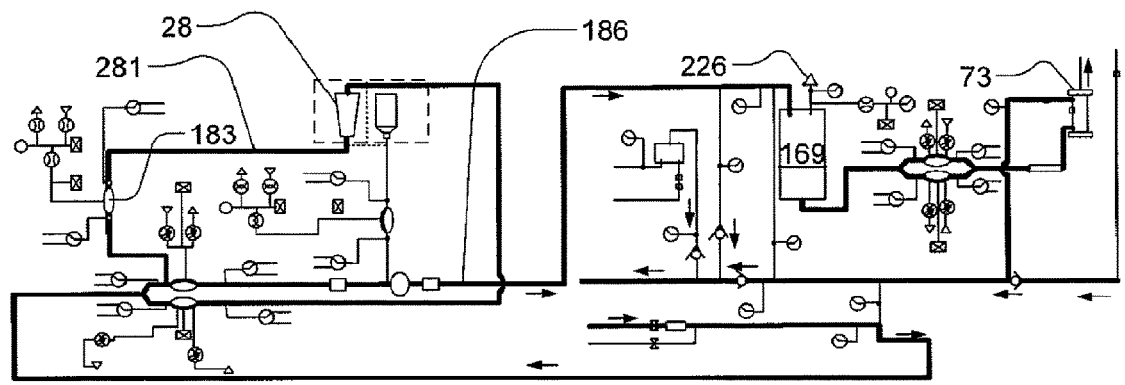
FIGS. 22A-22D illustrate integrity tests according to certain embodiments of the invention.
Figure 22B:
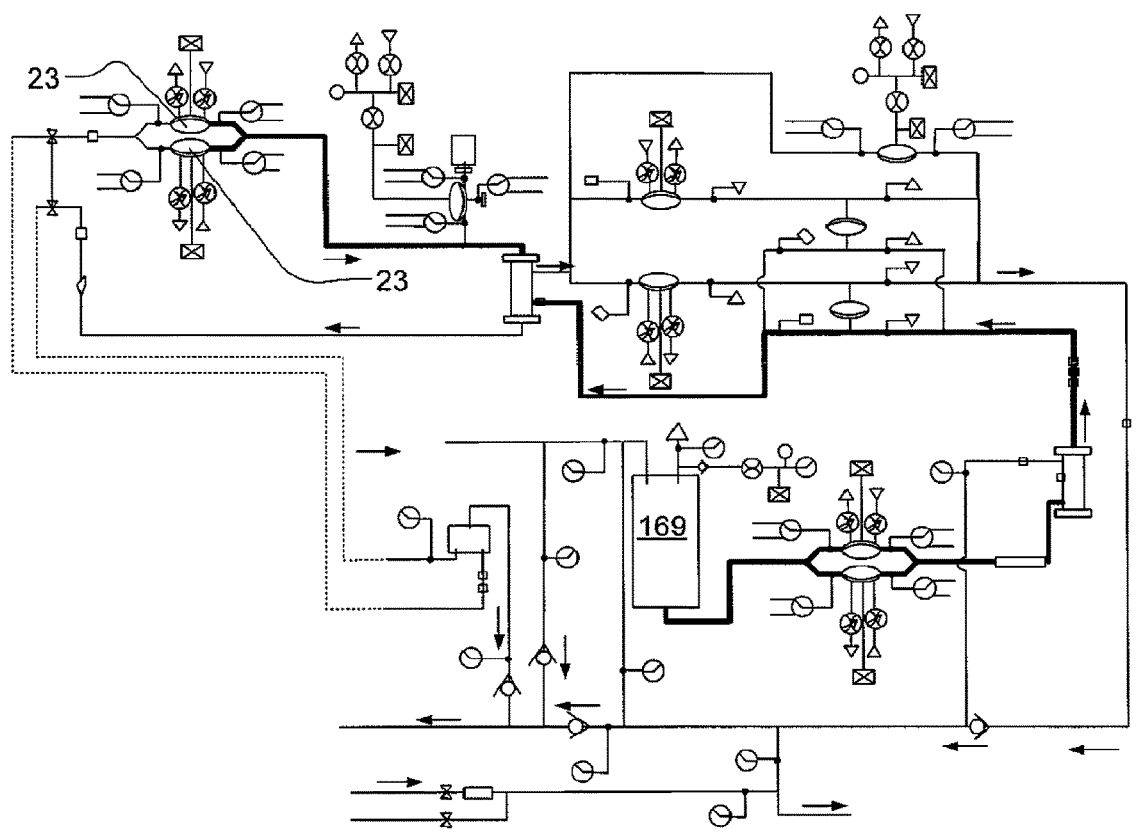
Figure 22C:
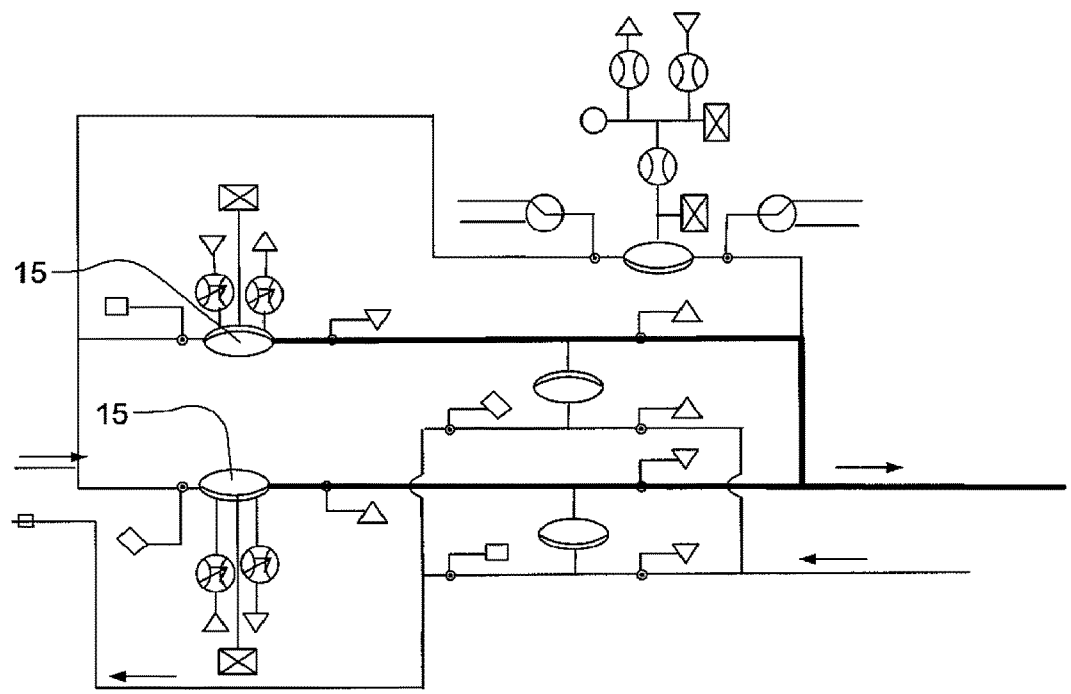

The mixing circuit is primed by first pushing water with pump 183, through line 281 and bicarbonate source 28, then through each of the pumps and through line 186 to dialysate tank 169. Dialysate tank 169 is vented so air that is pushed through bubbles to the top and leaves through vent 226. Once air has been primed out of dialysate tank 169, the tank is filled with water, then the priming flow continues from the dialysate tank through ultrafilter 73 to the drain. This can be seen in FIG. 22A. Water is then primed as previously discussed (see FIG. 17). Next, the blood flow pod pumps 23 are filled with water from dialysate tank 169, as is shown in FIG. 22B, while balancing pumps 15 are emptied, as is shown in FIG. 22C.

Figure 22D:
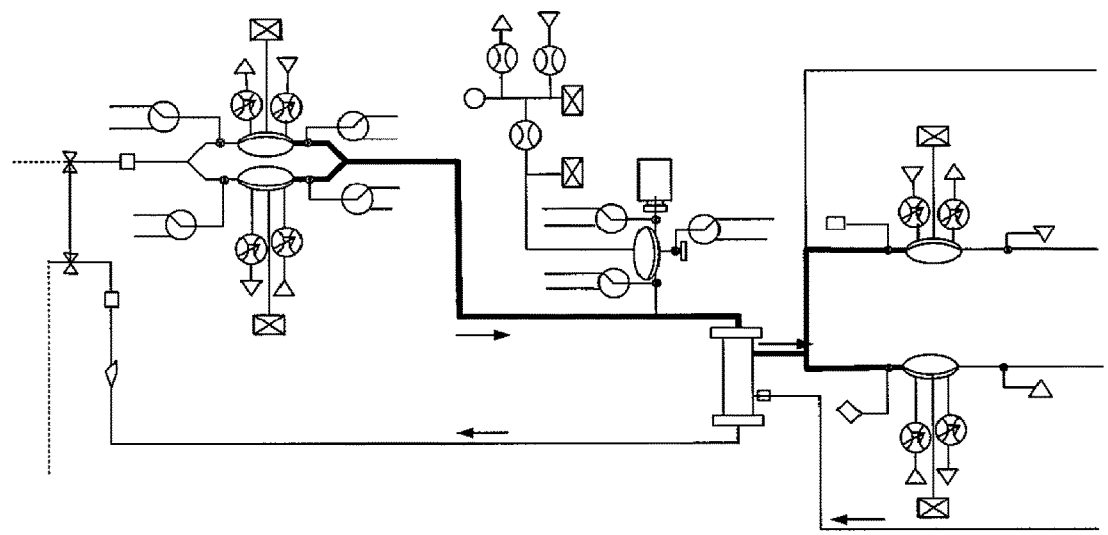

The test is conducted by using the blood flow pump to push each chamber of water across dialyzer 14 to balancing pump chambers 15, which start empty (FIG. 22C) and are vented to the atmosphere so that they are present at atmospheric pressure on the dialysate side of dialyzer 14. See FIG. 22D. Each of the blood flow circuit chambers delivers using a specific pressure and the end-of-stroke is determined to determine the flow rate.

Another integrity test is the ultrafilter flow test. In this test, the dialysate tank is filled with water, the ultrafilter is primed by pumping water from the dialysate tank through the ultrafilter and out line 731, and water is pumped through the ultrafilter, controlling flow rate, monitoring the delivery pressure required to maintain flow.

Another set of embodiments are directed to disinfection and rinsing of the system. This process removes any material which may have accumulated during therapy, and kills any active pathogens. Typically, heat is used, although in some cases, a disinfectant may be added. Water is maintained using the dialysate tank and replenished as necessary as water is discharged.

Figure 23:
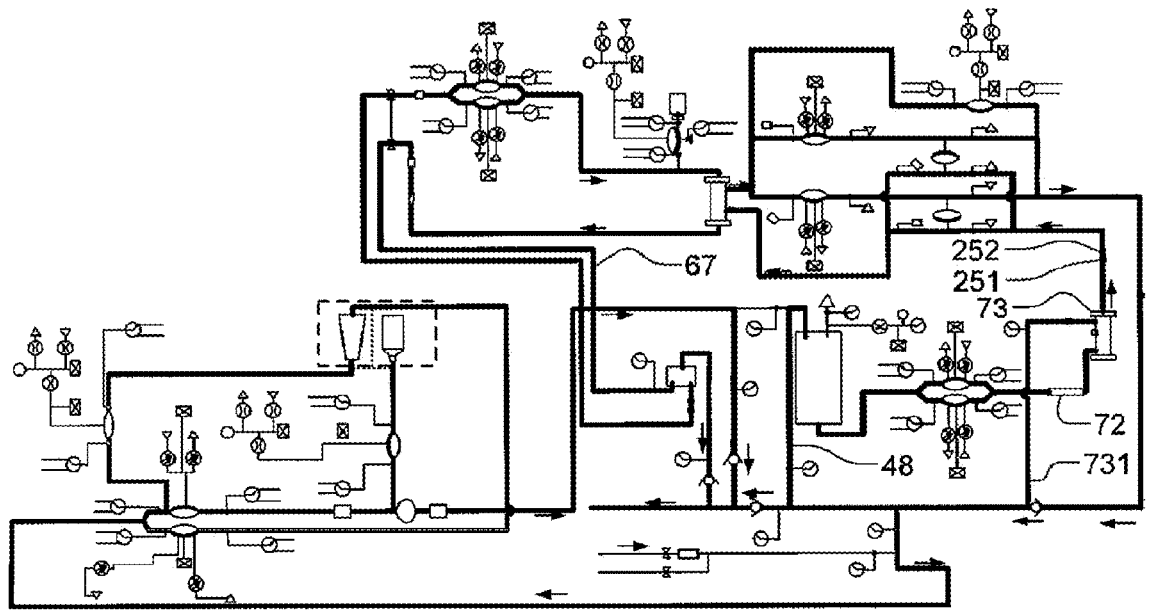
FIG. 23 illustrates a recirculating flow path, in another embodiment of the invention.

A recirculating flow path is shown in FIG. 23. The flow along this path is essentially continuous, and uses conduits 67 to connect the blood flow circuit with the directing circuit. The main flow path is heated using heater 72, which is used to increase the water temperature within the recirculating flow path, e.g., to a temperature that can kill any active pathogens that may be present. Most of the water is recirculated, although some is diverted to drain. Note that lines 48 and 731 are kept open in this example to ensure that these lines are properly disinfected. In addition, the flow paths through ultrafilter 73 can be periodically selected to purge air from the ultrafilter, and/or to provide recirculating flow through this path. Temperature sensors (e.g., sensors 251 and 252) can be used to ensure that proper temperatures are met. Non-limiting examples of such sensors can be seen in a U.S. patent application Ser. No. 12/038,474, filed Feb. 27, 2008, published as US PGPub No. 2008/0253427 on Oct. 16, 2008, entitled "Sensor Apparatus Systems, Devices and Methods," incorporated herein by reference.

Figure 24A:
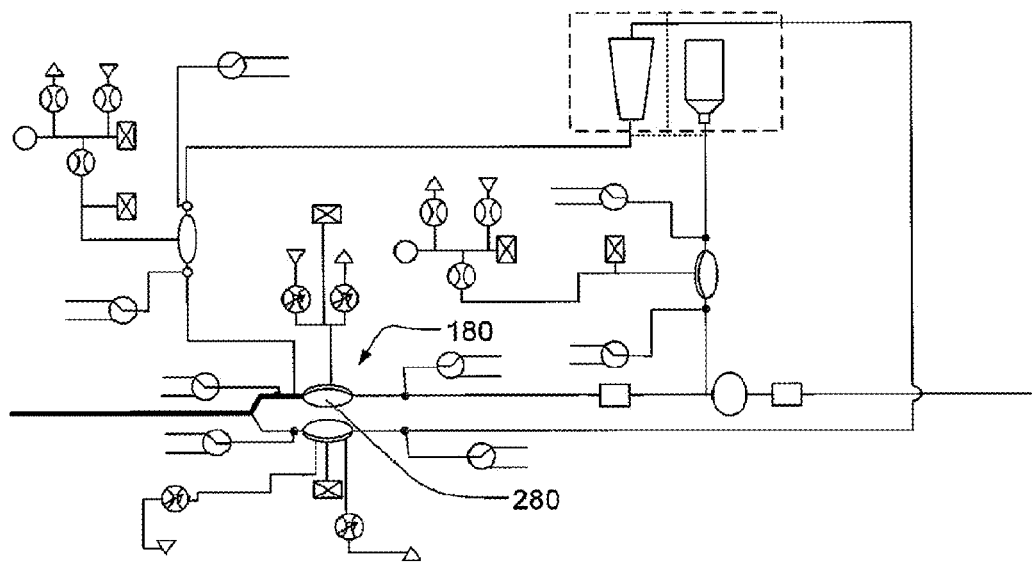
FIGS. 24A-24D illustrate the priming of a system with dialysate, in yet another embodiment of the invention.
Figure 24B:
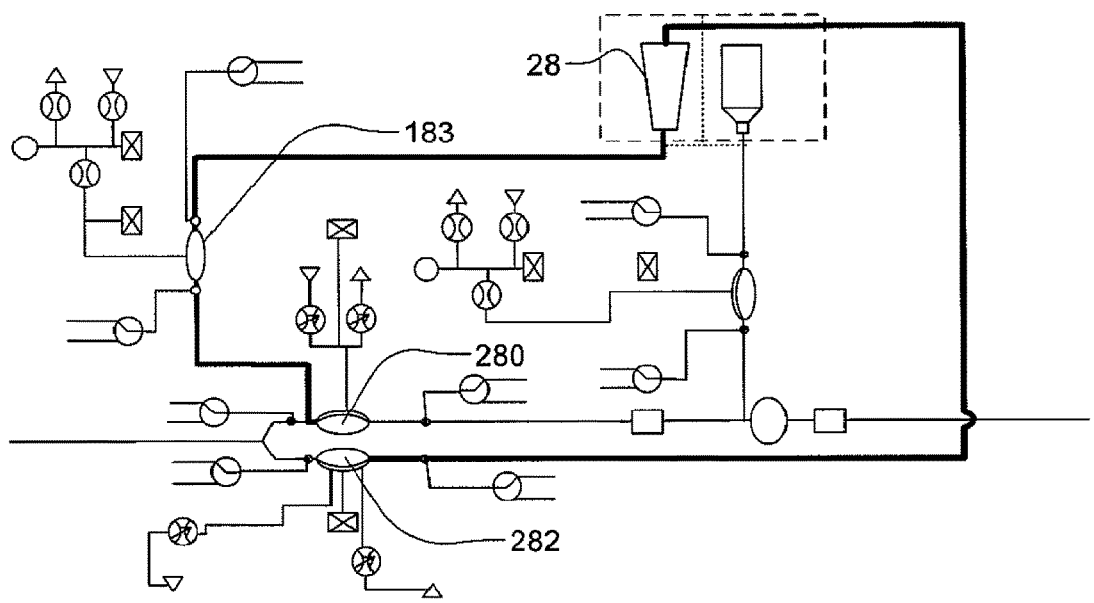
Figure 24D:
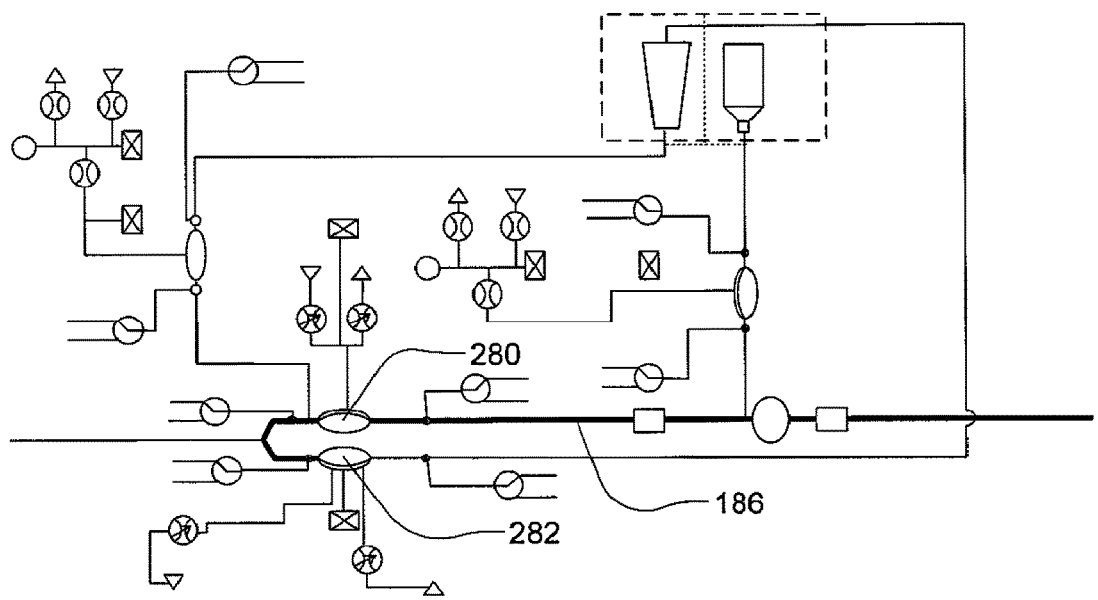
Figure 24C:
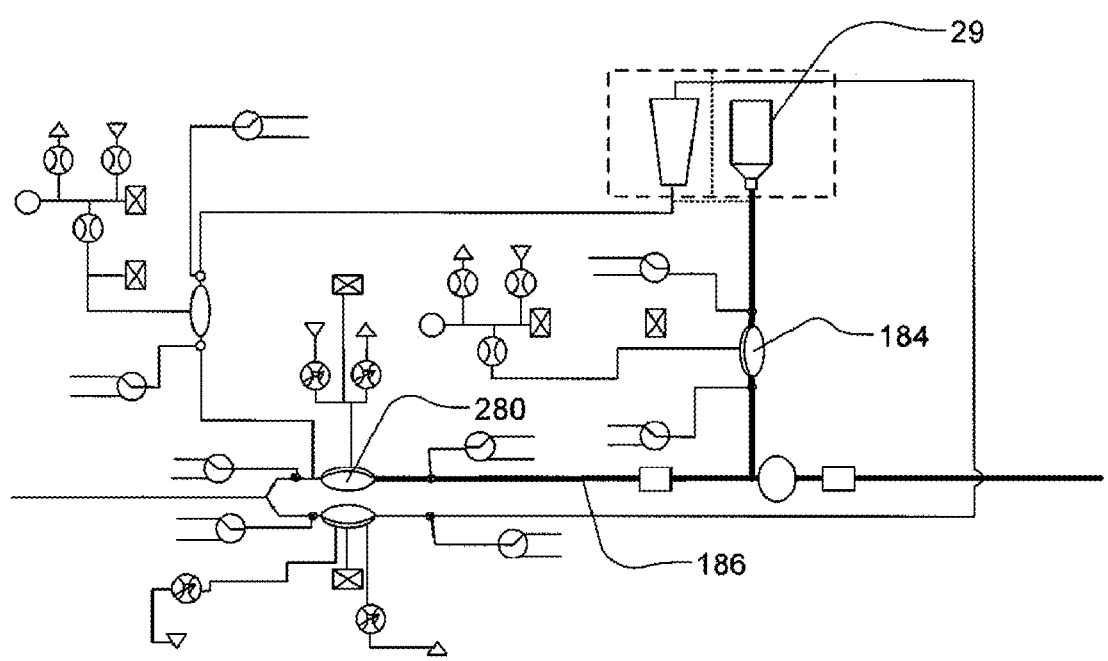

In one set of embodiments, the system is primed with dialysate as follows. In this operation, pod pump 280 is filled with water (FIG. 24A), and then water is pushed backwards through pump 183 to expel air from the top of bicarbonate source 28. The air is collected in pod pump 282. See FIG. 24B. Next, the air in pod pump 282 is expelled through pod pump 280 and line 186 to dialysate tank 169. Vent 226 in dialysate tank 169 is opened so that the air can leave the system (FIG. 24C). In addition, acid may be pumped in from acid source 29. Bicarbonate concentrate from bicarbonate source 28 and water are then mixed. Pump 183 is used to provide water pressure sufficient to fill bicarbonate source 28 with water, as is shown in FIG. 24D.

The acid and bicarbonate solutions (and sodium chloride solution, if a separate sodium chloride source is present) are then metered with incoming water to prepare the dialysate. Sensors 178 and 179 are used to ensure that the partial mixtures of each ingredient with water is correct. Dialysate that does not meet specification is emptied to the drain, while good dialysate is pumped into dialysate tank 14.

In another set of embodiments, the anticoagulant pump is primed. Priming the pump removes air from the heparin pump and the flow path, and ensures that the pressure in the anticoagulant vial is acceptable. The anticoagulant pump can be designed such that air in the pump chamber flows up into the vial. The test is performed by closing all of the anticoagulant pump fluid valves, measuring the external volume, charging the FMS chamber with vacuum, opening valves to draw from the vial into the pumping chamber, measuring the external volume (again), charging the FMS chamber with pressure, opening the valves to push fluid back into the vial, and then measuring the external volume (again). Changes in external volume that result from fluid flow should correspond to the known volume of the pumping chamber. If the pumping chamber cannot fill from the vial, then the pressure in the vial is too low and air must be pumped in. Conversely, if the pumping chamber cannot empty into the vial, then the pressure in the vial is too high and some of the anticoagulant must be pumped out of the vial. Anticoagulant pumped out of the vial during these tests can be discarded, e.g., through the drain.

In yet another set of embodiments, the system is rinsed with dialysate while the patient is not connected. This can be performed before or after treatment. Prior to treatment, dialysate may be moved and a portion sent to the drain to avoid accumulating sterilant in the dialysate. After treatment, this operation rinses the blood path with dialysate to push any residual blood to the drain. The flow paths used in this operation are similar to the flow paths used with water, as discussed above.

Figure 25:
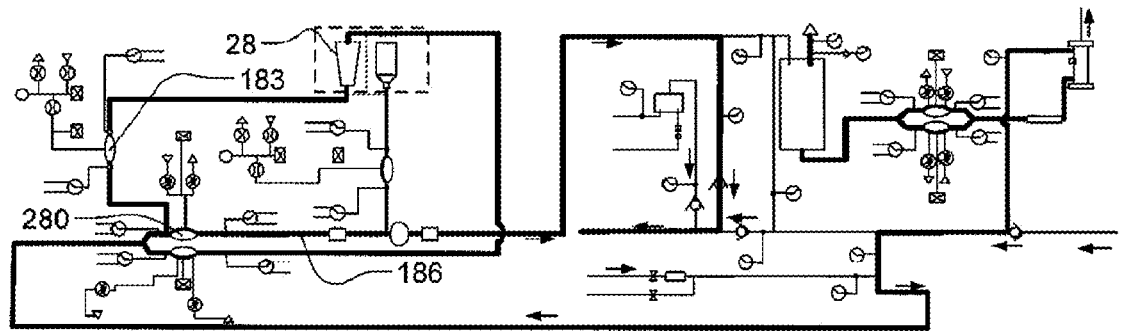
FIG. 25 illustrates the priming of an anticoagulant pump, in still another embodiment of the invention.

Acid concentrate may be pumped out of the mixing chamber. Pump 184 is activated so that pod pump 280 can draw out acid from pump 184 and acid source 29, to be mixed in line 186 and sent to the drain. Similarly, bicarbonate may be pumped out of the mixing chamber as is shown in FIG. 25. Pump 183 is used to draw water from bicarbonate source 28, then pod pump 280 is used to pass the water into line 186 to the drain.

Figure 26A:
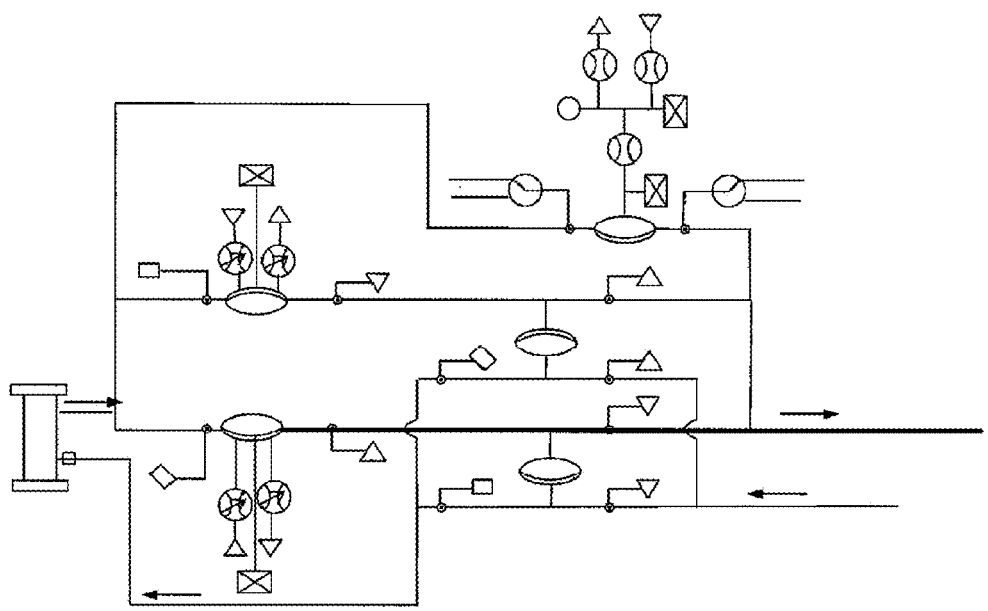
FIGS. 26A-26F illustrate the removal of dialysate from a blood flow circuit, in one embodiment of the invention.
Figure 26B:
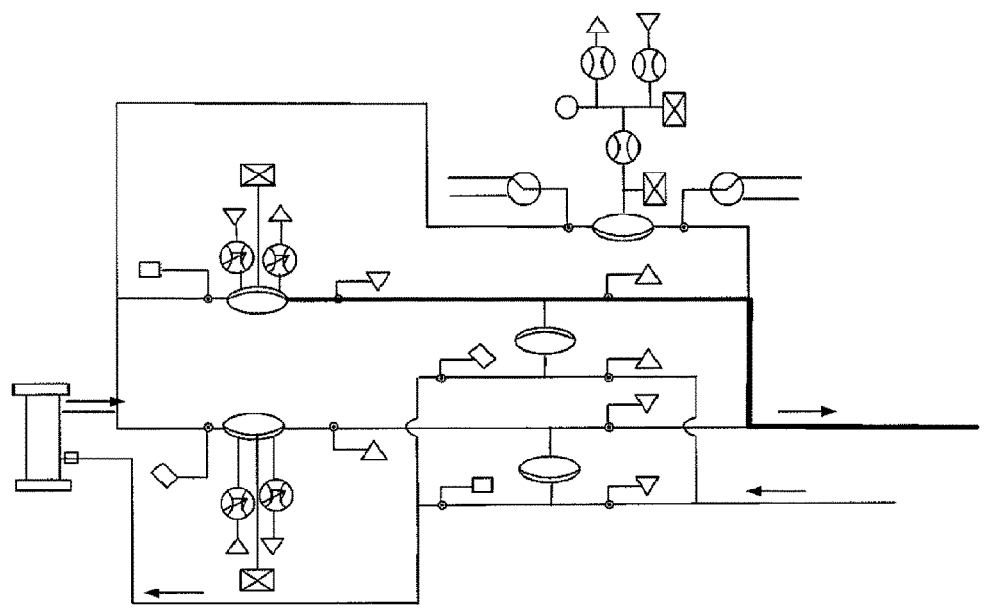
Figure 26C:
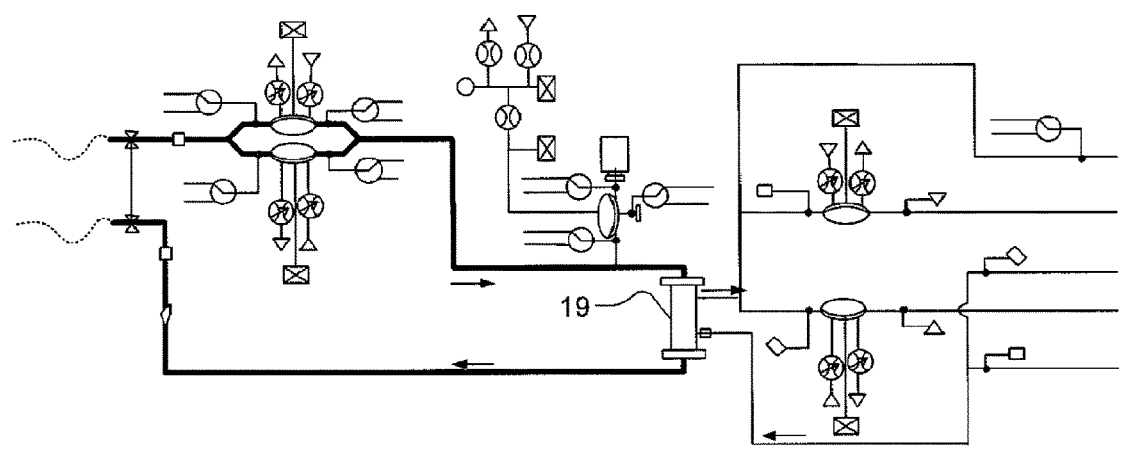
Figure 26D:
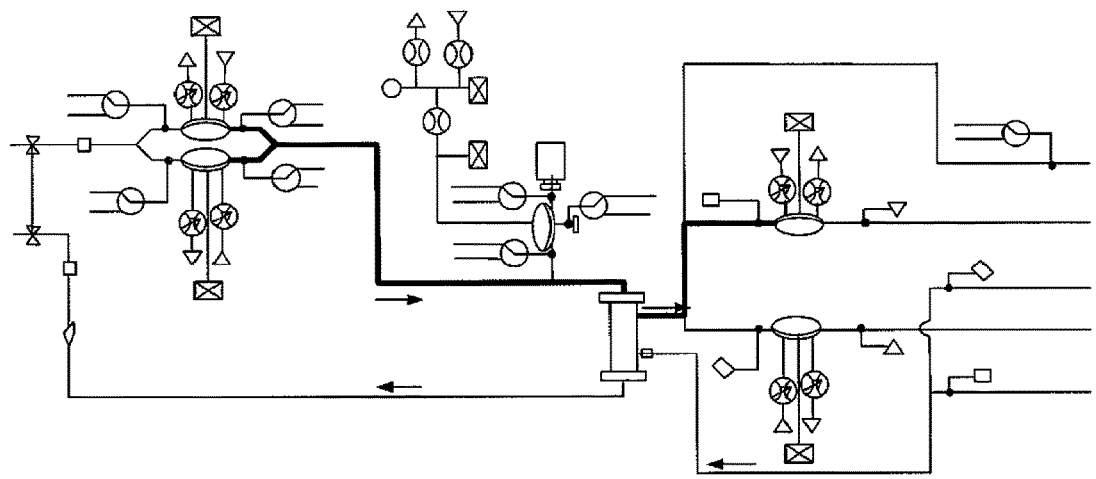
Figure 26E:
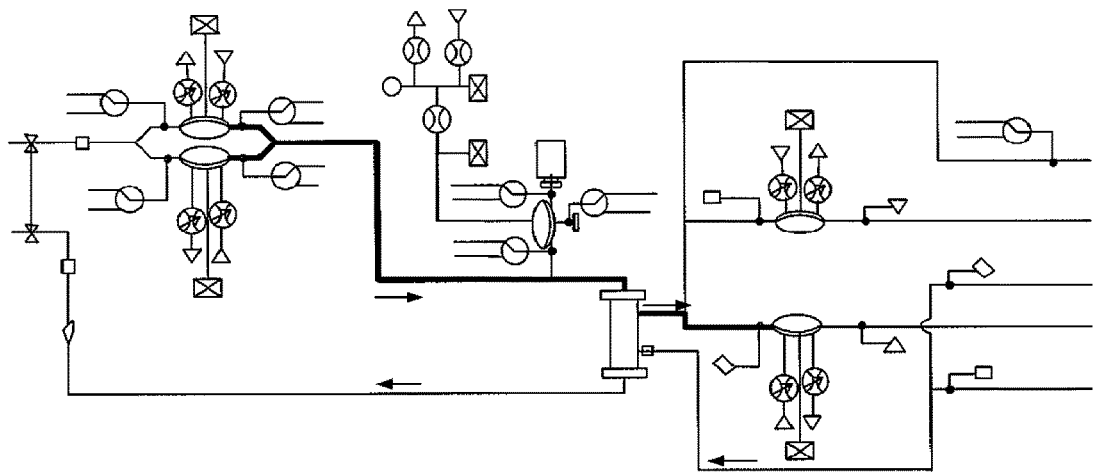
Figure 26F:
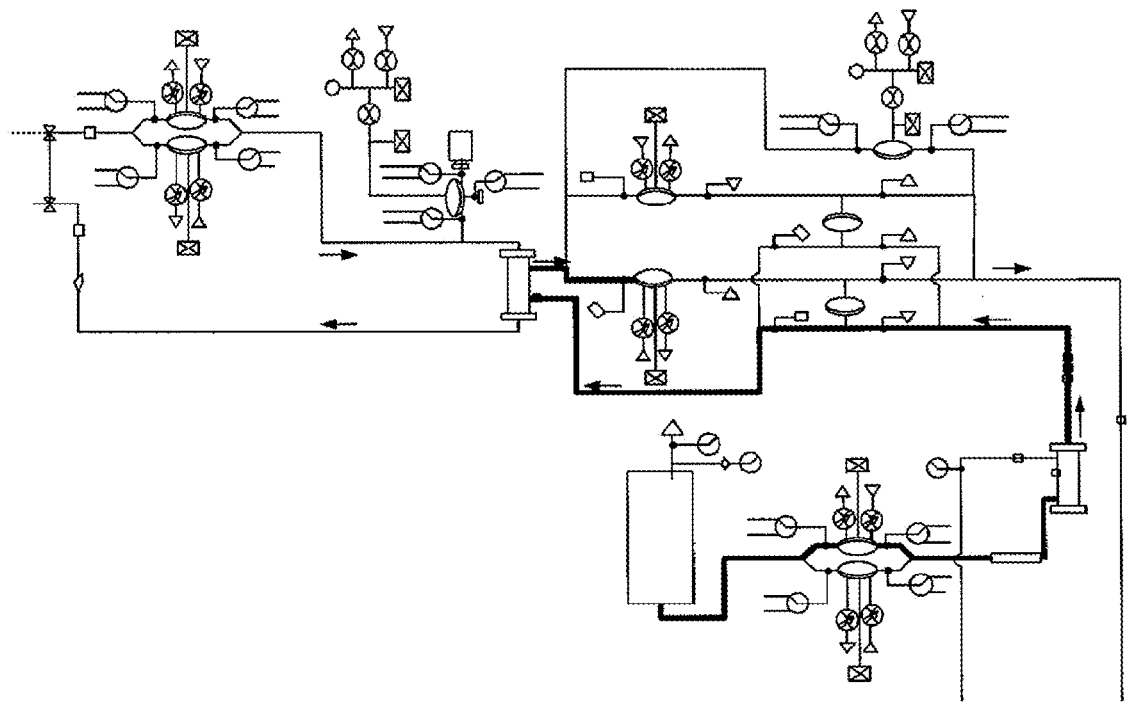

In still another set of embodiments, dialysate prime is removed from the blood flow circuit, to avoid giving the patient the priming fluid. FIGS. 26A and 26B show fluid leaving each of the balancing pump chambers and being expelled to the drain. Next, the dialysate side of dialyzer 14 is closed, while blood is drawn into the blood flow path from the patient (FIG. 26C). The patient connections are then occluded while the blood flow pump chambers 23 push the priming fluid across the dialyzer to the balancing circuit (FIGS. 26D and 26E). This fluid is then pushed to drain, as previously discussed. This operation can be repeated as necessary until sufficient priming fluid has been removed. Afterwards, the balancing pumps are then refilled with fresh dialysate, keeping the patient connections occluded, as is shown in FIG. 26F.

Figure 27A:
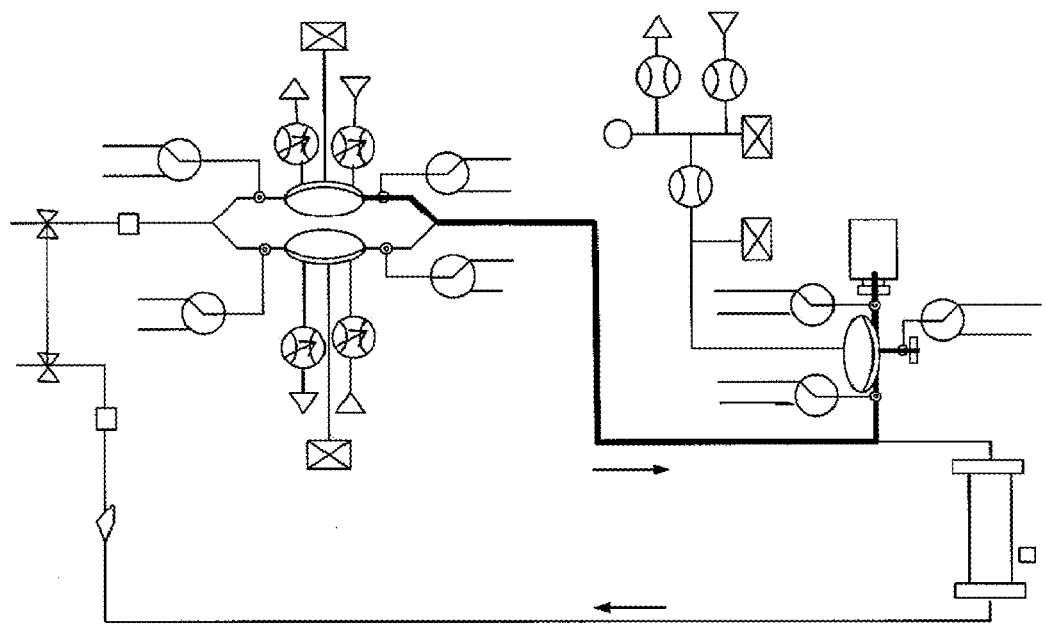
FIGS. 27A-27C illustrate the delivery of a bolus of anticoagulant to a patient, in another embodiment of the invention.
Figure 27B:
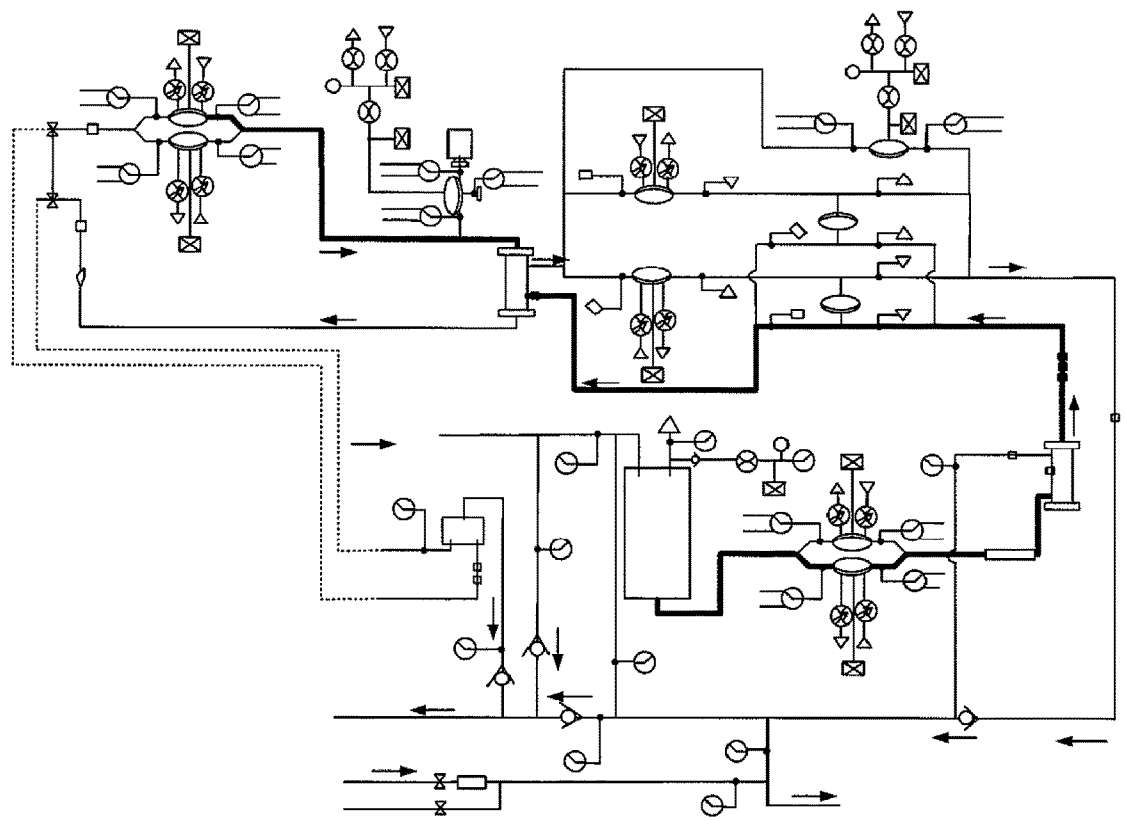
Figure 27C:
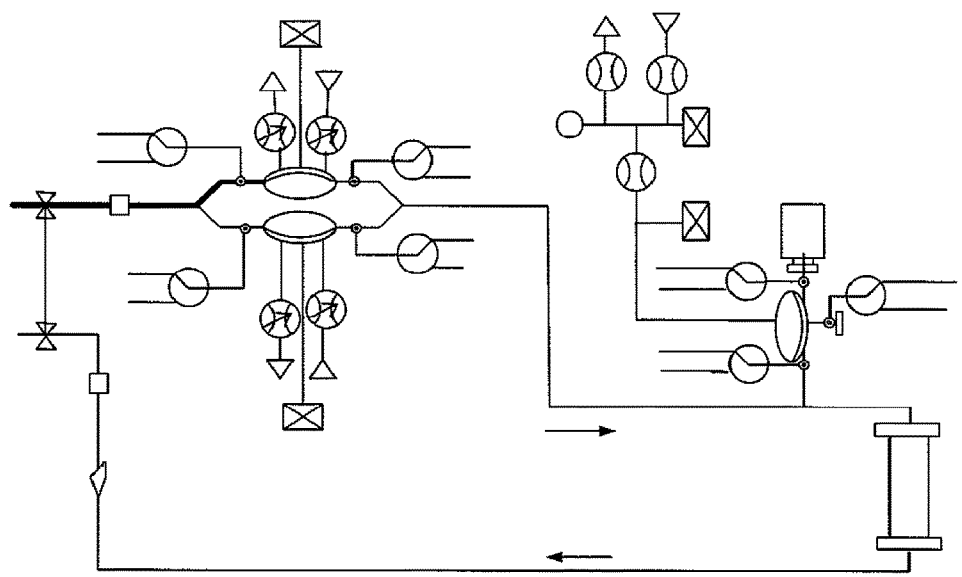

In yet another set of embodiments, a bolus of anticoagulant may be delivered to the patient. Initially, a bolus of anticoagulant is pumped from the vial (or other anticoagulant supply) to one chamber of pump 13, as is shown in FIG. 27A. The anticoagulant pump alternates between pumping air into the vial and pumping anticoagulant out of the vial, thereby keeping the pressure relatively constant. The remaining volume is then filled with dialysate (FIG. 27B). The combined fluids are then delivered to the patient down arterial line 203, as shown in FIG. 27B. In some cases, the same pump chamber may be refilled with dialysate again (see FIG. 27B), and that volume delivered to the patient also, to ensure that all of the anticoagulant has been properly delivered.

In still another set of embodiments, the system may perform push-pull hemodiafiltration. In such cases, blood flow pump 13 and balancing pumps 15 can be synchronized to pass fluid back and forth across the dialyzer. In hemodiafiltration, hydrostatic pressure is used to drive water and solute across the membrane of the dialyzer from the blood flow circuit to the balancing circuit, where it is drained. Without wishing to be bound by any theory, it is believed that larger solutes are more readily transported to the used dialysate due to the convective forces in hemodiafiltration.

Figure 28:
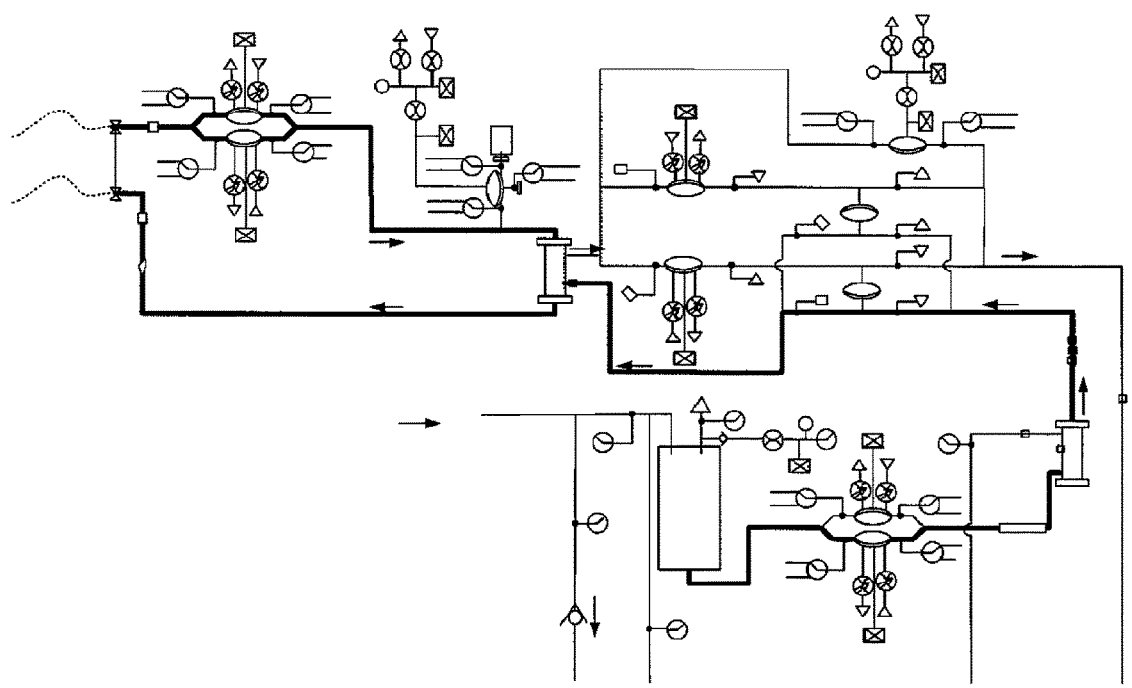
FIG. 28 illustrates solution infusion, in one embodiment of the invention.

In one set of embodiments, solution infusion may be used to delivery fluid to the patient. As is shown in FIG. 28, pump 159 in the directing circuit is used to push fluid across dialyzer 14 into the blood flow circuit, which thus causes delivery of fluid (e.g., dialysate) to the patient.

According to another set of embodiments, after repeated use, the dialyzer can lose its efficiency or even the ability to function at all as a result of compounds adhering to and building up on the membrane walls in the dialyzer. Any standard measure of dialyzer clearance determination may be used. However, one method of measuring how much build-up has accumulated in the dialyzer, i.e., how much the dialyzer's clearance has deteriorated, a gas is urged into the blood side of the dialyzer, while a liquid is held on the dialysate side of the dialyzer. By measuring the volume of gas in the dialyzer, the clearance of the dialyzer may be calculated based on the volume of gas measured in the dialyzer.

Alternatively, in other embodiments, because of the pneumatic aspects of the present system, clearance may be determined as follows. By applying a pressure differential along the dialyzer and measuring the flow rate of the dialyzer, the clearance of the dialyzer may then be correlated/determined or calculated, based on the pressure differential and the flow rate. For example, based on a known set of correlations or pre-programmed standards including a correlation table or mathematical relationship. For example, although a look-up table may be used, or a determined mathematical relationship may also be used.

The dialyzer's clearance can also be measured using a conductivity probe in the blood tube plug-back recirculation path. After treatment the patient connects the blood tubes back into the disinfection ports. The fluid in the blood tubes and dialyzer may be recirculated through these disinfection port connections, and the conductivity of this solution may be measured as it passes through the conductivity measurement cell in this recirculation path.

To measure the dialyzer clearance, pure water may be circulated through the dialysate path and the conductivity of the fluid flowing through the blood recirculation path is continuously monitored. The pure water takes ions from the solution in the blood flow circuit recirculation path at a rate which is proportional to the clearance of the dialyzer. The clearance of the dialyzer may be determined by measuring the rate at which the conductivity of the solution in the blood flow circuit recirculation path changes.

The dialyzer's clearance can be measured by circulating pure water on one side and dialysate on the other, and measuring the amount of fluid passing through the dialyzer using conductivity.

In one set of embodiments, in case of a power failure, it may be desirable to return as much blood to the patient as possible. Since one embodiment of the hemodialysis system uses compressed gas to actuate various pumps and valves used in the system, a further embodiment takes advantage of this compressed gas to use it in case of power failure to return blood in the system to the patient. In accordance with this procedure and referring to FIG. 29A, dialysate is pushed across the dialyzer 14, rinsing blood residing blood flow circuit 10 back to the patient. Compressed air is used to push dialysate across the dialyzer 14. A valve 77 releases the compressed air to initiate this function. This method may be used in situations where electrical power loss or some other failure prevents the dialysis machine from rinsing back the patient's blood using the method normally employed at the end of treatment.

As compressed air is used to increase the pressure on the dialysate side of the dialyzer 14 and force dialysate through the dialyzer to the blood side, thereby pushing the patient's blood back to the patient, the patient, or an assistant, monitors the process and clamps the tubes between the blood flow circuit and the patient once adequate rinse back has been achieved.

In one embodiment, a reservoir 70 is incorporated into the hemodialysis system and is filled with compressed air prior to initiating treatment. This reservoir 70 is connected to the dialysate circuit 20 through a manually actuated valve 77. When the treatment is finished or aborted, this valve 77 is opened by the patient or an assistant to initiate the rinse-back process. The membrane of the dialyzer 14 allows dialysate to pass through, but not air. The compressed air displaces dialysate until the patient tubes are clamped, or the dialysate side of the dialyzer is filled with air.

In another embodiment, a reservoir containing compressed air is provided as an accessory to the dialysis machine. If the treatment is terminated early due to a power failure or system failure of the dialysis machine, this reservoir may be attached to the dialysate circuit on the machine to initiate the rinse-back process. As in the previous embodiment, the rinse-back process is terminated when the patient tubes are clamped, or the dialysate side of the dialyzer is filled with air.

Figure 29A:
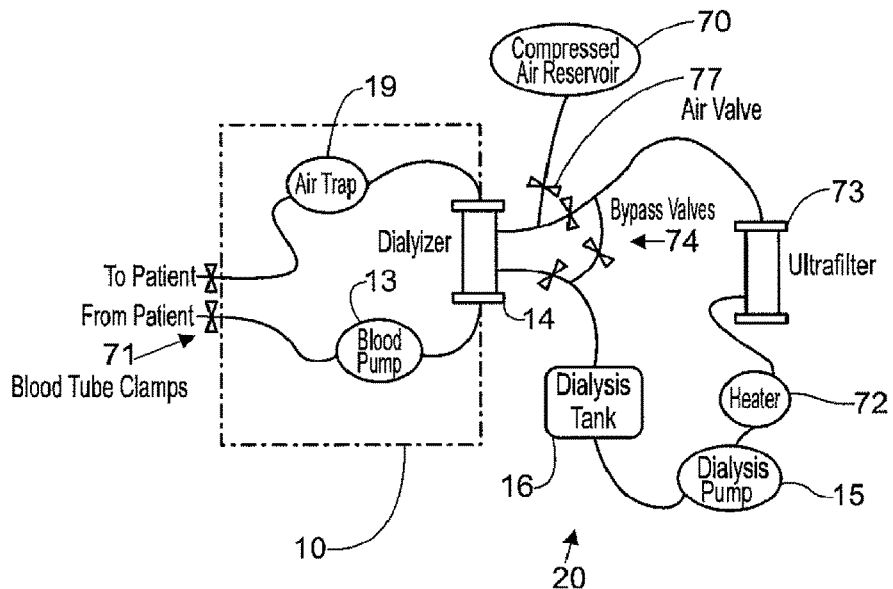
FIGS. 29A-29B are schematic representations showing how an emergency rinse-back procedure can be implemented.
Figure 29B:
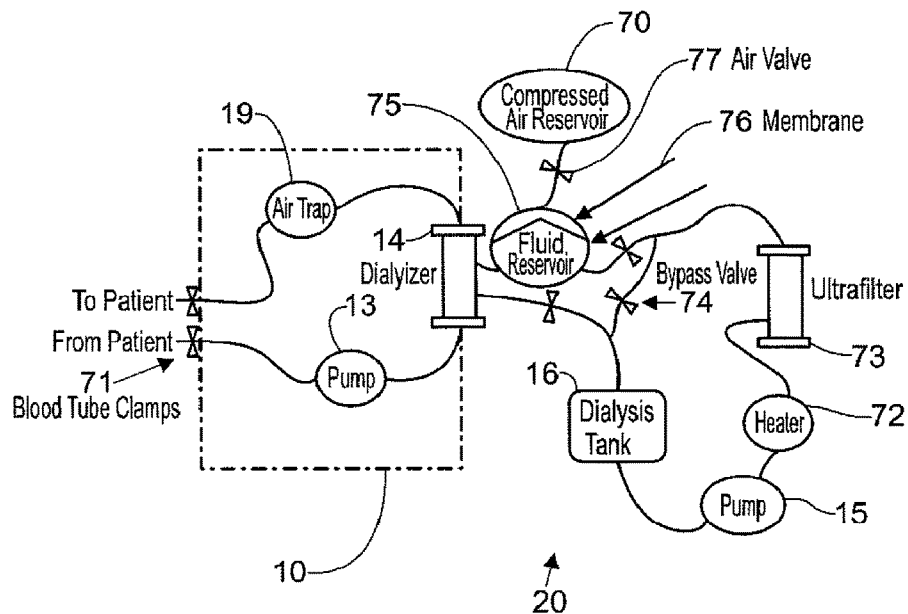

In yet another embodiment shown in FIG. 29B, an air reservoir 70 is incorporated into the system and attached to a fluid reservoir 75 with a flexible diaphragm 76 separating the air from the dialysate fluid. In this case, the compressed air pushes the diaphragm 76 to increase the pressure in the dialysate circuit 20 rather than having the compressed air enter the dialysate circuit. The volume of the dialysate that is available to be displaced is determined by the volume of the fluid chamber 75. The rinse-back process is terminated when the patient tubes are clamped, or when all of the fluid is expelled and the diaphragm 76 bottoms out against the wall of the fluid chamber 75.

In any of these embodiments, the operation of the systems or methods may be tested periodically between treatments by running a program on the dialysate machine. During the test the user interface prompts the user to actuate the rinse-back process, and the machine monitors the pressure in the dialysate circuit to ensure successful operation.

In the systems depicted in FIGS. 29A and 29B, blood is drawn from the patient by the blood flow pump 13, pushed through the dialyzer 14 and returned to the patient. These components and the tubing that connects them together make up the blood flow circuit 10. The blood contained in the blood flow circuit 10 should be returned to the patient when the treatment is finished or aborted.

The dialysate solution is drawn from the dialysate tank 169 by the dialysate pump 159, and passed through the heater 72 to warm the solution to body temperature. The dialysate then flows through the ultrafilter 73 which removes any pathogens and pyrogens which may be in the dialysate solution. The dialysate solution then flows through the dialyzer to perform the therapy and back to the dialysate tank.

The bypass valves 74 may be used to isolate the dialyzer 14 from the rest of the dialysate circuit 20. To isolate the dialyzer 14, the two valves connecting the dialysate circuit 20 to the dialyzer are closed, and the one shunting dialysate around the dialyzer is opened.

This rinse-back procedure may be used whether or not the dialyzer 14 is isolated and is used when the treatment is ended or aborted. The dialysate machine is turned off or deactivated so the pumps are not running. When the patient is ready for rinse-back, air valve 77 is opened by the patient or an assistant. The air in the compressed air reservoir 70 flows toward the dialysate circuit 20, increasing the pressure on the dialysate side of the dialyzer 14. This increase in pressure may be achieved by allowing the air to enter the dialysate circuit directly, as shown in FIG. 29A or indirectly by pushing on the diaphragm 76 shown in FIG. 29B.

The air pressure on the dialysate side of the dialyzer forces some dialysate solution through the dialyzer 14 into the blood flow circuit. This dialysate solution displaces the blood, rinsing the blood back to the patient. The patient or an assistant can observe the rinse process by looking at the dialyzer 14 and the blood tubes. The dialysate solution starts in the dialyzer, displacing the blood and making it appear much clearer. This clearer solution progresses from the dialyzer toward the patient. When it reaches the patient the blood tube clamps 71 are used to pinch the tubing to terminate the rinse-back process. If one line rinses back sooner than the other the quicker line may be clamped first and the slower line may be clamped later.

Once the rinse-back is completed and the blood lines are clamped the patient may be disconnected from the dialysis machine.

The implementation of one embodiment of the system and method is shown in FIG. 29A takes advantage of the hydrophilic nature of the material used to make the tiny tubes in the dialyzer 14. When this material is wet, the dialysate solution can pass through but air cannot. Where the embodiment shown in FIG. 29A is implemented, air may enter the dialyzer 14 but it will not pass across to the blood flow circuit 10.

In either implementation, the volume of dialysate that may be passed through the dialyzer 14 is limited. This limitation is imposed by the size of the compressed air reservoir 70, the volume of dialysate solution contained in the dialyzer 14 and in the case of the implementation shown in FIG. 7B the size of fluid reservoir 75. It is advantageous to limit the volume of dialysate that may be pushed across the dialyzer because giving too much extra fluid to the patient counteracts the therapeutic benefit of removing fluid during the therapy.

Another aspect of the invention is generally directed to a user interface for the system. The user interface may be operated by an individual, such as the patient, a family member, assistant, professional care provider, or service technician, to input options, such as treatment options, and to receive information, such as information about the treatment protocol, treatment status, machine status/condition, and/or the patient condition. The user interface may be mounted on the treatment device and controlled by one or more processors in the treatment device. In another embodiment, the user interface may be a remote device that may receive, transmit, or transmit and receive data or commands related to the treatment protocol, treatment status, and/or patient condition, etc. The remote device may be connected to the treatment device by any suitable technique, including optical and/or electronic wires, wireless communication utilizing Bluetooth, RF frequencies, optical frequencies, IR frequencies, ultrasonic frequencies, magnetic effects, or the like, to transmit and/or receive data and/or commands from or to the treatment device. In some cases, an indication device may be used, which can indicate when data and/or a command has been received by the treatment device or the remote device. The remote device may include input devices such as a keyboard, touch screen, capacitive input device, or the like to input data and/or commands to the treatment device.

In some embodiments, one or more processors of the treatment device may have a unique identification code, and the remote device may include the capability to read and learn the unique identification code of the treatment. Alternatively, the user can program in the unique identification code. The treatment device and the remote device may use a unique identification code to substantially avoid interference with other receivers, including other treatment device.

In one set of embodiments, the treatment device may have one or more processors that are connected to a web-enabled server and the user interface device may be run on this web-enabled server. In one embodiment, the device uses an external CPU (e.g., a GUI, graphical user interface) to communicate via Internet protocol to the embedded web server in or connected to the treatment device. The web page may be served up inside the device and the GUI may communication directly via 802.11b or other such wired or wireless Ethernet equivalent. The GUI may be operated by an individual, such as the patient, a family member, assistant, professional care provider, or service technician, to input options, such as treatment options, and to receive information, such as information about the treatment protocol, treatment status, machine status/condition, and/or the patient condition.

In another embodiment, the embedded web server in or connected to the treatment device may communicate to an appropriate site on the Internet. The Internet site may require a password or other user identification to access the site. In another embodiment, the user may have access to different information depending on the type of user and the access provider. For example, a patient or professional caregiver may have full access to patient treatment options and patient information, while a family member may be given access to certain patient information, such as the status and duration remaining for a given treatment or frequency of treatments. The service technician, dialysis center, or treatment device provider may access other information for troubleshooting, preventive maintenance, clinical trials, and the like. Use of the web-enabled server may allow more than one individual to access patient information at the same time for a variety of purposes.

The use of a remote device, e.g., via wired or wireless communication, Internet protocol, or through an Internet site utilizing a web enabled server, could allow a dialysis center to more effectively monitor each patient and/or more efficiently monitor a larger number of patients simultaneously. In some embodiments, the remote device can serve as a nocturnal monitor or nocturnal remote alert to monitor the patient during nocturnal dialysis treatment and to provide an alarm if the patient's condition does not meet certain parameters. In some cases, the remote device may be used to provide alarms to the patient, a family member, assistant, professional care provider, or service technician. These alarms could alert an individual to certain conditions such as, but not limited to, a fluid leak, an occlusion, temperature outside normal parameters, and the like. These alarms may be audible alarms, visual alarms, and/or vibratory alarms.

Figure 60:
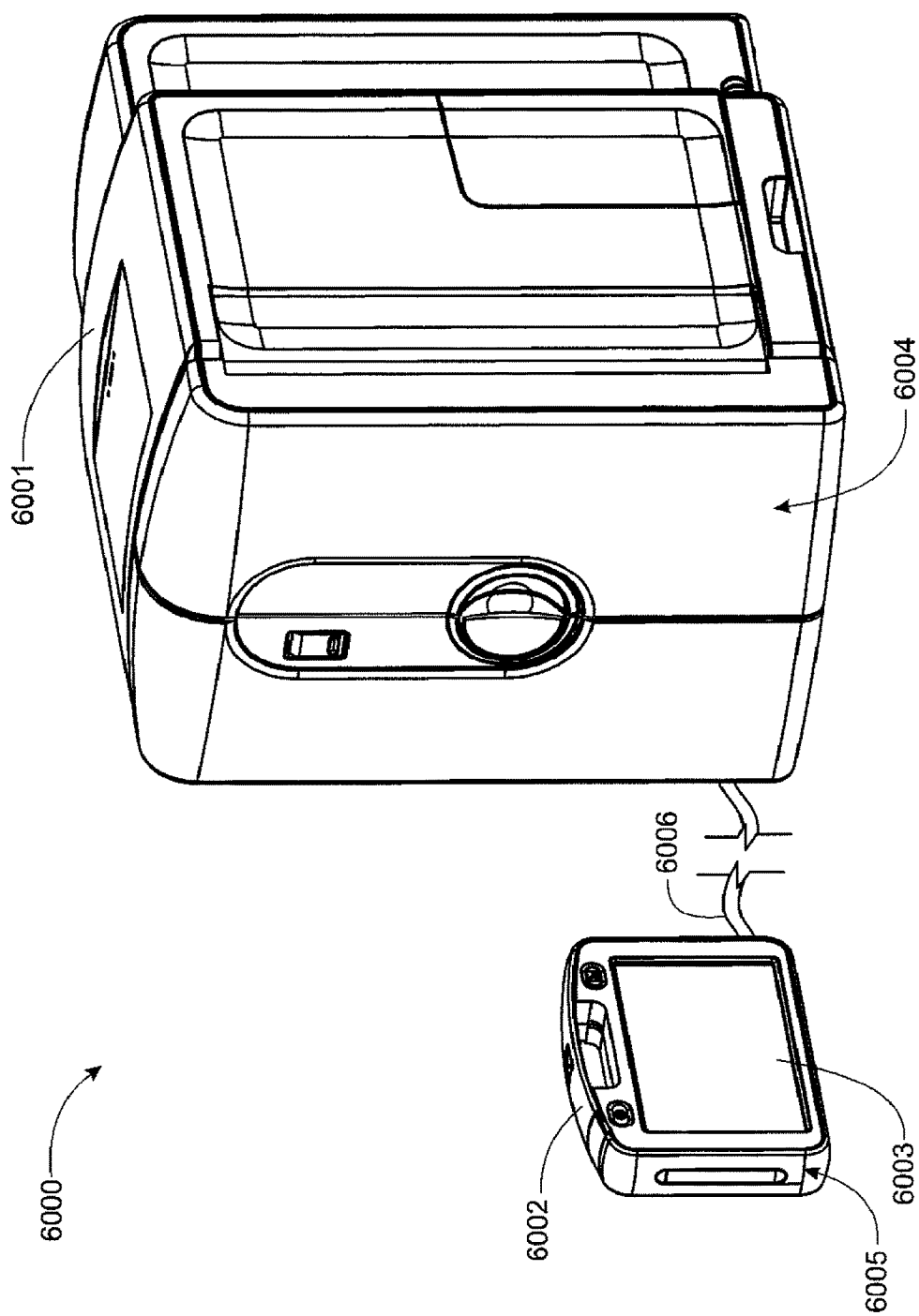
FIG. 60 is a perspective view of an exemplary embodiment of a user interface/treatment device combination.

An exemplary embodiment of a user interface/treatment device combination is shown in FIG. 60. In particular, FIG. 60 shows a perspective view of an exemplary hemodialysis system 6000 comprising a dialysis unit 6001 and a user interface unit 6002. In this embodiment, the dialysis unit 6001 comprises a housing 6004 that contains suitable components for performing hemodialysis. For example, the dialysis unit 6001 may include the mixing circuit 25, blood flow circuit 10, balancing circuit 143 and external dialysate circuit 142 described, for example, in connection with FIG. 2A. The dialysis unit 6001 may also include all patient access connections and dialysate fluidic connections needed for operation of the system 6000.

The user interface unit 6002 comprises a user interface 6003 that a user, such as a hemodialysis patient, may use to control operation of the dialysis unit 6001 via a connection 6006. The connection 6006 may comprise any suitable data connection such as a bus, a wireless connection, a connection over a local area network (e.g., an Ethernet local area network), and/or a connection over a wide area network (e.g., the Internet). The user interface unit 6002 further comprises a housing 6005 that contains components for enabling operation of the user interface. In the example of FIG. 60, the user interface 6003 comprises a display screen with a touch sensitive overlay to allow touch control and interaction with a graphical user interface presented on the screen. However, many other types of user interfaces are possible, such as a screen with a separate input mechanism, such as a keyboard and/or pointing device. The user interface 6002 may also include other features, such as push buttons, a speaker, a microphone for receiving voice commands, and so on.

While the hemodialysis system 6000 of FIG. 60 comprises a user interface unit 6002 remote from and physically coupled to a dialysis unit 6001, many alternative arrangements are possible. For example, the user interface unit 6002 may be mounted to or within dialysis unit 6001. For convenience, a user interface unit 6002 so mounted may be moveable from its mount for use in different locations and positions.

Figure 61:
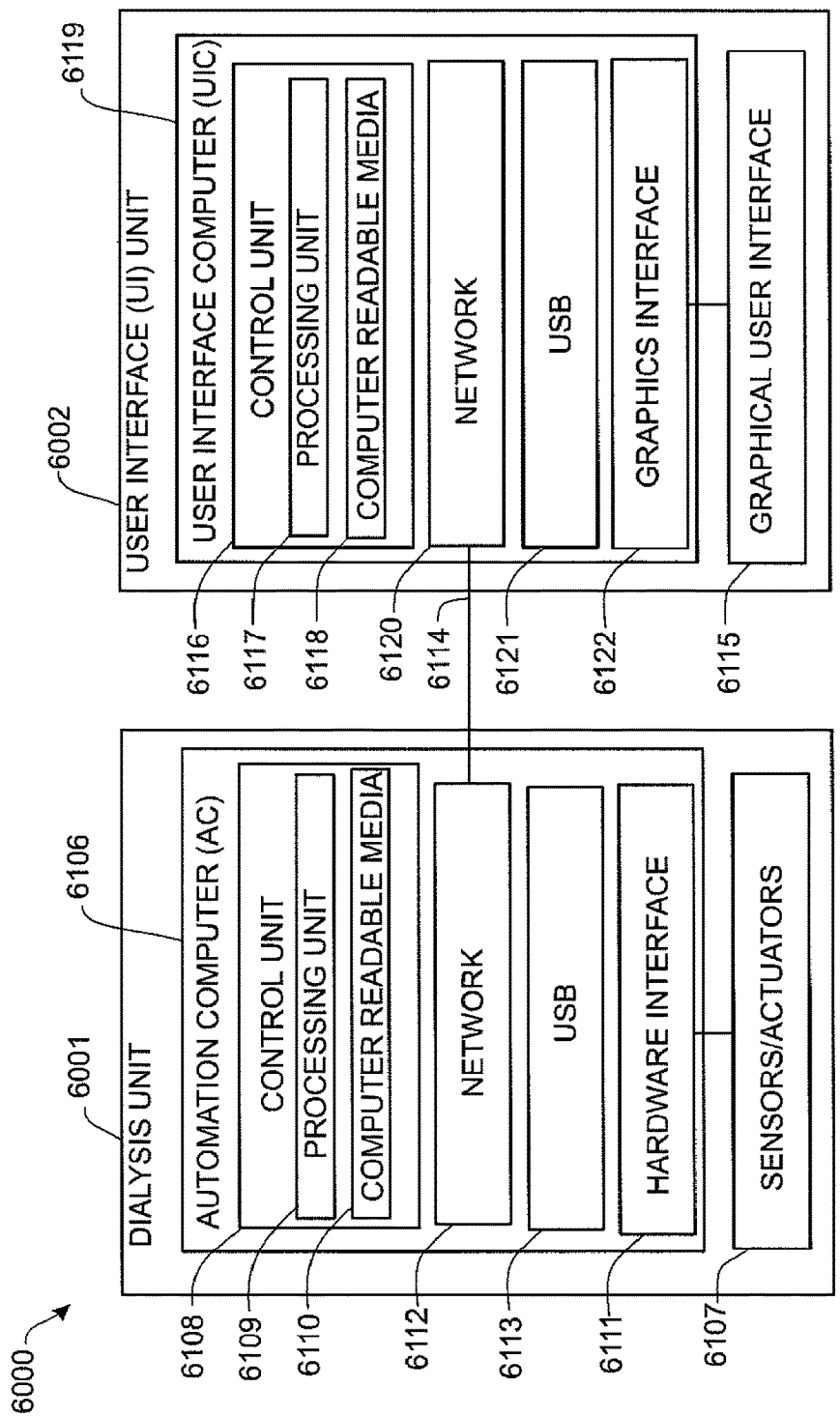
FIG. 61 is a schematic view of an exemplary hardware configuration for each of the dialysis unit and the user interface unit shown in FIG. 60.

FIG. 61 shows an exemplary hardware configuration for each of the dialysis unit 6001 and the user interface unit 6002. The dialysis unit 6001 comprises an automation computer (AC) 6106 that controls hardware actuators and sensors 6107 that deliver and monitor hemodialysis-related therapy. The automation computer 6106 comprises a control unit 6108 that includes a processing unit 6109 and computer readable media 6110. The processing unit 6109 comprises one or more processors that may execute instructions and operate on data stored on the computer readable media 6110. The data may, for example, relate to hemodialysis processes that have been or may be performed on a patient. The instructions may comprise, for example, an operating system (e.g., Linux), application programs, program modules, and/or other encoded instructions that perform particular processes.

The computer readable media 6110 may comprise any available media that can be accessed by the processing unit 6109. For example, computer readable media 6110 may comprise computer storage media and/or communication media. Computer storage media may include any one or more of volatile and/or nonvolatile memory and removable and/or non-removable media implemented in any method or technology for storage of information, such as computer readable instructions, data structures, program modules or other data. Examples of such computer storage media includes, but is not limited to, RAM, ROM, solid state disks, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by the processing unit 6109. Communication media typically embodies computer readable instructions, data structures, program modules or other data in a modulated data signal, such as a carrier wave or other transport mechanism, and includes any information delivery media. The term "modulated data signal" means a signal that has one or more of its characteristics set or changed in such a manner as to encode information in the signal. By way of example, communication media may include wired media, such as a wired network or direct-wired connection, and/or wireless media, such as acoustic, RF, infrared and other wireless media.

The various components of the automation computer 6106, including the computer readable media 6110 and the processing unit 6109, may be electrically coupled via a system bus. The system bus may comprise any of several types of bus structures including a memory bus or memory controller, a peripheral bus, and a local bus using any of a variety of bus architectures. By way of example, such architectures may include Industry Standard Architecture (USA), Micro Channel Architecture (MCA), Enhanced ISA (EISA), Video Electronics Standards Associate (VESA), and Peripheral Component Interconnect (PCI).

The automation computer 6106 may further include a universal serial bus (USB) interface 6113 so that various input and/or output devices may be coupled to the control unit 6108. Examples of such input and/or output devices include a monitor, speakers, a printer, a keyboard, a pointing device (e.g., a mouse), a scanner, personal digital assistants, a microphone and other peripheral devices. USB is merely one exemplary type of interface that may be used to connect peripheral devices. Other interfaces may alternatively be used.

As discussed above, dialysis unit 6001 includes components for performing and monitoring hemodialysis processes. Such components include sensors and actuators 6107. To couple the control unit 6108 to the sensors and actuators 6107, the automation computer may include a hardware interface 6111. The hardware interface 6111 may provide inputs to and receive outputs from the sensors and actuators 6107.

Automation computer 6106 may further comprise a network interface 6112 to allow the computer to connect with networked devices, such as those within a local area network (LAN) and/or a wide area network (WAN). For example, the network interface 6112 may allow the dialysis unit 6001 to exchange data with the user interface unit 6002 over a network 6114, which may comprise a LAN, such an Ethernet LAN, and/or a WAN, such as the Internet, and may be wired or wireless. Of course, the dialysis unit 6001 may alternatively or additionally exchange data with the user interface unit 6002 over a bus or other data connection.

The user interface unit 6002 comprises a user interface computer 6119 that controls a user interface, such as graphical user interface 6115 that displays information to and receives inputs from the user. Like the automation computer 6106, the user interface computer 6119 comprises a control unit 6116 having a processing unit 6117 and computer readable media 6118, a USB interface 6121 and a network interface 6120, each of which may be the same as or similar to their counterparts in the automation computer 6119. In addition, the user interface computer 6119 may include a graphics interface 6122 to couple the control unit 6116 to the graphical user interface 6115.

Figure 62:
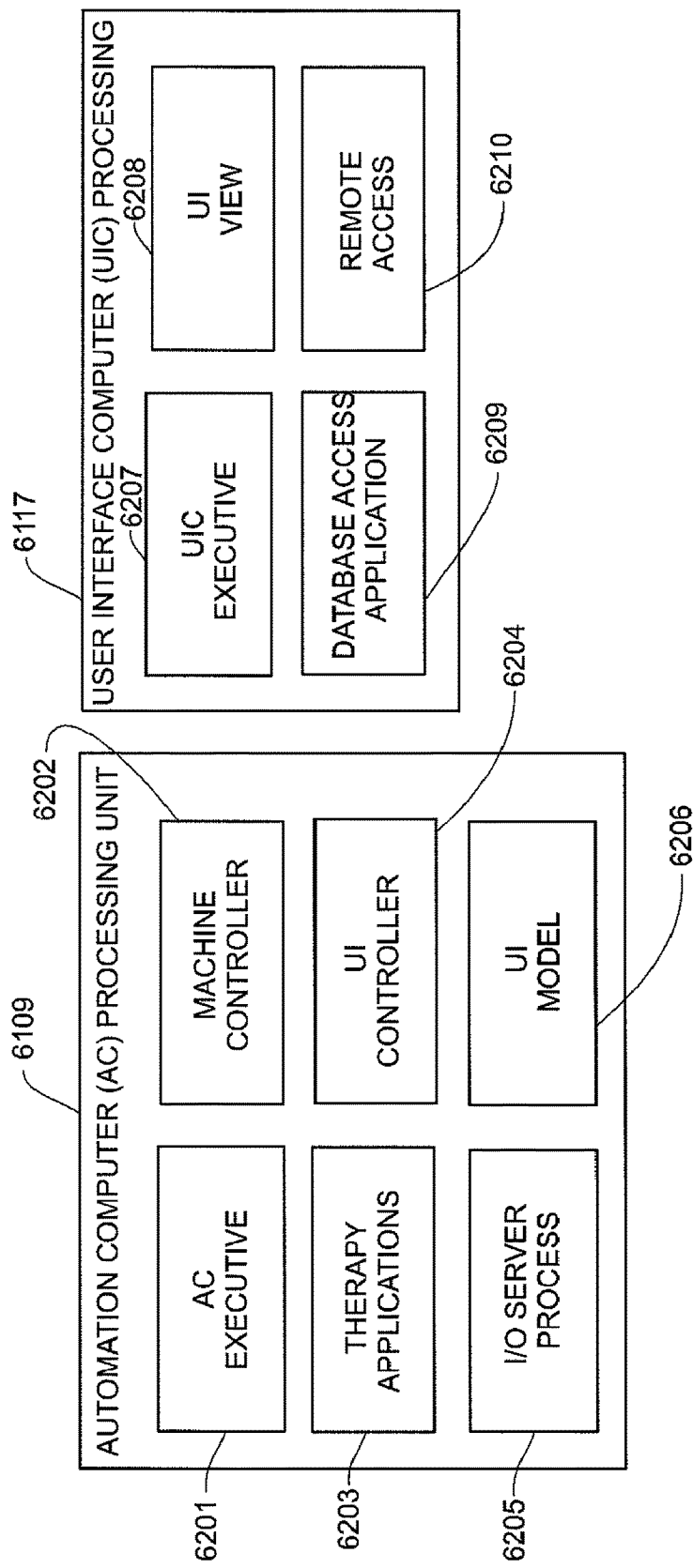
FIG. 62 is a schematic view showing exemplary software processes that may execute on the automation computer and user interface computer shown in FIG. 61.

FIG. 62 schematically shows various exemplary software processes that may execute on the processing units 6109 and 6117 of automation computer 6106 and user interface computer 6119, respectively. The processes shown may be lauched and monitored by an executive process. For example, the AC processing unit 6109 and UIC processing unit 6117 may respectively include AC Executive 6201 and the UIC Executive 6207 to launch the processes within the given processing unit and provide a communications mechanism to determine the running status of the child processes. In particular, the AC Executive 6201 and the UIC Executive 6207 may detect hung processes. When a child process terminates or fails, each executive process may take appropriate action to ensure that the system continues to operate in a safe manner. This may involve terminating processes, leading to system shutdown, or restarting processes that are not safety-critical. The AC Executive 6201 and the UIC Executive 6207 may use a Linux parent-child process relationship to receive notifications from the operating system about the termination of child processes. This allows handling of anomalous process terminations as well as expected terminations during a power-off sequence. The automation computer 6106 and the UIC Executives 6201 and 6207 may have a message interface between them to share information about their running processes. The status information may be shared on a periodic basis to allow a coherent view of state of all system processes on both processor units 6109 and 6117.

As shown in the example of FIG. 62, the AC processing unit 6109 includes an I/O Server Process 6205. The I/O Server Process 6205 directly accesses hardware, such as sensors and actuators, of the dialysis unit, and provides an interface to allow other processes to request read and write operations. For example, the I/O Server Process 6205 may provide an interface for the Machine Controller 6202 to read from and write to the sensors and actuators, thereby isolating the Machine Controller from the details of the hardware. In the embodiment described, only the Machine Controller 6202 may communicate with the I/O Server Process 6205. The interface may be a synchronous message queue.

The Machine Controller 6202, mentioned above, serves as an interface for controlling machine operations and reporting machine operational status. In particular, the Machine Controller 6202 implements controllers that read sensors and set actuators via the I/O Server Process 6205. These controllers are designed to allow functions (e.g., pumping and heating) to be programmed with a variety of parameters (e.g., flow rates, phases, pressures, and temperatures) in order to support the various hemodialysis therapies that may be performed. The configuration of the controllers may be established by state machines that implement high-level machine functions, such as priming and disinfection. The state machines configure flow paths and controller set points based on the capabilities of the machine and the high level commands received from the Therapy Applications 6203, described below. The Machine Controller 6202 may also perform safety cross checks on various sensors to maintain a safe, effective therapy. Machine status and health information may be recorded by the Machine Controller 6202 to a database.

The Therapy Applications 6203 drive the patient's therapy by commanding the Machine Controller 6202 to perform individual operations relating to hemodialysis processes. In particular, the Therapy Applications 6203 may run state machines that implement therapies and control the modes of the system. The state machines may, for example, control priming the system with dialysate, connecting the patient to the machine, dialyzing the patient, rinsing the patient's blood back to their body, cleaning the machine, disinfecting the machine, running tests on the machine components, replacing old or worn out components, and waiting for the patient to return for their next treatment. The Therapy Applications 6203 issue commands to and request status information from the Machine Controller 6202 in order to implement the therapy operations. In order to obtain patient, therapy and machine information the Therapy Applications 6203 may interface with a database to access information and store treatment status information. The Therapy Applications 6203 may be used as an interface by the User Interface Model 6206 process, discussed below, to forward user selections and report therapy status back to the user interface.

Like the Therapy Applications 6203, the User Interface (UI) Model 6206 runs on the AC processing unit 6109. The UI Model 6206 aggregates information describing the current state of the system and patient, and supports changes to the state of the system via operator input. The UI Model 6206 separates the content of the user interface display from non-content related aspects (e.g., presentation) by allowing the content of the user interface to change without affecting the underlying software that controls the user interface display. Thus, changes to the UI Model 6206 may be made without affecting the visual experience provided by the user interface. The UI Model 6206 does not have a display directly associated with it; rather, it commands the GUI 6115 of the user interface unit 6002 (FIG. 61) to display screens and return information. For example, when a user navigates to a new screen, the UI Model 6206 may send information to the user interface unit 6002 to be used in generating the new screen. The UI Model 6206 may also validate user data received from the user interface unit 6002 and, once validated, and forward the user data or commands based thereon to the Therapy Applications 6203.

To create the interactive displays for the GUI 6115 of the user interface unit 6002 (FIG. 61), the UI View Process 6208 runs on the UI processor 6117 of the user interface computer. The UI View Process 6208 need not keep track of screen flow or therapy state. Instead the UI View Process 6208 may receive from the UI Model 6206 running on the AC processing unit 6109 information specifying what and how to display the current state of a treatment to the user, as well as what may be input. As a result, the GUI 6115 may terminate and restart without impacting the system's operation. In addition, the GUI 6115 need not be responsible for validating user inputs. All inputs and commands received by the UI View 6208 may be sent to and validated by the UI Model 6206. Thus, all safety-critical aspects of the user interface may be handled by the UI Model 6206. Certain processes, such as those not safety-related, do not require the participation of the UI Model 6206. For example, allowing access to information stored in a database on the user interface computer may not require any functions to be performed by the UI Model 6206.

Also running on the UI processor 6117, a Remote Access Application 6210 provides an interface for external equipment. For example, the Remote Access Application 6210 may provide an interface for therapy monitoring, remote service, online assistance, and other external services, when authorized by a user. The Remote Access Application 6210 may be responsible for initiating a remote connection, validating the access, and supporting the communication from the remote site to the UI Model 6206.

A Database Access Application 6209 stores data to and retrieves data from one or more databases which may, for example, be located on the user interface computer 6119 (FIG. 61). The Database Access Application 6209 allows for record storage and retrieval, and provides a common access point for information required by the system, such as prescription, schedule, and history information. The Database Access Application 6209 may also manage database files to ensure they are backed up periodically.

As discussed in connection with FIG. 62, the functionality of the user interface software may be divided between the AC processing unit 6109 and the UIC processing unit 6117. The UI Model 6206 and UI Controller 6204 may cooperate to isolate the control of the UI data and state information on the automation computer 6106 so that software and screen design changes to the UI View 6208 will only affect the non-safety-critical software on the user interface computer 6119. Thus, while the UI Model 6206 may be tested and run at a safety-critical level, the UI View 6208 may run as a non-safety-critical process.

In general, therapy and machine state information displayed on the user interface computer 6119 originates only from the UI Model 6206. According to one exemplary embodiment, all data displayed on the user interface computer 6119 originates from the UI Model 6206, is taken directly from a database layer, or is temporary editing data entered by a user. The only local state information displayed or stored in the UI View 6208 may be this temporary editing data and details that allow for the local rendering of the information. In this manner, the UI Model 6208 may maintain and control the display of all validated data. Non-safety related data may be handled solely by the UI View 6208, if desired. For example, changes in the display language, or other display changes that do not impact safety-related content, may be performed using the UI View 6208 without any effect on the UI Model 6206.

It should be appreciated that the software processes shown in FIG. 62 and their association with processing units 6109 and 6117 represents just one example of a software configuration for performing the functions described above. The processes may be distributed in various alternative manners among processing units 6109 and 6117 and/or other local or remote processors. Further, not all processes may be required in the hemodialysis system. Certain processes may be omitted or modified while maintaining the functionality of a hemodialysis system.

Figure 63:
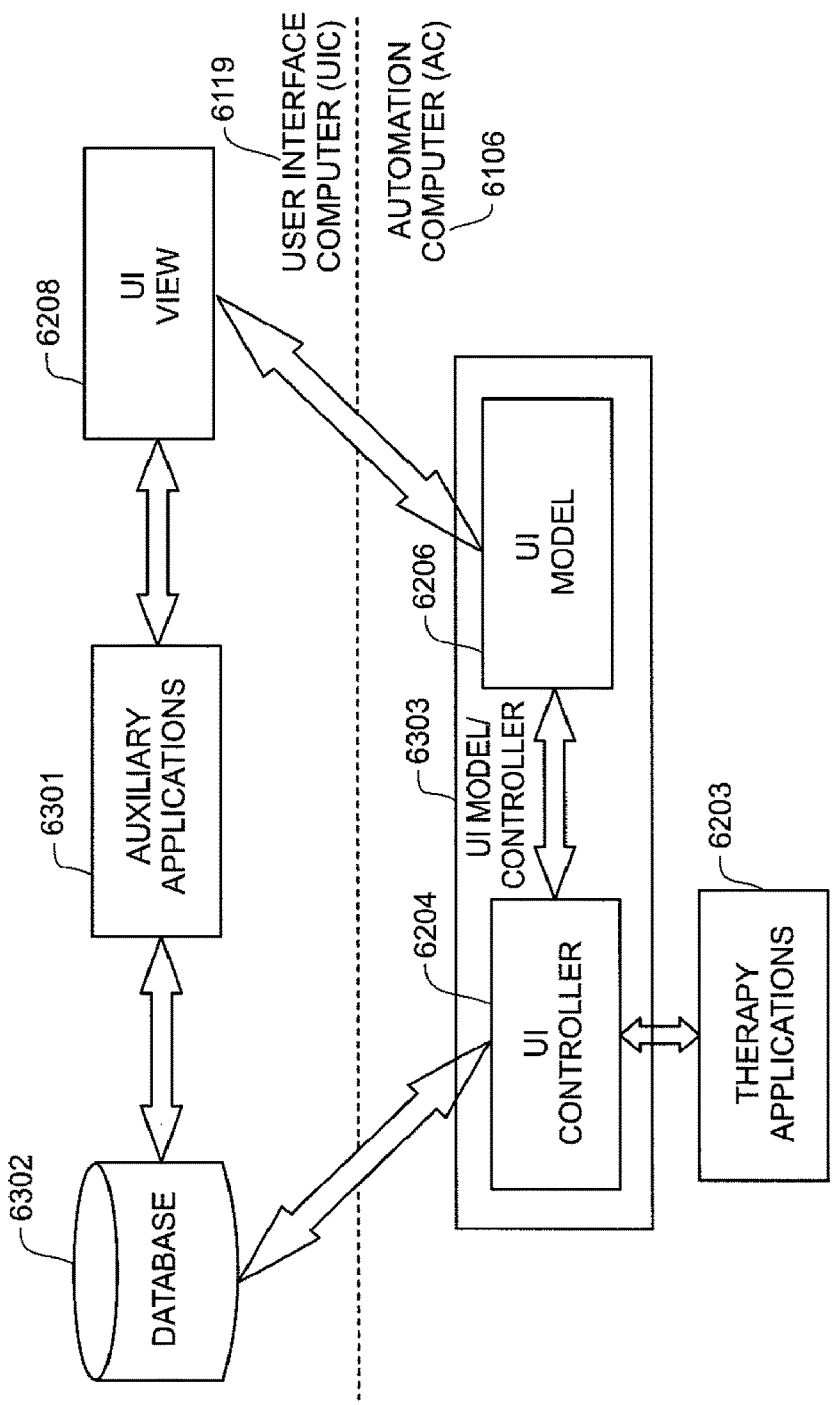
FIG. 63 is a schematic view showing an exemplary flow of information between and among the hardware and software components of the user interface computer and automation computer.

FIG. 63 shows an example of how information relating to the user interface may flow between and among the hardware and software components of the user interface computer 6119 and automation computer 6106. Information may flow and be handled so that safety-critical information is processed only at or below the UI Model layer. Safety-critical information relates to operations of the hemodialysis system. For example, safety-critical information may comprise a state of a dialysis process, a screen state of the graphical user interface, and/or the algorithms for implementing or monitoring therapies. In some cases, safety-critical information may be displayed by the graphical user interface. In such cases, the safety-critical information may comprise content that is material to the operations of the hemodialysis system. Non safety-critical information displayed by the user interface may comprise aspects of the display that relate to visual presentation and are not material to the operations of the hemodialysis system.

As shown in FIG. 63, the UI Model 6206, UI Controller 6204 and Therapy Applications 620, discussed in the connection with FIG. 62, run on the automation computer 6106. The UI View 6208 runs on the user interface computer 6119, along with Auxiliary Applications 6301. A database 6302, or an interface thereto (e.g., a database server) may also reside on the user interface computer 6119.

Considering first the flow of information between the UI View 6208 and UI Model 6206, the UI View operates as a client of the UI Model, as explained below. The UI View 6208 requests the current screen state from the UI Model 6206, and the UI Model answers the request. The answer dictates the major screen state of the UI View 6208. The UI Model 6206 may publish data and state information in sufficient detail so that the UI View 6208 can present various subsets of display information according to a level of detail requested by a user. For example, the UI View 6208 could present the same therapy state as either a summary or a step-by-step guide using the same information from the UI Model 6206. The presentation of the information may be based, for example, on a mode selected by a user (e.g., "expert" or "novice"). The UI Model 6206 may provide the ability for the UI View 6208 to record sub-state information, such as a current presentation mode, in the UI Model. This allows the GUI to resume operation in its prior state in the event of a user interface computer 6119 reset.

The UI Model 6206 may accept user-input data and requests, such as a request to start a therapy, from the UI View 6208. Data integrity of any information submitted via the UI View 6208 may be enhanced or ensured in several ways, such as by sending data submitted via the UI View 6208 through the UI Model 6206 for verification. That is, while data may be edited locally in the UI View 6208, the accepted data may be transferred to the UI Model 6206 to be verified and recorded into database 6302 and/or sent to the Therapy Applications 6203. Verification may comprise, for example, verifying that entered data is within an expected range. Any entered information may be then read back from the database 6302 by the UI Model 6206, and sent to the UI View 6208 for display to the user. This process may be used to ensure that data stored in the database 6302 is correct or as a user intended. Data integrity may also be enhanced by requesting verification, by the user or another party, of entered data.

As shown in FIG. 63, direct authority to control the Therapy Applications 6203 in response to inputs received from the user interface, and thereby affect machine state, may be limited to the UI Model/UI Controller 6303 running on the automation computer 6106. In addition, direct authority to change information in the database 6302 may be limited to the UI Model/UI Controller 6303. In this case, the UI View 6208 and Auxiliary Applications 6301 may have read access to the database for actions such a viewing a log, but may not have write access to the database 6302, at least under most circumstances. In this way, actions that could have safety-critical implications may be isolated on the automation computer 6106. Of course, in some situations, it may be desirable to allow the UI View 6208 and Auxiliary Applications 6301 to have limited write access to the database 6302, such as to write to a particular portion of the database or to write non safety-related data to the database. In addition, in some embodiments, it may be desirable to allow the UI View 6208 to directly control aspects of the Therapy Applications 6203.

The Auxiliary Applications 6301, discussed above, may comprise log or documentation viewers, for example. These Applications 6301 may run on the user interface computer 6119 and operate in their own process space. However, to enable the UI View 6208 to control these applications, the Auxiliary Applications 6301 may be clients of the UI View 6208. This allows the UI View 6208 to communicate with the applications in a standard manner and allows the UI View to monitor these processes.

The UI Controller 6204 may comprise a table-based hierarchical state machine (HSM) that determines the state of the screens displayed by the UI View 6208 based on data polled from the Therapy Applications 6203, local timeouts, and command requests or data received from the UI View 6208. As represented in FIG. 63, the UI Controller 6204 may access and write data to the database 6302 as required. The state of the HSM in the UI Controller 6204 may determine the major state of the set of screens displayed by the UI View 6208.

Figure 64:
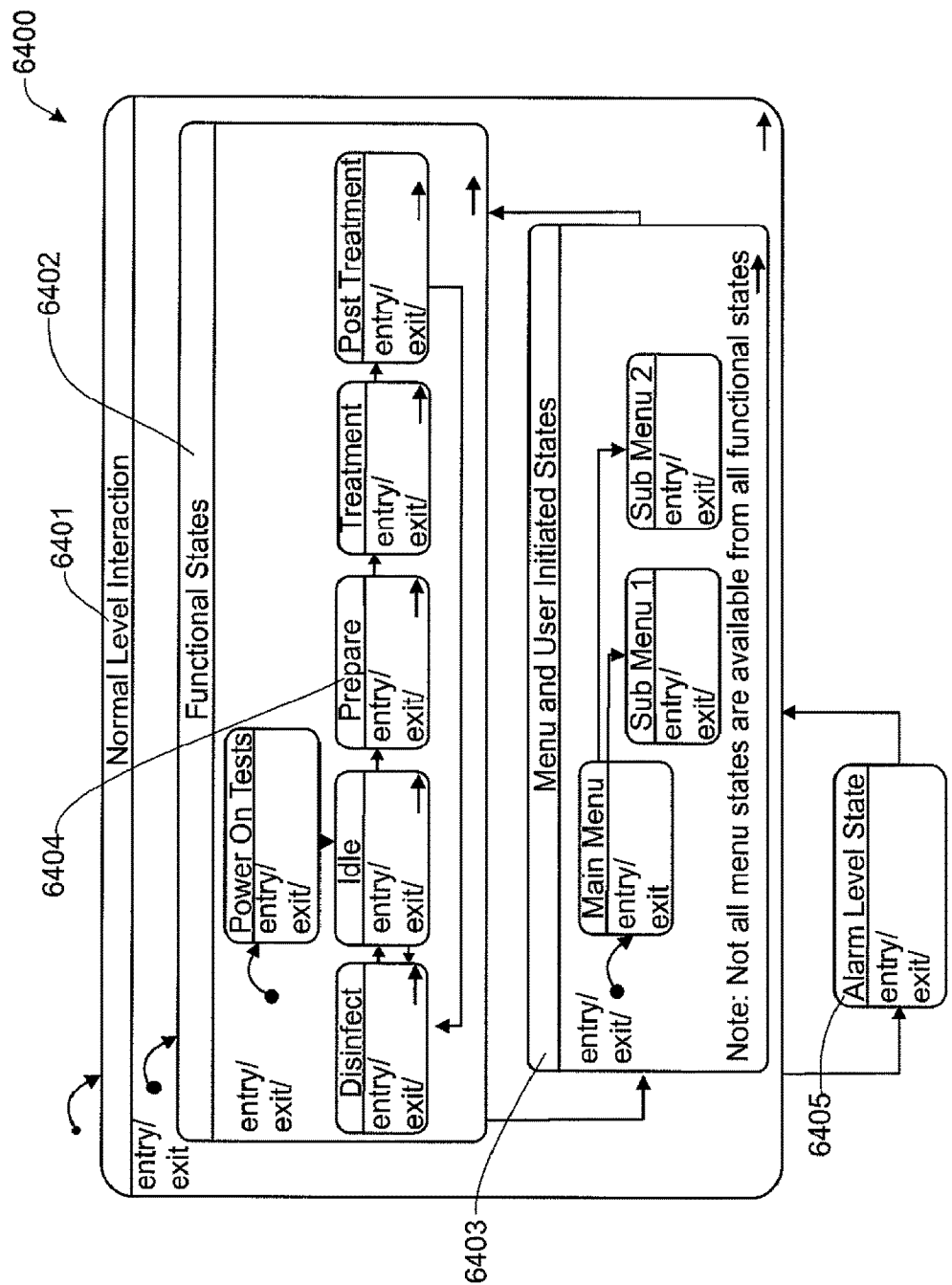
FIG. 64 is a schematic view of an exemplary hierarchical state machine (HSM) that may be used by the UI Controller shown in FIG. 63.

An exemplary HSM that may be used by the UI Controller 6204 to determine the state of the screens displayed by the UI View 6208 is schematically shown in FIG. 64. As shown, the HSM 6400 determines the state of "normal" (i.e., non-alarm) level interactions 6401, including the current functional state 6402 of the user interface and the current menu state 6403. The HSM 6400 shown in FIG. 64 is merely exemplary, and may be implemented in a much more detailed manner. For example, the state designated "Prepare" 6404 may involve several states relating to preparation for treatment, including a "gather supplies" state, an "install chemicals" state, the entering of patient information, and a validation screen. The validation screen gives the user the opportunity to return to any of the prior data entry screens so that inaccurate information can be corrected before the "Prepare" state is exited. The HSM 6400 also shows an alarm state 6405 that may be triggered. The alarm state is described in connection with FIG. 65.

Figure 65:
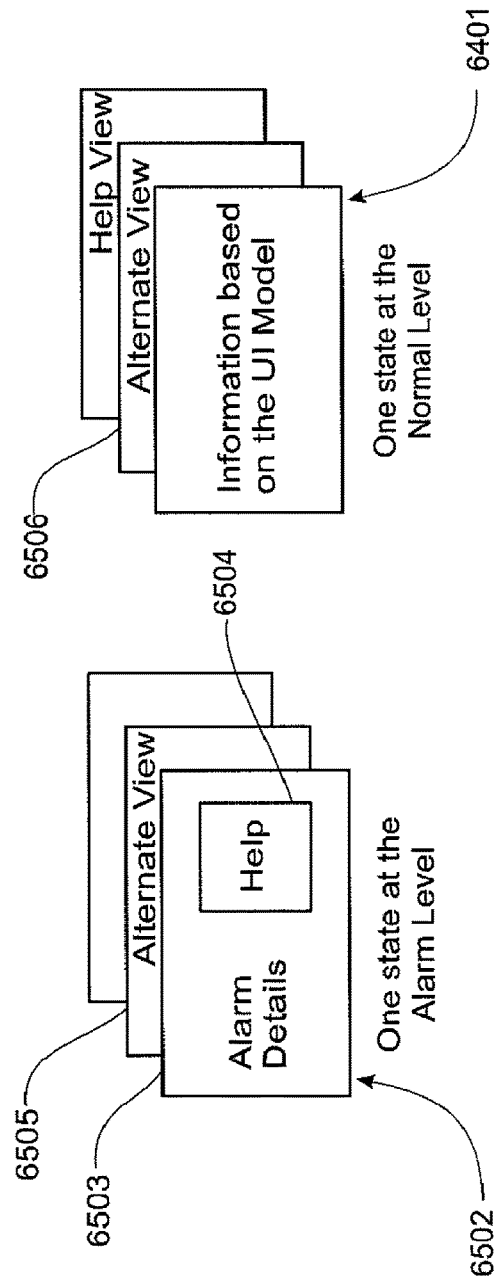
FIG. 65 is a schematic view of normal screen displays and alarm screen displays that may be displayed by the user interface shown in FIG. 61.

The UI View 6208 may have the ability to take over the screen display at any time in order to display alarms. An alarm condition may be triggered in certain circumstances to notify a user or other individual of an abnormal or otherwise noteworthy condition, such as a fluid leak, an occlusion, or an out-of-range temperature. When an alarm condition occurs, the state of the UI Controller 6204 may change. As shown in FIG. 65, when the UI View 6208 polls the UI Model 6206 for the current state, the UI View will change the display view from a normal state 6501 to an alarm state 6502 displaying alarm information 6503. When in an alarm condition, the UI View 6208 may prevent other information from blocking the display of the alarm. However, even during an alarm condition, the display may be configured such that a user may activate a "help" button to access additional information. In this case, help information 6504 may be laid out so that the help information covers only a portion of the view. Safety-critical logic of the alarm display, such as silencing logic, may be controlled in the automation computer 6106. For example, if a user would like an alarm to be silenced, an indication of the silencing request may be relayed back to the UI Model/UI Controller 6303, which can allow the audible alert to be silenced temporarily. In each of the alarm state and the normal state, alternate views 6505 and 6506, respectively, may be possible.

As explained above, when an alarm occurs, the normal UI View state is terminated so that the alarm state information can be displayed. Any local screen selection and/or editing data may be lost when the screen is changed. Since it may be desirable to preserve this information, the UI View 6208 may request that the UI Model/UI Controller 6303 stores information related to the screen displayed just prior to the alarm condition (i.e., the screen related to the normal state). At the conclusion of the alarm, if the normal state has not changed, the UI View 6208 may retrieve the stored information and restore the screen display. As an additional benefit, this feature may be used to restore the prior view in the event that the user interface computer 6119 is inadvertently reset.

The following are each incorporated herein by reference in their entireties: U.S. Provisional Patent Application Ser. No. 60/903,582, filed Feb. 27, 2007, entitled "Hemodialysis System and Methods"; U.S. Provisional Patent Application Ser. No. 60/904,024, filed Feb. 27, 2007, entitled "Hemodialysis System and Methods"; U.S. patent application Ser. No. 11/787,213, filed Apr. 13, 2007, published as US PGPub No. 2008/0058697 on Mar. 6, 2008, entitled "Heat Exchange Systems, Devices and Methods"; U.S. patent application Ser. No. 11/787,212, filed Apr. 13, 2007 and issued as U.S. Pat. No. 8,292,594 on Oct. 23, 2012, entitled "Fluid Pumping Systems, Devices and Methods"; U.S. patent application Ser. No. 11/787,112, filed Apr. 13, 2007 and issued as U.S. Pat. No. 7,794,141 on Sep. 14, 2010, entitled "Thermal and Conductivity Sensing Systems, Devices and Methods"; U.S. patent application Ser. No. 11/871,680, filed Oct. 12, 2007 and issued as U.S. Pat. No. 8,273,049 on Sep. 25, 2012, entitled "Pumping Cassette"; U.S. patent application Ser. No. 11/871,712, filed Oct. 12, 2007 and issued as U.S. Pat. No. 8,317,492 on Nov. 27, 2012, entitled "Pumping Cassette"; U.S. patent application Ser. No. 11/871,787, filed Oct. 12, 2007, published as US PGPub No. 2008/0253911 on Oct. 16, 2008, entitled "Pumping Cassette"; U.S. patent application Ser. No. 11/871,793, filed Oct. 12, 2007, published as US PGPub No. 2008/0253912 on Oct. 16, 2008, entitled "Pumping Cassette"; and U.S. patent application Ser. No. 11/871,803, filed Oct. 12, 2007 and issued as U.S. Pat. No. 7,967,022 on Jun. 28, 2011, entitled "Cassette System Integrated Apparatus." In addition, the following are incorporated by reference in their entireties: U.S. Pat. No. 4,808,161, issued Feb. 28, 1989, entitled "Pressure-Measurement Flow Control System"; U.S. Pat. No. 4,826,482, issued May 2, 1989, entitled "Enhanced Pressure Measurement Flow Control System"; U.S. Pat. No. 4,976,162, issued Dec. 11, 1990, entitled "Enhanced Pressure Measurement Flow Control System"; U.S. Pat. No. 5,088,515, issued Feb. 18, 1992, entitled "Valve System with Removable Fluid Interface"; and U.S. Pat. No. 5,350,357, issued Sep. 27, 1994, entitled "Peritoneal Dialysis Systems Employing a Liquid Distribution and Pumping Cassette that Emulates Gravity Flow." Also incorporated herein by reference are U.S. patent application Ser. No. 12/038,474, published as US PGPub No. 2008/0253427 on Oct. 16, 2008, entitled "Sensor Apparatus Systems, Devices and Methods," filed on Feb. 27, 2008; U.S. patent application Ser. No. 12/038,648, entitled "Cassette System Integrated Apparatus," filed on Feb. 27, 2008 and issued as U.S. Pat. No. 8,042,563 on Oct. 25, 2011; and U.S. patent application Ser. No. 12/072,908, filed Feb. 27, 2008 and issued as U.S. Pat. No. 8,246,826 on Aug. 21, 2012, entitled "Hemodialysis Systems and Methods."

In addition, the following applications are hereby incorporated herein by reference in their entireties: U.S. patent application Ser. No. 12/198,947, filed Aug. 27, 2008, published as US PGPub No. 2010/0057016 on Mar. 4, 2010, entitled "Occluder for a Medical Infusion System"; U.S. patent application Ser. No. 12/199,055, filed Aug. 27, 2008, published as US PGPub No. 2009/0114582 on May 7, 2009, entitled "Enclosure for a Portable Hemodialysis System"; U.S. patent application Ser. No. 12/199,062, published as US PGPub No. 2010/0051529 on Mar. 4, 2010, filed Aug. 27, 2008, entitled "Dialyzer Cartridge Mounting Arrangement for a Hemodialysis System"; U.S. patent application Ser. No. 12/199,068, filed Aug. 27, 2008, published as US PGPub No. 2009/0101549 on Apr. 23, 2009, entitled "Modular Assembly for a Portable Hemodialysis System"; U.S. patent application Ser. No. 12/199,077, filed Aug. 27, 2008, published as US PGPub No. 2009/0105629 on Apr. 23, 2009, entitled "Blood Circuit Assembly for a Hemodialysis System"; U.S. patent application Ser. No. 12/199,166, filed Aug. 27, 2008, published as US PGPub No. 2009/0107335 on Apr. 30, 2009, entitled "Air Trap for a Medical Infusion Device"; U.S. patent application Ser. No. 12/199,176, filed Aug. 27, 2008, published as US PGPub No. 2010/0056975 on Mar. 4, 2010, entitled "Blood Line Connector for a Medical Infusion Device"; U.S. patent application Ser. No. 12/199,196, filed Aug. 27, 2008, published as US PGPub No. 2010/0051551 on Mar. 4, 2010, entitled "Reagent Supply for a Hemodialysis System"; and U.S. Patent Application Ser. No. 61/092,239 entitled "Control System and Methods for Hemodialysis Device."

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A cassette-based fluid balancing system, comprising:
a first liquid flow path connecting a first inlet to a first outlet;
a second liquid flow path connecting a second inlet to a second outlet;
a control fluid path configured for controlling a diaphragm pump;
said pump comprising a rigid vessel containing a diaphragm dividing the rigid vessel into a control compartment and a liquid pumping compartment, the control compartment of said pump being in fluidic communication with the control fluid path and the liquid pumping compartment being in fluidic communication with the second liquid flow path;
a balancing chamber comprising a flexible diaphragm dividing the chamber into two liquid compartments, a first liquid compartment in fluidic communication with the first liquid flow path and a second liquid compartment in fluidic communication with the second liquid flow path;
the balancing chamber configured to balance flow between the first liquid flow path and the second liquid flow path; and
a first valve interposed between the liquid pumping compartment of the diaphragm pump and the second liquid compartment of the balancing chamber, said first valve under control of a controller; wherein
the controller is configured to operate the first valve using pulse-width modulation.

2. The system of claim 1, further comprising a second valve interposed between the second liquid compartment of the balancing chamber and the second outlet, wherein the controller is configured to operate the second valve so that it is closed while the first valve is operated using pulse-width modulation.

3. The system of claim 2, wherein while the second valve is closed, the controller operates the first valve using pulse-width modulation in a manner to provide a lower or more controlled pressure to the second liquid in the second liquid flow path as the first valve is being closed.

4. The system of claim 2, further comprising a third valve interposed between the first liquid compartment of the balancing chamber and the first inlet, wherein said first, second and third valves comprise membrane valves actuated by a control fluid, and wherein said second and third valves share a common control fluid line, causing said second and third valves to be opened together or closed together simultaneously.

5. A cassette-based fluid balancing system, comprising:
a first liquid flow path connecting a first inlet to a first outlet;
a second liquid flow path connecting a second inlet to a second outlet;
a control fluid path configured for controlling a diaphragm pump;
said pump comprising a rigid vessel containing a diaphragm dividing the rigid vessel into a control compartment and a liquid pumping compartment, the control compartment of said pump being in fluidic communication with the control fluid path and the liquid pumping compartment being in fluidic communication with the second liquid flow path;
a balancing chamber comprising a rigid chamber with a flexible diaphragm dividing the chamber into two liquid compartments, a first liquid compartment in fluidic communication with the first liquid flow path and a second liquid compartment in fluidic communication with the second liquid flow path;
the balancing chamber configured to balance flow between the first liquid flow path and the second liquid flow path; and
a first membrane valve interposed between the liquid pumping compartment of the diaphragm pump and the second liquid compartment of the balancing chamber, said first membrane valve under control of a control system comprising at least one controller; wherein
the control system is configured to control application of a closing pressure to the first membrane valve so that pressure applied during closure of the first membrane valve is less than pressure applied to maintain the first membrane valve closed, and to control operation of the fluid balancing system so that the balancing chamber balances flow between the first liquid flow path and the second liquid flow path by displacing a volume of a first liquid in the first liquid compartment as a substantially equal volume of a second liquid is pumped into the second liquid compartment.

6. The system of claim 5, further comprising a second membrane valve interposed between the second liquid compartment of the balancing chamber and the second outlet, wherein the control system is configured to operate the second membrane valve so that it is maintained in a closed position while the first membrane valve is being closed.

7. The system of claim 6, wherein while pressure is applied to the second membrane valve to maintain it in a closed position, the control system operates the first membrane valve in a manner to apply a lower pressure or a more controlled pressure increase to the first membrane valve as it is being closed than the pressure being applied to the second membrane valve.

8. The system of claim 6, further comprising a third membrane valve interposed between the first liquid compartment of the balancing chamber and the first inlet, wherein said first, second and third membrane valves are actuated by a control fluid, and wherein said second and third membrane valves share a common control fluid line, causing said second and third membrane valves to be opened together or closed together simultaneously.

9. A cassette-based fluid balancing system for a hemodialysis apparatus, comprising:
  a first dialysate flow path connecting a first inlet to a first outlet;
  a second dialysate flow path connecting a second inlet to a second outlet;
  a control fluid path configured for controlling a diaphragm pump;
  said pump comprising a rigid vessel containing a diaphragm dividing the rigid vessel into a control compartment and a dialysate pumping compartment, the control compartment of said pump being in fluidic communication with the control fluid path and the dialysate pumping compartment being in fluidic communication with the second dialysate flow path;
  a balancing chamber comprising a rigid chamber with a flexible diaphragm dividing the chamber into two dialysate compartments, a first dialysate compartment in fluidic communication with the first dialysate flow path and a second dialysate compartment in fluidic communication with the second dialysate flow path;
  the balancing chamber configured to balance flow between the first dialysate flow path and the second dialysate flow path; and
  a first membrane valve interposed between the dialysate pumping compartment of the diaphragm pump and the second dialysate compartment of the balancing chamber, said first membrane valve under control of a control system comprising at least one controller; wherein
  the control system is configured to control application of a closing pressure to the first membrane valve so that pressure applied during closure of the first membrane valve is less than pressure applied to maintain the first membrane valve closed, and to control operation of the fluid balancing system so that the balancing chamber balances flow between the first dialysate flow path and the second dialysate flow path by displacing a volume of a first dialysate in the first dialysate compartment as a substantially equal volume of a second dialysate is pumped into the second dialysate compartment.

10. The system of claim 9, further comprising a second membrane valve interposed between the second dialysate compartment of the balancing chamber and the second outlet, wherein the control system is configured to operate the second membrane valve so that it is maintained in a closed position while the first membrane valve is being closed.

11. The system of claim 10, wherein while pressure is applied to the second membrane valve to maintain it in a closed position, the control system operates the first membrane valve in a manner to apply a lower pressure or a more controlled pressure increase to the first membrane valve as it is being closed than the pressure being applied to the second membrane valve.

12. The system of claim 10, further comprising a third membrane valve interposed between the first dialysate compartment of the balancing chamber and the first inlet, wherein said first, second and third membrane valves are actuated by a control fluid, and wherein said second and third membrane valves share a common control fluid line, causing said second and third membrane valves to be opened together or closed together simultaneously.

* * * * *

UNITED STATES PATENT AND TRADEMARK OFFICE
CERTIFICATE OF CORRECTION

PATENT NO.         : 9,115,708 B2                           Page 1 of 1
APPLICATION NO.    : 14/262178
DATED              : August 25, 2015
INVENTOR(S)        : Dirk A. van der Merwe et al.

It is certified that error appears in the above-identified patent and that said Letters Patent is hereby corrected as shown below:

In the Specification:

At column 33, line 24, the word "of" should read -- uf --;

At column 41, line 1, the word "normutritive" should read -- nonnutritive --;

At column 71, line 11, the word "USA" should read -- ISA --.

Signed and Sealed this
Ninth Day of February, 2016

Michelle K. Lee
*Director of the United States Patent and Trademark Office*

UNITED STATES PATENT AND TRADEMARK OFFICE
CERTIFICATE OF CORRECTION

PATENT NO. : 9,115,708 B2
APPLICATION NO. : 14/262178
DATED : August 25, 2015
INVENTOR(S) : Dirk A. van der Merwe et al.

Page 1 of 1

It is certified that error appears in the above-identified patent and that said Letters Patent is hereby corrected as shown below:

In the Specification:

At column 34, lines 43-44, reads "A non-limiting example of a balancing cassette is shown in FIGS. 41-45." It should read "A non-limiting example of a directing cassette is shown in FIGS. 41-45."

Signed and Sealed this
Fourteenth Day of June, 2016

Michelle K. Lee
*Director of the United States Patent and Trademark Office*